US009518015B2

(12) United States Patent
Torrens Jover et al.

(10) Patent No.: US 9,518,015 B2
(45) Date of Patent: Dec. 13, 2016

(54) EP1 RECEPTOR LIGANDS

(75) Inventors: Antoni Torrens Jover, Terrassa (ES); Ramon Mercè Vidal, Barcelona (ES); Francesc Xavier Caldentey Frontera, Tarragona (ES); Antonio David Rodríguez Garrido, O Grove (ES); Elena Carceller González, Sant Cugat Del Vallés (ES); Jordi Salas Solana, Granollers (ES)

(73) Assignee: LABORATORIOS DEL DR. ESTEVE, S.A., Barcelona (ES)

( * ) Notice: Subject to any disclaimer, the term of this patent is extended or adjusted under 35 U.S.C. 154(b) by 0 days.

(21) Appl. No.: 14/345,136

(22) PCT Filed: Sep. 14, 2012

(86) PCT No.: PCT/EP2012/068101
§ 371 (c)(1),
(2), (4) Date: Apr. 30, 2014

(87) PCT Pub. No.: WO2013/037960
PCT Pub. Date: Mar. 21, 2013

(65) Prior Publication Data
US 2014/0323475 A1 Oct. 30, 2014

Related U.S. Application Data

(60) Provisional application No. 61/543,566, filed on Oct. 5, 2011.

(30) Foreign Application Priority Data

Sep. 16, 2011 (EP) ..................... 11382296

(51) Int. Cl.
| | |
|---|---|
| *C07D 209/12* | (2006.01) |
| *C07D 209/34* | (2006.01) |
| *C07D 405/06* | (2006.01) |
| *C07D 209/42* | (2006.01) |
| *C07D 215/48* | (2006.01) |
| *C07D 235/06* | (2006.01) |
| *C07D 471/04* | (2006.01) |
| *C07D 209/08* | (2006.01) |
| *C07D 231/56* | (2006.01) |
| *C07D 401/06* | (2006.01) |
| *C07D 405/12* | (2006.01) |
| *C07D 241/42* | (2006.01) |
| *C07D 487/04* | (2006.01) |
| *C07D 265/36* | (2006.01) |

(52) U.S. Cl.
CPC .......... *C07D 209/42* (2013.01); *C07D 209/08* (2013.01); *C07D 209/12* (2013.01); *C07D 209/34* (2013.01); *C07D 215/48* (2013.01); *C07D 231/56* (2013.01); *C07D 235/06* (2013.01); *C07D 241/42* (2013.01); *C07D 265/36* (2013.01); *C07D 401/06* (2013.01); *C07D 405/06* (2013.01); *C07D 405/12* (2013.01); *C07D 471/04* (2013.01); *C07D 487/04* (2013.01)

(58) Field of Classification Search
CPC .... C07D 209/12; C07D 209/34; C07D 405/06
See application file for complete search history.

(56) References Cited

U.S. PATENT DOCUMENTS

2002/0082280 A1    6/2002   Sperl et al.

FOREIGN PATENT DOCUMENTS

| EP | 1 424 325 A1 | 6/2004 |
| WO | WO 2004/108686 A2 | 12/2004 |
| WO | WO 2005/040128 A1 | 5/2005 |
| WO | WO 2006/066968 A1 | 6/2006 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/1alzheimers.drug.aplindexhtml>.*
Vippagunta, et al. Advanced Drug Delivery Reviews 48 (2001) 3-26.*
International Search Report dated Oct. 30, 2012 issued in corresponding International application No. PCT/EP2012/068101.
Abe et al., "The neuroprotective effect of prostaglandin E2 EP1 receptor inhibition has a wide therapeutic window, is sustained in time and is not sexually dimorphic", Journal of Cerebral Blood Flow & Metabolism, vol. 29, pp. 66-72, 2009.
Asboth et al. "Prostaglandin $E_2$ Activates Phospholipase C and Elevates Intracellular Calcium in Cultured Myometrial Cells: Involvement of EP1 and EP3 Receptor Subtypes", Endocrinology, vol. 137, No. 6, pp. 2572-2579, 1996.
Baba et al., "Direct Activation of Rat Spinal Dorsal Horn Neurons by Prostaglandin E2", The Journal of Neuroscience, vol. 21, No. 5, pp. 1750-1756, Mar. 1, 2001.
Breyer et al., "Prostaglandin receptors: their role in regulating renal function", Current Opinion in Nephrology and Hypertension, vol. 9, pp. 23-29, 2000.
Candelario et al., "Regional distribution of the prostaglandin E2 receptor EP1 in the rat brain: accumulation in Purkinje cells of the cerebellum", Journal of Molecular Neuroscience, vol. 27, No. 3, pp. 303-310, 2005.

(Continued)

Primary Examiner — Shawquia Jackson
(74) Attorney, Agent, or Firm — Ostrolenk Faber LLP

(57) ABSTRACT

The present invention belongs to the field of EP1 receptor ligands. More specifically it refers to compounds of general formula (I) having great affinity and selectivity for the EP1 receptor. The invention also refers to the process for their preparation, to their use as medicament for the treatment and/or prophylaxis of diseases or disorders mediated by the EP1 receptor as well as to pharmaceutical compositions comprising them.

16 Claims, No Drawings

(56) References Cited

OTHER PUBLICATIONS

Coleman, R.A., "Prostanoid Receptors", The IUPHAR Receptor Compendium, pp. 338-353, 2000.

Dirig et al., "In vitro prostanoid release from spinal cord following peripheral inflammation: effects of substance P, NMDA and capsaicin", British Journal of Pharmacology, vol. 126, pp. 1333-1340, 1999.

Durrenberger et al., "Prostanoid receptor EP1 and Cox-2 in injured human nerves and a rat model of nerve injury: a time-course study", BMC Neurology, vol. 6, No. 1, pp. 1-11, 2006.

Gabriel et al., "High Throughput Screening Technologies for Direct Cyclic AMP Measurement", ASSAY and Drug Development Technologies, vol. 1, No. 2, pp. 291-302, 2003.

Giblin et al., "The discovery of 6-[2-(5-chloro-2-{[(2,4-difluorophenyl)-methyl]oxy}phenyl)-1-cyclopenten-1-yl]-2-pyridinecarboxylic acid, GW848687X, a potent and selective prostaglandin $EP_1$ receptor antagonist for the treatment of inflammatory pain", Bioorganic & Medicinal Chemistry Letters, vol. 17, pp. 385-389, 2007.

Guay et al., "Carrageenan-induced Paw Edema in Rat Elicits a Predominant Prostaglandin $E_2$ ($PGE_2$) Response in the Central Nervous System Associated with the Induction of Microsomal $PGE_2$ Synthase-1", The Journal of Biological Chemistry, vol. 279, No. 23, pp. 24866-24872, 2004.

Hönemann et al., "The Inhibitory Effect of Bupivacaine on Prostaglandin $E_2$ ($EP_1$) Receptor Functioning: Mechanism of Action", Anesthesia & Analgesia, vol. 93, pp. 628-634, 2001.

Hall et al., "$EP_1$ Antagonists for the treatment of inflammatory pain", Current Opinion in Drug Discovery & Development, vol. 10, No. 5, pp. 597-612, 2007.

Hall et al., "Discovery of GSK345931A: An $EP_1$ receptor antagonist with efficacy in preclinical models of inflammatory pain", Bioorganic & Medicinal Chemistry Letters, vol. 19, pp. 479-501, 2009.

Johansson et al., "Contribution of peripheral versus central EP1 prostaglandin receptors to inflammatory pain", Neuroscience Letters, vol. 495, pp. 98-101, 2011.

Kawahara et al., "A Prostaglandin $E_2$ Receptor Subtype $EP_1$ Receptor Antagonist (ONO-8711) Reduces Hyperalgesia, Allodynia, and C-fos Gene Expression in Rats with Chronic Nerve Constriction", Anesthesia & Analgesia, vol. 93, pp. 1012-1017, 2001.

Lee et al., "Urodynamic Effects of a Novel $EP_1$ Receptor Antagonist in Normal Rats and Rats With Bladder Outlet Obstruction", The Journal of Urology, vol. 177, pp. 1562-1567, 2007.

Lee et al., "Hypoxia regulates $PGE_2$ release and EP1 receptor expression in osteoblastic cells", J Cell Physiol, vol. 212, No. 1, pp. 182-188, 2007.

Li et al., "Suppressed Microglial E Prostanoid Receptor 1 Signaling Selectively Reduces Tumor Necrosis Factor Alpha and Interleukin 6 Secretion from Toll-like Receptor 3 Activation", GLIA, vol. 59, pp. 569-576, 2011.

Lin et al., "Prostaglandin $E_2$ Receptor EP4 Contributes to Inflammatory Pain Hypersensitivity", The Journal of Pharmacology and Experimental Therapeutics, vol. 319, No. 3, pp. 1096-1103, 2006.

Ma et al., "Four PGE2 EP receptors are up-regulated in injured nerve following partial sciatic nerve ligation", Experimental Neurology, vol. 183, pp. 581-592, 2003.

Miki et al., "P1J-1-2 ONO-8130, an EP1 antagonist, strongly attenuates cystitis-related bladder pain caused by cyclophosphamide in mice", pp. 1.

Minami et al., "Allodynia evoked by intrathecal administration of prostaglandin $E_2$ to conscious mice", PAIN, vol. 57, pp. 217-223, 1994.

Minami et al., "Characterization of EP receptor subtypes responsible for prostaglandin $E_2$-induced pain responses by use of $EP_1$ and $EP_3$ receptor knockout mice", British Journal of Pharmacology, vol. 133, pp. 438-444, 2001.

Mizuguchi et al., "Roles of prostaglandin $E_2$-EP1 receptor signaling in regulation of gastric motor activity and emptying", American Journal of Physiol Gastrointest Liver Physiol, vol. 299, pp. G1078-G1086, 2010.

Moriyama et al., "Sensitization of TRPVI by $EP_1$ and IP reveals peripheral nociceptive mechanism of prostaglandins", Molecular Pain, vol. 1, No. 3, pp. 1-13, 2005.

Nakayama et al., "Role of Prostaglandin Receptor $EP_1$ in the Spinal Dorsal Horn in Carrageenan-induced Inflammatory Pain", Anesthesiology, vol. 97, pp. 1254-1262, 2002.

Nakayama et al., "Role of Prostaglandin receptor subtype $EP_1$ in prostaglandin $E_2$-induced nociceptive transmission in the rat spinal dorsal horn" Brain Research vol. 1010, pp. 62-28, 2004.

Narumiya et al., "Prostanoid Receptors: Structures, Properties and Functions", Physiological Reviews, vol. 79, No. 4, pp. 1193-1226, 1999.

Niho et al., "Suppression of azoxymethane-induced colon cancer development in rats by a prostaglandin E receptor $EP_1$-selective antagonist", Cancer Sci, vol. 96, No. 5, pp. 260-264, 2005.

Oida et al., "In situ hybridization studies of prostacyclin receptor mRNA expression in various mouse organs", British Journal of Pharmacology, vol. 116, pp. 2828-2837, 1995.

Oka et al., "Biphasic alteration in the trigeminal nociceptive neuronal responses after intracerebroventricular injection of prostaglandin $E_2$ in rats", Brain Research, vol. 749, pp. 354-357, 1997.

Oka et al., "Contrasting effects of E type prostaglandin (EP) receptor agonists on core body temperature in rats" Brain Research, vol. 968, pp. 256-262, 2003.

Okada et al., "ONO-8539, A Novel EP1 Receptor Antagonist, Suppresses Bladder Hyperactivity Via Excessive Production of Prostaglandin E2 9PGE2) Induced by Intravesical Instillation of ATP Urodynamic Evaluation of Cynomolgus Monkeys", Eur Urol Suppl, vol. 9, No. 2, pp. 72, 2010.

Omote et al., "The Effects of Peripheral Administration of a Novel Selective Antagonist for Prostaglandin E Receptor Subtype $EP_1$, ONO-8711, in a Rat Model of Postoperative Pain", Anesthesiology and Analgesia, vol. 92, pp. 233-238, 2001.

Omote et al., "Effects of a Novel Selective Agonist for Prostaglandin Receptor Subtype $EP_4$ on Hyperalgesia and Inflammation in Monoarthritic Model", Anesthesiology, vol. 97, No. 1, pp. 170-176, 2002.

Rahal et al., "Increased Severity of Renal Impairment in Nephritic Mice Lacking the $EP_1$ receptor", Canadian Journal of Physiol Pharmacol., vol. 84, pp. 877-885, 2006.

Samad et al., "Prostanoids and pain: unraveling mechanisms and revealing therapeutic targets", Trends in Molecular Medicine, vol. 8, No. 8, pp. 390-396, 2002.

Sarkar et al., "The Prostaglandin E2 Receptor-1 (EP-1) Mediates Acid-Induced Visceral Pain Hypersensitivity in Humans", Gastroenterology, vol. 124, pp. 18-25, 2003.

Schlötzer-Schrehardt et al., "Expression and Localization of FP and EP Prostanoid Receptor Subtypes in Human Ocular Tissues", Investigative Ophthalmology & Visual Science, vol. 43, No. 5, pp. 1475-1487., 2002.

Syriatowicz et al., "Hyperalgesia Due to Nerve Injury: Role of Prostaglandins", Neuroscience, vol. 94, No. 2, pp. 587-594, 1999.

Teramura et al., "Prostaglandin E1 Facilitate Primary Afferent Activity From the Urinary Bladder in the Rat Using Selective EP1-receptor antagonist (ONO-8711)", BJU INT, vol. 86, No. 3, pp. 1, 2000.

Watanabe et al., "Role of the Prostaglandin E Receptor Subtype $EP_1$ in Colon Carcinogenesis", Cancer Research, vol. 59, pp. 5093-5096, 1999.

Wilbraham et al., "Safety, Tolerability and Pharmacokinetic of Multiple Ascending Doses of the EP-1 Receptor Antagonist ONO-8539, A potential New and Novel Therapy to Overactive Bladder in Healthy Young and Elderly Subjects", Eur Urol Suppl, vol. 9, No. 2, pp. 250, 2010.

Woodward et al., "The Molecular Biology and the Ocular Distribution of Prostanoid Receptors", Survey of Ophthalmology, vol. 41, Suppl. 2, pp. S15-S21, 1997.

(56) References Cited

OTHER PUBLICATIONS

Zhang et al., "EP1-/-Mice Have Enhanced Osteoblast Differentiation and Accelerated Fracture Repair", Journal of Bone and Mineral Research, vol. 26, No. 4, pp. 792-802, 2011.

* cited by examiner

EP1 RECEPTOR LIGANDS

CROSS REFERENCE TO RELATED APPLICATIOS

The present application is a 35 U.S.C. §371 National Phase conversion of PCT/EP2012/068101, filed Sep. 14, 2012, which claims benefit of European Application No. 11382296.9, filed Sep. 16, 2011, and claims priority to U.S. Provisional Application No. 61/543,566, filed Oct. 5, 2011 the disclosures of which are incorporated herein by reference. The PCT International Application was published in the English language.

FIELD OF THE INVENTION

The present invention belongs to the field of EP1 receptor ligands. More specifically it refers to compounds of general formula (I) having great affinity and selectivity for the EP1 receptor. The invention also refers to the process for their preparation, to their use as medicament for the treatment and/or prophylaxis of diseases or disorders mediated by the EP1 receptor as well as to pharmaceutical compositions comprising them.

BACKGROUND OF THE INVENTION

Prostanoids are a family of eicosanoids that comprise prostaglandins (PGs), prostacyclins (PGIs), and thromboxanes (Txs). Their receptors belong to the G-protein coupled receptor (GPCR) superfamily of receptors and may be grouped into five classes, namely, prostaglandin D (DP), prostaglandin E (EP), prostaglandin F (FP), prostaglandin I (IP), and Thromboxane A (TP) based on their sensitivity to five naturally occurring prostanoids, PGD2, PGE2, PGF2 [alpha], PGI2, and TxA2, respectively (Coleman, R. A., 2000).

Prostaglandins contribute to the sensitization of peripheral and central nociceptive neurons during peripheral inflammation (Dirig and Yaksh, 1999) and play an important role in the pathogenesis of neuropathic pain following nerve injury (Syriatowicz et al 1999; Kawahara et al, 2001; Samad et al, 2002; Ma and Eisenach, 2003; Durrenberger et al., 2006).

Prostaglandin E2 (PGE2) is considered to be the dominant pro-nociceptive prostanoid. Guay and colleagues, analyzing the concentrations of different prostaglandins in the cerebrospinal fluid, found that PGE2 was the most prevalent prostanoid and exhibited the highest increase after peripheral carrageenan-induced inflammation (Guay et al., 2004). PGE2 is generated in most cells in response to mechanical, thermal or chemical injury and inflammatory insult, resulting in sensitization or direct activation of nearby sensory nerve, endings. Its production requires the activity of at least one of the two cyclooxygenase isoforms, COX-1 constitutively expressed or COX-2 which is inducible and particularly relevant for inflammation-induced PGE2 formation. Therefore, non-selective inhibitors of COX-1 and COX-2, and selective COX-2 inhibitors provide good pain relief. However, the long-term use is associated with gastrointestinal or cardiovascular side effects, respectively.

Downstream components of the inflammatory cascade could be an alternative approach for the treatment of the PGE2 associated pain. PGE2 binds to four different G-protein coupled receptors named EP1, EP2, EP3 and EP4 (Narumiya et al., 1999).

Studies employing antagonists suggest that blocking EP1, EP2, EP3 or EP4 receptors may reduce certain types of pain (Oka et al. 1997; Omote et al., 2002; Lin et al, 2006) and agonists increase nociceptive responses (Minami et al., 1994). Among these PGE2 receptor subtypes, most of drug discovery studies have focused on the EP1 receptors (Hall et al., 2007).

EP1 receptor stimulation mediates increases in intracellular calcium ions, facilitating neurotransmitter release (Asboth et al., 1996). EP1 receptor is preferentially expressed in primary sensory neurons, including their spinal cord terminals (Oidda et al., 1995) although it is also distributed in other tissues (Breyer et al., 2000; Schlötzer-Schrehardt et al., 2002). In the brain, marked differences in the level of EP1 expression among the cerebral regions were found. The strongest levels of EP1 mRNA were found in parietal cortex and cerebellum, followed in descending order by frontal cortex and striatum. The hypothalamus, hippocampus and brain stem displayed a low-level EP1 mRNA signal (Candelario-Jalil et al., 2005). In the spinal cord, several studies have reported the effects of PGE2 on neuronal excitability or synaptic transmission (Baba et al., 2001) and pain transmission (Nakayama et al., 2004). Therefore, EP1 receptor antagonists, blocking the positive feedback cascade mediated by $PGE_2$, may result in analgesic efficacy. In this regard, using EP receptor deficient mice, a prominent contribution of EP1 receptors has been described (Minami et al., 2001). EP1–/– knockout mice demonstrated a role of this receptor in mediating peripheral heat sensitization after subcutaneous PGE2 injection (Moriyama et al. 2005; Johansson et al. 2011), and EP1 receptor antagonism has been reported to reduce mechanical hyperalgesia in nerve injured rats (Kawahara et al., 2001), in the carrageenan model (Nakayama et al. 2002), or in the incisional model of postoperative pain (Omote et al 2002). Moreover, EP1 antagonists demonstrated analgesic activity in a complete Freund's adjuvant model of knee joint arthritis (Giblin et al, 2007; Hall et al, 2009). It has also been reported that the contribution of PGE2 in human visceral pain hypersensitivity is mediated through the EP1 receptor (Sarkar et al., 2003).

In addition to being useful for modulating pain, EP1 antagonists may also be useful for the treatment or prevention of other EP1 receptor-mediated diseases such as motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases.

In turn, EP1 receptor agonists also may have a number of utilities. These include, but are not limited to treatment of influenza, bone fracture healing, bone disease, glaucoma, ocular hypertension, dysmenorrhoea, pre-term labour, immune disorders, osteoporosis, asthma, allergy, fertility, male sexual dysfunction, female sexual dysfunction, periodontal disease, gastric ulcer, and renal disease. EP receptor agonists may also be useful for expansion of hematopoietic stem cell populations.

Based on the above mentioned results coming from animal and human studies, EP1 receptor has been identified as a selective target for the development of new potential therapies for the treatment of those disorders where PGE2 action is involved. In view of the potential therapeutic applications of agonists and antagonists of the EP1 receptor, a great effort is being directed to find selective ligands. Despite intense research efforts in this area, very few compounds with selective EP1 activity have been reported.

There is thus still a need to find compounds having pharmacological activity towards the EP1 receptor, being both effective and selective, and having good "druggability" properties, i.e. good pharmaceutical properties related to administration, distribution, metabolism and excretion.

The present invention hereby provide some novel compounds complying with the above mentioned properties.

OBJECT OF THE INVENTION

The present invention discloses novel compounds with great affinity to EP1 receptors which might be used for the treatment of EP1-related disorders or diseases.

Specifically, it is an object of the invention a compound of general formula I:

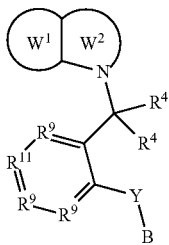

I wherein:
$W^1$ is phenyl or a 6-membered heteroaromatic ring containing 1 or 2 N atoms, wherein $W^1$ is substituted by one $R^1$ and optionally substituted by, one or more $R^2$;
$W^2$ is a 5- or 6-membered heterocyclic ring that contains 1 N atom and can additionally contain 1 or 2 heteroatoms selected from the group consisting of N, O, and S; wherein said ring is aromatic, partially unsaturated or saturated, and which is optionally substituted by one or more $R^3$;
$R^1$ is —$R^6$-$R^7$;
each $R^2$ is independently selected from the group consisting of H, halogen, $C_{1-6}$-alkyl, $C_{1-6}$-haloalkyl, —O—$C_{1-6}$-alkyl, —O—$C_{1-6}$-haloalkyl, hydroxy$C_{1-6}$-alkyl, CN, —$NR^{14}COR^{15}$, —$NR^{14}SO_2R^{15}$ and —$SO_2R^{15}$;
each $R^3$ is independently selected from the group consisting of H, halogen, $C_{1-6}$-alkyl $C_{1-6}$-haloalkyl, —O—$C_{1-6}$-alkyl, —O—$C_{1-6}$-haloalkyl, hydroxy$C_{1-6}$-alkyl, —$C_{1-4}$-alkylene-$OR^{14}$, —$C_{2-4}$-alkenylene-COON, =O and CN;
each $R^4$ is independently selected from the group consisting of H and $C_{1-6}$-alkyl, or both $R^4$ together with the C atom to which they are bonded form a $C_{3-6}$cycloalkyl;
$R^5$ is selected from the group consisting of H, halogen, $C_{1-6}$-haloalkyl, —O—$C_{1-6}$-alkyl, —O—$C_{1-6}$-haloalkyl, —OH, $C_{1-6}$-alkyl, $C_{3-6}$cycloalkyl and —$SO_2R^{15}$;
$R^6$ is selected from the group consisting of a direct bond, —$C_{1-4}$-alkylene-, —O—$C_{1-4}$-alkylene- and —$C_{2-4}$-alkenylene-;

$R^7$ is selected from the group consisting of —$CO_2H$, —$SO_3H$, 5-tetrazolyl, —$OPO_3H_2$, —$PO_3H_2$, —$CONR^{12}R^{12}$—$CONH$—$SO_2R^{12}$, —$NR^{14}CONR^{14}$—$SO_2R^{15}$ and —$SO_2$—$NHCOR^{15}$,
Y is selected from the group consisting of —$C_{2-4}$-alkylene-, —O—$C_{1-4}$-alkylene-, —$C_{2-4}$-alkenylene-, —$C_{1-4}$-alkylene-O—, —$NR^{13}$—$C_{1-4}$-alkylene-$NR^{13}$—;
B is selected from the group consisting of $C_{2-6}$-alkyl, $C_{2-6}$ alkenyl and Cy, any of them optionally substituted by one or more $R^8$;
each $R^8$ is independently selected from the group consisting of halogen, $C_{1-6}$-haloalkyl, —O—$C_{1-6}$-alkyl, —O—$C_{1-6}$-haloalkyl, $C_{1-6}$-alkyl, —OH, —CN, —$CH_2OR^{14}$ and —$CONR^{12}R^{12}$;
each $R^9$ is independently selected from the group consisting of $CR^{10}$ and N;
each $R^{10}$ is independently selected from the group consisting of H, halogen, $C_{1-6}$-alkyl, $C_{1-6}$-haloalkyl, —O—$C_{1-6}$-alkyl, —O—$C_{1-6}$-haloalkyl and hydroxy$C_{1-6}$-alkyl;
$R^{11}$ is $CR^5$ or N,
each $R^{12}$ is independently selected from the group consisting of H, $C_{1-6}$-alkyl, $C_{1-6}$-haloalkyl, —$NR^{14}R^{14}$ and $C_{3-6}$cycloalkyl;
each $R^{13}$ is independently selected from the group consisting of H, $C_{1-6}$-alkyl, $C_{1-6}$-haloalkyl, and $C_{3-6}$cycloalkyl;
each $R^{14}$ is independently selected from the group consisting of H and $C_{1-6}$-alkyl;
each $R^{15}$ is independently selected from the group consisting of $C_{1-6}$-alkyl;
Cy is a 3-6 membered monocyclic or 8-12 membered polycyclic ring which can be carbocyclic or heterocyclic containing 1 to 3 heteroatoms selected from N, O and S and which can be aromatic, partially unsaturated or saturated and wherein one or more C or S atoms in Cy can be oxidized to form CO, SO or $SO_2$;
with the proviso that when W1 and W2 is a benzimidazole, $R^6$ and $R^7$ are not at the same time respectively a —O—$C_{1-4}$-alkylene- and a —$CO_2H$ or that $R^7$ is not —$CONH$—$SO_2R^{12}$; and the salts, solvates and prodrugs thereof.

It is also an object of the invention the process for the preparation of compounds of general formula (I).

In another aspect, the invention relates to a compound of general formula (I) for use as a medicament.

Yet another object of the invention is a compound of general formula (I) for use in the treatment and/or prophylaxis of diseases or disorders mediated by the EP1 receptor. This includes but is not limited to diseases such as inflammatory related pain including low back and neck pain, skeletal pain, post-partum pain, toothache, sprains and straits, myositis, neuralgia, synovitis, arthritis, including rheumatoid arthritis, degenerative joint diseases, gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases.

It is another object of the invention a pharmaceutical composition comprising at least one compound of general formula (I) and at least one pharmaceutically acceptable carrier, additive, adjuvant or vehicle.

DETAILED DESCRIPTION OF THE INVENTION

In a first aspect the invention relates to compounds of general formula (I):

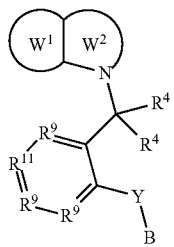

I wherein:

$W^1$ is phenyl or a 6-membered heteroaromatic ring containing 1 or 2 N atoms,
wherein $W^1$ is substituted by one $R^1$ and optionally substituted by one or more $R^2$;

$W^2$ is a 5- or 6-membered heterocyclic ring that contains 1 N atom and can additionally contain 1 or 2 heteroatoms selected from the group consisting of N, O, and S; wherein said ring is aromatic, partially unsaturated or saturated, and which is optionally substituted by one or more $R^3$;

$R^1$ is —$R^6$-$R^7$;

each $R^2$ is independently selected from the group consisting of H, halogen, $C_{1-6}$-alkyl, $C_{1-6}$-haloalkyl, —O—$C_{1-6}$-alkyl, —O—$C_{1-6}$-haloalkyl, hydroxy$C_{1-6}$-alkyl, CN, —$NR^{14}COR^{15}$, —$NR^{14}SO_2R^{15}$ and —$SO_2R^{15}$;

each $R^3$ is independently selected from the group consisting of H, halogen, $C_{1-6}$-alkyl $C_{1-6}$-haloalkyl, —O—$C_{1-6}$-alkyl, —O—$C_{1-6}$-haloalkyl, hydroxy$C_{1-6}$-alkyl, —$C_{1-4}$-alkylene-$OR^{14}$, —$C_{2-4}$-alkenylene-COOH, =O and CN;

each $R^4$ is independently selected from the group consisting of H and $C_{1-6}$-alkyl, or both $R^4$ together with the C atom to which they are bonded form a $C_{3-6}$cycloalkyl;

$R^5$ is selected from the group consisting of H, halogen, $C_{1-6}$-haloalkyl, —O—$C_{1-6}$-alkyl, —O—$C_{1-6}$-haloalkyl, —OH, $C_{1-6}$-alkyl, $C_{3-6}$cycloalkyl and —$SO_2R^{15}$;

$R^6$ is selected from the group consisting of a direct bond, —$C_{1-4}$-alkylene-, —O—$C_{1-4}$-alkylene- and —$C_{2-4}$-alkenylene-;

$R^7$ is selected from the group consisting of —$CO_2H$, —$SO_3H$, 5-tetrazolyl, —$OPO_3H_2$, —$PO_3H_2$, —$CONR^{12}R^{12}$—$CONH$—$SO_2R^{12}$, —$NR^{14}CONR^{14}$—$SO_2R^{15}$ and —$SO_2$—$NHCOR^{15}$;

Y is selected from the group consisting of —$C_{2-4}$-alkylene-, —O—$C_{1-4}$-alkylene-, —$C_{2-4}$-alkenylene-, —$C_{1-4}$-alkylene-O—, —$NR^{13}$—$C_{1-4}$-alkylene- and —$C_{1-4}$-alkylene-$NR^{13}$—;

B is selected from the group consisting of $C_{2-6}$-alkyl, $C_{2-6}$-alkenyl and Cy, any of them optionally substituted by one or more $R^8$;

each $R^8$ is independently selected from the group consisting of halogen, $C_{1-6}$-haloalkyl, —O—$C_{1-6}$-alkyl, —O—$C_{1-6}$-haloalkyl, $C_{1-6}$-alkyl, —OH, —CN, —$CH_2OR^{14}$ and —$CONR^{12}R^{12}$;

each $R^9$ is independently selected from the group consisting of $CR^{10}$ and N;

each $R^{10}$ is independently selected from the group consisting of H, halogen, $C_{1-6}$-alkyl, $C_{1-6}$-haloalkyl, —O—$C_{1-6}$-alkyl, —O—$C_{1-6}$-haloalkyl and hydroxy$C_{1-6}$-alkyl;

$R^{11}$ is $CR^5$ or N, each $R^{12}$ is independently selected from the group consisting of H, $C_{1-6}$-alkyl $C_{1-6}$-haloalkyl, —$NR^{14}R^{14}$ and $C_{3-6}$cycloalkyl;

each $R^{13}$ is independently selected from the group consisting of H, $C_{1-6}$-alkyl $C_{1-6}$-haloalkyl, and $C_{3-6}$cycloalkyl;

each $R^{14}$ is independently selected from the group consisting of H and $C_{1-6}$-alkyl;

each $R^{15}$ is independently selected from the group consisting of $C_{1-6}$-alkyl;

Cy is a 3-6 membered monocyclic or 8-12 membered polycyclic ring which can be carbocyclic or heterocyclic containing 1 to 3 heteroatoms selected from N, O and S and which can be aromatic, partially unsaturated or saturated and wherein one or more C or S atoms in Cy can be oxidized to form CO, SO or $SO_2$;

with the proviso that when W1 and W2 is a benzimidazole, $R^6$ and $R^7$ are not at the same time, respectively a —O—$C_{1-4}$-alkylene- and a —$CO_2H$ or that $R^7$ is not —CONH—$SO_2R^{12}$;

and the salts, solvates and prodrugs thereof.

Also included within the scope of the invention are the isomers, polymorphs, isotopes, salts, solvates and prodrugs of the compounds of formula (I). Any reference to a compound of formula (I) throughout the present specification includes a reference to any isomer, polymorph, isotope, salt, solvate or prodrug of such compound of formula I.

The compounds of formula I may exist in different physical forms, i.e. amorphous and crystalline forms. Moreover, the compounds of the invention may have the ability to crystallize in more, than one form, a characteristic which is known as polymorphism. Polymorphs can be distinguished by various physical properties well known in the art such as X-ray diffraction pattern, melting point or solubility. All physical forms of the compounds of formula I, including all polymorphic forms ("polymorphs") thereof, are included within the scope of the invention.

Some of the compounds of the present invention may exist as several optical isomers and/or several diastereoisomers. Diastereoisomers can be separated by conventional techniques such as chromatography or fractional crystallization. Optical isomers can be resolved by conventional techniques of optical resolution to give optically pure isomers. This resolution can be carried out on any chiral synthetic intermediate or on the products of formula I. Optically pure isomers can also be individually obtained using enantiospecific synthesis. The present invention covers all individual isomers as well as mixtures thereof (for example racemic mixtures or mixtures of diastereomers), whether obtained by synthesis or by physically mixing them.

In addition, any formula given herein is intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{36}S$, $^{18}F$, $^{36}Cl$, and $^{125}I$, respectively. Such isotopically labelled compounds are useful in metabolic studies (preferably with 14C), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. In addition to the unlabeled form, all isotopically labeled forms of the compounds of formula I are included within the scope of the invention.

"Halogen" or "halo" as referred in the present invention represent fluorine, chlorine, bromine or iodine.

The term "alkyl," alone or in combination, means an acyclic radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, heptyl, octyl, and the like. Where no specific substitution is specified, alkyl radicals may be optionally substituted with groups consisting of hydroxy, sulfhydryl, methoxy, ethoxy, amino, cyano, chloro, and fluoro. The carbon atom content of various hydrocarbon-containing moieties is indicated by suffix designating a lower and upper number of carbon atoms in the moiety. Thus, for example, '$C_{1-6}$-alkyl' refers to alkyl of 1 to 6 carbon atoms, inclusive.

The term "alkenyl," alone or in combination, means an acyclic radical, linear or branched, preferably containing from 1 to about 6 carbon atoms and containing at least one double bond. Examples of such radicals include ethenyl, propenyl, isopropenyl, butenyl, isobutenyl, sec-butenyl tert-butenyl and the like. Where no specific substitution is specified, alkenyl radicals may be optionally substituted with groups consisting of hydroxy, sulfhydryl, methoxy, ethoxy, amino, cyano, chloro, and fluoro. The carbon atom content of various hydrocarbon-containing moieties is indicated by suffix designating a lower and upper number of carbon atoms in the moiety. Thus, for example, 'C1-6-alkenyl' refers to alkenyl of 1 to 6 carbon atoms, inclusive.

An "alkylene" linking group preferably contains 1-4 carbon atoms and represents for example methylene, ethylene, propylene, butylene. The carbon atom content of various hydrocarbon-containing moieties is indicated by suffix designating a lower and upper number of carbon atoms in the moiety. Thus, for example, 'C1-4-alkylene' refers to an alkylene of 1 to 4 carbon atoms, inclusive.

An "alkenylene" linking group preferably contains 2 to 4 carbon atoms and represents for example ethenylene, 1,3-propenylene, 1,4-but-1-enylene, 1,4-but-2-ethylene. The carbon atom content of various hydrocarbon-containing moieties is indicated by suffix designating a lower and upper number of carbon atoms in the moiety. Thus, for example, 'C2-4-alkenylene' refers to alkenylene of 2 to 4 carbon atoms, inclusive.

"Cycloalkyl" is preferably a monocyclic cycloalkyl containing from three to six carbon atoms. Examples include cyclopropyl, cyclobutyl, cyclopentyl, and cyclohexyl. The carbon atom content of various hydrocarbon-containing moieties is indicated by suffix designating a lower and upper number of carbon atoms in the moiety. Thus, for example, 'C3-6-cycloalkyl' refers to cycloalkyl of 3 to 6 carbon atoms, inclusive. The term "carbocyclic", "carbocyclic ring" and "carbocyclyl" refer to a saturated, unsaturated or aromatic mono- or multi-ring cycloalkyl only formed from carbon atoms.

The terms "heterocycle", "heterocyclic ring" and "heterocyclyl" refer to a saturated, unsaturated or aromatic mono- or multi-ring cycloalkyl wherein one or more carbon atoms is replaced by N, S, or O. The terms "heterocycle", "heterocyclic ring system," and "heterocyclyl" include fully saturated ring structures such as piperazinyl, dioxanyl, tetrahydrofuranyl, oxiranyl, aziridinyl, morpholinyl, pyrrolidinyl, piperidinyl, thiazolidinyl, and others. The terms "heterocycle", "heterocyclic ring system," and "heterocyclyl" also include partially unsaturated ring structures such as dihydrofuranyl, dihydropyrrolyl, pyrazolinyl, imidazolinyl, pyrrolinyl, chromanyl, dihydrothienyl, and others. The term "heterocycle", "heterocyclic ring system," and "heterocyclyl" also include aromatic structures such as pyridyl, pyrimidinyl, pyridazinyl, pyrazinyl, thienyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted.

The term "heteroaromatic ring" refers to an aromatic heterocyclic ring. Examples of "heteroaromatic ring" include pyridyl, pyrimidinyl, pyridazinyl, pyrazinyl, thionyl, furanyl, pyrrolyl, pyrazolyl, imidazolyl, oxazolyl, isoxazolyl, thiazolyl, isothiazolyl, triazolyl, oxadiazolyl, thiadiazolyl, and tetrazolyl, optionally substituted.

The term "ring" or "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems.

The term "monocyclic ring" refers to a ring system composed of a single ring.

The term "polycyclic ring" refers to a ring system composed of at least two rings.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts; this term must be understood as equivalent to "pharmaceutically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These pharmaceutically acceptable salts may be formed with cations or bases and, in the context of this invention, are understood to be salts formed by at least one compound used in accordance with the invention—normally an acid (deprotonated) —such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), especially including hydrates and alcoholates, for example methanolate.

The term "prodrug" is used in its broadest sense and encompasses those derivatives that are converted in vivo to the compounds of the invention. Examples of prodrugs include, but are not limited to, derivatives and metabolites of the compounds of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

The terms "prevention", "preventing", "preventive" "prevent" and "prophylaxis" refer to the capacity of a therapeutic to avoid, minimize or difficult the onset or development of a disease or condition before its onset.

The terms "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, terminated, such that the subject no longer experiences the condition.

In a particular and preferred embodiment of the present invention each $R^9$ in the general formula (I) is $CR^{10}$ and each $R^{10}$ is preferably H.

In another preferred embodiment of the invention each $R^4$ is H.

In still another particular embodiment, Y preferably is —O—$C_{1-4}$-alkylene- or —$C_{1-4}$-alkylene-O— and more preferably —O—$CH_2$— or —$CH_2$—O—. In a preferred embodiment, Y is —O—$C_{1-4}$-alkylene-. In a more preferred embodiment, Y is —O—$CH_2$—.

In another embodiment $R^{11}$ is $CR^5$ and $R^5$ is selected from the group consisting of H, halogen, $C_{1-6}$-haloalkyl, —O—$C_{1-6}$-alkyl, —O—$C_{1-6}$-haloalkyl, —OH and $C_{1-6}$-alkyl.

In another preferred embodiment of the invention $R^5$ is selected from the group consisting of H, halogen and —$C_{1-6}$-haloalkyl.

Another preferred embodiment is that in which B is Cy, this being preferably phenyl, $C_{3-6}$-cycloalkyl, $C_{2-6}$-alkyl, $C_{2-6}$ alkenyl or a 5-6 membered monocyclic heterocycle containing 1 or 2 N atom which can be aromatic, partially unsaturated or saturated, any of them optionally substituted by one or more $R^8$.

In another embodiment B is phenyl or cyclopropyl, any of them optionally substituted by one or more $R_8$.

In another embodiment B is phenyl and $C_{2-6}$-alkyl

In a preferred embodiment B is preferably a phenyl optionally substituted by 1-5 $R^8$, more preferably by 1-4 $R^8$.

In another embodiment B is:

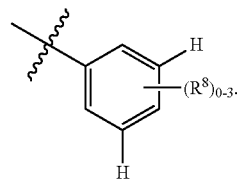

In another embodiment B is

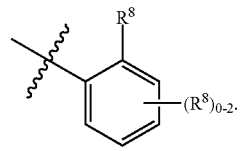

In another embodiment B is

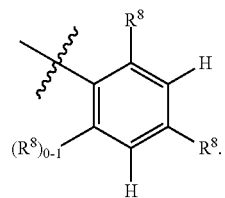

In another embodiment $R^8$ is independently selected from the group consisting of halogen, $C_{1-6}$-haloalkyl, —O—$C_{1-6}$-alkyl, —O—$C_{1-6}$-haloalkyl, $C_{1-6}$-alkyl, and —OH.

In another embodiment $R^8$ is selected from the group consisting of halogen and —$C_{1-6}$-haloalkyl.

In a particular embodiment of the invention

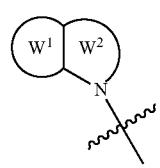 [SMILES: *NCC]

represents

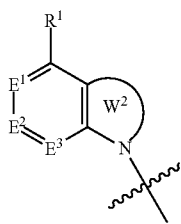

where $E^1$, $E^2$ and $E^3$ are $CR^2$; or one of $E^1$, $E^2$ or $E^3$ is N and the others are $CR^2$; or two of $E^1$, $E^2$ or $E^3$ are N and the other is $CR^2$.

In another embodiment $E^1$, $E^2$ and E3 are $CR^2$.
In another embodiment $E^1$ is N and $E^2$ and $E^3$ are $CR^2$.
In another embodiment $E^2$ is N and $E^1$ and $E^3$ are $CR^2$.
In another embodiment $E^3$ is N and $E^1$ and $E^2$ are $CR^2$.
In another embodiment $E^1$ and $E^3$ are N and $E^2$ is $CR^2$.
In another particular embodiment of the invention

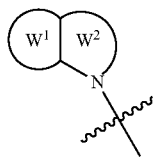

represents

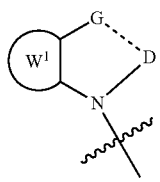

where G is selected from the group consisting of $CR^3$, $CR^3R^3$, $OCR^3R^3$, $OCR^3$, $CR^3R^3$—$CR^3R^3$ and N;
D is selected from the group consisting of $CR^3$, $CR^3R^3$ and N;
and - - - represents a single bond or a double bond.

In another embodiment G is selected from the group consisting of $CR^3$, $CR^3R^3$, O, S and N.
In another embodiment G is selected from the group consisting of $CR^3$=$CR^3$, $CR^3R^3$—$CR^3R^3$, N—$CR^3$, N—$CR^3R^3$, $CR^3R^3$—N, O—$CR^3$, O—$CR^3R^3$, $CR^3R^3$—O, S—$CR^3$, S—$CR^3R^3$ and $CR^3R^3$—S.
In another embodiment G is selected from the group consisting of $CR^3$, $CR^3R^3$ and N.
In another embodiment G is $CR^3R^3$—$CR^3R^3$.
In another embodiment G is selected from the group consisting of $CR^3$, $CR^3R^3$, N, $CR^3$=$CR^3$; $CR^3R^3$—$CR^3R^3$, N—$CR^3$, N—$CR^3R^3$, $CR^3R^3$—N;
In another embodiment G is selected from the group consisting of $CR^3$, $CR^3R^3$, N and $CR^3R^3$—$CR^3R^3$.

In another embodiment

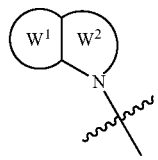 [SMILES: *NCC]

represents

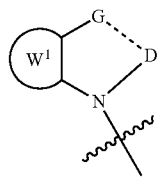

G is selected from the group consisting of $CR^3$, $CR^3R^3$ and N;
D is selected from the group consisting of $CR^3$, $CR^3R^3$ and N;
- - - represents a single bond or a double bond.

In another embodiment

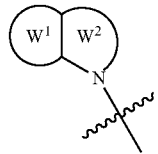 [SMILES: *NCC]

represents

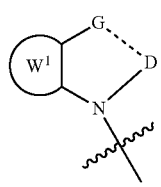

G is selected from the group consisting of $CR^3R^3$—$CR^3R^3$;
D is selected from the group consisting of $CR^3$, $CR^3R^3$ and N;
- - - represents a single bond or a double bond.

In another embodiment D is selected from the group consisting of $CR^3$, $CR^3R^3$ and N.

In another embodiment

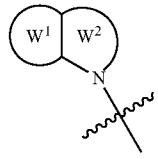

is selected from the group consisting of

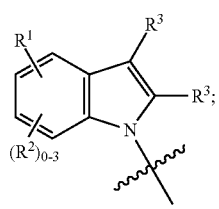 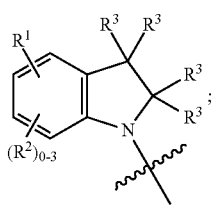

-continued
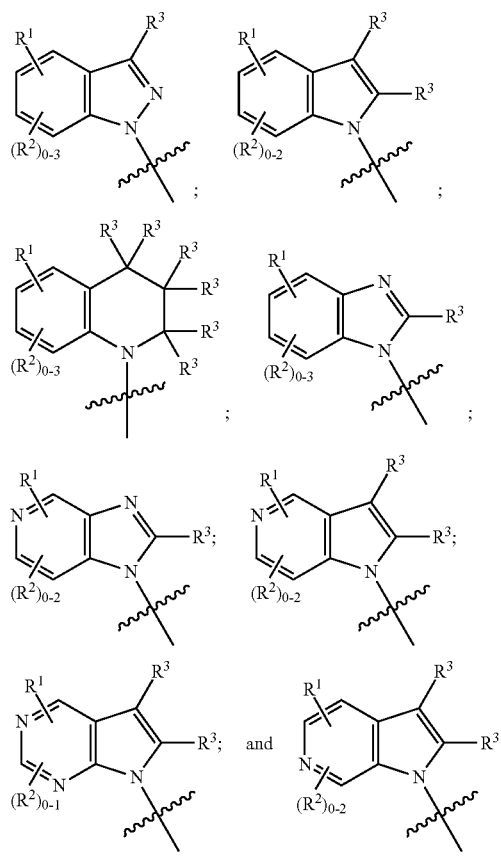
In a preferred embodiment of the invention
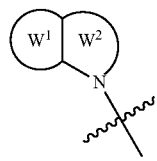 [SMILES: *NCC]
is selected from the group consisting of
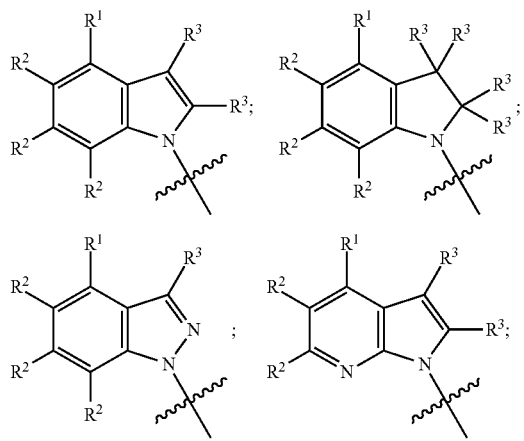
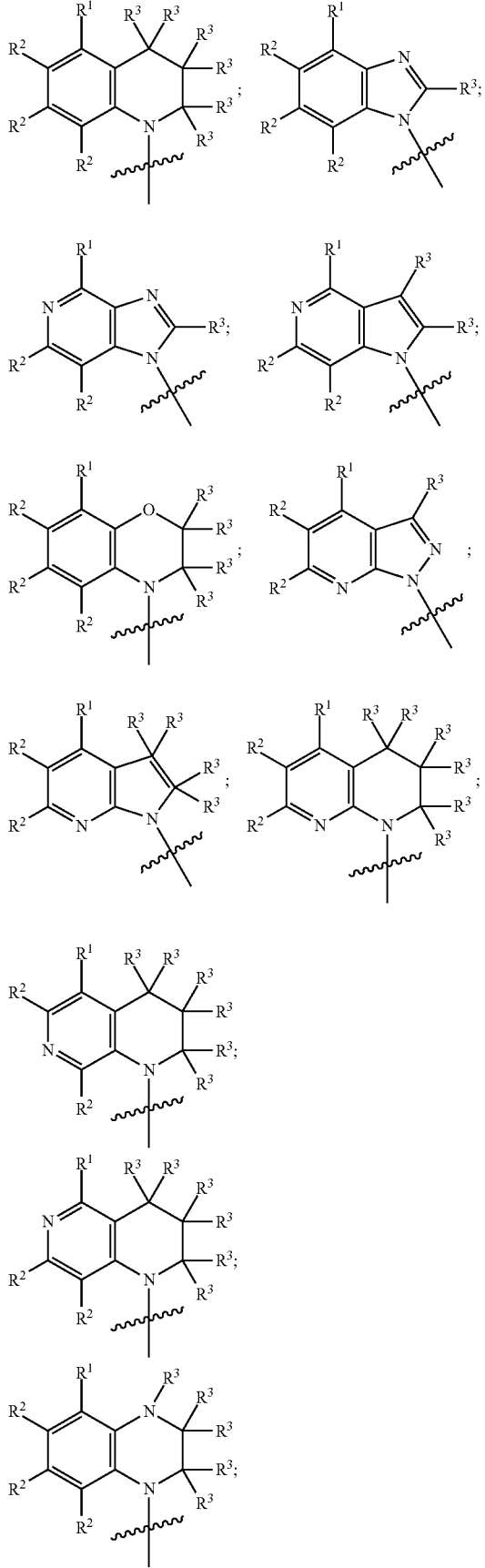

-continued

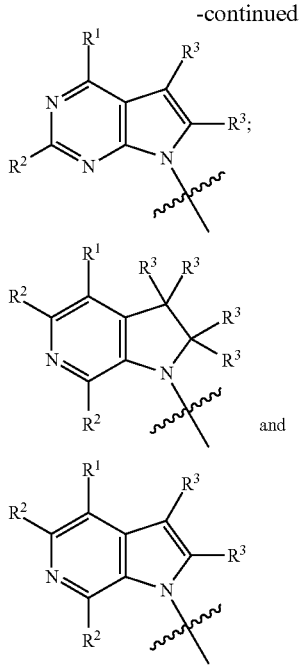

and

In another preferred embodiment

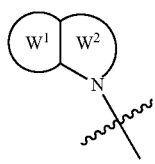 [SMILES: *NCC]

represents

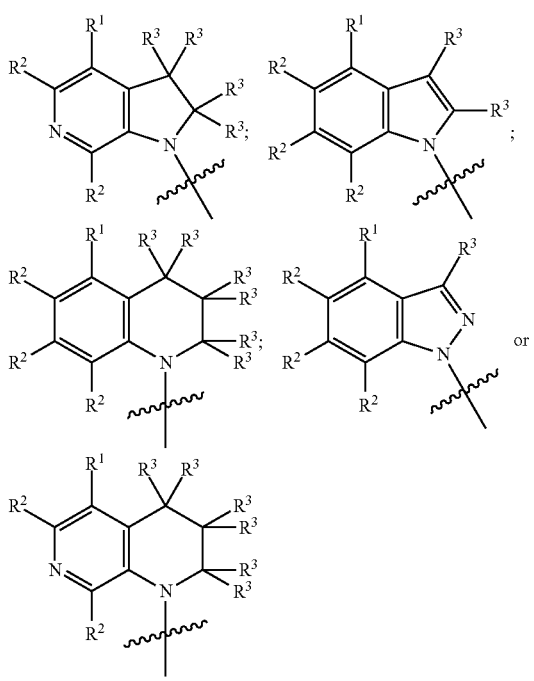

or

In another preferred embodiment

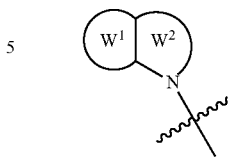

represents

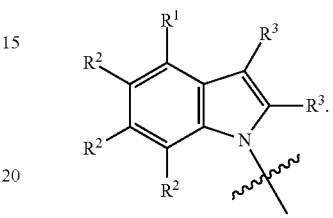

In another preferred embodiment

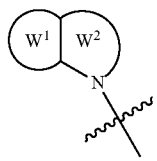 [SMILES: *NCC]

represents

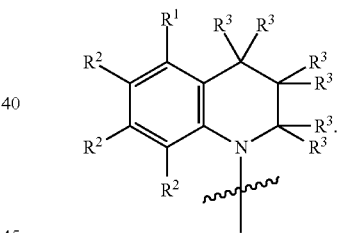

In another embodiment $R^6$ is a direct bond.

In another embodiment $R^7$ is selected from the group consisting of —$CO_2H$, —$SO_3H$ and 5-tetrazolyl.

In another embodiment $R^7$ is —$CO_2H$.

Another preferred embodiment of the invention is that in which $R^6$ is a direct bond and $R^7$ is —$CO_2H$.

In a particular embodiment $R^2$ is independently selected from the group consisting of H, halogen, $C_{1-6}$-alkyl, $C_{1-6}$-haloalkyl, —O—$C_{1-6}$-alkyl, —O—$C_{1-6}$-haloalkyl, hydroxy$C_{1-6}$-alkyl and CN.

In another embodiment $R^2$ is independently selected from the group consisting of H and halogen.

In another embodiment $R^3$ is H.

In another embodiment, each $R^2$ is independently selected from the group consisting of H and halogen and each $R^3$ is H.

Among all the compounds encompassed by the general formula (I) the following compounds are particularly preferred:

(E)-1-(5-chloro-2-(4-chloro-2-fluorostyryl)benzyl)-1H-indole-4-carboxylic acid, 1-(2-(benzyloxy)-5-bromobenzyl)-1H-indole-4-carboxylic acid,
1-(2-(benzyloxy)-5-(trifluoromethyl)benzyl)-1H-indole-4-carboxylic acid,
1-(5-bromo-2-((4-fluorobenzyl)oxy)benzyl)-1H-indole-4-carboxylic acid,
1-(5-chloro-2-((4-fluorobenzyl)oxy)benzyl)-1H-indole-4-carboxylic acid,
1-(2-((4-chloro-2-fluorobenzyl)oxy)-5-(trifluoromethyl)benzyl)-1H-indole-4-carboxylic acid,
1-(5-chloro-2-(cyclopropylmethoxy)benzyl)-1H-indole-4-carboxylic acid,
1-(5-bromo-2-(cyclopropylmethoxy)benzyl)-1H-indole-4-carboxylic acid,
1-(5-bromo-2-((4-chloro-2-fluorobenzyl)oxy)benzyl)-1H-indole-4-carboxylic acid,
1-(4-chloro-2-isobutoxybenzyl)-1H-indole-4-carboxylic acid,
1-(5-chloro-2-((4-(trifluoromethyl)benzyl)oxy)benzyl)-1H-indole-4-carboxylic acid,
1-(5-chloro-2-((2-chloro-4-fluorobenzyl)oxy)benzyl)-1H-indole-4-carboxylic acid,
1-(5-chloro-2-((2,3,5,6-tetrafluorobenzyl)oxy)benzyl)-1H-indole-4-carboxylic acid,
1-(2-((2,4-bis(trifluoromethyl)benzyl)oxy)-5-chlorobenzyl)-1H-indole-4-carboxylic acid,
1-(5-chloro-2-((2,4,5-trifluorobenzyl)oxy)benzyl)-1H-indole-4-carboxylic acid,
1-(5-fluoro-2-((2,4,5-trifluorobenzyl)oxy)benzyl)-1H-indole-4-carboxylic acid,
1-(2-((3-bromo-4-fluorobenzyl)oxy)-5-chlorobenzyl)-1H-indole-4-carboxylic acid,
1-(5-fluoro-2-((4-fluoro-2-(trifluoromethyl)benzyl)oxy)benzyl)-1H-indole-4-carboxylic acid,
1-(2-((2-chloro-4-fluorobenzyl)oxy)-5-fluorobenzyl)-1H-indole-4-carboxylic acid,
1-(5-fluoro-2-((4-fluoro-2-(trifluoromethyl)benzyl)oxy)benzyl)-1H-indole-4-carboxylic acid,
1-(5-chloro-2-((2,3,4-trifluorobenzyl)oxy)benzyl)-1H-indole-4-carboxylic acid,
1-(5-bromo-2-((2,3,4-trifluorobenzyl)oxy)benzyl)-1H-indole-4-carboxylic acid,
1-(5-chloro-2-(1-(2,4-difluorophenyl)ethoxy)benzyl)-1H-indole-4-carboxylic acid,
1-(2-((3-bromo-4-fluorobenzyl)oxy)-5-fluorobenzyl)-1H-indole-4-carboxylic acid,
1-(5-bromo-2-((3-bromo-4-fluorobenzyl)oxy)benzyl)-1H-indole-4-carboxylic acid,
1-(5-bromo-2-((4-fluoro-2-(trifluoromethyl)benzyl)oxy)benzyl)-1H-indole-4-carboxylic acid,
1-(5-bromo-2-((2-chloro-4-fluorobenzyl)oxy)benzyl)-1H-indole-4-carboxylic acid,
1-(3-bromo-2-((4-bromo-2-fluorobenzyl)oxy)-5-chlorobenzyl)-1H-indole-4-carboxylic acid,
1-(5-chloro-2-((2,5-difluorobenzyl)oxy)benzyl)-1H-indole-4-carboxylic acid,
1-(5-chloro-2-((2-chloro-5-fluorobenzyl)oxy)benzyl)-1H-indole-4-carboxylic acid,
1-(5-chloro-2-((2-chloro-4,5-difluorobenzyl)oxy)benzyl)-1H-indole-4-carboxylic acid,
1-(2-((2,5-difluorobenzyl)oxy)-5-fluorobenzyl)-1H-indole-4-carboxylic acid,
1-(2-((2,6-difluorobenzyl)oxy)-5-fluorobenzyl)-1H-indole-4-carboxylic acid,
1-(5-fluoro-2-((3,4,5-trifluorobenzyl)oxy)benzyl)-1H-indole-4-carboxylic acid,
1-(5-fluoro-2-((4-fluorobenzyl)oxy)benzyl)-1H-indole-4-carboxylic acid,
1-(2-((2-chloro-4,5-difluorobenzyl)oxy)-5-fluorobenzyl)-1H-indole-4-carboxylic acid,
1-(2-((2,6-difluorobenzyl)oxy)-5-(trifluoromethyl)benzyl)-1H-indole-4-carboxylic acid,
1-(2-((2-chloro-5-fluorobenzyl)oxy)-5-fluorobenzyl)-1H-indole-4-carboxylic acid,
1-(2-((2,5-difluorobenzyl)oxy)-5-(trifluoromethyl)benzyl)-1H-indole-4-carboxylic acid,
1-(3-bromo-5-chloro-2-((2,6-difluorobenzyl)oxy)benzyl)-1H-indole-4-carboxylic acid,
1-(5-chloro-2-((3,5-difluorobenzyl)oxy)benzyl)-1H-indole-4-carboxylic acid,
1-(1-(5-chloro-2-((4-chloro-2-fluorobenzyl)oxy)phenyl)ethyl)-1H-indole-4-carboxylic acid,
1-(5-chloro-2-((2,4-difluorobenzyl)oxy)benzyl)-1H-indole-4-carboxylic acid,
1-(2-(benzyloxy)-5-chlorobenzyl)-1H-indole-4-carboxylic acid,
1-(5-chloro-2-((2-fluorobenzyl)oxy)benzyl)-1H-indole-4-carboxylic acid,
1-(2-((4-bromo-2-fluorobenzyl)oxy)-5-chlorobenzyl)-1H-indole-4-carboxylic acid,
1-(5-chloro-2-((2-fluoro-4-(trifluoromethyl)benzyl)oxy)benzyl)-1H-indole-4-carboxylic acid,
1-(5-chloro-2-((4-chloro-2-fluorobenzyl)oxy)benzyl)-1H-indole-4-carboxylic acid,
1-(2-((3-fluorobenzyl)oxy)-5-(trifluoromethyl)benzyl)-1H-indole-4-carboxylic acid,
1-(2-((4-bromo-2-fluorobenzyl)oxy)-5-(trifluoromethyl)benzyl)-1H-indole-4-carboxylic acid,
1-(2-((2,4-difluorobenzyl)oxy)-5-(trifluoromethyl)benzyl)-1H-indole-4-carboxylic acid,
1-(2-((2-fluorobenzyl)oxy)-5-(trifluoromethyl)benzyl)-1H-indole-4-carboxylic acid,
1-(2-((2,4-difluorobenzyl)oxy)-5-fluorobenzyl)-1H-indole-4-carboxylic acid,
1-(2-((2,4-difluorobenzyl)oxy)benzyl)-1H-indole-4-carboxylic acid,
1-(5-bromo-2-((4-bromo-2-fluorobenzyl)oxy)benzyl)-1H-indole-4-carboxylic acid,
1-(2-((4-bromo-2-fluorobenzyl)oxy)-5-fluorobenzyl)-1H-indole-4-carboxylic acid,
1-(5-chloro-2-((4-chloro-2,6-difluorobenzyl)oxy)benzyl)-1H-indole-4-carboxylic acid,
1-(2-((4-bromo-2,6-difluorobenzyl)oxy)-5-chlorobenzyl)-1H-indole-4-carboxylic acid,
1-(3,5-dichloro-2-((4-chloro-2-fluorobenzyl)oxy)benzyl)-1H-indole-4-carboxylic acid,
1-(5-bromo-2-((4-chloro-2,6-difluorobenzyl)oxy)benzyl)-1H-indole-4-carboxylic acid,
1-((3-((4-chloro-2-fluorobenzyl)oxy)pyridin-2-yl)methyl)-1H-indole-4-carboxylic acid,
3-(1-(5-chloro-2-((4-chloro-2-fluorobenzyl)benzyl)-1H-indol-4-yl)propanoic acid,
1-(5-chloro-2-(4-chloro-2-fluorophenethyl)benzyl)-1H-indole-4-carboxylic acid,
1-(5-chloro-2-(cyclopropylmethoxy)benzyl)-1H-indole-5-carboxylic acid,
1-(5-fluoro)-2-((2,4,5-trifluorobenzyl)oxy)benzyl)-1H-indole-5-carboxylic acid,
1-(2-((2-chloro-4-fluorobenzyl)oxy)-5-fluorobenzyl)-1H-indole-5-carboxylic acid,
1-(5-chloro-2-((4-fluoro-2-(trifluoromethyl)benzyl)oxy)benzyl)-1H-indole-5-carboxylic acid, 1-(2-((3-bromo-4-fluorobenzyl)oxy)-5-fluorobenzyl)-1H-indole-5-carboxylic acid,
1-(5-bromo-2-((4-fluoro-2-(trifluoromethyl)benzyl)oxy)benzyl)-1H-indole-5-carboxylic acid,
1-(5-bromo-2-((2-chloro-4-fluorobenzyl)oxy)benzyl)-1H-indole-5-carboxylic acid,
1-(5-fluoro-2-((3,4,5-trifluorobenzyl)oxy)benzyl)-1H-indole-5-carboxylic acid,
1-(2-((2-chloro-4,5-difluorobenzyl)oxy)-5-fluorobenzyl)-1H-indole-5-carboxylic acid,
1-(2-((2-chloro-5-fluorobenzyl)oxy)-5-fluorobenzyl)-1H-indole-5-carboxylic acid,
1-(5-bromo-2-((2,4-difluorobenzyl)oxy)benzyl)-1H-indole-5-carboxylic acid,
1-(2-((4-bromo-2-fluorobenzyl)oxy)-5-(trifluoromethyl)benzyl)-1H-indole-5-carboxylic acid,
1-(5-chloro-2-((4-chloro-2-fluorobenzyl)oxy)benzyl)-1H-indole-5-carboxylic acid,
1-(5-chloro-2-((4-fluorobenzyl)oxy)benzyl)-1H-indole-5-carboxylic acid,
1-(5-chloro-2-((2,4-difluorobenzyl)oxy)benzyl)-1H-indole-5-carboxylic acid,
(E)-3-(1-(2-(benzyloxy)-5-(trifluoromethyl)benzyl)-1H-indol-4-yl)acrylic acid,
(E)-3-(1-(5-bromo-2-(cyclopropylmethoxy)benzyl)-1H-indol-4-yl)acrylic acid,
(E)-3-(1-(5-chloro-2-(cyclopropylmethoxy)benzyl)-1H-indol-4-yl)acrylic acid,
(E)-3-(1-(5-chloro-2-((2,4-difluorobenzyl)oxy)benzyl)-1H-indol-4-yl)acrylic acid,
(E)-3-(1-(5-chloro-2-((4-chloro-2-fluorobenzyl)oxy)benzyl)-1H-indol-4-yl)acrylic acid,
2-((1-(2-((4-chloro-2-fluorobenzyl)oxy)-5-(trifluoromethyl)benzyl)-1H-indol-4-yl)oxy)acetic acid,
2-((1-(5-chloro-2-(cyclopropylmethoxy)benzyl)-1H-indol-4-yl)oxy)acetic acid,
2-((1-(5-chloro-2-(cyclopropylmethoxy)benzyl)-1H-indol-4-yl)oxy)acetic acid,
1-(2-(benzyloxy)-5-bromobenzyl)-1H-indole-6-carboxylic acid,
1-(5-chloro-2-((2,4-difluorobenzyl)oxy)benzyl)-1H-indole-6-carboxylic acid,
3-(1-(5-chloro-2-((4-chloro-2-fluorobenzyl)oxy)benzyl)-1H-indol-4-yl)propanoic acid,
1-(5-chloro-2-((4-chloro-2-fluorobenzyl)oxy)benzyl)-1H-pyrrolo[2,3-b]pyridine-4-carboxylic acid,
1-(5-chloro-2-((2,4-difluorobenzyl)oxy)benzyl)-1H-pyrrolo[2,3-b]pyridine-4-carboxylic acid,
1-(5-chloro-2-((4-chloro-2-fluorobenzyl)oxy)benzyl)-1H-benzo[d]imidazole-4-carboxylic acid,
1-(5-chloro-2-((4-chloro-2-fluorobenzyl)oxy)benzyl)indoline-4-carboxylic acid,
1-(5-chloro-2-((4-chloro-2-fluorobenzyl)oxy)benzyl)-1,2,3,4-tetrahydroquinoline-5-carboxylic acid,
1-(5-chloro-2-((2,4-difluorobenzyl)oxy)benzyl)-1,2,3,4-tetrahydroquinoline-5-carboxylic acid,
7-(5-chloro-2-((4-chloro-2-fluorobenzyl)oxy)benzyl)-7H-pyrrolo[2,3-d]pyrimidine-4-carboxylic acid,
7-(5-chloro-2-((2,4-difluorobenzyl)oxy)benzyl)-7H-pyrrolo[2,3-d]pyrimidine-4-carboxylic acid,
1-(5-chloro-2-((2,4-difluorobenzyl)oxy)benzyl)-7-fluoro-1H-indole-4-carboxylic acid,
1-{2-[(2,4-difluorobenzyl)oxy]-5-methoxybenzyl}-1H-indole-4-carboxylic acid,
1-[5-chloro-2-(cyclohexylmethoxy)benzyl]-1H-indole-4-carboxylic acid,
1-[5-chloro-2-(cyclopentylmethoxy)benzyl]-1H-indole-4-carboxylic acid,
1-(5-fluoro-2-propoxybenzyl)-1H-indole-4-carboxylic acid,
1-(5-chloro-2-(cyclopentyloxy)benzyl)-1H-indole-4-carboxylic acid,
1-(5-chloro-2-propoxybenzyl)-1H-indole-4-carboxylic acid,
1-(5-chloro-2-(2-(tetrahydro-2H-pyran-4-yl)ethoxy)benzyl)-1H-indole-4-carboxylic acid,
1-(5-fluoro-2-isobutoxybenzyl)-1H-indole-4-carboxylic acid,
1-(2-isobutoxybenzyl)-1H-indole-4-carboxylic acid,
1-[5-chloro-2-(2,2-difluoroethoxy)benzyl]-1H-indole-4-carboxylic acid,
1-[5-chloro-2-(2-fluoroethoxy)benzyl]-1H-indole-4-carboxylic acid,
1-[5-chloro-2-(2,2,2-trifluoroethoxy)benzyl]-1H-indole-4-carboxylic acid,
1-[5-chloro-2-(neopentyloxy)benzyl]-1H-indole-4-carboxylic acid,
4-(5-chloro-2-cyclobutoxybenzyl)-3-oxo-3,4-dihydro-2H-benzo[b][1,4]oxazine-8-carboxylic acid,
4-(5-bromo-2-(4-chloro-2-fluorobenzyloxy)benzyl)-3-oxo-3,4-dihydro-2H-benzo[b][1,4]oxazine-8-carboxylic acid,
4-(5-chloro-2-(2-fluoro-2-methylpropoxy)benzyl)-3,4-dihydro-2H-benzo[b][1,4]oxazine-8-carboxylic acid
4-(5-chloro-2-((4-chloro-2-fluorobenzyl)oxy)benzyl)-3,4-dihydro-2H-benzo[b][1,4]oxazine-8-carboxylic acid,
4-(5-chloro-2-((2,4-difluorobenzyl)oxy)benzyl)-3,4-dihydro-2H-benzo[b][1,4]oxazine-8-carboxylic acid,
4-(2-((4-chloro-2-fluorobenzyl)oxy)benzyl)-3,4-dihydro-2H-benzo[b][1,4]oxazine-8-carboxylic acid,
4-(2-(benzyloxy)benzyl)-3,4-dihydro-2H-benzo[b][1,4]oxazine-8-carboxylic acid,
4-(2-((2-chloro-4-fluorobenzyl)oxy)-5-fluorobenzyl)-3,4-dihydro-2H-benzo[b][1,4]oxazine-8-carboxylic acid,
4-(2-((2,4-difluorobenzyl)oxy)benzyl)-3,4-dihydro-2H-benzo[b][1,4]oxazine-8-carboxylic acid,
1-(2-((2-chlorobenzyl)oxy)-5-fluorobenzyl)-1H-indazole-4-carboxylic acid,
1-(5-chloro-2-((4-chloro-2-fluorobenzyl)oxy)benzyl)-1H-indazole-4-carboxylic acid,
1-(5-chloro-2-(2-fluoro-2-methylpropoxy)benzyl)-1H-indazole-4-carboxylic acid,
1-(5-chloro-2-((2-fluorobenzyl)oxy)benzyl)-1H-indazole-4-carboxylic acid,
1-(2-((2-chlorobenzyl)oxy)-5-methylbenzyl)-1H-indazole-4-carboxylic acid,
1-(5-fluoro-2-((2-fluorobenzyl)oxy)benzyl)-1H-indazole-4-carboxylic acid,
1-(2-((2-fluorobenzyl)oxy)-5-methylbenzyl)-1H-indazole-4-carboxylic acid,
1-(5-chloro-2-((2-chlorobenzyl)oxy)benzyl)-1H-indazole-4-carboxylic acid,
1-(5-chloro-2-(3-fluoro-2-methylpropoxy)benzyl)-1H-indazole-4-carboxylic acid,
1-(5-chloro-2-propoxybenzyl)-1H-indazole-4-carboxylic acid,
1-(5-chloro-2-(cyclopentyloxy)benzyl)-1H-indazole-4-carboxylic acid,
1-(5-fluoro-2-isobutoxybenzyl)-1H-indazole-4-carboxylic acid,
1-(5-fluoro-2-propoxybenzyl)-1H-indazole-4-carboxylic acid, 1-(5-bromo-2-(4-chloro-2-fluorobenzyloxy)benzyl)-1H-indazole-4-carboxylic acid,
1-(5-chloro-2-cyclobutoxybenzyl)-1H-indazole-4-carboxylic acid,
1-(5-chloro-2-(neopentyloxy)benzyl)-1H-indazole-4-carboxylic acid,
1-(5-chloro-2-((4-chloro-2-fluorobenzyl)oxy)benzyl)-1H-pyrrolo[3,2-c]pyridine-4-carboxylic acid,
1-(2-((2,4-difluorobenzyl)oxy)benzyl)-7-fluoro-1H-indole-4-carboxylic acid,
1-(5-chloro-2-((4-chloro-2-fluorobenzyl)oxy)benzyl)-3-(hydroxymethyl)-1H-indole-4-carboxylic acid,
1-(5-chloro-2-((2,4-difluorobenzyl)oxy)benzyl)-3-(hydroxymethyl)-1H-indole-4-carboxylic acid,
1-(2-((2,4-difluorobenzyl)oxy)benzyl)-3-(hydroxymethyl)-1H-indole-4-carboxylic acid,
1-(2-((4-chloro-2-fluorobenzyl)oxy)benzyl)-3-(hydroxymethyl)-1H-indole-4-carboxylic acid,
1-(2-((2,4-difluorobenzyl)oxy)-5-fluorobenzyl)-3-(hydroxymethyl)-1H-indole-4-carboxylic acid,
1-(2-((4-chloro-2-fluorobenzyl)oxy)-5-fluorobenzyl)-3-(hydroxymethyl)-1H-indole-4-carboxylic acid,
1-(5-chloro-2-(2-fluoro-2-methylpropoxy)benzyl)-3-(hydroxymethyl)-1H-indole-4-carboxylic acid,
1-(2-cyclobutoxy-5-fluorobenzyl)-3-(hydroxymethyl)-1H-indole-4-carboxylic acid,
1-(5-fluoro-2-((4-fluorobenzyl)oxy)benzyl)-3-(hydroxymethyl)-1H-indole-4-carboxylic acid,
1-(5-chloro-2-((4-fluorobenzyl)oxy)benzyl)-3-(hydroxymethyl)-1H-indole-4-carboxylic acid,
1-(5-chloro-2-(3-fluoro-2-methylpropoxy)benzyl)-3-(hydroxymethyl)-1H-indole-4-carboxylic acid,
1-(5-chloro-2-((2,4-difluorobenzyl)oxy)benzyl)-3-(hydroxymethyl)-1H-pyrrolo[2,3-b]pyridine-4-carboxylic acid,
1-(5-chloro-2-((4-chloro-2-fluorobenzyl)oxy)benzyl)-3-(hydroxymethyl)-1H-pyrrolo[2,3-b]pyridine-4-carboxylic acid,
1-(5-chloro-2-((4-chloro-2-fluorobenzyl)oxy)benzyl)-3-(2-hydroxyethyl)-1H-indole-4-carboxylic acid,
1-(5-chloro-2-((2,4-difluorobenzyl)oxy)benzyl)-3-(2-hydroxyethyl)-1H-indole-4-carboxylic acid,
1-(5-fluoro-2-isobutoxybenzyl)-3-(2-hydroxyethyl)-1H-indole-4-carboxylic acid,
1-(5-chloro-2-isobutoxybenzyl)-3-(2-hydroxyethyl)-1H-indole-4-carboxylic acid,
1-(5-chloro-2-(2-fluoro-2-methylpropoxy)benzyl)-3-(2-hydroxyethyl)-1H-indole-4-carboxylic acid,
1-(2-((2,4-difluorobenzyl)oxy)-5-fluorobenzyl)-3-(2-hydroxyethyl)-1H-indole-4-carboxylic acid,
1-(5-chloro-2-(3-fluoro-2-methylpropoxy)benzyl)-3-(2-hydroxyethyl)-1H-indole-4-carboxylic acid,
(E)-3-(2-carboxylatovinyl)-1-(5-chloro-2-((4-chloro-2-fluorobenzyl)oxy)benzyl)-1H-indole-4-carboxylic acid,
(E)-3-(2-carboxylatovinyl)-1-(5-chloro-2-((2,4-difluorobenzyl)oxy)benzyl)-1H-indole-4-carboxylic acid,
1-(5-chloro-2-((2,4-difluorobenzyl)oxy)benzyl)-1H-pyrrolo[2,3-c]pyridine-4-carboxylic acid,
1-(5-chloro-2-((4-chloro-2-fluorobenzyl)oxy)benzyl)-1H-pyrrolo[2,3-c]pyridine-4-carboxylic acid,
1-(5-chloro-2-((2,4-difluorobenzyl)oxy)benzyl)indoline-4-carboxylic acid,
1-(5-chloro-2-(2-fluoro-2-methylpropoxy)benzyl)indoline-4-carboxylic acid,
1-(5-chloro-2-((4-chloro-2-fluorobenzyl)oxy)benzyl)indoline-4-carboxylic acid,
1-(2-((2-chloro-4-fluorobenzyl)oxy)-5-fluorobenzyl)indoline-4-carboxylic acid,
1-(5-chloro-2-isobutoxybenzyl)indoline-4-carboxylic acid,
1-(5-fluoro-2-isobutoxybenzyl)indoline-4-carboxylic acid,
1-(5-chloro-2-cyclobutoxybenzyl)indoline-4-carboxylic acid,
1-(2-((2,4-difluorobenzyl)oxy)benzyl)-1,2,3,4-tetrahydroquinoline-5-carboxylic acid,
1-(5-chloro-2-((2,4-difluorobenzyl)oxy)benzyl)-1,2,3,4-tetrahydroquinoline-5-carboxylic acid,
1-(5-chloro-2-(cyclobutylmethoxy)benzyl)-1,2,3,4-tetrahydroquinoline-5-carboxylic acid,
1-(5-chloro-2-isobutoxybenzyl)-1,2,3,4-tetrahydroquinoline-5-carboxylic acid,
1-[5-chloro-2-(1,2-dimethylpropoxy)benzyl]-1,2,3,4-tetrahydroquinoline-5-carboxylic acid,
1-[5-chloro-2-(2-fluoro-2-methylpropoxy)benzyl]-1,2,3,4-tetrahydroquinoline-5-carboxylic acid,
1-[5-chloro-2-(cyclobutyloxy)benzyl]-1,2,3,4-tetrahydroquinoline-5-carboxylic acid,
1-{5-chloro-2-[(2-methylprop-2-enyl)oxy]benzyl}-1,2,3,4-tetrahydroquinoline-5-carboxylic acid,
1-[5-chloro-2-(3-fluoro-2-methylpropoxy)benzyl]-1,2,3,4-tetrahydroquinoline-5-carboxylic acid,
1-[5-chloro-2-(2-fluoropropoxy)benzyl]-1,2,3,4-tetrahydroquinoline-5-carboxylic acid,
1-(5-chloro-2-{[2-(fluoromethyl)prop-2-enyl]oxy}benzyl)-1,2,3,4-tetrahydroquinoline-5-carboxylic acid,
1-(5-chloro-2-((4-chloro-2-fluorobenzyl)oxy)benzyl)-1,2,3,4-tetrahydroquinoline-5-sulfonic acid,
1-(5-chloro-2-((2,4-difluorobenzyl)oxy)benzyl)-1,2,3,4-tetrahydroquinoline-5-sulfonic acid,
1-(2-((4-chloro-2-fluorobenzyl)oxy)benzyl)-1,2,3,4-tetrahydroquinoline-5-sulfonic acid,
N-((1-(5-chloro-2-((2,4-difluorobenzyl)oxy)benzyl)-1,2,3,4-tetrahydroquinolin-5-yl)sulfonyl)acetamide,
N-((1-(5-chloro-2-((4-chloro-2-fluorobenzyl)oxy)benzyl)-1,2,3,4-tetrahydroquinolin-5-yl)sulfonyl)acetamide,
1-(5-chloro-2-((4-chloro-2-fluorobenzyl)oxy)benzyl)-3-(hydroxymethyl)-1H-indazole-4-carboxylic acid,
1-(5-chloro-2-(2-fluoro-2-methylpropoxy)benzyl)-3-(hydroxymethyl)-1H-indazole-4-carboxylic acid,
1-(5-chloro-2-(cyclopentyloxy)benzyl)-1,2,3,4-tetrahydroquinoline-5-carboxylic acid,
1-(5-chloro-2-(propooxy)benzyl)-1,2,3,4-tetrahydroquinoline-5-carboxylic acid,
1-(2-(4-chloro-2-fluorobenzyloxy)-5-methylbenzyl)-1,2,3,4-tetrahydroquinoline-5-carboxylic acid,
1-(5-chloro-2-(neopentyloxy)benzyl)-1,2,3,4-tetrahydroquinoline-5-carboxylic acid,
4-(2-(4-chloro-2-fluorobenzyloxy)-5-methylbenzyl)-3,4-dihydro-2H-benzo[b][1,4]oxazine-8-carboxylic acid,
4-(5-fluoro-2-isobutoxybenzyl)-3,4-dihydro-2H-benzo[b][1,4]oxazine-8-carboxylic acid,
4-(5-chloro-2-isobutoxybenzyl)-3,4-dihydro-2H-benzo[b][1,4]oxazine-8-carboxylic acid,
4-(5-chloro-2-cyclobutoxybenzyl)-3,4-dihydro-2H-benzo[b][1,4]oxazine-8-carboxylic acid,
4-(5-chloro-2-(cyclopropylmethoxy)benzyl)-3,4-dihydro-2H-benzo[b][1,4]oxazine-8-carboxylic acid,
4-(5-chloro-2-(neopentyloxy)benzyl)-3,4-dihydro-2H-benzo[b][1,4]oxazine-8-carboxylic acid, 1-(5-chloro-2-(3-methoxypropoxy)benzyl)indoline-4-carboxylic acid,
1-(5-chloro-2-(2-methoxyethoxy)benzyl)indoline-4-carboxylic acid,
1-(5-chloro-2-(cyclopropylmethoxy)benzyl)indoline-4-carboxylic acid,
1-(5-chloro-2-(neopentyloxy)benzyl)indoline-4-carboxylic acid,
1-(5-chloro-2-((3-methyloxetan-3-yl)methoxy)benzyl)indoline-4-carboxylic acid,
(S)-1-(5-chloro-2-(3-hydroxy-2-methylpropoxy)benzyl)indoline-4-carboxylic acid,
1-(5-chloro-2-(4-chloro-2-fluorobenzyloxy)benzyl)-3-(methoxymethyl)-1H-indole-4-carboxylic acid,
1-(5-chloro-2-(4-chloro-2-fluorobenzyloxy)benzyl)-2-oxoindoline-4-carboxylic acid,
1-(2-(4-chloro-2-fluorobenzyloxy)-5-cyclopropylbenzyl)-1H-indazole-4-carboxylic acid,
1-(5-chloro-2-(4-chloro-2-fluorobenzyloxy)benzyl)-3-(methoxymethyl)-1H-indole-4-carboxylic acid,
1-{5-chloro-2-[(4-chloro-2-ethylbenzyl)oxy]benzyl}-1H-indole-4-carboxylic acid,
1-{5-chloro-2-[(4-chloro-2-fluorobenzyl)oxy]benzyl}-1H-pyrazolo[3,4-b]pyridine-4-carboxylic acid,
1-[5-chloro-2-(2-fluoro-2-methylpropoxy)benzyl]-1H-pyrazolo[3,4-b]pyridine-4-carboxylic acid,
1-[5-chloro-2-(cyclobutyloxy)benzyl]-1H-pyrazolo[3,4-b]pyridine-4-carboxylic acid,
1-{5-chloro-2-[(4-chloro-2-fluorobenzyl)oxy]benzyl}-2-oxo-1,2,3,4-tetrahydroquinoline-5-carboxylic acid,
1-{5-chloro-2-[(4-chloro-2-fluorobenzyl)oxy]benzyl}-2,3-dihydro-1H-pyrrolo[2,3-b]pyridine-4-carboxylic acid,
1-{5-chloro-2-[(2,4-difluorobenzyl)oxy]benzyl}-2,3-dihydro-1H-pyrrolo[2,3-b]pyridine-4-carboxylic acid,
1-{5-chloro-2-[(4-chlorobenzyl)oxy]benzyl}-2,3-dihydro-1H-pyrrolo[2,3-b]pyridine-4-carboxylic acid,
1-{5-chloro-2-[(2-fluorobenzyl)oxy]benzyl}-2,3-dihydro-1H-pyrrolo[2,3-b]pyridine-4-carboxylic acid,
1-{5-chloro-2-[(4-fluorobenzyl)oxy]benzyl}-2,3-dihydro-1H-pyrrolo[2,3-b]pyridine-4-carboxylic acid,
1-[5-chloro-2-(2-fluoro-2-methylpropoxy)benzyl]-2,3-dihydro-1H-pyrrolo[2,3-b]pyridine-4-carboxylic acid,
1-(5-chloro-2-isobutoxybenzyl)-2,3-dihydro-1H-pyrrolo[2,3-b]pyridine-4-carboxylic acid,
1-{5-chloro-2-[(4-chloro-2-fluorobenzyl)oxy]benzyl}-4-(1H-tetrazol-5-yl)-2,3-dihydro-1H-pyrrolo[2,3-b]pyridine,
8-{5-chloro-2-[(2,4-difluorobenzyl)oxy]benzyl}-5,6,7,8-tetrahydro-1,8-naphthyridine-4-carboxylic acid,
8-{5-chloro-2-[(4-chloro-2-fluorobenzyl)oxy]benzyl}-5,6,7,8-tetrahydro-1,8-naphthyridine-4-carboxylic acid,
1-{5-chloro-2-[(4-chloro-2-fluorobenzyl)oxy]benzyl}-1,2,3,4-tetrahydro-1,7-naphthyridine-5-carboxylic acid,
1-{5-chloro-2-[(2,4-difluorobenzyl)oxy]benzyl}-1,2,3,4-tetrahydro-1,7-naphthyridine-5-carboxylic acid,
1-{5-chloro-2-[(2,4-difluorobenzyl)oxy]benzyl}-1,2,3,4-tetrahydro-1,6-naphthyridine-5-carboxylic acid,
1-{5-chloro-2-[(4-chloro-2-fluorobenzyl)oxy]benzyl}-1,2,3,4-tetrahydro-1,6-naphthyridine-5-carboxylic acid,
1-{5-chloro-2-[(4-chloro-2-fluorobenzyl)oxy]benzyl}-1,2,3,4-tetrahydroquinoxaline-5-carboxylic acid,
1-{5-chloro-2-[2-(2,4-difluorophenyl)ethoxy]benzyl}-1H-indole-4-carboxylic acid,
1-{5-chloro-2-[(4-chloro-2-fluorobenzyl)oxy]benzyl}-N-(methylsulfonyl)-1H-indole-4-carboxamide,
1-{5-chloro-2-[(4-chloro-2-fluorobenzyl)oxy]benzyl}-N-(methylsulfonyl)-1H-indole-4-carboxamide,
1-(5-chloro-2-isobutoxybenzyl)-N-(methylsulfonyl)-2,3-dihydro-1H-pyrrolo[2,3-b]pyridine-4-carboxamide,
1-{5-chloro-2-[(4-chloro-2-fluorobenzyl)oxy]benzyl}-N-(methylsulfonyl)-1,2,3,4-tetrahydroquinoline-5-carboxamide,
1-{5-chloro-2-[(4-chloro-2-fluorobenzyl)oxy]benzyl}-N-[(dimethylamino)sulfonyl]-1,2,3,4-tetrahydroquinoline-5-carboxamide,
1-{5-chloro-2-[(4-chloro-2-fluorobenzyl)oxy]benzyl}-N-[(dimethylamino)sulfonyl]-1,2,3,4-tetrahydroquinoline-5-carboxamide,
N-({1-(5-chloro-2-[(4-chloro-2-fluorobenzyl)oxy]benzyl}-1,2,3,4-tetrahydroquinolin-5-yl]amino}carbonyl)methanesulfonamide,
1-{5-chloro-2-[(4-chloro-2-fluorobenzyl)oxy]benzyl}-N-(methylsulfonyl)-2,3-dihydro-1H-pyrrolo[2,3-b]pyridine-4-carboxamide,
1-{5-chloro-2-[(2,4-difluorobenzyl)oxy]benzyl}-1,2,3,4-tetrahydro-1,7-naphthyridine-5-carboxylic acid,
1-{2-[(4-chloro-2-fluorobenzyl)oxy]benzyl}-1,2,3,4-tetrahydro-1,7-naphthyridine-5-carboxylic acid,
1-{2-[(2,4-difluorobenzyl)oxy]benzyl}-1,2,3,4-tetrahydro-1,7-naphthyridine-5-carboxylic acid,
1-[5-chloro-2-(2-fluoro-2-methylpropoxy)benzyl]-1,2,3,4-tetrahydro-1,7-naphthyridine-5-carboxylic acid
1-{2-[(2,4-difluorobenzyl)oxy]-5-fluorobenzyl}-1,2,3,4-tetrahydro-1,7-naphthyridine-5-carboxylic acid
1-(2-((2,4-difluorobenzyl)oxy)-5-methylbenzyl)-1,2,3,4-tetrahydro-1,7-naphthyridine-5-carboxylic acid
1-{2-[(4-chloro-2-fluorobenzyl)oxy]-5-fluorobenzyl}-1,2,3,4-tetrahydro-1,7-naphthyridine-5-carboxylic acid
1-{2-[(4-chloro-2-fluorobenzyl)oxy]-5-methylbenzyl}-1,2,3,4-tetrahydro-1,7-naphthyridine-5-carboxylic acid
4-(2-cyclobutoxy-5-fluorobenzyl)-3,4-dihydro-2H-benzo[b][1,4]oxazine-8-carboxylic acid,
1-{5-chloro-2-[(4-chloro-2-fluorobenzyl)oxy]benzyl}-2,3-dihydro-1H-pyrrolo[2,3-c]pyridine-4-carboxylic acid,
1-(5-chloro-2-cyclobutoxybenzyl)-2-oxoindoline-4-carboxylic acid
1-(5-chloro-2-(2-fluoro-2-methylpropoxy)benzyl)-2-oxoindoline-4-carboxylic acid and the salts, solvates and prodrugs thereof.

In another embodiment, the sodium salt of the previous compounds is preferred.

In another aspect the invention refers to a process for preparing the compounds of the invention.

The compounds of the invention may be made by a variety of methods, including standard chemistry. Any previously defined variable will continue to have the previously defined meaning unless otherwise indicated. Illustrative general synthetic methods are set out below and then the preparation of specific compounds of the invention is described in more detail in the Experimental Section.

For instance, a process for preparing compounds of general formula (I) comprises the reaction between a compound of general formula (II):

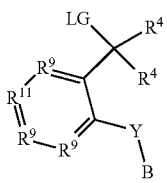

wherein LG is a leaving group, preferably bromo, with a compound of general formula (III), or a protected form thereof where the $R^7$ group in $W^1$ is protected:

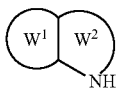

followed if necessary by the removal of any protecting group that may be present.

In general, a compound of formula III is preferably used in protected form, i.e. with the $R^7$ group in W1 protected with a suitable protecting group. If III is reacted with II in protected form, a subsequent step to remove the protecting group on $R^7$ will be required to yield a compound of formula I, which is performed under standard conditions well known in the art. When in a compound of formula III $R^7$ is —$CO_2H$, compound III is used in protected form as an ester, and therefore the acid must be deprotected after the reaction of II with III under standard conditions; a suitable set of conditions comprises the treatment of the corresponding ester with NaOH (10%), in tetrahydrofuran or methanol at about 50° C.

A compound of formula I thus obtained can be converted into a salt using standard procedures. For example, when $R^7$ in a compound of formula I is —$CO_2H$, the sodium salt can be obtained for example by treatment of the corresponding carboxylic acid with sodium tert-butoxide in methanol at room temperature.

The process for the synthesis of compound of general formula I can be summarised as follows:

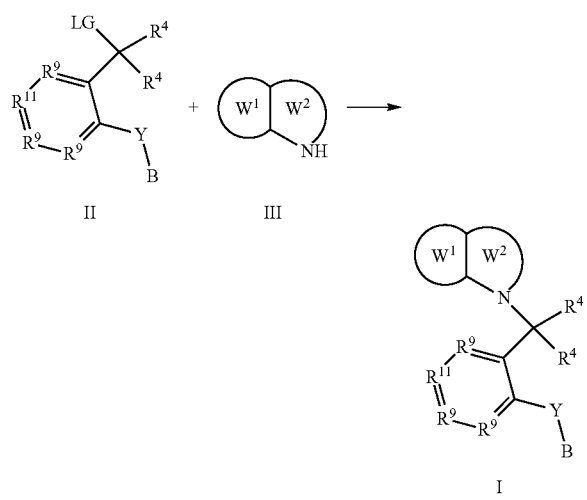

In the above scheme $W^1$, $W^2$, $R^4$, Y, B, $R^9$ and $R^{11}$ have the meaning previously defined and LG represents a leaving group. A leaving group is a group that in an heterolytic bond cleavage keeps the electron pair of the bond. Suitable leaving groups are well known in the art and include Cl, Br, I and —O—$SO_2R^{14}$, wherein $R^{14}$ is F, $C_{1-4}$-alkyl, $C_{1-4}$-haloalkyl, or optionally substituted phenyl. The preferred leaving groups are: Cl, Br, I, tosylate, mesylate, triflate, nonaflate and fluorosulphonate.

Preferably, compounds of formula (II) wherein LG is bromo are used.

Compounds of formula (II) and (III) are suitably reacted together in the presence of a base in an inert organic solvent which includes, aromatic hydrocarbons such as toluene, o-, m-, p-xylene; halogenated hydrocarbons such as methylene chloride, chloroform, and chlorobenzene; ethers such as diethylether, diisopropyl ether, tert-butyl methyl ether, 5 dioxane, anisole, and tetrahydrofuran; nitriles such as acetonitrile and propionitrile; ketones such as acetone, methyl ethyl ketone, diethyl ketone and tert-butyl methyl ketone; alcohols such as methanol, ethanol, n-propanol, n-butanol, tert-butanol and also DMF (N,N-dimethylformamide), DMSO (N,N-dimethyl sulfoxide) and water. The preferred list of solvents includes DMSO, DMF, acetonitrile and THF. Mixtures of these solvents in varying ratios can also be used. Suitable bases are, generally, inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, lithium oxide, sodium oxide, magnesium oxide and calcium oxide; alkali metal hydrides and alkaline earth metal hydrides such as lithium hydride, sodium hydride, potassium hydride and calcium hydride; alkali metal, amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogencarbonates and alkaline earth metal hydrogencarbonates such as sodium hydrogencarbonate; organometallic compounds, particularly alkali-metal alkyls such as methyl lithium, butyllithium, phenyl lithium; alkyl magnesium halides such as methyl magnesium chloride, and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, N-methylpiperidine, pyridine. Sodium hydroxide, Sodium methoxide, Sodium ethoxide, potassium hydroxide, potassium carbonate and triethylamine are especially preferred. Suitably the reaction may be effected in the presence of a phase transfer catalyst such as tetra-n-butylammonium hydrogensulphate and the like. The inert atmosphere may be maintained by using inert gases such as $N_2$, Ar or He. Reaction times may vary from 1 to 24 hrs, preferably from 2 to 6 hours, whereafter, if desired, the resulting compound is transformed into a salt thereof.

The starting compounds of general formula (II) can be prepared in several ways. A general scheme of preparation of compound of formula (II) is represented below:

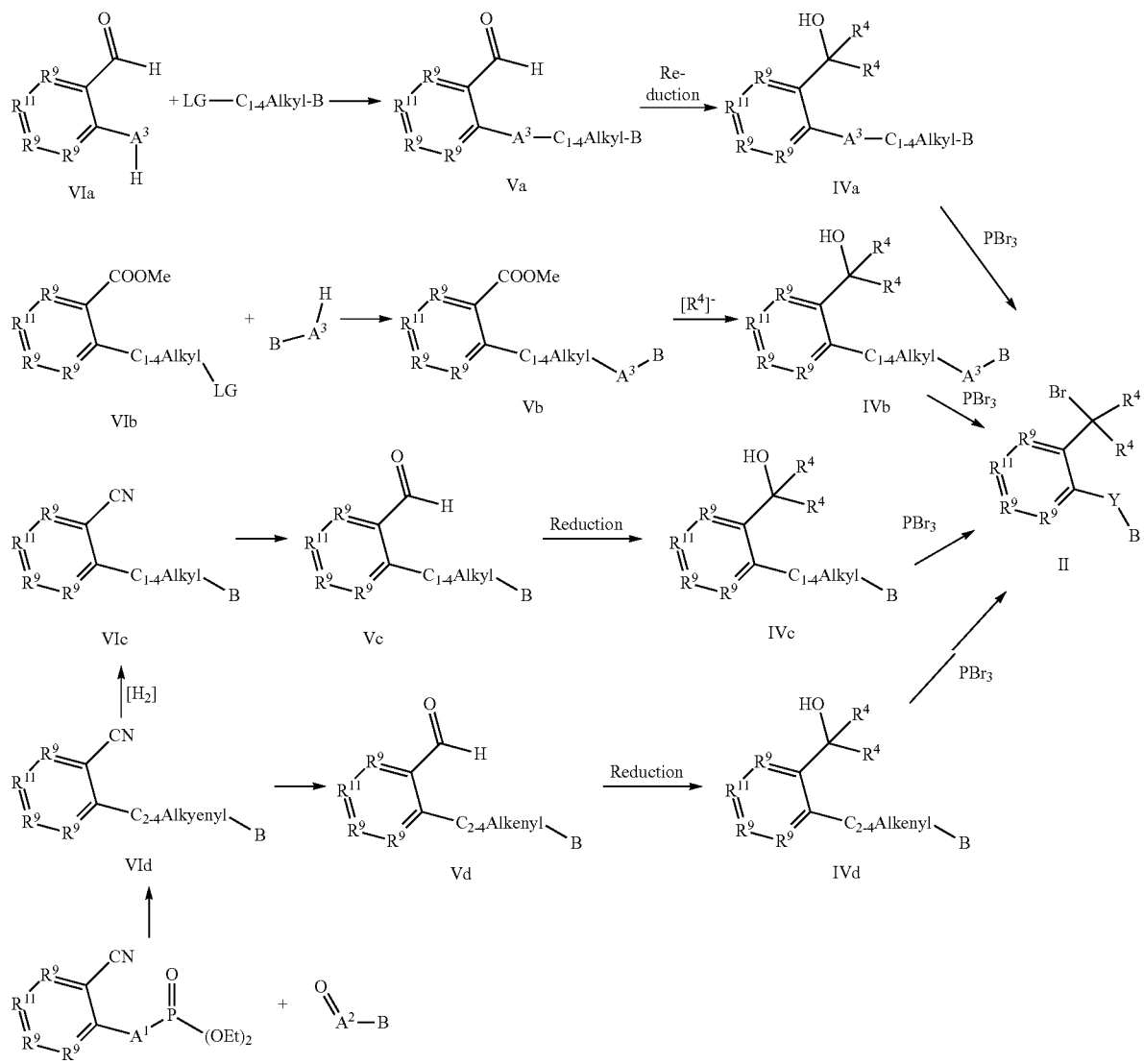

In the above scheme:
LG represents a leaving group. A leaving group is a group that in an heterolytic bond cleavage keeps the electron pair of the bond. Suitable leaving groups are well known in the art and include Cl, Br, I and —O—SO$_2$R$^{16}$, wherein R$^{16}$ is F, C$_{1-4}$-alkyl, C$_{1-4}$-haloalkyl, or optionally substituted phenyl. The preferred leaving groups are: Cl, Br, I, tosylate, mesylate, triflate, nonaflate and fluorosulphonate.

A$^1$ represents a C$_{1-2}$-alkylene group.

A$^2$ represents —C$_n$-alkyl-CO—C$_m$-alkyl-B, wherein n and m independently have a value of 0 to 2 and wherein n+m≤2.

A$^3$ represents either an —O— or —NR$^{13}$—.

all remaining substituents have the same meanings as previously defined in relation to a compound of formula (I).

Suitable reaction conditions for the preparation a compound of formula (II) include conventional methods for converting the hydroxyl group of the compounds of formula (IVa), (IVb), (IVc) and (IVd) to a leaving group, for example Br. When LG=bromo, the compound of formula (IV) may be reacted with phosphorous tribromide in a solvent, e.g. dichloromethane, at reduced temperatures, e.g. less than 0° C. Such transformations are well known to those skilled in the art and are described in for example L. G. Wade, Jr., Organic Chemistry, 6th ed., p. 477, Pearson/Prentice Hall, Upper Saddle River, New Jersey, USA, 2005.

Suitable reaction conditions for the preparation a compound of formula (IV) include conventional methods for reducing the carbonyl group of the compounds of formula (V) to a hydroxyl group. The reduction step may be carried out using a reducing agent such as NaBH$_4$, NaCNBH$_3$, LiAlH$_4$, LiBH$_4$ or Zn(BH$_4$)$_2$. For compounds of formula (Va), (Vc) and (Vd), preferably, the reduction step is carried out using NaBH$_4$. Preferably, an excess of NaBH$_4$ is used. Preferably, the reduction step is carried out in an alcohol solvent. Typical alcohols are methanol, ethanol, isopropanol, and mixtures thereof. A preferred alcohol is methanol. For compounds of formula (Vb) preferably, the reduction step is carried out using LiAlH$_4$. Preferably, an excess of LiAlH$_4$ is used. Preferably, the reduction step is carried out in an alkylether solvent. Typical alkylether solvents are tetrahydrofuran, diethylether, dioxane, diisopropylether, and mixtures thereof. A preferred alkylether is tetrahydrofuran. Such transformations are well known to those skilled in the art and are described in for example Banfi, L.; Narisano, E.; Riva, R.; Stiasni, N.; Hiersemann, M. "Sodium Borohydride" in Encyclopedia of Reagents for Organic Synthesis (Ed: L. Paquette) 2004, J. Wiley & Sons, New York.; and Seyden-Penne, J. "Reductions by the Alumino- and Borohydrides in Organic Synthesis"; VCH-Lavoisier: Paris, 1991.

Suitable reaction conditions for the preparation a compound of formula (Va) and (Vb) include conventional methods for the alkylation of the compounds of formula (VIa) and (VIb) wherein $A^3$ represents either an —O— or —$NR^{13}$—. A suitable LG group is bromine or chloride. The alkylation reaction of the compounds of formula (VIa) and (VIb) may be carried out in an inert organic solvent such as tetrahydrofuran or dimethylformamide at ambient or elevated temperature, optionally in the presence of a suitable base such as potassium or cesium carbonate or a strong base such as sodium t-butoxide or lithium bis(trimethylsilyl) amide (LiHMDS).

Suitable reaction conditions for the preparation a compound of formula (Vc) and ⁻(Vd) include conventional methods for reducing the cyano group of the compounds of formula (VIc) and (VId) to a hydroxyl group. The reduction step may be carried out using a reducing agent such as DIBA-H in an inert organic solvent such as hexane, heptane or cyclohexane, at ambient or low temperature, preferably from 0° C. to 5° C.

Intermediates of formula (VI) wherein $A^3$ represents either an —O— or —$NR^{13}$—, are commercially available, or may readily be prepared by methods known to those skilled in the art, for example from suitable commercially available starting materials.

Compounds of formula (III) are either commercially available or can be obtained by conventional methods.

Particular embodiments of the preparation of compounds of general formula (II) and (III) are provided below in the experimental section under the heading "Intermediate compounds".

Certain substituents in any of the reaction intermediates described above and in the compounds of formula (I) may be converted to other substituents by conventional methods known to those skilled in the art. Examples of such transformations include the Wittig reaction of an aldehyde group to give an alkene group; hydrolysis of esters, alkylation of hydroxy and amino groups; and formation of salts of carboxylic acids. Such transformations are well known to those skilled in the art and are described in for example, Richard Larock, *Comprehensive Organic Transformations,* 2nd edition, Wiley-VCH, ISBN 0-471-19031-4.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. In some instances it may be appropriate to use protecting groups to prevent reactions between one or more groups or moieties. Such procedures are familiar to those skilled in the art (see, for example, "Protective groups in organic synthesis" by T. W. Greene and P. G. M. Wuts (John Wiley & sons 10 1999) or "Protecting Groups" by P. J. Kocienski (Georg Thieme Verlag 1994).

An additional aspect of the invention relates to the therapeutic use of the compounds of general formula (I). As mentioned above, compounds of general formula (I) show a strong affinity to EP1 receptors. For this reason, they are suitable for the treatment and/or the prophylaxis of disorders and diseases mediated by EP1 receptors.

Compounds of the invention are particularly useful for modulating pain. The compounds of the present invention can treat or prevent the pain associated with several pathological conditions comprising, among others, inflammatory related pain (Hall et al. 2007) including low back and neck pain, skeletal pain, post-partum pain, toothache, sprains and straits, myositis, neuralgia, synovitis, arthritis, including rheumatoid arthritis, degenerative joint diseases (osteoarthritis), gout and ankylosing spondylitis, bursitis, burns including radiation and corrosive chemical injuries and sunburns; postoperative pain (Omote et al. 2001) including dental procedures; neuropathic pain (Kawahara et al. 2001); visceral pain (Sarkar et al. 2003); tension headache; cluster headaches; migraine and the like.

Moreover, by inhibition of prostanoid-induced smooth muscle contraction by antagonizing contractile prostanoids or mimicking relaxing prostanoids, EP1 modulators may be used in the treatment of motility -related disorders (with or without pain) such as as gastroinstestinal disorders (Sarkar et al. 2003; Mizuguchi et al 2010) and urinary incontinence and other urinary tract diseases (Teramura et al. 2000; Lee et al. 2007; Okada et al., 2010; Wilbraham et al 2010; Miki et al 2010), dysmenorrhea and preterm labour.

The compounds of the invention can also be useful in prostaglandin-mediated proliferation disorders such as in diabetic retinopathy and tumour angiogenesis, cancer (Watanabe et al. 1999; Niho et al. 2005), the inhibition of cellular neoplasic transformations and metastatic tumour growth.

They can further be used in the treatment of neurodegenerative diseases (including senile dementia, Alzheimer's disease, Pick's disease, Huntingdon's chorea, Parkinson's disease, Creutzfeldt-Jakob disease, or Amyotrophic Lateral Sclerosis) (Li et al. 2011), neuroprotection/stroke (Abe et al 2009), glaucoma (Woodward et al 1997), bone loss (osteoporosis) and the proportion of bone formation (treatment of fractures) (Zhang et al 2011; Lee et al. 2007) and other bone diseases such as Paget's disease.

As PGE2-induced hyperthermia in the rat is mediated predominantly through the EP1 receptor (Hönemann et al. 2001; Oka et al. 2003) different kinds of fever as rheumatic fever, symptoms associated with influenza or other viral infections as well as common cold can be also target diseases for EP1 modulators.

The compounds of the invention can also have a cytoprotective activity in patients under different gastrointestinal disorders as related with chemotherapy, or irritable bowel disease. Other diseases that can be treated or prevented with the compounds of the invention include gastrointestinal bleeding, coagulation disorders including anaemia such as hypoprothrombinemia, haemophilia or other bleeding problems; kidney diseases (nephritis (Rahal et al. 2006), particularly mesangial proliferative glomerulonephritis and nephritic syndrome); thrombosis, and occlusive vascular diseases.

In this sense, compounds of formula (I) are suitable to treat or to prevent diseases or disorders comprising inflammatory related pain including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; common cold, gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases.

The invention thus relates to a compound of formula (I) for use in the treatment and/or prophylaxis of an EP1-mediated disease or disorder. In one embodiment, the EP1-mediated disease or disorder is selected from the group consisting of pain, motility-related disorders, gastrointestinal disorders, urinary tract diseases, cancer, neurodegenerative diseases, stroke; glaucoma, bone diseases, fever, coagulation disorders and occlusive vascular diseases. In a preferred embodiment, the EP1-mediated disease or disorder is pain. In another embodiment, the EP1-mediated disease or disorder is selected from the group consisting of inflammatory related pain including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; common cold, gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases. In a preferred embodiment, the EP1-mediated disease or disorder is pain comprising inflammatory related pain, including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns; postoperative pain; neuropathic pain; visceral pain; tension headache; cluster headaches; migraine.

A related aspect refers to the use of at least one compound of general formula (I) for the manufacture of a medicament for the treatment and/or prophylaxis diseases or disorders mediated by EP1 receptors or in which EP1 receptors are involved.

In one embodiment, the EP1-mediated disease or disorder is selected from the group consisting of pain, motility-related disorders, gastrointestinal disorders, urinary tract diseases, cancer, neurodegenerative diseases, stroke, glaucoma, bone diseases, fever, coagulation disorders and occlusive vascular diseases. In a preferred embodiment, the EP1-mediated disease or disorder is pain. In another embodiment, the EP1-mediated disease or disorder is selected from the group consisting of inflammatory related pain including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns; postoperative pain; neuropathic pain; visceral pain; tension headache; cluster headaches; migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hypertermia including different types of fever as rheumatic fever; symptoms associated with influenza or other viral infections; common cold, gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases. In another embodiment, the EP1-mediated disease or disorder is selected from the group consisting of inflammatory related pain (including low back and neck pain, skeletal pain, post-partum pain, toothache, sprains and straits, myositis, neuralgia, synovitis, arthritis, including rheumatoid arthritis, degenerative joint dieases (such as osteoarthritis), gout and ankylosing spondylitis, bursitis, burns including radiation and corrosive chemical injuries and sunburns); postoperative pain; neuropathic pain; visceral pain; tension headache; cluster headaches; and migraine.

An aspect of the invention related to the therapeutic use of the compounds of general formula (I) is a method of treatment and/or prophylaxis of disorders and diseases mediated by EP1 receptors which comprises administering to a patient in need thereof a therapeutically effective amount of at least one compound of general formula (I). In one embodiment, the EP1-mediated disease or disorder is selected from the group consisting of pain, motility-related disorders, gastrointestinal disorders, urinary tract diseases, cancer, neurodegenerative diseases, stroke, glaucoma, bone diseases, fever, coagulation disorders and occlusive vascular diseases. In a preferred embodiment, the EP1-mediated disease or disorder is pain. In another embodiment, the EP1-mediated disease or disorder is selected from the group consisting of inflammatory related pain including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns; postoperative pain; neuropathic pain; visceral pain; tension headache; cluster headaches;

migraine; motility-related disorders including gastrointestinal disorders, urinary incontinence and other urinary tract diseases; dysmenorrhea; preterm labour; diabetic retinopathy; tumour angiogenesis; cancer; metastatic tumour growth; neurodegenerative diseases including senile dementia, Alzheimer's disease, Pick's disease, Huntington's chorea, Parkinson's disease, Creutzfeldt-Jakob disease, or amyotrophic lateral sclerosis; neuroprotection/stroke; glaucoma; osteoporosis; bone fractures; Paget's disease; hyperthermia including different types of fever as rheumatic fever; symptoms associated with influenza or other viral infections; common cold, gastrointestinal disorders related with chemotherapy or irritable bowel syndrome; gastrointestinal bleeding; coagulation disorders including anaemia, hypoprothrombinemia, haemophilia or other bleeding problems; kidney diseases including nephritis, particularly mesangial proliferative glomerulonephritis and nephritic syndrome; thrombosis and occlusive vascular diseases. In another embodiment, the EP1-mediated disease or disorder is selected from the group consisting of inflammatory related pain (including low back and neck pain, skeletal pain, post-partum pain, toothache, sprains and straits, myositis, neuralgia, synovitis, arthritis, including rheumatoid arthritis, degenerative joint diseases (such as osteoarthritis), gout and ankylosing spondylitis, bursitis, burns including radiation and corrosive chemical injuries and sunburns); postoperative pain; neuropathic pain; visceral pain; tension headache; cluster headaches; and migraine.

The amount of active ingredient that must be administered to the patient depends on the patient's weight, the type of application, the condition and, severity of the disease. Normally, in human beings 1 to 1500 mg of the active compound is administered daily in one or several doses.

A further aspect of the invention regards a pharmaceutical composition which comprises a compound of general formula (I), and at least a pharmaceutically acceptable carrier, additive, adjuvant or vehicle.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are tablets, pills, chewing gums, capsules, granules, drops or syrups. Suitable preparations for parenteral applications are solutions, suspensions, reconstitutable dry preparations or sprays.

The compounds of the invention as deposits in dissolved form or in patches, for percutaneous application.

Skin applications include ointments, gels, creams, lotions, suspensions or emulsions.

The preferred form of rectal application is by means of suppositories.

In the following paragraphs, some specific examples of preparation of intermediate compounds (II) and (III) and compounds of formula (I) are provided, together with examples of the biological activity of the compounds of the invention.

EXPERIMENTAL SECTION

The following abbreviations are used along the experimental section:
ACN: Acetonitrile
AcOH: Acetic acid
CDI: 1,1'-Carbonyldiimidazole
DAST: Diethylaminosulfur trifluoride
DBU: 1,8-Diazabicyclo[5.4.0]undec-7-ene
DCM: Dichloromethane
DIBAL-H: Diisobutylaluminium hydride
DIPEA: N,N-Diisopropylethylamine
DMAP: 4-(Dimethylamino)pyridine
DMF: Dimethylformamide
DMSO: Dimethyl sulfoxide
DPPA: Diphenyl phosphoryl azide
Dppf: 1,1'-Bis(diphenylphosphino)ferrocene
EDCl.HCl: N-(3-Dimethylaminopropyl)-N'-ethylcarbodiimide hydrochloride
EDTA: Ethylenediaminetetraacetic acid
$Et_2O$: Diethyl ether
EtAcO: Ethyl acetate
EtOH: Ethanol
Hex: hexane
HMTA: Hexamethylenetetramine
HPLC: High Performance Liquid Chromatography
LC-MS: Liquid chromatography-mass spectrometry
LDA: Lithium diisopropylamide
MeI: Iodomethane
MEM-Cl: 2-Methoxyethoxymethyl chloride
MeOH: Methanol
MES: 2-(N-Morpholino)ethanesulfonic acid
Me-THF: 2-Methyltetrahydrofurane
MsCl: Methanesulfonyl chloride
NaAcO: Sodium acetate
$NaBH(OAc)_3$: Sodium triacetoxyborohydride
NaHMDS: Sodium hexamethyldisilazide
NBS: N-bromosuccinimide
n-BuLi: Butyllithium
NMR: Nuclear magnetic resonance
Pd/C: Palladium on carbon
$Pd(OAc)_2$: Palladium(II) acetate
$P(OEt)_3$: Triethylphosphite
$Pd(PPh_3)_4$: Tetrakis(triphenylphosphine)palladium
PPTS: Pyridinium p-toluenesulfonate
p-TsCl: p-Toluenesulfonyl chloride
p-TsOH: p-Toluenesulfonic acid
Rf: Retention factor
RT: Room temperature
TBAF: Tetrabutylammonium fluoride
t-BuONa: Sodium tert-butoxide
TEA: Triethylamine
TFA: Trifluoroacetic acid
THF: Tetrahydrofurane
TLC: Thin layer cromatography
$TMSN_3$: Trimethylsilyl azide
tr: Retention time
X-Phos: 2-Dicyclohexylphosphino-2',4',6'-triisopropylbiphenyl Intermediate Compounds Intermediate Compound 1

Synthesis of 2-(bromomethyl)-4-chloro-1-((2,4-difluorobenzyl)oxy)benzene a) To a solution of 5-chloro-2-hydroxybenzaldehyde (2.04 g, 13 mmol) in DMF, potassium carbonate (2.64 g, 15.6 mmol) and 1-(bromomethyl)-2,4-difluorobenzene (2.83 g, 13.7 mmol) were added. The resulting yellow mixture was stirred at 40° C. overnight.

Then, it was diluted with water and HCl 1M was added until neutral pH was reached.

The mixture was extracted with EtAcO (×3) and the combined organic phase washed with brine and dried over MgSO$_4$.

b) The white solid obtained after removing the solvent (3.67 g, 100%) was suspended in 25 mL of absolute EtOH. The mixture was cooled at 0° C. and then 560 mg (14.7 mmol) of NaBH$_4$ were added. After 10 minutes the white suspension had turned into a colourless solution and TLC showed no starting material left. It was diluted with water and HCl 1M was added until acid pH was reached. The mixture was extracted with EtAcO (×3) and the combined organic phase washed with brine and dried over MgSO$_4$. Solvent was evaporated to yield 3.42 g (12 mmol, 93%) of (5-chloro-2-((2,4-difluorobenzyl)oxy)phenyl)methanol.

c) To a solution of 3.42 g of (5-chloro-2-((2,4-difluorobenzyl)oxy)phenyl)methanol in 50 mL dry DCM under argon and at 0° C. PBr$_3$ (3.25 g, 12 mmol) was added dropwise. The solution was stirred at 0° C. for 90 minutes, then at room temperature overnight. A saturated solution of sodium hydrogen carbonate was then added until neutral pH was reached. The mixture diluted with dichloromethane and water. The organic phase was separated, washed with water then dried over Na$_2$SO$_4$ and evaporated to dryness. The crude was purified by column chromatography eluting with Hex/EtAcO 8:2. 2-(bromomethyl)-4-chloro-1-((2,4-difluorobenzyl)oxy)benzene was obtained as a white solid (3.67 g, 88%).

$^1$H NMR (400 MHz CDCl$_3$) δ 7.59 (1H, m), 7.36 (1H, d), 7.26 (1H, dd,), 6.96 (1H, m), 6.89 (2H, m), 5.17 (2H, s), 4.53 (2H, s).

The following compounds were prepared using the same procedure as in intermediate compound 1:

| Intermediate compound | Compound name | Starting materials | NMR |
|---|---|---|---|
| 1a | 2-(bromomethyl)-4-chloro-1-((2,5-difluorobenzyl)oxy)benzene | 5-chloro-2-hydroxybenzaldehyde and 2-(bromomethyl)-1,4-difluorobenzene | $^1$H NMR (400 MHz, CDCl$_3$) δ 7.40-7.31 (m, 2H), 7.30-7.23 (m, 1H), 7.13-6.97 (m, 2H), 6.88 (d, 1H), 5.20 (s, 2H), 4.54 (s, 2H). |
| 1b | 2-(bromomethyl)-4-chloro-1-((2-chloro-4,5-difluorobenzyl)oxy)benzene | 5-chloro-2-hydroxybenzaldehyde and 1-(bromomethyl)-2-chloro-4,5-difluorobenzene | $^1$H NMR (400 MHz, CDCl$_3$) δ 7.52 (dd, 1H), 7.35 (d, 1H), 7.29-7.23 (m, 2H), 6.82 (d, 1H), 5.15 (s, 2H), 4.53 (s, 2H). |
| 1c | 2-(bromomethyl)-4-chloro-1-((2-chloro-5-fluorobenzyl)oxy)benzene | 5-chloro-2-hydroxybenzaldehyde and 2-(bromomethyl)-1-chloro-4-fluorobenzene | $^1$H NMR (400 MHz, CDCl$_3$) δ 7.43-7.36 (m, 1H), 7.35 (d, 1H), 7.27-7.21 (m, 1H), 7.03-6.96 (m, 1H), 6.83 (d, 1H), 5.19 (s, 2H), 4.55 (s, 2H). |
| 1d | 2-(bromomethyl)-4-fluoro-1-((2,5-difluorobenzyl)oxy)benzene | 5-fluoro-2-hydroxybenzaldehyde and 2-(bromomethyl)-1,4-difluorobenzene | $^1$H NMR (400 MHz, CDCl$_3$) δ 7.33 (ddd, 1H), 7.11-7.03 (m, 2H), 7.02-6.95 (m, 2H), 6.87 (dd, 1H), 5.17 (s, 2H), 4.54 (s, 2H). |
| 1e | 2-(bromomethyl)-4-fluoro-1-((2,6-difluorobenzyl)oxy)benzene | 5-fluoro-2-hydroxybenzaldehyde and 2-(bromomethyl)-1,3-difluorobenzene | $^1$H NMR (400 MHz, CDCl$_3$) δ 7.42-7.31 (m, 1H), 7.07 (dd, 1H), 7.01-6.95 (m, 4H), 5.18 (s, 2H), 4.56 (s, 2H). |
| 1f | 2-(bromomethyl)-4-fluoro-1-((4-fluorobenzyl)oxy)benzene | 5-fluoro-2-hydroxybenzaldehyde and 1-(bromomethyl)-4-fluorobenzene | $^1$H NMR (400 MHz, CDCl$_3$) δ 7.45 (dd, 2H), 7.15-7.02 (m, 3H), 6.96 (td, 1H), 6.84 (dd, 1H), 5.08 (s, 2H), 4.53 (s, 2H). |
| 1g | 2-(bromomethyl)-4-fluoro-1-((3,4,5-trifluorobenzyl)oxy)benzene | 5-fluoro-2-hydroxybenzaldehyde and 5-(bromomethyl)-1,2,3-trifluorobenzene | $^1$H NMR (400 MHz, CDCl$_3$) δ 7.17-7.06 (m, 3H), 6.97 (td, 1H), 6.79 (dd, 1H), 5.05 (s, 2H), 4.53 (s, 2H). |

-continued

| Intermediate compound | Compound name | Starting materials | NMR |
|---|---|---|---|
| 1h | 2-(bromomethyl)-4-fluoro-1-((2-chloro-4,5-difluorobenzyl)oxy)benzene | 5-fluoro-2-hydroxybenzaldehyde and 1-(bromomethyl)-2-chloro-4,5-difluorobenzene | $^1$H NMR (400 MHz, CDCl$_3$) δ 7.53 (dd, 1H), 7.27 (dd, 2H), 7.11 (dd, 1H), 7.02-6.95 (m, 1H), 6.84 (dd, 1H), 5.14 (s, 2H), 4, 55 (s, 2H). |
| 1i | 2-(bromomethyl)-4-trifluoromethyl-1-((2,6-difluorobenzyl)oxy)benzene | 2-hydroxy-5-(trifluoromethyl)benzaldehyde and 2-(bromomethyl)-1,3-difluorobenzene | $^1$H NMR (400 MHz, CDCl$_3$) δ 7.63-7.52 (m, 2H), 7.39-7.31 (m, 1H), 7.13 (d, 1H), 7.00-6.89 (m, 2H), 5.25 (s, 2H), 4.47 (s, 2H). |
| 1j | 2-(bromomethyl)-4-fluoro-1-((2-chloro-5-fluoro-benzyl)oxy)benzene | 5-fluoro-2-hydroxybenzaldehyde and 2-(bromomethyl)-1-chloro-4-fluorobenzene | $^1$H NMR (400 MHz, CDCl$_3$) δ 7.41 (dd, 1H), 7.37 (dd, 1H), 7.11 (dd, 1H), 7.04-6.94 (m, 2H), 6.84 (dd, 1H), 5.19 (s, 2H), 4.57 (s, 2H). |
| 1k | 2-(bromomethyl)-4-trifluoromethyl-1-((2,5-difluorobenzyl)oxy)benzene | 2-hydroxy-5-(trifluoromethyl)benzaldehyde and 2-(bromomethyl)-1,4-difluorobenzene | $^1$H NMR (400 MHz, CDCl$_3$) δ 7.61 (d, 1H), 7.56 (dd, 1H), 7.09 (d, 1H), 6.76-6.71 (m, 2H), 5.18 (s, 2H), 4.59 (s, 2H). |
| 1l | 2-(bromomethyl)-6-bromo-4-chloro-1-((2,6-difluorobenzyl)oxy)benzene | 3-bromo-5-chloro-2-hydroxybenzaldehyde and 2-(bromomethyl)-1,3-difluorobenzene | $^1$H NMR (400 MHz, CDCl$_3$) δ 7.54 (d, 1H), 7.42-7.32 (m, 2H), 6.94-7.00 (m, 2H), 5.22 (s, 2H), 4.50 (s, 2H). |
| 1m | 2-(bromomethyl)-4-chloro-1-((3,5-difluorobenzyl)oxy)benzene | 5-chloro-2-hydroxybenzaldehyde and 1-(bromomethyl)-3,5-difluorobenzene | $^1$H NMR (400 MHz, CDCl$_3$) δ 7.35 (d, 1H), 7.22 (dd, 1H), 7.02-7.00 (m, 2H), 6.82-6.74 (m, 2H), 5.12 (s, 2H), 4.53 (s, 2H). |
| 1n | 2-(bromomethyl)-4-chloro-1-((4-chloro-2-fluorobenzyl)oxy)benzene | 5-chloro-2-hydroxybenzaldehyde and 1-(bromomethyl)-4-chloro-2-fluorobenzene | $^1$H NMR (400 MHz CDCl$_3$) δ 7.56 (1H, t), 7.36 (1H, d), 7.26 (1H, dd), 7.22 (1H, dd), 7.17 (1H, dd), 6.89 (1H, d), 5.19 (2H, s), 4.53 (2H, s). |
| 1p | 4-bromo-1-(bromomethyl)-2-((3,5-dichlorobenzyl)oxy)benzene | 4-bromo-2-hydroxybenzaldehyde and 1-(bromomethyl)-3,5-dichlorobenzene | $^1$H NMR (400 MHz CDCl$_3$) δ 7.41 (2H, m), 7.37 (1H, t), 7.25 (1H, d), 7.14 (1H, dd), 7.04 (1H, d), 5.10 (2H, s), 4.55 (2H, s). |
| 1q | 1-(benzyloxy)-2-(bromomethyl)-4-chlorobenzene | 5-chloro-2-hydroxybenzaldehyde and (bromomethyl)benzene | $^1$H NMR (400 MHz CDCl$_3$) δ 7.50-7.35 (5H, m), 7.23 (1H, dd), 6.87 (1H, d), 5.16 (2H, s), 4.55 (2H, s). |
| 1r | 2-(bromomethyl)-4-chloro-1-((2-fluorobenzyl)oxy)benzene | 5-chloro-2-hydroxybenzaldehyde and 1-(bromomethyl)-2-fluorobenzene | $^1$H NMR (400 MHz CDCl$_3$) δ 7.62 (1H, t), 7.40-7.32 (2H, m), 7.28-7.19 (2H, m), 7.11 (1H, t), 6.90 (1H, d), 5.23 (2H, s), 4.55 (2H, s). |

| Intermediate compound | Compound name | Starting materials | NMR |
|---|---|---|---|
| 1s | 4-bromo-1-((2-(bromomethyl)-4-chlorophenoxy)methyl)-2-fluorobenzene | 5-chloro-2-hydroxybenzaldehyde and 4-bromo-1-(bromomethyl)-2-fluorobenzene | $^1$H NMR (400 MHz CDCl$_3$) δ 7.49 (1H, t), 7.36 (1H, dd), 7.35 (1H, dd), 7.32 (1H, dd), 7.25 (1H, dd), 6.87 (1H, d), 5.17 (2H, s), 4.52 (2H, s). |
| 1t | 2-(bromomethyl)-4-chloro-1-((2-fluoro-4-(trifluoromethyl)benzyl)oxy)benzene | 5-chloro-2-hydroxybenzaldehyde 1-(bromomethyl)-2-fluoro-4-(trifluoromethyl)benzene | $^1$H NMR (400 MHz CDCl$_3$) δ 7.79 (1H, t), 7.51 (1H, d), 7.40 (1H, d), 7.37 (1H, d), 7.27 (1H, dd), 6.88 (1H, d), 5.27 (2H, s), 4.54 (2H, s). |
| 1u | 2-(bromomethyl)-1-((3-fluorobenzyl)oxy)-4-(trifluoromethyl)benzene | (trifluoro2-hydroxy-5-methyl)benzaldehyde and 1-(bromomethyl)-3-fluorobenzene | $^1$H NMR (400 MHz CDCl$_3$) δ 7.64 (1H, d), 7.55 (1H, dd), 7.40 (1H, m), 7.28-7.23 (2H, m), 7.06 (1H, td), 6.98 (1H, d), 5.23 (2H, s), 4.61 (2H, s). |
| 1v | 4-bromo-1-((2-(bromomethyl)-4-(trifluoromethyl)phenoxy)methyl)-2-fluorobenzene | 2-hydroxy-5-(trifluoromethyl)benzaldehyde and 4-bromo-1-(bromomethyl)-2-fluorobenzene | $^1$H NMR (400 MHz CDCl$_3$) δ 7.63 (1H, d), 7.57 (1H, dd), 7.50 (1H, t), 7.37 (1H, dd), 7.33 (1H, dd), 7.02 (1H, d), 5.24 (2H, s), 4.57 (2H, s). |
| 1x | 2-(bromomethyl)-1-((2-fluorobenzyl)oxy)-4-(trifluoromethyl)benzene | 2-hydroxy-5-(trifluoromethyl)benzaldehyde and 1-(bromomethyl)-2-fluorobenzene | $^1$H NMR (400 MHz CDCl$_3$) δ 7.64-7.53 (3H, m), 7.35 (1H, q), 7.22 (1H, t), 7.12 (1H, t), 7.05 (1H, d), 5.31 (2H, s), 4.60 (2H, s). |
| 1y | 4-bromo-2-(bromomethyl)-1-((2,4-difluorobenzyl)oxy)benzene | 5-bromo-2-hydroxybenzaldehyde and 1-(bromomethyl)-2,4-difluorobenzene | $^1$H NMR (400 MHz CDCl$_3$) δ 7.60-7.53 (1H, m), 7.49 (1H, d), 7.40 (1H, dd), 6.98-6.84 (3H, m), 5.19 (2H, s), 4.51 (2H, s). |
| 1z | 1-((2-(bromomethyl)phenoxy)methyl)-2,4-difluorobenzene | 2-hydroxybenzaldehyde and 1-(bromomethyl)-2,4-difluorobenzene | $^1$H NMR (400 MHz CDCl$_3$) δ 7.65-7.60 (1H, m), 7.37 (1H, dd), 7.31 (1H, td), 7.00-6.85 (4H, m), 5.20 (2H, s), 4.61 (2H, s). |
| 1aa | 4-bromo-1-((4-bromo-2-(bromomethyl)phenoxy)methyl)-2-fluorobenzene | 5-bromo-2-hydroxybenzaldehyde and 4-bromo-1-(bromomethyl)-2-fluorobenzene | $^1$H NMR (400 MHz CDCl$_3$) δ 7.50-7.30 (5H, m), 6.85 (1H, d), 5.17 (2H, s), 4.52 (2H, s). |
| 1ab | 4-bromo-1-((2-(bromomethyl)-4-fluorophenoxy)methyl)-2-fluorobenzene | 5-fluoro-2-hydroxybenzaldehyde and 4-bromo-1-(bromomethyl)-2-fluorobenzene | $^1$H NMR (400 MHz CDCl$_3$) δ 7.50 (1H, t), 7.36 (1H, dd), 7.31 (1H, dd), 7.11 (1H, dd), 7.01-6.97 (1H, m), 6.88 (1H, dd), 5.16 (2H, s), 4.54 (2H, s). |
| 1ac | 2-((2-(bromomethyl)-4-chlorophenoxy)methyl)-5-chloro-1,3-difluorobenzehe | 5-chloro-2-hydroxybenzaldehyde and 2-(bromomethyl)-5-chloro-1,3-difluorobenzene | $^1$H NMR (400 MHz CDCl$_3$) δ 7.34 (1H, d), 7.27 (1H, dd), 7.11-6.97 (3H, m), 5.16 (2H, s), 4.44 (2H, s). |

| Intermediate compound | Compound name | Starting materials | NMR |
|---|---|---|---|
| 1ad | 5-bromo-2-((2-(bromomethyl)-4-chlorophenoxy)methyl)-1,3-difluorobenzene | 5-chloro-2-hydroxybenzaldehyde and 2-(bromomethyl)-5-bromo-1,3-difluorobenzene | $^1$H NMR (400 MHz CDCl$_3$) δ 7.32 (1H, d), 7.26 (1H, dd), 7.21-7.15 (2H, m), 6.97 (1H, d), 5.13 (2H, s), 4.44 (2H, s). |
| 1ae | 2-((4-bromo-2-(bromomethyl)phenoxy)methyl)-5-chloro-1,3-difluorobenzene | 5-bromo-2-hydroxybenzaldehyde and 2-(bromomethyl)-5-chloro-1,3-difluorobenzene | $^1$H NMR (400 MHz CDCl$_3$) δ 7.48 (1H, d), 7.41 (1H, dd), 7.21-7.15 (2H, m), 6.93 (1H, d), 5.15 (2H, s), 4.43 (2H, s). |
| 1af | 1-(bromomethyl)-3,5-dichloro-2-((4-chloro-2-fluorobenzyl)oxy)benzene | 3,5-dichloro-2-hydroxybenzaldehyde and 1-(bromomethyl)-4-chloro-2-fluorobenzene | $^1$H NMR (400 MHz CDCl$_3$) δ 7.58 (1H, t), 7.39 (1H, d), 7.33 (1H, d), 7.23 (1H, dd), 7.17 (1H, dd), 5.18 (2H, s), 4.46 (2H, s). |
| 1ag | 2-(bromomethyl)-3-((4-chloro-2-fluorobenzyl)oxy)pyridine | 3-hydroxypicolinaldehyde and 1-(bromomethyl)-4-chloro-2-fluorobenzene | $^1$H NMR (400 MHz CDCl$_3$) δ 8.22 (1H, dd), 7.55 (1H, t), 7.28-7.15 (4H, m), 5, 21 (2H, s), 4.68 (2H, s). |
| 1ah | 2-(bromomethyl)-1-((3,5-difluorobenzyl)oxy)-4-fluorobenzene | 5-fluoro-2-hydroxybenzaldehyde and 1-(bromomethyl)-3,5-difluorobenzene | $^1$H NMR (400 MHz CDCl$_3$) δ 7.12 (1H, dd), 7.05-6.98 (3H, m), 6.83-6.80 (2H, m), 5.13 (2H, s), 4.57 (2H, s). |
| 1ai | 1-(benzyloxy)-4-bromo-2-(bromomethyl)benzene | 5-bromo-2-hydroxybenzaldehyde and (bromomethyl)benzene | $^1$H NMR (400 MHz, CDCl$_3$) δ 7.48-7.43 (3H, m), 7.43-7.37 (2H, m), 7.35 (2H, m), 5.14 (2H, s), 4.53 (2H, s). |
| 1aj | 1-(benzyloxy)-2-(bromomethyl)-4-(trifluoromethyl)benzene | 2-hydroxy-5-(trifluoromethyl)benzaldehyde and (bromomethyl)benzene | $^1$H NMR (400 MHz, CDCl$_3$) δ 7.61 (1H, d), 7.52 (1H, dd), 7.49-7.47 (2H, m), 7.43-7.39 (2H, m), 7.37-7.33 (1H, m), 6.98 (1H, d), 5.21 (2H, s), 4.59 (2H, s). |
| 1ak | 4-bromo-2-(bromomethyl)-1-(4-fluorobenzyloxy)benzene | 5-bromo-2-hydroxybenzaldehyde and 1-(bromomethyl)-4-fluorobenzene | 'H NMR (400 MHz, CDCl$_3$) δ 7.50-7.40 (m, 3H), 7.50-7.40 (1H, dd), 7.36 (1H, dd), 7.14-7.04 (1H, m), 6.78 (1H, d), 5.09 (2H, s), 4.50 (2H, s). |
| 1al | 2-(bromomethyl)-4-chloro-1-(4-fluorobenzyloxy)benzene | 5-chloro-2-hydroxybenzaldehyde and 1-(brombmethyl)-4-fluorobenzene | $^1$H NMR (400 MHz, CDCl$_3$) δ 7.44 (2H, dd), 7.33 (1H, d), 7.22 (1H, dd), 7.14-7.01 (2H, m), 6.83 (1H, d), 5.09 (2H, s), 4.51 (2H, s). |

-continued

| Intermediate compound | Compound name | Starting materials | NMR |
|---|---|---|---|
| 1am | 2-(bromomethyl)-1-(4-chloro-2-fluorobenzyloxy)-4-(trifluoromethyl)benzene | 2-hydroxy-5-(trifluoromethyl)benzaldehyde and 1-(bromomethyl)-4-chloro-2-fluorobenzene | $^1$H NMR (400 MHz, CDCl$_3$) δ 7.62 (1H, d), 7.54 (1H, t), 7.21 (1H, dd), 7.16 (1H, dd), 7.00 (1H, d), 5.24 (s, 2H), 4.56 (s, 2H). |
| 1an | 2-(bromomethyl)-4-chloro-1-((4-(trifluoromethyl)benzyl)oxy)benzene | 5-chloro-2-hydroxybenzaldehyde and 1-(bromomethyl)-2-fluoro-4-(trifluoromethyl)benzene | $^1$H NMR (400 MHz, CDCl$_3$) δ 7.46 (2H, dd), 7.32 (1H, d), 7.22 (1H, dd), 7.14-7.01 (2H, m), 6.83 (1H, d), 5.09 (2H, s), 4.51 (2H, s). |
| 1ap | 4-bromo-2-(bromomethyl)-1-(4-chloro-2-fluorobenzyloxy)benzene | 5-bromo-2-hydroxybenzaldehyde and 1-(bromomethyl)-4-chloro-2-fluorobenzene | $^1$H NMR (400 MHz, CDCl$_3$) δ 7.53 (1H, t), 7.47 (1H, d), 7.38 (1H, dd), 7.19 (1H, dd), 7.14 (1H, dd), 6.81 (1H, d), 5.16 (s, 2H), 4.49 (2H, s). |
| 1aq | 2-(bromomethyl)-4-chloro-1-(cyclopropylmethoxy)benzene | 5-chloro-2-hydroxybenzaldehyde and (bromomethyl)cyclopropane | $^1$H NMR (400 MHz, CDCl$_3$) δ 7.31 (1H, d), 7.20 (1H, dd), 6.76 (1H, d), 4.52 (2H, s), 3.87 (2H, d), 1.39-1.15 (1H, m), 0.75-0.53 (2H, m), 0.48-0.28 (2H, m). |
| 1ar | 4-bromo-2-(bromomethyl)-1-(cyclopropylmethoxy)benzene | 5-bromo-2-hydroxybenzaldehyde and (bromomethyl)cyclopropane | $^1$H NMR (400 MHz, CDCl$_3$) δ 7.45 (1H, d), 7.34 (1H, dd), 6.72 (1H, d), 4.51 (2H, s), 3.87 (2H, d), 1.35-1.25 (1H, m), 0.70-0.56 (2H, m), 0.45-0.32 (2H, m). |
| 1as | 3-((2-(bromomethyl)-4-chlorophenoxy)methyl)-1,2,4,5-tetrafluorobenzene | 5-chloro-2-hydroxybenzaldehyde and 3-(bromomethyl)-1,2,4,5-tetrafluorobenzene | $^1$H NMR (400 MHz, CDCl$_3$) δ 7.32 (1H, d), 7.19 (1H, dd), 6.81 (1H, d), 6.57 (1H, m), 5.16 (2H, s), 4.56 (2H, s). |
| 1at | 1-((2,4-bis(trifluoromethyl)benzyl)oxy)-2-(bromomethyl)-4-chlorobenzene | 5-chloro-2-hydroxybenzaldehyde and 1-(bromomethyl)-2,4-bis(trifluoromethyl)benzene | $^1$H NMR (400 MHz, CDCl$_3$) δ 8.06 (1H, d), 7.96 (1H, s), 7.89 (1H, d), 7.37 (1H, d), 7.24 (1H, dd), 6.78 (1H, d), 5.39 (2H, s), 4.56 (2H, s). |
| 1au | 2-(bromomethyl)-4-chloro-1-((2-chloro-4-fluorobenzyl)oxy)benzene | 5-chloro-2-hydroxybenzaldehyde and 1-(bromomethyl)-2-chloro-4-fluorobenzene | $^1$H NMR (400 MHz, CDCl$_3$) δ 7.61 (1H, dd), 7.35 (1H, d), 7.24 (1H, dd), 7.18 (1H, dd), 7.05 (1H, td), 6.84 (1H, d), 5.18 (2H, s), 4.53 (2H, s). |
| 1av | 4-bromo-2-(bromomethyl)-1-((2-chloro-4-fluorobenzyl)oxy)benzene | 5-bromo-2-hydroxybenzaldehyde and 1-(bromomethyl)-2-chloro-4-fluorobenzene | $^1$H NMR (400 MHz, CDCl$_3$) δ 7.61 (1H, dd), 7.48 (1H, d), 7.38 (1H, dd), 7.18 (1H, dd), 7.04 (1H, td), 6.80 (1H, d), 5.18 (2H, s), 4.53 (2H, s). |

-continued

| Intermediate compound | Compound name | Starting materials | NMR |
|---|---|---|---|
| 1ax | 1-((2-(bromomethyl)-4-chlorophenoxy)methyl)-2,4,5-trifluorobenzene | 5-chloro-2-hydroxybenzaldehyde and 1-(bromomethyl)-2,4,5-trifluorobenzene | $^1$H NMR (400 MHz, CDCl$_3$) δ 7.47-7.40 (1H, m), 7.19 (1H, dd), 7.02-6.94 (2H, m), 6.86 (1H, dd), 5.12 (2H, s), 4.52 (2H, s). |
| 1ay | 2-bromo-4-((2-(bromomethyl)-4-chlorophenoxy)methyl)-1-fluorobenzene | 5-chloro-2-hydroxybenzaldehyde and 2-bromo-4-(bromomethyl)-1-fluorobenzene | $^1$H NMR (400 MHz, CDCl$_3$) δ 7.67 (1H, dd), 7.44 (1H, d), 7.43-7.27 (2H, m), 7.15 (1H, t), 6.76 (1H, d), 5.07 (2H, s), 4.50 (2H, s). |
| 1az | 1-((2-(bromomethyl)-4-chlorophenoxy)methyl)-2,3,4-trifluorobenzene | 5-chloro-2-hydroxybenzaldehyde and 1-(bromomethyl)-2,3,4-trifluorobenzene | $^1$H NMR (400 MHz, CDCl$_3$) δ 7.48 (1H, d), 7.39 (1H, dd), 7.35-7.27 (1H, m), 7.02 (1H, tdd), 6.81 (1H, d), 5.16 (2H, s), 4.48 (2H, s). |
| 1ba | 2-(bromomethyl)-1-((2-chloro-4-fluorobenzyl)oxy)-4-fluorobenzene | 5-fluoro-2-hydroxybenzaldehyde and 1-(bromomethyl)-2-chloro-4-fluorobenzene | $^1$H NMR (400 MHz, CDCl$_3$) δ 7.62 (1H, dd), 7.17 (1H, dd), 7.10 (1H, dd), 7.05 (1H, td), 7.01-6.94 (1H, m), 6.86 (1H, dd), 5.17 (2H, s), 4.55 (2H, s). |
| 1bb | 1-((2-(bromomethyl)-4-fluorophenoxy)methyl)-2,4,5-trifluorobenzene | 5-fluoro-2-hydroxybenzaldehyde and 1-(bromomethyl)-2,4,5-trifluorobenzene | $^1$H NMR (400 MHz, CDCl$_3$) δ 7.51-7.40 (1H, m), 7.09 (1H, dd), 7.02-6.94 (2H, m), 6.86 (1H, dd), 5.12 (2H, s), 4.52 (2H, s). |
| 1bc | 2-(bromomethyl)-4-fluoro-1-((4-fluoro-2-(trifluoromethyl)benzyl)oxy)benzene | 5-fluoro-2-hydroxybenzaldehyde and 1-(bromomethyl)-4-fluoro-2-(trifluoromethyl)benzene | $^1$H NMR (400 MHz, CDCl$_3$) δ 7.85 (1H, dd), 7.42 (1H, dd), 7.31 (1H, td), 7.10 (1H, dd), 7.04-6.93 (1H, m), 6.81 (1H, dd), 5.28 (2H, s), 4.55 (2H, s). |
| 1bd | 2-(bromomethyl)-4-chloro-1-((4-fluoro-2-(trifluoromethyl)benzyl)oxy)benzene | 5-chloro-2-hydroxybenzaldehyde and 1-(bromomethyl)-4-fluoro-2-(trifluoromethyl)benzene | $^1$H NMR (400 MHz, CDCl$_3$) δ 7.84 (1H, dd), 7.43 (dd, J = 8.8, 2.7 Hz, 1H), 7.35 (d, J = 2.6 Hz, 1H), 7.30 (td, J = 8.3, 2.7 Hz, 1H), 7.23 (dd, J = 8.8, 2.6 Hz, 1H), 6.79 (d, J = 8.8 Hz, 1H), 5.29 (s, 1H), 4.54 (s, 1H). |
| 1be | 1-((4-bromo-2-(bromomethyl)phenoxy)methyl)-2,3,4-trifluorobenzene | 5-bromo-2-hydroxybenzaldehyde and 1-(bromomethyl)-2,3,4-trifluorobenzene | $^1$H NMR (400 MHz, CDCl$_3$) δ 7.48 (1H, d), 7.39 (1H, dd), 7.35-7.27 (1H, m), 7.02 (1H, tdd), 6.81 (1H, d), 5.16 (2H, s), 4.48 (2H, s). |
| 1bf | 2-bromo-4-((2-(bromomethyl)-4-fluorophenoxy)methyl)-1-fluorobenzene | 5-fluoro-2-hydroxybenzaldehyde and 2-bromo-4-(bromomethyl)-1-fluorobenzene | $^1$H NMR (400 MHz, CDCl$_3$) δ 7.69 (1H, dd), 7.44-7.37 (1H, m), 7.44-7.37 (1H, m), 7.15 |

| Intermediate compound | Compound name | Starting materials | NMR |
|---|---|---|---|
| | | | (1H, t), 7.09 (1H, dd), 6.96 (1H, ddd), 6.82 (1H, dd), 5.06 (2H, s), 4.52 (2H, s). |
| 1bg | 2-bromo-4-((4-bromo-2-(bromomethyl)phenoxy)methyl)-1-fluorobenzene | 5-bromo-2-hydroxybenzaldehyde and 2-bromo-4-(bromomethyl)-1-fluorobenzene | $^1$H NMR (400 MHz, CDCl$_3$) δ 7.69 (1H, dd), 7.47 (1H, d), 7.44-7.28 (2H, m), 7.15 (1H, t), 6.76 (1H, d), 5.07 (2H, s), 4.50 (2H, s). |
| 1bh | 4-bromo-2-(bromomethyl)-1-((4-fluoro-2-(trifluoromethyl)benzyl)oxy)benzene | 5-bromo-2-hydroxybenzaldehyde and 1-(bromomethyl)-4-fluoro-2-(trifluoromethyl)benzene | $^1$H NMR (400 MHz, CDCl$_3$) δ 7.83 (1H, dd), 7.49 (1H, d), 7.43 (1H, dd), 7.37 (1H, dd), 7.30 (1H, td), 6.74 (1H, d), 5.28 (2H, s), 4.53 (2H, s). |
| 1bi | 1-bromo-2-((4-bromo-2-fluorobenzyl)oxy)-3-(bromomethyl)-5-chlorobenzene | 3-bromo-5-chloro-2-hydroxybenzaldehyde and 4-bromo-1-(bromomethyl)-2-fluorobenzene | $^1$H NMR (400 MHz, CDCl$_3$) δ 7.57-7.51 (2H, m), 7.37 (2H, dd), 7.31 (1H, dd), 5.14 (2H, s), 4.46 (2H, s). |
| 1bj | 2-(bromomethyl)-1-1(2,4-difluorobenzyl)oxy]-4-methoxybenzene | 2-hydroxy-5-methoxy-benzaldehyde 1-(bromomethyl)-2,4-difluorobenzene | $^1$H-NMR (CDCl$_3$, 250 MHz, δ): 7.57 (dd, J = 15.0, 8.4 Hz, 1H, ArH); 6.99-6.78 (m, 5H, ArH); 5.12 (s, 2H, CH2); 4.55 (s, 2H, CH2); 3.77 (s, 3H, OCH3). |
| 1bk | 2-(bromomethyl)-4-chloro-1-(cyclohexylmethoxy)benzene | 5-chloro-2-hydroxy-benzaldehyde and (bromomethyl)cyclohexane | * |
| 1bl | 2-(bromomethyl)-4-chloro-1-(cyclopentylmethoxy)benzene | 5-chloro-2-hydroxy-benzaldehyde and (bromomethyl)cyclopentane | * |
| 1bm | 2-(bromomethyl)-4-fluoro-1-propoxybenzene | 5-fluoro-2-hydroxy-benzaldehyde and 1-iodopropane | $^1$H NMR (300 MHz, CDCl3) δ: 7.09-6.89 (m, 2H, ArH); 6.83-6.75 (m, 1H, ArH); 4.51 (s, 2H); 3.96 (t, J = 6.4 Hz, 2H); 1.97-1.74 (m, 2H); 1.08 (t, J = 7.41 Hz, 3H). |
| 1bn | 2-(bromomethyl)-4-chloro-1-(cyclopentyloxy)benzene | 5-chloro-2-hydroxy-benzaldehyde and 1-iodocyclopentane | $^1$H NMR (300 MHz, CDCl3) δ: 7.31-7.16 (m, 2H, ArH); 6.78 (d, J = 8.74 Hz, 1H, ArH); 4.85-4.77 (m, 1H); 4.44 (s, 2H); 1.98-1.76 (m, 6H); 1.71-1.56 (m, 2H). |
| 1bo | 2-(bromomethyl)-4-chloro-1-propoxybenzene | 5-chloro-2-hydroxy-benzaldehyde and 1-iodopropane | $^1$H NMR (300 MHz, CDCl3) δ: 7.35-7.17 (m, 2H, ArH); 6.78 (d, J = 8.76 Hz, 1H, ArH); 4.49 (s, 2H); 3.97 (t, J = 6.4 Hz, 2H); 1.98-1.74 (m, 2H); 1.08 (t, J = 7.44 Hz, 3H). |
| 1bp | 1-(bromomethyl)-2-isobutoxybenzene | salicylaldehyde and 1-iodo-2-methylpropane | * |

-continued

| Intermediate compound | Compound name | Starting materials | NMR |
|---|---|---|---|
| 1bq | 2-(bromomethyl)-4-chloro-1-(2,2-difluoroethoxy)benzene | 5-chloro-2-hydroxy-benzaldehyde and 1,1-difluoro-2-iodoethane | * |
| 1br | 2-(bromomethyl)-4-chloro-1-(2-fluoro-ethoxy)benzene | 5-chloro-2-hydroxy-benzaldehyde and 2-fluoroethyl-4-methylbenzenesulfonate | * |
| 1bs | 2-(bromomethyl)-4-chloro-1-(2,2,2-tri-fluoroethoxy)benzene | 5-chloro-2-hydroxy-benzaldehyde and 1,1,1-trifluoro-2-iodoethane | * |
| 1bt | 2-(bromomethyl)-4-chloro-1-(neo-pentyloxy)benzene | 5-chloro-2-hydroxy-benzaldehyde and 1-iodo-2,2-dimethylpropane | * |
| 1bu | 2-(bromomethyl)-4-chloro-1-(2-fluoro-2-methylpropoxy)benzene | 5-chloro-2-hydroxy-benzaldehyde and 2-fluoro-2-methylpropyl trifluoromethanesulfonate (prepared following the method described in: Limanto, J. et al *J. Org. Chem.* 2005, 70, 2372-2375) | * |
| 1bv | 2-(bromomethyl)-1-((4-chloro-2-fluorobenzyl)oxy)-4-fluorobenzene | 5-fluoro-2-hydroxy-benzaldehyde and 1-(bromomethyl)-4-chloro-2-fluorobenzene | * |
| 1bw | 2-(bromomethyl)-4-chloro-1-(cyclobutyl-methoxy)benzene | 5-chloro-2-hydroxy-benzaldehyde and cyclobutylmethyl 4-methylbenzenesulfonate | ** |

* Intermediate compouns used directly in the next step without further analysis.
** LC-MS (method 4): $t_R$ = 1.55 [M − H]$^-$ = 289

Intermediate Compound 2

Synthesis of 2-(1-bromoethyl)-4-chloro-1-((4-chloro-2-fluorobenzyl)oxy)benzene a) 1-(5-chloro-2-((4-chloro-2-fluorobenzyl)oxy)phenyl)ethanol To a solution of 5-chloro-2-((4-chloro-2-fluorobenzyl)oxy)benzaldehyde (200 mg, 0.67 mmol) in dry diethyl ether, a solution of methylmagnesium bromide 3 M in ether (0.45 mL, 1.34 mmol) was added at 0° C. under nitrogen atmosphere. Mixture was stirred and allowed to reach room temperature. After 3 h, TLC showed no starting material left. It was treated with a saturated solution of ammonium chloride, diluted with water and extracted with diethyl ether (×3). The combined organic phases were washed with brine and dried over MgSO$_4$. Solvent was removed under vacuum to yield the crude desired product in quantitative yield.

b) The title compound was obtained following the general procedure as described intermediate compound 1 (step c) using 1-(5-chloro-2-((4-chloro-2-fluorobenzyl)oxy)phenyl) ethanol as starting material.

$^1$H NMR (400 MHz, CDCl$_3$) δ 7.52 (t, 1H), 7.49 (d, 1H), 7.24-7.17 (m, 2H), 7.15 (dd, 1H), 6.85 (d, 1H), 5.59 (q, 1H), 5.20-5.09 (m, 2H), 2.00 (d, 3H).

Intermediate Compound 3

Synthesis of 2-(bromomethyl)-4-chloro-1-(1-(2,4-difluorophenyl)ethoxy)benzene

The title compound was obtained following the general procedure described in intermediate compound 1 (step a, b, c) using 5-chloro-2-hydroxybenzaldehyde and 1-(1-bromo-ethyl)-2,4-difluorobenzene as starting materials.

$^1$H NMR (400 MHz, CDCl$_3$) δ 7.61 (1H, dd), 7.35 (1H, d), 7.24 (1H, dd), 7.18 (1H, dd), 7.05 (1H, td), 6.84 (1H, d), 5.15 (1H, m), 4.53 (2H, s), 1.72 (3H, d).

Intermediate Compound 4

Synthesis of 4-bromo-1-((4-bromo-2-(bromomethyl)benzyl)oxy)-2-fluorobenzene a) To a solution of 2.80 g (13 mmol) of 5-bromo-2-methylbenzoic acid in 11 mL of MeOH, 2.5 mL of HCl 4.0 M (10 mmol) in dioxane were added.
The reaction was heated at 70° C. and stirred at that temperature overnight.
Then, the mixture was concentrated, cooled to 0° C. and neutralized with saturated NaHCO$_3$. The resulting mixture was extracted with DCM and evaporated to obtain methyl 5-bromo-2-methylbenzoate as yellow oil (2.8 g, 94%), which solidified into needles.

b) 2.8 g (12.2 mmol) of 5-bromo-2-methylbenzoate was dissolved in 19 mL of CCl$_4$ and then NBS (2.6 g, 14.7 mmol) and benzoyl peroxide (0.28 g, 0.9 mmol) were added. The resulting yellow mixture was heated to 80° C. and stirred at that temperature overnight.

The solid was removed by filtration and washed with DCM. The yellow filtrate was concentrated and purified by column chromatography over silica gel eluting with hex/EtAcO 95:5 then 9:1 to yield methyl 5-bromo-2-(bromomethyl)benzoate.

c) To a solution of 255 mg (0.7 mmol) of methyl 5-bromo-2-(bromomethyl)benzoate and 111 mg (0.6 mmol) of 4-bromo-2-fluorophenol in 2 mL of dry DMF, $K_2CO_3$ (117 mg, 0.85 mmol) was added. Reaction was stirred at 50° C. overnight.

Then, it was allowed to cool to room temperature. Water was added and a white precipitated appeared. The mixture was extracted with EtAcO (×3), and the organic phases combined and washed with a 10% solution of NaCl in water. It was dried with anhydrous $Na_2SO_4$, filtered and the solvent evaporated. The compound was purified by column chromatography over silica gel eluting with cyclohexane/EtAcO 9:1

Methyl 5-bromo-2-((4-bromo-2-fluorophenoxy)methyl)benzoate (290 mg, 98%) was obtained as a white solid.

d) To a solution of 290 mg (0.7 mmol) of methyl 5-bromo-2-((4-bromo-2-fluorophenoxy)methyl)benzoate in 4 mL of dry THF cooled at 0° C. under argon, 0.8 mL of $LiAlH_4$ 1.0M in THF were added dropwise.

After 5 minutes TLC showed that there was no starting material left. Wet EtAcO was used to quench the reaction. The resulting mixture was dried over anhydrous $Na_2SO_4$ and then filtered through celite. After solvent evaporation (5-bromo-2-((4-bromo-2-fluorophenoxy)methyl)phenyl)methanol (267 mg, 99%) was obtained as white needles.

e) The title compound was obtained following the general procedure described in intermediate compound 1 (step c) using 4-bromo-1-((4-bromo-2-(bromomethyl)benzyl)oxy)-2-fluorobenzene as starting material.

$^1$H NMR (400 MHz $CDCl_3$) δ 7.57 (1H, d), 7.49 (1H, dd), 7.35-7.28 (2H, m), 7.23-7.20 (1H, m), 6.95 (1H, t), 5.21 (2H, s), 4.57 (2H, s).

Intermediate Compound 5

Synthesis of 2-(Bromomethyl)-4-chloro-1-(4-chloro-2-fluorophenethyl)benzene a) 2-(Bromomethyl)-5-chlorobenzonitrile 5-chloro-2-methylbenzonitrile (2.5 g, 16.5 mmol) was dissolved in carbon tetrachloride (40 mL), and N-bromosuccinimide (2.94 g, 16.5 mmol) was added, followed by benzoyl peroxide (0.107 g, 0.33 mmol). The mixture was refluxed for 4 h, and the white succinimide residue was filtered off. The solvent was evaporated under reduced pressure and the residue was chromatographed on silica gel eluting with Hexanes:EtAcO (1:0 to 9:1). One pure fraction was collected (2.05 g, 54% yield) as a white crystalline solid.

$^1$H NMR (400 MHz, $CDCl_3$) δ 7.65 (1H, d), 7.57 (1H, dd), 7.50 (1H, d), 4.60 (2H, s).

b) Diethyl 4-chloro-2-cyanobenzylphosphonate

A solution of 2-(bromomethyl)-5-chlorobenzonitrile (1.95 g, 8.46 mmol) and $P(OEt)_3$ (3.63 mL, 21.15 mmol) in toluene were heated to 140° C. for 4 hours. Excess of $P(OEt)_3$ was removed in vacuo, and the product was extracted with ethyl acetate. Combined organic extracts were dried over $MgSO_4$. Column chromatography on silica gel gave the desired product as a slightly yellow oil (2.1 g, 86% yield).

$^1$H NMR (400 MHz, $CDCl_3$) δ 7.65-7.58 (1H, m), 7.51 (2H, m), 4.19-4.00 (4H, m), 3.37 (2H, d), 1.29 (6H, t).

c) (E)-5-Chloro-2-(4-chloro-2-fluorostyryl)benzonitrile

To a solution of 4-chloro-2-fluorobenzaldehyde (1.43 g, 9.04 mmol) and diethyl 4-chloro-2-cyanobenzylphosphonate (2.6 g, 9.04 mmo) in THF (50 mL) was added potassium tertbutoxide (2.03 g, 18.1 mmol) at room temperature, the reaction was stirred for 3 hours. The mixture was then poured into water and extracted with ethyl acetate. After removing the solvent under vacuum, the crude product was purified by crystallization with methanol (2.6 g, 9.04 mmol).

$^1$H NMR (400 MHz, $CDCl_3$) δ 7.76 (1H, d), 7.67-7.53 (3H, m), 7.39 (2H, dd), 7.22-7.11 (2H, m).

d) 5-Chloro-2-(4-chloro-2-fluorophenethyl)benzonitrile (E)-5-Chloro-2-(4-chloro-2-fluorostyryl)benzonitrile was dissolved in THF and a catalytic amount of Pd/C was added. The reaction vessel was purged with $H_2$ and kept under $H_2$ (1 atm) for 24 h at room temperature. The reaction mixture was filtered over Celite and concentrated to give the desired product as a white solid.

$^1$H NMR (400 MHz, $CDCl_3$) δ 7.59 (1H, d), 7.45 (1H, dd), 7.15 (1H, d), 7.08-7.00 (3H, m), 3.13-3.01 (2H, m), 3.04-2.76 (2H, m).

e) 5-Chloro-2-(4-chloro-2-fluorophenethyl)benzaldehyde

In a dry Schlenk flask 5-chloro-2-(4-chloro-2-fluorophenethyl)benzonitrile (410 mg, 1.39 mmol) was dissolved in 20 mL of dry dichloromethane. The solution is cooled to 0° C. and 1.54 mL of DIBAL-H in hexane (c=1 mol/l) was added dropwise via syringe while the temperature is maintained below 5° C. After 20 minutes the cooling bath is removed and the mixture is stirred at room temperature. When TLC indicates the absence of starting material, 10 mL of diluted hydrochloric acid were carefully added. The mixture is demulsified by addition of aq. sat. NaCl solution and the aqueous phase was extracted with dichloromethane. The combined organic phases were dried with $MgSO_4$, filtered and concentrated at rotavap. The crude product is purified by flash chromatography ($SiO_2$, hexanes/$Et_2O$, 9:1). The product was obtained as a white solid.

$^1$H NMR (400 MHz, $CDCl_3$) δ 10.14 (1H, s), 7.79 (1H, d), 7.44 (1H, dd), 7.13 (1H, d), 7.08-6.87 (3H, m), 3.26 (2H, t), 2.89 (2H, t).

f) 2-(Bromomethyl)-4-chloro-1-(4-chloro-2-fluorophenethyl)benzene

The title compound was obtained following the general procedure described in intermediate compound 1 (steps b, c) using 5-chloro-2-(4-chloro-2-fluorophenethyl)benzaldehyde as starting material.

$^1$H NMR (500 MHz, $CDCl_3$) δ 7.40 (1H, d), 7.20 (1H, dd), 7.11-6.99 (4H, m), 4.67 (2H, s), 2.99-2.75 (4H, m).

Intermediate Compound 6

Synthesis of (E)-2-(Bromomethyl)-4-chloro-1-(4-chloro-2-fluorostyryl)benzene a) (E)-5-Chloro-2-(4-chloro-2-fluorostyryl)benzaldehyde

In a dry Schlenk flask (E)-5-Chloro-2-(4-chloro-2-fluorostyryl)benzonitrile (335 mg, 1.15 mmol) was dissolved in 20 mL of dry dichloromethane. The solution is cooled to 0° C. and 1.34 mL of DIBAL-H in hexane (c=1 mol/l) was added dropwise via syringe while the temperature is maintained below 5° C. After 20 minutes the cooling bath is removed and the mixture is stirred at room temperature. When TLC indicates the absence of starting material, 10 mL of diluted hydrochloric acid were carefully added. The mixture is demulsified by addition of aq. sat. NaCl solution and the aqueous phase was extracted with dichloromethane. The combined organic phases were dried with $MgSO_4$, filtered and concentrated at rotavap. The product was obtained as a white solid and used in the next step without further purification.

b) (E)-2-(Bromomethyl)-4-chloro-1-(4-chloro-2-fluorostyryl)benzene

The title compound was obtained following the general procedure described intermediate compound 1 (steps b, c) using (E)-5-chloro-2-(4-chloro-2-fluorostyryl)benzaldehyde as starting material.

$^1$H NMR (500 MHz, $CDCl_3$) δ 7.58 (1H, d), 7.52 (1H, t), 7.41 (2H, dd), 7.31 (1H, dd), 7.18-7.06 (3H, m), 4.81 (2H, s).

Intermediate Compound 7

Synthesis of methyl 7-fluoro-1H-indole-4-carboxylate a) 2-(Bromomethyl)-4-chloro-1-(4-chloro-2-fluorophenethyl)benzene

At −40° C., vinylmagnesium bromide (75 mmol) in tetrahydrofuran (75 mL) was added dropwise, in the course of 30 min, to a solution of 4-bromo-1-fluoro-2-nitrobenzene (5.5 g, 25 mmol) in tetrahydrofuran (100 mL). After 1 h at −40° C., the mixture was poured into a saturated aqueous solution (50 mL) of ammonium chloride. The organic layer was evaporated. The crude was submitted to flash chromatography through silica gel to obtain 1.2 g (22% yield) of 4-bromo-7-fluoro-1H-indole.

b) Methyl 7-fluoro-1H-indole-4-carboxylate

Under inert atmosphere (glove box), in a stainless steel high pressure reactor with a capacity of 25 mL and equipped with a magnetic stirrer were placed 4-bromo-7-fluoro-1H-indole (150 mg, 0.7 mmol), tetrakis(triphenylphosphane)palladium(0) (162 mg, 0.14 mmol), dry methanol (3 mL) and triethylamine (196 µL, 1.4 mmol). The system was purged three times with CO and pressurized to 25 bar. The reactor was warmed to 100° C. and stirred at 600 rpm overnight. Then was cooled to RT and the product was concentrated under reduced pressure. The crude was submitted to flash chromatography through silica gel to obtain 41 mg (30% yield) of the desired product.

$^1$H NMR (400 MHz, $CDCl_3$) δ 8.60 (1H, s NH), 7.89 (1H, dd), 7.38-7.35 (1H, m), 7.21 (1H, td), 6.94 (1H, dd), 3.98 (3H, s).

Intermediate Compound 8

Synthesis of methyl 7H-pyrrolo[2,3-d]pyrimidine-4-carboxylate a) 4-iodo-7H-pyrrolo[2,3-d]pyrimidine

A mixture of 4-chloro-7H-pyrrolo[2,3-d]pyrimidine (336 mg, 2.15 mmol) and 3.5 mL of 57% hydriodic acid was stirred at room temperature for 16 hours. The solid was filtered off, suspended in 3 mL of water and brought to pH=8 with aqueous ammonia solution. The suspension was cooled down to 0° C. and the solid was filtered off, washed with cold water and dried to give the desired product (410 mg). The product contains about 10% of the starting material.

b) Methyl 7H-pyrrolo[2,3-d]pyrimidine-4-carboxylate

Under inert atmosphere (glove box), in a stainless steel high pressure reactor with a capacity of 25 mL and equipped with a magnetic stirrer were placed 4-iodo-7H-pyrrolo[2,3-d]pyrimidine (300 mg, 1.22 mmol), tetrakis(triphenylphosphane)palladium(0) (283 mg, 0.25 mmol), dry methanol (4 mL) and triethylamine (342 µL, 2.5 mmol). The system was purged three times with CO and pressurized to 5 bar. The reactor was warmed to 100° C. and stirred at 600 rpm overnight. Then was cooled to RT and the product was concentrated under reduced pressure. The crude was submitted to flash chromatography through silica gel to obtain 200 mg (92% yield) of the desired product.

$^1$H NMR (500 MHz, $CDCl_3$) δ 10.27 (1H, s NH), 9.08 (1H, s), 7.58 (1H, dd), 7.16 (1H, d), 4.11 (3H, s).

Intermediate Compound 9

Synthesis of 4-(2-(2-(bromomethyl)-4-chlorophenoxy)ethyl)tetrahydro-2H-pyran

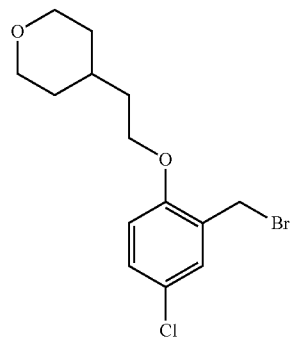 [SMILES: Clc1ccc(OCCC2CCOCC2)c(CBr)c1]

a) To a suspension of 180 mg (7.5 mmol) of NaH 60% in mineral oil in 5 mL of benzene under argon and cooled at 0° C. 1.5 mL (7.5 mmol) of triethyl phosphonoacetate was added dropwise (caution: gases evolve). The mixture was stirred at 0° C. for 20 min, then 250 mg (2.5 mmol) of dihydro-2H-pyran-4(3H)-one was added. Reaction was stirred at room temperature for 2 hours. Then it was quenched with a saturated solution of NH$_4$Cl, extracted with EtAcO and the combined organic layers washed with water and brine and dried over MgSO$_4$. The crude was purified by column chromatography over silica gel eluting with mixtures of hex/EtAcO 95:5 to 8:2. The desired compound ethyl 2-(dihydro-2H-pyran-4(3H)-ylidene)acetate was quantitatively obtained.

b) To a solution of 425 mg (2.5 mmol) of ethyl 2-(dihydro-2H-pyran-4(3H)-ylidene)acetate in 15 mL of MeOH, 133 mg of Pd on carbon 10% was added. Hydrogen atmosphere was set (1 atm, with a balloon) and the reaction was stirred at room temperature overnight. It was filtered through a pad of celite washing with abundant EtAcO. After removing the solvent the desired compound ethyl 2-(tetrahydro-2H-pyran-4-yl)acetate was obtained as a colorless oil (99%).

c) To a solution of 425 mg (2.5 mmol) of ethyl 2-(tetrahydro-2H-pyran-4-yl)acetate in 10 mL of dry THF cooled at 0° C. under argon, a 2.71 mL of a solution of LiAlH$_4$ 1M in THF was added. Bubbling was observed. It was stirred at room temperature for 30 min. Then it was quenched with wet EtAcO, dried with MgSO$_4$ and filtered through celite, washing with abundant EtAcO. After removing the solvent the desired compound, 2-(tetrahydro-2H-pyran-4-yl)ethanol, was obtained (300 mg, 93%).

d) To a solution of 300 mg (2.2 mmol) of 2-(tetrahydro-2H-pyran-4-yl)ethanol in 10 mL of DCM at 0° C. TEA (0.38 mL, 2.7 mmol) and methanesulfonyl chloride (0.19 mL, 2.5 mmol) were added. The mixture was allowed to warm to room temperature and stirred at this temperature overnight. The reaction was stirred with saturated NaHCO$_3$ for 15 min and the aqueous phase was extracted with DCM (×3). The combined organic layers were dried over MgSO$_4$, filtered and concentrated to quantitatively yield 2-(tetrahydro-2H-pyran-4-yl)ethyl methanesulfonate as a colorless oil.

e) To a solution of 465 mg (2.2 mmol) of 2-(tetrahydro-2H-pyran-4-yl)ethyl methanesulfonate in 11 mL of acetone LiBr (970 mg, 11.1 mmol) was added. The resulting mixture was stirred at 50° C. for 5 hours. Then, it was allowed to cool to room temperature and the solvent was evaporated. Water was added and the mixture was extracted with DCM (×3). The combined extracts were dried over MgSO$_4$, filtered and the solvent removed. The crude was purified by column chromatography over silica gel eluting with mixtures hexane/EtAcO. 4-(2-bromoethyl)tetrahydro-2H-pyran was obtained as a colorless oil (200 mg, 46%).

f) To a solution of 5-chloro-2-hydroxybenzaldehyde 162 mg (1.0 mmol) in DMF (2 mL), 172 mg of K$_2$CO$_3$ (1.2 mmol) and 4-(2-bromoethyl)tetrahydro-2H-pyran (200 mg, 1.0 mmol) were added. Reaction was stirred at 40° C. overnight. Then, it was allowed to cool to room temperature. Water was added and a white precipitated appeared. The mixture was extracted with EtAcO (×3), and the organic phases combined and washed with a 10% solution of NaCl in water. It was dried with anhydrous Na$_2$SO$_4$, filtered and the solvent evaporated to obtain 5-chloro-2-(2-(tetrahydro-2H-pyran-4-yl)ethoxy)benzaldehyde (220 mg, 80%).

g) To a suspension of 220 mg of 5-chloro-2-(2-(tetrahydro-2H-pyran-4-yl)ethoxy)benzaldehyde in 4 mL of absolute ethanol cooled at 0° C. NaBH$_4$ (37 mg, 1.0 mmol) was added. After 15 minutes TLC showed no starting material left. Reaction was quenched with HCl 1M and extracted with EtAcO (×3), washed with water, dried over anhydrous MgSO$_4$ and filtered. (5-chloro-2-(2-(tetrahydro-2H-pyran-4-yl)ethoxy)phenyl)methanol was quantitatively obtained.

h) To a solution of (5-chloro-2-(2-(tetrahydro-2H-pyran-4-yl)ethoxy)phenyl)methanol (222 mg, 0.82 mmol) in 4 mL of DCM, cooled at 0° C. under argon, PBr$_3$ (77 μL, 0.82 mmol) was slowly added. The reaction was stirred at 0° C. for 1 h, then at room temperature overnight. It was quenched with a saturated solution of NaHCO$_3$, extracted with DCM and the combined organic extracts were washed with a saturated solution of NaCl, dried over anhydrous Na$_2$SO$_4$, filtered and the solvent evaporated. 4-(2-(2-(bromomethyl)-4-chlorophenoxy)ethyl)tetrahydro-2H-pyran was obtained as a white solid (200 mg, 73%).

$^1$H NMR CDCl$_3$ (400 MHz) 7.32 (1H, d, J=3.4 MHz), 7.23 (1H, dd, J=11.7, 3.4 MHz), 6.79 (1H, d, J=11.7 MHz), 4.49 (2H, s), 4.08 (2H, t, J=8.2 MHz), 3.98 (2H, dd, J=14.6, 5.0 MHz), 3.43 (2H, td, J=14.6, 2.5 MHz), 1.94-1.31 (7H, m).

The following compounds were prepared using the same procedure (steps f, g and h) as in 4-(2-(2-(bromomethyl)-4-chlorophenoxy)ethyl)tetrahydro-2H-pyrane.

| Intermediate compound | Compound name | Starting materials | NMR |
|---|---|---|---|
| 9a | 2-(bromomethyl)-4-chloro-1-((2-chlorobenzyl)oxy)benzene | 5-chloro-2-hydroxybenzaldehyde and 1-(bromomethyl)-2-chlorobenzene | $^1$H NMR (300 MHz, CDCl$_3$) δ 7.68-7.57 (m, 1H), 7.45-7.38 (m, 1H), 7.37-7.27 (m, 3H), 7.23 (dd, 1H), 6.85 (d, 1H), 5.24 (s, 2H), 4.56 (s, 2H). |
| 9b | 2-(bromomethyl)-1-((2-chlorobenzyl)oxy)-4-fluorobenzene | 5-fluoro-2-hydroxybenzaldehyde and 1-(bromomethyl)-2-chlorobenzene | $^1$H NMR (300 MHz, CDCl$_3$) δ 7.69-7.59 (m, 1H), 7.41 (dd, 1H), 7.34-7.27 (m, 2H), 7.10 (dd, 1H), 6.97 (ddd, 1H), 6.86 (dd, 1H), 5.22 (s, 2H), 4.58 (s, 2H). |
| 9c | 2-(bromomethyl)-4-fluoro-1-((2-fluorobenzyl)oxy)benzene | 5-fluoro-2-hydroxybenzaldehyde and 1-(bromomethyl)-2-fluorobenzene | $^1$H NMR (300 MHz, CDCl$_3$) δ 7.67-7.51 (m, 1H), 7.33 (tdd, 1H), 7.19 (td, 1H), 7.14-7.03 (m, 2H), 7.01-6.85 (m, 2H), 5.20 (s, 2H), 4.54 (s, 2H). |
| 9d | 2-(bromomethyl)-1-((2-chlorobenzyl)oxy)-4-methylbenzene | 2-hydroxy-5-methylbenzaldehyde and 1-(bromomethyl)-2-chlorobenzene | $^1$H NMR (300 MHz, CDCl$_3$) δ 7.71-7.62 (m, 1H), 7.40 (dd, 1H), 7.35-7.21 (m, 2H), 7.17 (d, 1H), 7.11-7.01 (m, 1H), 6.81 (d, 1H), 5.23 (s, 2H), 4.62 (s, 2H), 2.28 (s, 3H). |
| 9e | 2-(bromomethyl)-1-((2-fluorobenzyl)oxy)-4-methylbenzene | 2-hydroxy-5-methylbenzaldehyde and 1-(bromomethyl)-2-fluorobenzene | $^1$H NMR (300 MHz, CDCl$_3$) δ 7.62 (td, 1H), 7.30 (ddd, 1H), 7.23-7.03 (m, 4H), 6.85 (d, 1H), 5.20 (s, 2H), 4.58 (s, 2H), 2.28 (s, 3H). |
| 9f | 1-((2-(bromomethyl)phenoxy)methyl)-4-chloro-2-fluorobenzene | 2-hydroxybenzaldehyde and 1-(bromomethyl)-4-chloro-2-fluorobenzene | $^1$H NMR (300 MHz, CDCl$_3$) δ 7.58 (t, 1H), 7.36 (dd, 1H), 7.33-7.25 (m, 1H), 7.21-7.12 (m, 2H), 7.03-6.85 (m, 2H), 5.19 (s, 2H), 4.60 (s, 2H). |

| Intermediate compound | Compound name | Starting materials | NMR |
|---|---|---|---|
| 9g | 2-(bromomethyl)-4-chloro-1-((4-chlorobenzyl)oxy)benzene | 5-chloro-2-hydroxybenzaldehyde and 1-(bromomethyl)-4-chlorobenzene | $^1$H NMR (300 MHz, CDCl$_3$) δ 7.51-7.31 (m, 5H), 7.23 (dd, 1H), 6.83 (d, 1H), 5.12 (s, 2H), 4.53 (s, 2H). |
| 9h | 2-(bromomethyl)-4-fluoro-1-isobutoxybenzene | 5-fluoro-2-hydroxybenzaldehyde and 1-bromo-2-methylpropane | $^1$H NMR (300 MHz, CDCl$_3$) δ 7.06 (dd, 1H), 6.95 (ddd, 1H), 6.77 (dd, 1H), 4.52 (s, 2H), 3.76 (d, 2H), 2.14 (hept, 1H), 1.08 (d, 6H). |
| 9i | 2-(bromomethyl)-1-cyclobutoxy-4-fluorobenzene | 5-fluoro-2-hydroxybenzaldehyde and bromocyclobutane | $^1$H NMR (300 MHz, CDCl$_3$) δ 7.06 (dd, 1H), 6.92 (ddd, 1H), 6.65 (dd, 1H), 4.65 (p, 1H), 4.51 (s, 2H), 2.52-2.35 (m, 2H), 2.30-2.10 (m, 2H), 1.94-1.81 (m, 1H), 1.76-1.61 (m, 1H). |
| 9j | 2-(bromomethyl)-4-chloro-1-cyclobutoxybenzene | 5-chloro-2-hydroxybenzaldehyde and bromocyclobutane | $^1$H NMR (300 MHz, CDCl$_3$) δ 7.30 (d, 1H), 7.18 (dd, 1H), 6.64 (d, 1H), 4.67 (p, 1H), 4.49 (s, 2H), 2.57-2.36 (m, 2H), 2.27-2.14 (m, 2H), 2.01-1.82 (m, 1H), 1.78-1.62 (m, 1H). |

Intermediate Compound 10

Synthesis of sodium 1,2,3,4-tetrahydroquinoline-5-sulfonate a) Thionyl chloride (4.2 mL) was added dropwise over 30 min to water (25 mL), cooled to 0° C., maintaining the temperature of the mixture 0-7° C. The solution was allowed to warm to 18° C. over 17 h. CuCl (15 mg, 0.14 mmol) was added, and the resulting yellow-green solution was cooled to −3° C.

b) Concentrated hydrochloric acid (14 mL) was cooled to 0° C. for the portionwise addition of quinolin-5-amine (2 g, 13.9 mmol). This was allowed to warm slightly between additions. After complete addition and at −5° C. a solution of sodium nitrite (1.053 g, 15.3 mmol) in water (4 mL) was added dropwise over 45 min, maintaining the temperature of the reaction mixture between −5 to 0° C.

c) The slurry from step b, was cooled to −5° C. and added dropwise to the solution obtained from step a over 30 min, maintaining the temperature of the reaction mixture between −3 to 0° C. (the slurry from step b was maintained at −5° C. throughout the addition). When the addition was complete, the reaction mixture was agitated at 0° C. for 90 min. The solid precipitated was filtered, washed with water and dried under vacuum at 40° C. to give quinoline-5-sulfonyl chloride (1.5 g, 48% yield) as a red-orange solid.

$^1$H NMR (400 MHz, Chloroform-d) δ 9.18 (dt, J=8.7, 0.8 Hz, 1H), 9.12 (dd, J=4.3, 1.6 Hz, 1H), 8.57 (d, J=8.5 Hz, 1H), 8.45 (dd, J=7.6, 1.2 Hz, 1H), 7.89 (dd, J=8.5, 7.6 Hz, 1H), 7.75 (dd, J=8.8, 4.3 Hz, 1H).

d) Quinoline-5-sulfonyl chloride (500 mg, 2.2 mmol) was suspended in 10 mL of dioxane at RT. Sodium hydroxide (88 mg, 2.2 mmol) in 5 mL of water was added followed by the addition of 1 mg of DMAP. The progress of the reaction was followed by hplc-mass. After 3 h at 60° C. the solvents were removed under vacuum: The solid obtained was washed with cold EtAcO.

$^1$H NMR (400 MHz, DMSO-d6) δ 9.18 (dd, J=8.7, 1.7 Hz, 1H), 8.88 (dd, J=4.1, 1.8 Hz, 1H), 7.98 (2H), 7.68 (t, J=7.8 Hz, 1H), 7.54 (dd, J=8.6, 4.1 Hz, 1H).

e) 330 mg of quinoline-5-sulfonic acid (1.43 mmol) were suspended in MeOH (25 mL) and Pd/C 10% was added (200 mg). The mixture was hydrogenated (H$_2$ balloon) at RT. The progress of the reaction was followed by hplc-mass. After 4 hours the suspension was passed through a plug of Celite. The filtrate was evaporated and the product was obtained as colorless oil (330 mg, 98% yield).

$^1$H NMR (500 MHz, Deuterium Oxide) δ 7.31 (dd, J=7.8, 1.2 Hz, 1H), 7.14 (t, J=7.9 Hz, 1H), 6.86 (dd, J=8.1, 1.3 Hz, 1H), 3.26-3.20 (m, 2H), 3.10 (t, J=6.5 Hz, 2H), 1.98-1.90 (m, 2H).

Intermediate Compound 11

Synthesis of methyl 3-formyl-1H-indole-4-carboxylate

To a stirred solution of 573 mg (3.27 mmol) of methyl 1H-indole-4-carboxylate in 6 mL of anhydrous DMF under dry argon atmosphere, 0.9 mL (9.8 mmol) of phosphorus chloride oxide was added at 0° C. and the resulting mixture was stirred at room temperature for 1 h. Then, the reaction mixture was poured into cold saturated NaH$_2$CO$_3$ aqueous solution and stirred for 30 min. The resultant mixture was extracted with EtAcO (×3). The combined organic layer was dried over anhydrous Na$_2$SO$_4$ and filtered. Then, the filtrate was condensed under reduced pressure and purified by silica gel flash column chromatography to provide methyl 3-formyl-1H-indole-4-carboxylate as a white solid (400 mg, 60%).

$^1$H NMR (300 MHz, Chloroform-d) δ 10.49 (s, 1H), 9.93 (br s, 1H, NH), 8.05 (d, J=3.3 Hz, 1H), 7.83 (dd, J=7.5, 1.0 Hz, 1H), 7.64 (dd, J=8.2, 1.0 Hz, 1H), 7.31 (t, J=7.9 Hz, 1H), 4.00 (s, 3H).

Intermediate Compound 12

Synthesis of ethyl 3-formyl-1H-pyrrolo[2,3-b]pyridine-4-carboxylate a) Under inert atmosphere (glove box), in a stainless steel high pressure reactor with a capacity of 100 mL and equipped with a magnetic stirrer were placed 4-bromo-1H-pyrrolo[2,3-b]pyridine (1.03 g, 5.2 mmol), Bis(benzonitrile) palladium(II) chloride (21 mg, 0.05 mmol), dppf (87 mg, 0.16 mmol), degassed ethanol (45 mL) and triethylamine (876 µL, 6.3 mmol). The system was purged three times with CO and pressurized to 25 bar. The reactor was warmed to 130° C. and stirred at 600 rpm overnight. Then was cooled to RT and DCM was added. The organic phase was washed with water, dried with MgSO$_4$ and concentrated under reduced pressure. The crude was submitted to flash chromatography through silica gel eluting with Cyclohexane:

EtAcO (4:1 to 2:1) to obtain 700 mg (70% yield) of ethyl 1H-pyrrolo[2,3-b]pyridine-4-carboxylate as a slightly yellow solid.

$^1$H NMR (300 MHz, CDCl$_3$) δ 8.59 (s, 1H), 7.90 (dd, J=8.4, 4.8 Hz, 1H), 7.36 (t, J=2.8 Hz, 1H), 7.22 (dd, J=5.6, 3.3 Hz, 1H), 6.94 (dd, J=10.4, 8.4 Hz, 1H), 4.45 (q, J=7.1 Hz, 2H), 1.46 (t, J=7.1 Hz, 3H).

b) ethyl 1H-pyrrolo[2,3-b]pyridine-4-carboxylate (387 mg, 2.0 mmol) was suspended in 4 mL of AcOH 33%. HMTA (428 mg, 3.1 mmol) was added in one portion and the suspension was refluxed overnight. After 16 hours the mixture was cooled to RT and water was added. The reaction was filtrated and washed with water to give the desired product as a white solid.

$^1$H NMR (300 MHz, DMSO-d6) δ 13.06 (br s, 1H, NH), 10.09 (s, 1H), 8.55 (s, 1H), 8.47 (d, J=4.8 Hz, 1H), 7.48 (d, J=4.9 Hz, 1H), 4.40 (q, J=7.1 Hz, 2H), 1.30 (t, J=7.1 Hz, 3H).

Intermediate Compound 13

Synthesis of methyl 3-formyl-1H-indazole-4-carboxylate

Procedure according to WO 2011/140325

$^1$H NMR (300 MHz) CDCl$_3$ 10.81 (1H, s), 8.10 (1H, d, J=8.4 MHz), 8.10 (1H, d, J=7.2 MHz), 7.56 (1H, t, J=7.8 MHz).

Intermediate Compound 14

Synthesis of N-((1,2,3,4-tetrahydroquinolin-5-yl)sulfonyl)acetamide a) An aqueous solution of NH$_4$OH (45 mL of 30% w/v) was added to a cold (0° C.) solution of quinoline-5-sulfonyl chloride (1 g, 4.4 mmol) in dioxane (35 mL) and the reaction was allowed to proceed overnight at RT. Water was added and extracted twice with EtAcO and twice with DCM. The combined organic fractions were dried and the solvent was evaporated to afford quinoline-5-sulfonamide as a slightly brown solid/750 mg, 82% yield)

$^1$H NMR (400 MHz, Chloroform-d) δ 9.13-8.92 (m, 2H), 8.36 (d, J=7.9 Hz, 2H), 7.80 (t, J=7.9 Hz, 1H), 7.61 (dd, J=8.7, 4.1 Hz, 1H), 4.95 (s, 2H).

b) Acetic anhydride (1 mL, 10.1 mmol) and DMAP (123 mg, 1.01 mmol) were added to a suspension of quinoline-5-sulfonamide (700 mg, 3.36 mmol) in pyridine 2 mL and the reaction was allowed to proceed at RT with stirring for 6 h. HPLC-mass spectra showed complete conversion. EtAcO (150 mL) was added and this solution was washed twice with NH$_4$Cl sat (50 mL) and H$_2$O (2×50 mL). The organic fraction was dried (Mg$_2$SO$_4$) and the solvent was removed in vacuo to afford N-(quinolin-5-ylsulfonyl)acetamide as a slightly yellow solid. (350 mg, 42% yield)

$^1$H NMR (300 MHz, Chloroform-d) δ 9.12-8.96 (m, 2H), 8.53 (dd, J=7.5, 1.3 Hz, 1H), 8.43 (dt, J=8.4, 1.1 Hz, 1H), 7.86 (dd, J=8.5, 7.5 Hz, 1H), 7.61 (dd, J=8.8, 4.2 Hz, 1H), 2.05 (s, 3H).

c) 330 mg of N-(quinolin-5-ylsulfonyl)acetamide (1.32 mmol) were suspended in MeOH (25 mL) and Pd/C 10% was added (281 mg). The mixture was hydrogenated (H$_2$ balloon) at RT. The progress of the reaction was followed by hplc-mass.

3 h-complete conversion. The suspension was passed through a plug of Celite, and the solvent removed using a rotatory evaporator. (330 mg, 98% yield) Slightly brown foam.

$^1$H NMR (500 MHz, Chloroform-d) δ 7.39 (dd, J=7.9, 1.1 Hz, 1H), 7.08 (t, J=8.0 Hz, 1H), 6.69 (dd, J=8.1, 1.2 Hz, 1H), 3.36-3.26 (m, 2H), 3.10 (t, J=6.4 Hz, 2H), 2.11 (s, 3H), 2.01-1.92 (m, 2H).

Intermediate Compound 15

Synthesis of (1H-indol-7-yl)boronic acid

KH (62 mg, 1.53 mmol) was suspended in anhydrous THF (0.4 ml) under an argon atmosphere at 0° C. in a flask protected from light. 7-Bromoindole (300 mg, 1.53 mmol) in anhydrous THF (2.6 ml) was added and the mixture stirred for 15 min. After cooling to −78° C. a solution of tBuLi in pentane (3.1 mmol), previously cooled to −78° C., was added dropwise. The mixture was brought to rt and stirred for 15 min and re-cooled to −78° C. B(OMe)$_3$ (341 μl, 1.53 mmol) was added and stirring was continued for a further 3 h at rt. H$_2$O (5 ml) was added and the mixture was extracted with EtAcO (2×10 ml). The aqueous phase was acidified to pH 1 with 10% HCl and was re-extracted with EtAcO (3×10 ml). The combined organic extracts were dried over anhydrous MgSO$_4$ and filtered. The solvents were evaporated leaving the crude indolylboronic acid as a pale brown oil.

$^1$H NMR (400 MHz, Chloroform-d) δ 9.52 (s, 1H), 8.03 (dd, J=7.1, 1.2 Hz, 1H), 7.98-7.92 (m, 1H), 7.43 (dd, J=3.2, 2.2 Hz, 1H), 7.33 (dd, J=7.8, 7.0 Hz, 1H), 6.68 (dd, J=3.3, 2.0 Hz, 1H).

Intermediate Compound 16

Synthesis of methyl 3,4-dihydro-2H-benzo[b][1,4]oxazine-8-carboxylate

To a solution of methyl 2-hydroxy-3-nitrobenzoate (11.1 mmol, 2.18 g) in EtAcO (55 mL), 10% Pd/C was added. It was stirred at room temperature under H$_2$ atmosphere (1 atm) until consumption of starting material (TLC). It was filtered through Celite washing with more EtAcO. The solvent was removed under vacuum and the brownish solid was used without further purification.

b) To a solution of methyl 3-amino-2-hydroxybenzoate (11 mmol, 1.84 g) in dry DMF (55 mL), were added oven-dried K$_2$CO$_3$ (33 mmol, 4.56 g) and 1,2-dibromoethane (13.2 mmol, 1.14 mL). It was stirred at 120° C. until consumption of starting material. Then, it was cooled, quenched with water and extracted with EtAcO (×3). The organic phases were washed with brine (×2) and solvent was evaporated. The crude product was purified by column chromatography, eluting with cyclohexane/EtAcO 2:1, to yield methyl 3,4-dihydro-2H-benzo[b][1,4]oxazine-8-carboxylate as a brown oil (81%).

$^1$H NMR (400 MHz, CDCl$_3$) δ 7.15 (dd, 1H), 6.79-6.68 (m, 2H), 4.36-4.30 (m, 2H), 3.95 (s, 1H), 3.88 (s, 3H), 3.47-3.40 (m, 3H).

Intermediate Compound 17

Synthesis of ethyl 8-isobutoxy-1,2,3,4-tetrahydroquinoline-5-carboxylate a) To a solution of 5-bromohydroxyquinoline in DMF, K$_2$CO$_3$ was added giving a bright yellow solution. 2-Methylbromopropane was added dropwise and the mixture was stirred at 80° C. untill total consumption of the starting quinolone. Then it was cooled, quenched with water and extracted with EtAcO (×3); the organic phases were washed with brine (×2) and dried with MgSO$_4$. Solvent was removed and the crude product was purified by SiO$_2$ CombiFlash chromatography, eluting with a gradient of cyclohexane/EtAcO from 9:1 to 1:1. The pure, product was obtained as a yellowish solid (60% yield).

$^1$H NMR (400 MHz, Chloroform-d) δ 8.97 (dd, 1H), 8.48 (dd, 1H), 7.70 (d, 1H), 7.52 (dd, 1H), 6.93 (d, 1H), 3.98 (d, 2H), 2.39 (hept, 1H), 1.11 (d, 6H).

b) Under inert atm (glove box), in a stainless high pressure reactor equipped with a stir bar, were placed 5-bromo-8-isobutoxyquinoline, palladium catalyst, dppf, degassed TEA and degassed EtOH. The system was purged with CO (×3) and pressurized to 25 bar. The reactor was warmed to 130° C. and stirred at 600 rpm overnight. Then the system was cooled, depressurized and the mixture diluted with DCM. This organic phase was washed with water, dried with MgSO$_4$ and solvents were removed under vacuum. The crude product was purified by SiO$_2$ CombiFlash chromatography, eluting with a gradient of cyclohex/EtAcO from 9:1 to 1:1, yielding the pure product as a yellow oil (91%).

$^1$H NMR (300 MHz, Chloroform-d) δ 9.46 (dd, 1H), 8.98 (dd, 1H), 8.31 (d, 1H), 7.53 (dd, 1H), 7.03 (d, 1H), 4.44 (q, 2H), 4.06 (d, 2H), 2.42 (hept, 1H), 1.45 (t, 4H), 1.12 (d, 6H).

c) To a solution of ethyl 8-isobutoxyquinoline-5-carboxylate in acetic acid, sodium cyanoborohydride was added carefully in three portions, over 15 minutes at room temperature. After 2 h, there was no starting material left (TLC). The mixture was diluted with water, basified with NaOH 2M, extracted with DCM (×5), washed with brine and dried over MgSO$_4$. The crude product was purified by SiO$_2$ Combiflash chromatography, eluting with a gradient of cyclohex/EtAcO from 9:1 to 1:1. The pure product was obtained as colorless oil (60% yield).

$^1$H NMR (300 MHz, Chloroform-d) δ 7.27 (d, 2H), 6.59 (d, 1H), 4.38 (s, 1H), 4.29 (q, 3H), 3.78 (d, 2H), 3.44-3.25 (m, 2H), 3.12 (t, 2H), 2.13 (hept, 1H), 2.03-1.83 (m, 2H), 1.36 (t, 3H), 1.04 (d, 6H).

Intermediate Compound 18

Synthesis of (E)-methyl 3-(3-ethoxy-3-oxoprop-1-en-1-yl)-1H-indole-4-carboxylate To a suspension of NaH 60% in mineral oil (118 mg, 3.0 mmol) in 5 mL of benzene under argon and cooled at 0° C. triethyl phosphonoacetate (0.6 mL, 3.0 mmol) was added dropwise (caution: gases evolve). The mixture was stirred at 0° C. for 20 min, then dihydromethyl 3-formyl-1H-indole-4-carboxylate (200 mg, 1.0 mmol) was added as a solution in 5 mL of benzene. Reaction was stirred at room temperature for 2 hours. Then it was quenched with a saturated solution of NH$_4$Cl, extracted with EtAcO and the combined organic layers washed with water and brine and dried over MgSO$_4$. The crude was purified by column chromatography over silica gel eluting with mixtures of cyclohexane/EtAcO. (E)-methyl 3-(3-ethoxy-3-oxoprop-1-en-1-yl)-1H-indole-4-carboxylate was obtained (220 mg, 82%).

$^1$H NMR CDCl$_3$ (300 MHz) 8.99 (1H, bs), 8.42 (1H, d, J=15.8 MHz), 7:80 (1H, d, J=7.7 MHz), 7.68 (1H, d, J=2.7 MHz), 7.58 (1H, d, J=7.7 MHz), 7.27 (1H, t, J=7.7 MHz), 6.16 (1H, d, J=15.8 MHz), 4.28 (2H, q, J=7.1 MHz), 4.01 (3H, s), 1.35 (3H, t, J=7.1 MHz).

Intermediate Compound 19

Synthesis of 2-(bromomethyl)-4-chloro-1-(3-fluoro-2-methylpropoxy)benzene a) 3-hydroxy-2-methylpropyl 4-methylbenzenesulfonate p-TsCl (1.00 g, 5.25 mmol) was added to a solution of 2-methylpropane-1,3-diol (2.30 mL, 26.23 mmol) and TEA (1.50 mL, 10.50 mmol) in DCM (20 mL) and stirred at room temperature. After 4 h, the reaction mixture was diluted with DCM (40 mL) and washed with water (30 mL). The organic layer was dried over anhydrous Na$_2$SO$_4$ and filtered. After removal of the solvent, the residue was purified by column chromatography on silica gel (15→50% EtAcO/hexanes), affording 0.86 g of 3-hydroxy-2-methylpropyl 4-methylbenzenesulfonate [Rf=0.40 (40% EtAcO/hexanes), colorless oil, 67% yield].

LC-MS ESI+ m/z: 245 (M+1, 99%) (method 5).

b) 5-chloro-2-(3-hydroxy-2-methylpropoxy)benzaldehyde

Following the general procedure, the title compound was obtained in 46% yield (pale yellow oil) after stirring at 80° C. for 17 h, using 5-chloro-2-hydroxybenzaldehyde (2.27 g, 14.48 mmol), K$_2$CO$_3$ (2.00 g, 14.48 mmol) and 3-hydroxy-2-methylpropyl 4-methylbenzenesulfonate (2.95 g, 12.07 mmol) as starting materials.

LC-MS ESI+ m/z 229 (M+1, 92%) (method 5).

c) 3-(4-chloro-2-formylphenoxy)-2-methylpropyl trifluoromethanesulfonate

Tf$_2$O (1.67 mL, 6.12 mmol) was added dropwise to a solution of 5-chloro-2-(3-hydroxy-2-methylpropoxy)benzaldehyde (1.40 g, 6.12 mmol) and DIPEA (2.10 mL, 12.24 mmol) in DCM (20 mL) cooled at −78° C. After 15 min, the reaction mixture was diluted with DCM (20 mL) and washed with water (20 mL). The organic layer was dried over anhydrous Na$_2$SO$_4$ and filtered. After removal of the solvent, 2.90 g of 3-(4-chloro-2-formylphenoxy)-2-methylpropyl trifluoromethanesulfonate were obtained [Rf=0.60 (40% EtAcO/hexanes), brown solid, 100% yield], that were used without further purification.

d) 5-chloro-2-(3-fluoro-2-methylpropoxy)benzaldehyde

TBAF (9.18 mL of 1 M solution in THF, 9.18 mmol) was added dropwise to a solution of 3-(4-chloro-2-formylphenoxy)-2-methylpropyl trifluoromethanesulfonate (2.20 g, 6.12 mmol) in THF (20 mL) cooled at 0° C., and the mixture was allowed to reach room temperature. After 2 h, the solvent was removed by rotatory evaporation and the resulting residue was dissolved in EtAcO (40 mL) and washed with water (30 mL). The organic layer was dried over anhydrous Na$_2$SO$_4$ and filtered. After removal of the solvent, the residue was purified by column chromatography on silica gel (5→15% EtAcO/hexanes), affording 0.63 g of 5-chloro-2-(3-fluoro-2-methylpropoxy)benzaldehyde [Rf=0.70 (30% EtAcO/hexanes), pale yellow oil, 45% yield].

LC: purity 93% (method 5).

$^1$H-NMR (CDCl$_3$, 250 MHz, δ): 10.42 (s, 1H, CHO); 7.77 (d, J=2.9 Hz, 1H, ArH); 7.48 (dd, J=9.0, 2.9 Hz, 1H, ArH);

6.95 (d, J=9.0 Hz, 1H, ArH); 4.68-4.38 (m, 2H); 4.12-3.98 (m, 2H); 2.52-2.27 (m, 1H); 1.13 (dd, J=6.8, 1.0 Hz, 3H).

e) [5-chloro-2-(3-fluoro-2-methylpropoxy)phenyl]methanol

Following the general procedure described in intermediate compound 1, section b, the title compound was obtained in 73% yield (colorless oil), using 5-chloro-2-(3-fluoro-2-methylpropoxy)benzaldehyde (0.66 g, 2.86 mmol) and NaBH$_4$ (0.11 g, 2.86 mmol) as starting materials.
LC: purity 96% (method 5).
$^1$H-NMR (CDCl$_3$, 250 MHz, δ): 7.30 (d, J=2.8 Hz, 1H, ArH); 7.20 (dd, J=8.6, 2.8 Hz, 1H, ArH); 6.79 (d, J=8.6 Hz, 1H, ArH); 4.66 (s, 2H); 4.64-4.32 (m, 2H); 4.02-3.90 (m, 2H); 2.47-2.25 (m, 1H); 1.99 (br s, 1H, OH); 1.10 (d, J=7.8 Hz, 3H).

f) 2-(bromomethyl)-4-chloro-1-(3-fluoro-2-methylpropoxy)benzene

Following the general procedure described in intermediate compound 1, section c, the title compound was obtained in 98% yield (pale yellow oil), using [5-chloro-2-(3-fluoro-2-methylpropoxy)phenyl]methanol (0.48 g, 2.04 mmol) and PBr$_3$ (0.19 mL, 2.04 mmol) as starting materials.

Intermediate Compound 20

Synthesis of 2-(bromomethyl)-4-chloro-1-(2-fluoropropoxy)benzene a) 4-chloro-2-(1,3-dioxolan-2-yl)phenol A solution of 5-chloro-2-hydroxybenzaldehyde (5.00 g, 31.93 mmol), ethylene glycol (5.40 mL, 95.79 mmol) and p-TsOH (0.30 g, 1.60 mmol) in toluene (50 mL) was refluxed connected to a Dean-Stark apparatus. After 32 h, the reaction was allowed to reach room temperature, diluted with EtAcO (40 mL) and washed with water (2×30 mL). The organic layer was dried over anhydrous Na$_2$SO$_4$ and filtered. After removal of the solvent, the residue was purified by column chromatography on silica gel (5□10% EtAcO/hexanes), affording 3.40 g of 4-chloro-2-(1,3-dioxolan-2-yl)phenol [Rf=0.40 (20% EtAcO/hexanes), white solid, 53% yield].
$^1$H-NMR (CDCl$_3$, 250 MHz, δ): 7.72 (s, 1H, ArH); 7.25-7.17 (m, 2H, ArH+OH); 6.83 (d, J=7.7 Hz, 1H, ArH); 5.92 (s, 1H); 4.18-4.04 (m, 4H).

b) 1-[4-chloro-2-(1,3-dioxolan-2-yl)phenoxy]acetone

A mixture of 1-chloroacetone (0.29 mL, 3.59 mmol), K$_2$CO$_3$ (0.62 g, 4.49 mmol) and 4-chloro-2-(1,3-dioxolan-2-yl)phenol (0.60 g, 2.99 mmol) in DMF (15 mL) was stirred at room temperature for 2 h. The reaction mixture was poured over EtAcO (80 mL) and washed with water (2×30 mL); the organic layer was dried over anhydrous Na$_2$SO$_4$ and filtered. After removal of the solvent, the residue was purified by column chromatography on silica gel (40% EtAcO/hexanes), affording 0.69 g of 1-[4-chloro-2-(1,3-dioxolan-2-yl)phenoxy]acetone [Rf=0.25 (30% EtAcO/hexanes), pale yellow solid, 90% yield].
LC-MS ESI+ m/z: 257 (M+1, 98%) (method 5).
$^1$H-NMR (CDCl$_3$, 250 MHz, δ): 7.54 (d, J=2.7 Hz, 1H, ArH); 7.26 (dd, J=8.9, 2.7 Hz, 1H, ArH); 6.67 (d, J=8.9 Hz, 1H, ArH); 6.20 (s, 1H); 4.56 (s, 2H); 4.18-4.01 (m, 4H); 2.29 (s, 3H).

c) 1-[4-chloro-2-(1,3-dioxolan-2-yl)phenoxy]propan-2-ol

NaBH$_4$ (0.12 g, 3.20 mmol) was added in small portions to a solution of 1-[4-chloro-2-(1,3-dioxolan-2-yl)phenoxy]acetone (0.77 g, 2.99 mmol) in MeOH (15 mL) cooled at 0° C., observing gas evolution. After 10 min, the solvent was removed by rotatory evaporation and the resulting residue was dissolved in DCM (20 mL), acidified with HCl (aqueous solution 10%, 3 mL), and washed with water (20 mL). The organic layer was dried over anhydrous Na$_2$SO$_4$ and filtered. After removal of the solvent, the residue was purified by column chromatography on silica gel (30□45% EtAcO/hexanes), affording 0.53 g of 1-[4-chloro-2-(1,3-dioxolan-2-yl)phenoxy]propan-2-ol [Rf=0:33 (40% EtAcO/hexanes), colorless oil, 69% yield].
LC-MS ESI+ m/z: 259 (M+1, 93%) (method 5).

d) 2-[5-chloro-2-(2-fluoropropoxy)phenyl]-1,3-dioxolane

DAST (0.50 g, 3.07 mmol) was added dropwise to a solution of 1-[4-chloro-2-(1,3-dioxolan-2-yl)phenoxy]propan-2-ol (0.53 g, 2.05 mmol) in DCM (15 mL) cooled at 0° C., and the mixture was allowed to reach room temperature. After 1.5 h, the reaction mixture was diluted with DCM (15 mL) and washed with water (20 mL). The organic layer was dried over anhydrous Na$_2$SO$_4$ and filtered. After removal of the solvent, the residue was purified by column chromatography on silica gel (8→15% EtAcO/hexanes), affording 0.30 g of 2-[5-chloro-2-(2-fluoropropoxy)phenyl]-1,3-dioxolane [Rf=0.50 (20% EtAcO/hexanes), pale yellow oil, 58% yield].
LC-MS ESI+ m/z 261 (M+1, 97%) (method 5).

e) 5-chloro-2-(2-fluoropropoxy)benzaldehyde

PPTS (48 mg, 0.19 mmol) was added to a suspension of 2-[5-chloro-2-(2-fluoropropoxy)phenyl]-1,3-dioxolane (0.50 g, 1.92 mmol) in a mixture of water (1 mL) and acetone (5 mL), and the reaction was heated at reflux for 6 h. The reaction was allowed to reach room temperature and the volatiles were removed by rotatory evaporation; the resulting residue was dissolved in EtAcO (30 mL) and washed with water (30 mL) and NaOH (10%, 10 mL). The organic layer was dried over anhydrous Na$_2$SO$_4$ and filtered. After removal of the solvent, 0.42 g of 5-chloro-2-(2-fluoropropoxy)benzaldehyde were obtained [Rf=0.50 (20% EtAcO/hexanes), pale yellow oil, 100% yield, crude], that were used without further purification.
$^1$H-NMR (CDCl$_3$, 250 MHz, δ): 10.45 (s, 1H, CHO); 7.80 (d, J=2.7 Hz, 1H, ArH); 7.49 (dd, J=9.1, 2.7 Hz, 1H, ArH); 6.93 (d, J=9.1 Hz, 1H, ArH); 5.23-4.90 (m, 1H); 4.22-4.10 (m, 2H); 1.56-1.42 (m, 3H).

f) [5-chloro-2-(2-fluoropropoxy)phenyl]methanol

Following the general procedure described in intermediate compound 1, section b, the title compound was obtained in 71% yield (colorless oil), using 5-chloro-2-(2-fluoropropoxy)benzaldehyde (0.60 g, 2.77 mmol) and NaBH$_4$ (0.10 g, 2.77 mmol) as starting materials.

¹H-NMR (CDCl₃, 250 MHz, δ): 7.31 (d, J=2.8 Hz, 1H, ArH); 7.21 (dd, J=8.6, 2.8 Hz, 1H, ArH); 6.77 (d, J=8.6 Hz, 1H, ArH); 5.18-4.86 (m, 1H); 4.68 (dd, J=15.5, 13.5 Hz, 2H); 4.15-3.99 (m, 2H); 1.92 (br s, 1H, OH); 1.46 (dd, J=23.5, 6.5 Hz, 3H).

g) 2-(bromomethyl)-4-chloro-1-(2-fluoropropoxy)benzene

Following the general procedure described in intermediate compound 1, section c, the title compound was obtained in 91% yield (pale yellow oil), using [5-chloro-2-(2-fluoropropoxy)phenyl]methanol (0.46 g, 2.09 mmol) and PBr₃ (0.20 mL, 2.09 mmol) as starting materials.

Intermediate Compound 21

Synthesis of 5-chloro-2-(1,2-dimethylpropoxy)benzaldehyde a) N-(tert-butyl)-N-{(1E)-[5-chloro-2-(1,2-dimethylpropoxy)phenyl]methylene}-amine 3-methylbutan-2-ol (0.41 mL, 3.84 mmol) was added to a suspension of NaH [0.15 g (60% oil dispersion) 3.84 mmol] in 1,4-dioxane (10 mL) and heated at 50° C. After 30 min, a solution of N-(tert-butyl)-N-[(1E)-(5-chloro-2-fluorophenyl)methylene]amine (0.41 g, 1.92 mmol) in 6 mL of 1,4-dioxane was transferred via canula and the resulting mixture was heated at 70° C. for 15 h. The volatiles were removed by rotatory evaporation; the resulting residue was dissolved in EtAcO (40 mL) and washed with water (30 mL). The organic layer was dried over anhydrous Na₂SO₄ and filtered. After removal of the solvent, 0.60 g of N-(tert-butyl)-N-{(1E)-[5-chloro-2-(1,2-dimethylpropoxy)phenyl]methylene}amine were obtained [Rf=0.60 (10% EtAcO/hexanes), pale yellow oil, 100% yield, crude], that were used without further purification.

N-(tert-butyl)-N-[(1E)-(5-chloro-2-fluorophenyl)methylene]amine was prepared following the method described in: Larock, R. C. et al *J. Org. Chem.* 2001, 66, 8042-8051.

b) 5-chloro-2-(1,2-dimethylpropoxy)benzaldehyde

The crude N-(tert-butyl)-N-{(1E)-[5-chloro-2-(1,2-dimethylpropoxy)phenyl]methylene}amine, obtained in the previous step (1.92 mmol), was dissolved in a mixture of THF (6 mL), water (6 mL) and AcOH (1 mL) and stirred at room temperature. After 1 h, THF was removed by rotatory evaporation and the resulting residue was diluted with EtAcO (30 mL) and washed with water (20 mL) and NaOH (aqueous solution 10%, 5 mL). The organic layer was dried over anhydrous Na₂SO₄ and filtered. After removal of the solvent, 0.50 g of 5-chloro-2-(1,2-dimethylpropoxy)benzaldehyde were obtained [Rf=0.60 (10% EtAcO/hexanes), pale yellow oil, 100% yield, crude], that were used without further purification.

¹H-NMR (CDCl₃, 250 MHz, δ): 10.44 (s, 1H, CHO); 7.77 (d, J=2.8 Hz, 1H, ArH); 7.45 (dd, J=9.0, 2.8 Hz, 1H, ArH); 6.93 (d, J=9.0 Hz, 1H, ArH); 4.34-4.23 (m, 1H); 2.08-1.92 (m, 1H); 1.29 (d, J=6.2 Hz, 3H); 1.02 (d, J=6.9 Hz, 3H); 0.99 (d, 6.6 Hz, 3H).

c) [5-chloro-2-(1,2-dimethylpropoxy)phenyl]methanol

Following the general procedure described in intermediate compound 1, section b, the title compound was obtained in 77% yield (colorless oil), using 5-chloro-2-(1,2-dimethylpropoxy)benzaldehyde (0.44 g, 1.92 mmol) and NaBH₄ (0.04 g, 0.96 mmol) as starting materials.

LC: purity 99% (method 5).
¹H-NMR (CDCl₃, 250 MHz, δ): 7.27 (d, J=2.7 Hz, 1H, ArH); 7.18 (dd, J=8.8, 2.7 Hz, 1H, ArH); 6.78 (d, J=8.8 Hz, 1H, ArH); 4.72-4.57 (m, 2H); 4.27-4.16 (m, 1H); 2.30 (t, J=6.5 Hz, 1H, OH); 2.03-1.88 (m, 1H); 1.24 (d, J=6.0 Hz, 3H); 1.03-0.95 (m, 6H).

d) 2-(bromomethyl)-4-chloro-1-(1,2-dimethylpropoxy)benzene

Following the general procedure described in intermediate compound 1, section c, the title compound was obtained in 95% yield (colorless oil), using [5-chloro-2-(1,2-dimethylpropoxy)phenyl]methanol (0.33 g, 1.44 mmol) and PBr₃ (0.07 mL, 0.72 mmol) as starting materials.

Intermediate Compound 22

Synthesis of 2-(bromomethyl)-4-chloro-1-(cyclobutyloxy)benzene a) N-(tert-butyl)-N-{(1E)-[5-chloro-2-(cyclobutyloxy)phenyl]methylene}amine Cyclobutanol (0.20 mL, 2.55 mmol) was added to a stirred suspension of NaH [0.10 g (60% oil dispersion), 2.55 mmol] in 1,4-dioxane (8 mL) observing abundant gas evolution while a viscous solution was formed. After 20 min, a solution of N-(tert-butyl)-N-[(1E)-(5-chloro-2-fluorophenyl)methylene]amine (0.42 g, 1.96 mmol) in 4 mL of 1,4-dioxane was transferred via canula and the resulting mixture was heated at 70° C. After 15 h, the volatiles were removed by rotatory evaporation, rendering a sticky yellow solid, N-(tert-butyl)-N-{(1E)-[5-chloro-2-(cyclobutyloxy)phenyl]methylene}amine, that was used without further purification.

b) 5-chloro-2-(cyclobutyloxy)benzaldehyde

The crude N-(tert-butyl)-N-{(1E)-[5-chloro-2-(cyclobutyloxy)phenyl]methylene}amine obtained in the previous step (1.96 mmol) was dissolved in a mixture of THF (6 mL) and HCl (aqueous solution 10%, 5 mL) and stirred at room temperature. After 1 h, THF was removed by rotatory evaporation and the resulting residue was diluted with EtAcO (30 mL) and washed with NaOH (aqueous solution 10%, 10 mL). The organic layer was dried over anhydrous Na₂SO₄ and filtered. After removal of the solvent, the residue was purified by column chromatography on silica gel (5% EtAcO/hexanes), affording 0.16 g of 5-chloro-2-(cyclobutyloxy)benzaldehyde [Rf=0.40 (10% EtAcO/hexanes), colorless oil, 39% yield (2 steps)].

LC: purity 93% (method 5).
¹H-NMR (CDCl₃, 250 MHz, δ): 10.42 (s, 1H, CHO); 7.77 (d, J=2.8 Hz, 1H, ArH); 7.43 (dd, J=8.7, 2.8 Hz, 1H, ArH); 6.77 (d, J=8.7 Hz, 1H, ArH); 4.79-4.65 (m, 1H); 2.58-2.42 (m, 2H); 2.34-2.14 (m, 2H); 2.00-1.66 (m, 2H).

c) [5-chloro-2-(cyclobutyloxy)phenyl]methanol

Following the general procedure described in intermediate compound 1, section b, the title compound was obtained in 92% yield (white solid), using 5-chloro-2-(cyclobutyloxy) benzaldehyde (0.26 g, 1.23 mmol) and NaBH$_4$ (0.05 g, 1.23 mmol) as starting materials.

LC: purity 86% (method 5).

$^1$H-NMR (CDCl$_3$, 250 MHz, δ): 7.27 (d, J=2.8 Hz, 1H, ArH); 7.16 (dd, J=8.8, 2.8 Hz, 1H, ArH); 6.63 (d, J=8.8 Hz, 1H, ArH); 4.77-4.57 (m, 3H); 2.54-2.38 (m, 2H); 2.26-2.06 (m, 2H); 1.96-1.61 (m, 2H+OH).

d) 2-(bromomethyl)-4-chloro-1-(cyclobutyloxy) benzene

Following the general procedure described in intermediate compound 1, section c, the title compound was obtained in 90% yield (colorless oil), using [5-chloro-2-(cyclobutyloxy)phenyl]methanol (0.47 g, 2.21 mmol) and PBr$_3$ (0.10 mL, 1.10 mmol) as starting materials.

Intermediate Compound 23

Synthesis of 2-(bromomethyl)-4-chloro-1-[(2-methylprop-2-enyl)oxy]benzene

Following the general procedure described in intermediate compound 1, section a, the title compound was obtained in 81% yield (pale yellow oil) after stirring at room temperature for 1 h, using 5-chloro-2-hydroxybenzaldehyde (1.00 g, 6.38 mmol), NaH [0.28 g (60% oil dispersion), 7.03 mmol] and 3-bromo-2-methylprop-1-ene (0.86 g, 6.38 mmol) as starting materials.

LC-MS ESI+ m/z: 211 (M+1, 90%) (method 5).

b) {5-chloro-2-[(2-methylprop-2-enyl)oxy]phenyl}methanol

Following the general procedure described in intermediate compound 1, section b, the title compound was obtained in 50% yield (yellow oil), using 5-chloro-2-[(2-methylprop-2-enyl)oxy]benzaldehyde (0.54 g, 2.56 mmol) and NaBH$_4$ (0.05 g, 1.28 mmol) as starting materials.

LC-MS ESI– m/z: 181 (M−1, 99%) (method 5).

$^1$H-NMR (CDCl$_3$, 250 MHz, δ): 7.30 (d, J=2.8 Hz, 1H, ArH); 7.19 (dd, J=8.8, 2.8 Hz, 1H, ArH); 6.78 (d, J=8.8 Hz, 1H, ArH); 5.12-4.99 (m, 2H); 4.69 (d, J=6.3 Hz, 2H); 4.46 (s, 2H); 2.23 (t, J=6.3 Hz, 1H, OH); 1.83 (s, 3H).

c) 2-(bromomethyl)-4-chloro-1-[(2-methylprop-2-enyl)oxy]benzene

Following the general procedure described in intermediate compound 1, section c, the title compound was obtained in 81% yield (pale yellow oil), using {5-chloro-2-[(2-methylprop-2-enyl)oxy]phenyl}methanol (0.26 g, 1.23 mmol) and PBr$_3$ (0.12 mL, 1.23 mmol) as starting materials.

Intermediate Compound 24

Synthesis of 2-(bromomethyl)-4-chloro-1-{[2-(fluoromethyl)prop-2-enyl]oxy}benzene a) 5-chloro-2-{[2-(chloromethyl)prop-2-enyl]oxy}benzaldehyde Following the general procedure described in intermediate compound 1, section a, the title compound was obtained in 24% yield (white solid) after stirring at room temperature for 20 h, using 5-chloro-2-hydroxybenzaldehyde (0.50 g, 3.19 mmol), K$_2$CO$_3$ (0.53 g, 3.83 mmol) and 3-chloro-2-(chloromethyl)prop-1-ene (0.44 mL, 3.83 mmol) as starting materials. It was purified by column chromatography on silica gel (10→30% EtAcO/hexanes), Rf=0.40 (10% EtAcO/hexanes).

LC: purity 99% (method 5).

$^1$H-NMR (CDCl$_3$, 250 MHz, δ): 10.44 (s, 1H, CHO); 7.79 (d, J=2.7 Hz, 1H, ArH); 7.48 (dd, J=8.8, 2.7 Hz, 1H, ArH); 6.98 (d, J=8.8 Hz, 1H, ArH); 5.47-5.44 (m, 1H); 5.42-5.38 (m, 1H); 4.74 (br s, 2H); 4.20 (br s, 2H).

b) 5-chloro-2-{[2-(iodomethyl)prop-2-enyl]oxy}benzaldehyde

A solution of NaI (0.14 g, 0.98 mmol) and 5-chloro-2-{[2-(chloromethyl)prop-2-enyl]oxy}benzaldehyde (0.16 g, 0.65 mmol) was stirred at room temperature for 14 h. The volatiles were removed by rotatory evaporation; the resulting residue was dissolved in EtAcO (25 mL) and washed with water (10 mL). The organic layer was dried over anhydrous Na$_2$SO$_4$ and filtered. After removal of the solvent, 0.22 g of 5-chloro-2-{[2-(iodomethyl)prop-2-enyl]oxy}benzaldehyde were obtained [Rf=0.40 (10% EtAcO/hexanes), pale yellow oil, 100% yield, crude], that were used without further purification.

$^1$H-NMR (CDCl$_3$, 250 MHz, δ): 10.45 (s, 1H, CHO); 7.81 (d, J=2.8 Hz, 1H, ArH); 7.50 (dd, J=9.0, 2.8 Hz, 1H, ArH); 7.00 (d, J=9.0 Hz, 1H, ArH); 5.56-5.53 (m, 1H); 5.35-5.32 (m, 1H); 4.81 (br s, 2H); 4.03 (br s, 2H).

c) 5-chloro-2-{[2-(fluoromethyl)prop-2-enyl]oxy}benzaldehyde

TBAF (1.82 mL of 1 M solution in THF, 1.82 mmol) was added dropwise to a solution of 5-chloro-2-{[2-(iodomethyl)prop-2-enyl]oxy}benzaldehyde (0.21 g, 0.62 mmol) in THF (4 mL) and the mixture was stirred at room temperature. After 1 h, the reaction was diluted with EtAcO (30 mL) and washed with brine (20 mL). The organic layer was dried over anhydrous Na$_2$SO$_4$ and filtered. After removal of the solvent, the residue was purified by column chromatography on silica gel (8% EtAcO/hexanes), affording 0.03 g of 5-chloro-2-{[2-(fluoromethyl)prop-2-enyl]oxy}benzaldehyde [Rf=0.50 (10% EtAcO/hexanes), colorless oil, 21% yield (2 steps)].

$^1$H-NMR (CDCl$_3$, 250 MHz, δ): 10.43 (s, 1H, CHO); 7.79 (d, J=2.8 Hz, 1H, ArH); 7.48 (dd, J=9.1, 2.8 Hz, 1H, ArH); 6.96 (d, J=9.1 Hz, 1H, ArH); 5.46-5.42 (m, 2H); 4.99 (d, J=57.3 Hz, 2H); 4.71 (br s, 2H).

d) (5-chloro-2-{[2-(fluoromethyl)prop-2-enyl]oxy}phenyl)methanol

Following the general procedure described in intermediate compound 1, section b, the title compound was obtained in 56% yield (colorless oil), using 5-chloro-2-{[2-(fluoromethyl)prop-2-enyl]oxy}benzaldehyde (0.36 g, 1.56 mmol) and NaBH$_4$ (0.03 g, 0.78 mmol) as starting materials.

$^1$H-NMR (CDCl$_3$, 250 MHz, □): 7.32 (d, J=2.8 Hz, 1H, ArH); 7.20 (dd, J=8.5, 2.8 Hz, 1H, ArH); 6.80 (d, J=8.5 Hz, 1H, ArH); 5.42-5.38 (m, 2H); 4.97 (d, J=46.8 Hz, 2H); 4.68 (s, 2H); 4.63 (s, 2H).

e) 2-(bromomethyl)-4-chloro-1-{[2-(fluoromethyl)prop-2-enyl]oxy}benzene

Following the general procedure described in intermediate compound 1, section c, the title compound was obtained in 83% yield (pale yellow oil), using (5-chloro-2-{[2-(fluoromethyl)prop-2-enyl]oxy}phenyl)methanol (0.20 g, 0.85 mmol) and PBr₃ (0.08 mL, 0.85 mmol) as starting materials.

Intermediate Compound 25

Synthesis of (3-methyloxetan-3-yl)methyl trifluoromethanesulfonate

To a solution of (3-methyloxetan-3-yl)methanol (0.58 ml, 5.87 mmol) and TEA (1.63 ml, 11.75 mmol) in DCM (29 ml), trifluoromethanesulfonic anhydride (0.98 ml, 5.87 mmol) was added at 0° C. The reaction mixture was stirred at 0° C. for 1 h and then at room temperature for 1 h. It was cooled and saturated NaHCO₃ aqueous solution was added. The aqueous layer was extracted with EtAcO (×3). The combined organic layers were washed with brine dried (MgSO4) filtered and concentrated. After removal of the solvent, 1.20 g of the desired compound was obtained (87% yield, crude), that were used without further purification.

¹H NMR (300 MHz, DMSO-d6) δ: 4.48-4.13 (m, 2H); 3.58-3.02 (m, 4H); 1.17 (s, 3H).

The following compound was prepared using the same procedure as in intermediate compound 25:

| Intermediate compound | Compound name | Starting materials | NMR |
|---|---|---|---|
| 25a | (3-ethyloxetan-3-yl)methyl trifluoromethanesulfonate | (3-methyloxetan-3-yl)ethanol | ¹H NMR (300 MHz, DMSO-d6) δ: 4.44-4.25 (m, 2H); 3.52-2.99 (m, 4H); 1.17 (t, J = 7.1 Hz, 3H); 0.98-0.71 (m, 2H). |

Intermediate Compound 26

Synthesis of 3-{5-chloro-2-[(4-chloro-2-fluorobenzyl)oxy]benzyl}-1,2,3-oxathiazolidine 2,2-dioxide a) 2-({5-chloro-2-[(4-chloro-2-fluorobenzyl)oxy]benzyl}amino)ethanol 2-aminoethanol (5.98 mL, 98.9 mmol) was added dropwise to a solution of 2-(bromomethyl)-4-chloro-1-[(4-chloro-2-fluorobenzyl)oxy]benzene (4.50 g, 12.4 mmol) in ACN (50 mL) cooled at 0° C. The reaction was allowed to reach room temperature, while a white precipitate appeared. After 15 h, the volatiles were removed by rotatory evaporation. The residue was dissolved in EtAcO (100 mL) and washed with brine (100 mL) and water (50 mL); the organic layer was dried over anhydrous Na₂SO₄ and filtered. After removal of the solvent, 3.50 g of 2-({5-chloro-2-[(4-chloro-2-fluorobenzyl)oxy]benzyl}amino)ethanol were obtained [Rf=0.15 (5% MeOH/DCM), white solid, 82% yield], that were used without further purification.

LC-MS ESI+ m/z 344 (M+1, 86%) (method 5).

b) 3-{5-chloro-2-[(4-chloro-2-fluorobenzyl)oxy]benzyl}-1,2,3-oxathiazolidine 2-oxide A solution of SOCl₂ (0.81 mL, 11.1 mmol) in 10 mL of DCM was added dropwise to a suspension of 2-({5-chloro-2-[(4-chloro-2-fluorobenzyl)oxy]benzyl}amino)ethanol (3.48 g, 10.1 mmol) and imidazole (2.75 g, 40.4 mmol) in TEA (3.1 mL, 22.2 mmol) and DCM (100 mL) cooled at 0° C. The suspension turned into a yellowish solution, and the reaction was allowed to reach room temperature. After 4 h, the mixture was poured over DCM (60 mL) and washed with brine (2×40 mL); the organic layer was dried over anhydrous Na₂SO₄ and filtered. After removal of the solvent, 4.1 g of 3-{5-chloro-2-[(4-chloro-2-fluorobenzyl)oxy]benzyl}-1,2,3-oxathiazolidine 2-oxide were obtained [Rf=0.40 (20% EtAcO/hexanes), yellow oil, quantitative yield], that were used without further purification.

c) 3-{5-chloro-2-[(4-chloro-2-fluorobenzyl)oxy]benzyl}-1,2,3-oxathiazolidine 2,2-dioxide To an ice-cold solution of crude 3-{5-chloro-2-[(4-chloro-2-fluorobenzyl)oxy]benzyl}-1,2,3-oxathiazolidine 2-oxide (10.1 mmol) in ACN (60 mL) was added RuCl₃.H₂O (52 mg, 0.10 mmol), followed by NaIO₄ (3.24 g, 15.2 mmol), and then water (40 mL). The reaction was allowed to reach room temperature over 2 h and stirred for additional 5 h. The mixture was diluted with Et₂O (60 mL) and the organic phase was separated. The aqueous phase was extracted with Et₂O (2×40 mL). The combined organic phase was washed with NaHCO₃ (saturated aqueous solution, 2 ×40 mL), dried over anhydrous Na₂SO₄ and filtered. After removal of the solvent, the residue was purified by column chromatography on silica gel (20☐30% EtAcO/hexanes), affording 1.31 g of 3-{5-chloro-2-[(4-chloro-2-fluorobenzyl)oxy]benzyl}-1,2,3-oxathiazolidine 2,2-dioxide [Rf=0.30 (20% EtAcO/hexanes), white solid, 32% yield (3 steps)].

LC-MS ESI– m/z: 404 (M–1, 97%) (method 5).

¹H-NMR (CDCl₃, 250 MHz, δ): 7.51-7.10 (m, 5H, ArH); 6.92 (d, J=8.7 Hz, 1H, ArH); 5.10 (s, 2H); 4.56-4.48 (m, 2H); 4.26 (s, 2H); 3.52-3.43 (m, 2H).

The following compounds were prepared using the same procedure as in intermediate compound 26:

| Intermediate compound | Compound name | Starting materials | NMR |
|---|---|---|---|
| 26a | 3-{5-chloro-2-[(2,4-difluorobenzyl)oxy]benzyl}-1,2,3-oxathiazolidine 2,2-dioxide | 2-(bromomethyl)-4-chloro-1-[(2,4-difluorobenzyl)oxy]benzene | * |
| 26b | 3-{5-chloro-2-[(4-chlorobenzyl)oxy]benzyl}-1,2,3-oxathiazolidine 2,2-dioxide | 2-(bromomethyl)-4-chloro-1-[(4-chlorobenzyl)oxy]benzene | ¹H-NMR (CDCl₃, 250 MHz, δ): 7.40-7.32 (m, 5H, ArH); 7.25 (dd, J = 8.6, 2.8 Hz, 1H, ArH); 6.86 (d, J = 8.6 Hz, 1H, ArH); 5.05 (s, 2H); 4.55-4.48 (m, 2H); 4.27 (s, 2H); 3.51-3.44 (m, 2H). |
| 26c | 3-{5-chloro-2-[(2-fluorobenzyl)oxy]benzyl}-1,2,3-oxathiazolidine 2,2-dioxide | 2-(bromomethyl)-4-chloro-1-[(2-fluorobenzyl)oxy]benzene | ** |

-continued

| Intermediate compound | Compound name | Starting materials | NMR |
|---|---|---|---|
| 26d | 3-{5-chloro-2-[(4-fluorobenzyl)oxy]benzyl}-1,2,3-oxathiazolidine 2,2-dioxide | 5-chloro-2-[(4-fluorobenzyl)oxy]benzaldehyde | ¹H-NMR (CDCl₃, 250 MHz, δ): 7.43-7.02 (m, 6H, ArH); 6.88 (d, J = 9.0 Hz, 1H, ArH); 5.04 (s, 2H); 4.55-4.47 (m, 2H); 4.26 (s, 2H); 3.51-3.43 (m, 2H). |
| 26e | 3-[5-chloro-2-(2-fluoro-2-methylpropoxy)benzyl]-1,2,3-oxathiazolidine 2,2-dioxide | 5-chloro-2-(2-fluoro-2-methylpropoxy)benzaldehyde | *** |
| 26f | 3-(5-chloro-2-isobutoxybenzyl)-1,2,3-oxathiazolidine 2,2-dioxide | 2-(bromomethyl)-4-chloro-1-isobutoxybenzene | ¹H-NMR (CDCl₃, 250 MHz, δ): 7.33 (d, J = 2.5 Hz, 1H, ArH); 7.23 (dd, J = 8.8, 2.5 Hz, 1H, ArH); 6.80 (d, J = 8.8 Hz, 1H, ArH); 4.57-4.49 (m, 2H); 4.26 (s, 2H); 3.72 (d, J = 6.4 Hz, 2H); 3.54-3.46 (m, 2H); 2.19-2.02 (m, 1H); 1.03 (d, J = 6.8 Hz, 6H). |

\* LC-MS ESI– m/z: 388 (M – 1, 97%) (method 5).
\*\* LC-MS ESI+ m/z: 372 (M + 1, 97%) (method 5).
\*\*\* LC-MS ESI+ m/z: 338 (M + 1, 98%) (method 5).

Intermediate Compound 27

Synthesis of 1-{5-chloro-2-[(2,4-difluorobenzyl)oxy]phenyl}methanamine

A suspension of 5-chloro-2-[(2,4-difluorobenzyl)oxy]benzaldehyde (3.20 g, 12.4 mmol), NH₂OH.HCl (1.29 g, 18.6 mmol) and NaAcO (1.63 g, 19.8 mmol) in EtOH (25 mL) was heated at reflux for 30 min. The reaction was allowed to reach room temperature and EtOH was removed by rotatory evaporation. The resulting residue was dissolved in DCM (60 mL) and washed with brine (2×50 mL); the organic layer was dried over anhydrous Na₂SO₄ and filtered. After removal of the solvent, 3.60 g of 5-chloro-2-[(2,4-difluorobenzyl)oxy]benzaldehyde oxime were obtained. This solid was suspended in 25 mL of AcOH and Zn dust (3.24 g, 49.6 mmol) was added in small portions over 2 h. After 3 h, the reaction was filtered through a pad of celite, washing with MeOH. The volatiles were removed by rotatory evaporation and the resulting residue was dissolved in DCM (100 mL) and washed with an aqueous saturated solution of NaHCO₃ (50 mL); the organic layer was dried over anhydrous Na₂SO₄ and filtered. After removal of the solvent, the residue was purified by column chromatography on silica gel (7% DCM/MeOH), affording 1.70 g of 1-{5-chloro-2-[(2,4-difluorobenzyl)oxy]phenyl}methanamine [Rf=0.25 (10% DCM/MeOH), white solid, 52% yield].

LC-MS ESI+ m/z: 284 (M+1, 97%) (method 5).

¹H-NMR (CDCl₃, 250 MHz, δ): 7.49-7.38 (m, 1H, ArH); 7.24 (d, J=2.7 Hz, 1H, ArH); 7.18 (dd, J=8.8, 2.7 Hz, 1H, ArH); 6.96-6.81 (m, 3H, ArH); 5.08 (s, 2H); 3.80 (s, 2H); 1.61 (br s, 2H, NH₂).

The following compounds were prepared using the same procedure as in intermediate compound 27:

| Intermediate compound | Compound name | Starting materials | NMR |
|---|---|---|---|
| 27a | 1-{5-chloro-2-[(4-chloro-2-fluorobenzyl)oxy]phenyl}methanamine | 5-chloro-2-[(4-chloro-2-fluorobenzyl)oxy]benzaldehyde | ¹H-NMR (CDCl₃, 250 MHz, δ): 7.45-7.36 (m, 1H, ArH); 7.25 (d, J = 2.7 Hz, 1H, ArH); 7.21-7.11 (m, 3H, ArH); 6.84 (d, J = 8.7 Hz, 1H, ArH); 5.09 (s, 2H); 3.81 (s, 2H); 1.75 (br s, 2H, NH₂). |
| 27b | 1-{2-[(4-chloro-2-fluorobenzyl)oxy]phenyl}methanamine | 2-[(4-chloro-2-fluorobenzyl)oxy]benzaldehyde | ¹H-NMR (CDCl₃, 250 MHz, δ): 7.50 (t, J = 8.1 Hz, 1H, ArH); 7.37-7.22 (m, 2H, ArH); 7.17-7.04 (m, 2H, ArH); 6.95-6.85 (m, 2H, ArH); 5.17 (s, 2H); 4.16 (br s, 2H). |
| 27c | 1-{2-1(2,4-difluorobenzyl)oxy]phenyl}methanamine | 2-[(2,4-difluorobenzyl)oxy]benzaldehyde | ¹H-NMR (CDCl₃, 250 MHz, δ): 7.52-7.41 (m, 1H, ArH); 7.29-7.20 (m, 2H, ArH); 7.00-6.81 (m, 4H, ArH); 5.11 (s, 2H); 3.84 (s, 2H). |

-continued

| Intermediate compound | Compound name | Starting materials | NMR |
|---|---|---|---|
| 27d | 1-[5-chloro-2-(2-fluoro-2-methylpropoxy)phenyl]methanamine | 5-chloro-2-(2-fluoro-2-methyl-propoxy)benzaldehyde | $^1$H-NMR (CDCl$_3$, 250 MHz, δ): 7.32 (d, J = 2.6 Hz, 1H, ArH); 7.23 (dd, J = 8.7, 2.6 Hz, 1H, ArH); 6.79 (d, J = 8.7 Hz, 1H, ArH); 3.99 (d, J = 18.4 Hz, 2H); 3.98 (s, 2H); 1.49 (d, J = 21.4 Hz, 6H). |
| 27e | 1-{2-[(2,4-difluorobenzyl)oxy]-5-fluorophenyl}methanamine | 2-[(2,4-difluorobenzyl)oxy]-5-fluorobenzaldehyde | $^1$H-NMR (CDCl$_3$, 250 MHz, δ): 7.50-7.39 (m, 1H, ArH); 7.01 (dd, J = 8.8, 2.7 Hz, 1H, ArH); 6.96-6.81 (m, 4H, ArH); 5.07 (s, 2H); 3.82 (s, 2H). |
| 27f | 1-{2-[(2,4-difluorobenzyl)oxy]-5-methylphenyl}methanamine | 2-[(2,4-difluorobenzyl)oxy]-5-methylbenzaldehyde | $^1$H-NMR (CDCl$_3$, 250 MHz, δ): 7.52-7.40 (m, 1H, ArH); 7.11-6.74 (m, 5H, ArH); 5.08 (s, 2H); 3.81 (s, 2H); 2.29 (s, 3H). |
| 27g | 1-{2-[(4-chloro-2-fluorobenzyl)oxy]-5-fluorophenyl}methanamine | 2-[(4-chloro-2-fluorobenzyl)oxy]-5-fluorobenzaldehyde | $^1$H-NMR (CDCl$_3$, 250 MHz, δ): 7.46-7.37 (m, 1H, ArH); 7.20-7.10 (m, 2H, ArH); 7.05-6.99 (m, 1H, ArH); 6.94-6.84 (m, 2H, ArH); 5.08 (s, 2H); 3.83 (s, 2H). |
| 27h | 1-{2-[(4-chloro-2-fluorobenzyl)oxy]-5-methylphenyl}methanamine | 2-[(4-chloro-2-fluorobenzyl)oxy]-5-methylbenzaldehyde | $^1$H-NMR (DMSO-d6, 250 MHz, δ): 7.59 (t, J = 8.2 Hz, 1H, ArH); 7.50 (dd, J = 9.8, 2.2 Hz, 1H, ArH); 7.33 (dd, J = 8.2, 2.2 Hz, 1H, ArH); 7.14 (d, J = 1.6 Hz, 1H, ArH); 7.02-6.90 (m, 2H, ArH); 5.10 (s, 2H); 3.64 (s, 2H); 3.22 (br s, 2H); 2.22 (s, 3H). |

The following examples illustrate the scope of the invention.

EXAMPLES OF COMPOUNDS OF GENERAL FORMULA I

The following HPLC methods for LC-MS spectra have been used:

Method 1: X-Bridge C18, 2.5 μm 4.6×50 mm column; temperature: 35° C.; rate 1.5 mL/min; eluent: A=NH$_4$HCO3 10 mM, B=ACN; gradient: 98% A 0.5 min, 98 to 5% A in 4 min, 5% A 2 min, 5 to 98% A 0.75 min, 98% A 1.75 min.

Method 2: SunFire C18 3.5 um, 2.1×100 mm column; temperature 35° C.; rate 0.3 mL/min; eluent: A: ACN:MeOH (1:1), B: Water, C: Ammonium acetate 20 mM pH 7; gradient 10:85:5 (A:B:C) 3 min to 95:5 (A:C) in 17 min and 10 min 95:5 (A:C). The sample is previously solved in methanol.

Method 3: XDB-C18 5 um, 4.6×150 mm column; temperature 25° C.; rate 1 mL/min; eluent: A: Water (0.05% TFA), B: AcN; gradient 5% B to 95:5 (A:B) in 7 min and 4 min 95:5 (A:B).

Method 4: Acquity UPLC® BEH C18 1.7 μm; 2.1×50 mm column; temperature 40° C.; rate 0.5 mL/min; eluent: A=NH$_4$HCO3 10 mM, B=ACN; gradient: 90% A 0.25 min, 90 to 10% A in 2.75 min, 10% A 0.75 min, 10 to 90% A 0.01 min, 90% A 1.24 min.

Method 5: SunFire C18 5 um, 2.1×50 mm, rate 0.3 mL/min; eluent A: AcCN:MeOH (1:1), B: Ammonium acetate 5 mM pH 7; gradient 10:90 (A:B) 2 min, 10:90 (A:B) to 95:5 (A:B) in 2 min, 95:5 (A:B) 5 min. The sample is previously solved in methanol.

Example 1

(E)-1-(5-chloro-2-(4-chloro-2-fluorostyryl)benzyl)-1H-indole-4-carboxylic acid a) To a suspension of NaH 60% in mineral oil (17 mg, 0.42 mmol) in dry DMF (1 mL) at 0° C. was added a solution of methyl 1H-indole-4-carboxylate (70 mg, 0.4 mmol) in DMF (1 mL) dropwise. After 30 min, a solution of (E)-2-(bromomethyl)-4-chloro-1-(4-chloro-2-fluorostyryl)benzene (173 mg, 0.48 mmol) in 1 mL of DMF was added dropwise.

When TLC analysis showed total conversion, crushed ice was added and the solution was extracted with EtAcO (×3). Combined organic extracts were washed with water, brine and dried over Na2SO4. Column chromatography on silica gel gave (E)-methyl 1-(4-chloro-2-(4-chloro-2-fluorostyryl)benzyl)-1H-indole-4-carboxylate as a white solid (155 mg, 85% yield).

$^1$H NMR (500 MHz, CDCl3) δ 7.95 (1H, dd), 7.57 (1H, d), 7.49 (1H, d), 7.31 (1H, dd), 7.26 (1H, d), 7.21 (1H, dd), 7.19-7.11 (3H, m), 7.09 (1H, dd), 7.06-6.97 (2H, m), 6.82 (1H, d), 3.99 (3H, s).

b) In a sealed tube, were placed the compound obtained above (135 mg, 0.3 mmol), THF (4 mL) and a solution of LiOH (21 mg, 0.9 mmol) in 1 mL of water. The mixture was stirred at 80° C. until TLC showed no starting material left. Then, it was cooled to room temperature and acidified with HCl 1M. The mixture was extracted with EtAcO (×3). The organic phases were washed with brine, dried over Na2SO4 and filtered. The solvent was removed in vacuo, and the residue was chromatographed using dichloromethane:MeOH (9.5:0.5) as eluent to give 110 mg (84% yield) of the title compound (example 1) as a white solid.

$^1$H NMR (400 MHz, DMSO) δ 7.87-7.71 (4H, m), 7.63 (1H, d), 7.55 (1H, d), 7.48 (1H, dd), 7.38 (1H, dd), 7.33 (1H, dd), 7.21 (2H, dd), 7.05 (1H, dd), 6.66 (1H, d), 5.75 (2H, s).

LC-MS: $t_R$=9.59 [M+H]$^+$=472 (method 3).

The following compounds were prepared using the same methodology as in example 1 using methyl 1H-indole-4-carboxylate and the compound II specified as starting materials.

| Example | Compound name | Starting compound II | LC-MS Method | $t_R$ (min) | m/z [M + H]$^+$ |
|---|---|---|---|---|---|
| 2 | 1-(2-(benzyloxy)-5-bromobenzyl)-1H-indole-4-carboxylic acid | 1-(benzyloxy)-4-bromo-2-(bromomethyl)benzene | 1 | 3.32 | 436 |
| 3 | 1-(2-(benzyloxy)-5-(trifluoromethyl)benzyl)-1H-indole-4-carboxylic acid | 1-(benzyloxy)-2-(bromomethyl)-4-(trifluoromethyl)benzene | 1 | 3.37 | 426 |
| 4 | 1-(5-bromo-2-((4-fluorobenzyl)oxy)benzyl)-1H-indole-4-carboxylic acid | 4-bromo-2-(bromomethyl)-1-(4-fluorobenzyloxy)benzene | 1 | 3.34 | 454 |
| 5 | 1-(5-chloro-2-((4-fluorobenzyl)oxy)benzyl)-1H-indole-4-carboxylic acid | 2-(bromomethyl)-4-chloro-1-(4-fluorobenzyloxy)benzene | 1 | 3.31 | 410 |
| 6 | 1-(2-((4-chloro-2-fluorobenzyl)oxy)-5-(trifluoromethyl)benzyl)-1H-indole-4-carboxylic acid | 2-(bromomethyl)-1-(4-chloro-2-fluorobenzyloxy)-4-(trifluoromethyl)benzene | 1 | 3.58 | 478 |
| 7 | 1-(5-chloro-2-(cyclopropylmethoxy)benzyl)-1H-indole-4-carboxylic acid | 2-(bromomethyl)-4-chloro-1-(cyclopropylmethoxy)benzene | 1 | 3.19 | 356 |
| 8 | 1-(5-bromo-2-(cyclopropylmethoxy)benzyl)-1H-indole-4-carboxylic acid | 4-bromo-2-(bromomethyl)-1-(cyclopropylmethoxy)benzene | 1 | 3.22 | 400 |
| 9 | 1-(5-bromo-2-((4-chloro-2-fluorobenzyl)oxy)benzyl)-1H-indole-4-carboxylic acid | 4-bromo-2-(bromomethyl)-1-(4-chloro-2-fluorobenzyloxy)benzene | 1 | 3.53 | 488 |
| 10 | 1-(4-chloro-2-isobutoxybenzyl)-1H-indole-4-carboxylic acid | 4-bromo-1-(bromomethyl)-2-((3,5-dichlorobenzyl)oxy)benzene | 1 | 3.43 | 358 |
| 11 | 1-(5-chloro-2-((4-(trifluoromethyl)benzyl)oxy)benzyl)-1H-indole-4-carboxylic acid | 2-(bromomethyl)-4-chloro-1-((4-(trifluoromethyl)benzyl)oxy)benzene | 1 | 3.56 | 460 |
| 12 | 1-(5-chloro-2-((2-chloro-4-fluorobenzyl)oxy)benzyl)-1H-indole-4-carboxylic acid | 2-(bromomethyl)-4-chloro-1-((2-chloro-4-fluorobenzyl)oxy)benzene | 1 | 3.53 | 444 |

-continued

|  |  |  | LC-MS | | |
|---|---|---|---|---|---|
| Example | Compound name | Starting compound II | Method | $t_R$ (min) | m/z [M + H]$^+$ |
| 13 | 1-(5-chloro-2-((2,3,5,6-tetrafluorobenzyl)oxy)benzyl)-1H-indole-4-carboxylic acid | 3-((2-(bromomethyl)-4-chlorophenoxy)methyl)-1,2,4,5-tetrafluorobenzene | 1 | 3.38 | 464 |
| 14 | 1-(2-((2,4-bis(trifluoromethyl)benzyl)oxy)-5-chlorobenzyl)-1H-indole-4-carboxylic acid | 1-((2,4-bis(trifluoromethyl)benzyl)oxy)-2-(bromomethyl)-4-chlorobenzene | 1 | 3.79 | 528 |
| 15 | 1-(5-chloro-2-((2,4,5-trifluorobenzyl)oxy)benzyl)-1H-indole-4-carboxylic acid | 1-(2-(bromomethyl)-4-chlorophenoxy)methyl)-2,4,5-trifluorobenzene | 1 | 3.40 | 446 |
| 16 | 1-(5-fluoro-2-((2,4,5-trifluorobenzyl)oxy)benzyl)-1H-indole-4-carboxylic acid | 1-((2-(bromomethyl)-4-fluorophenoxy)methyl)-2,4,5-trifluorobenzene | 1 | 3.29 | 430 |
| 17 | 1-(2-((3-bromo-4-fluorobenzyl)oxy)-5-chlorobenzyl)-1H-indole-4-carboxylic acid | 2-bromo-4-((2-(bromomethyl)-4-chlorophenoxy)methyl)-1-fluorobenzene | 1 | 3.50 | 488 |
| 18 | 1-(5-fluoro-2-((4-fluoro-2-(trifluoromethyl)benzyl)oxy)benzyl)-1H-indole-4-carboxylic acid | 2-(bromomethyl)-4-fluoro-1-((4-fluoro-2-(trifluoromethyl)benzyl)oxy)benzene | 1 | 3.47 | 462 |
| 19 | 1-(2-((2-chloro-4-fluorobenzyl)oxy)-5-fluorobenzyl)-1H-indole-4-carboxylic acid | 2-(bromomethyl)-1-((2-chloro-4-fluorobenzyl)oxy)-4-fluorobenzene | 1 | 3.41 | 428 |
| 20 | 1-(5-fluoro-2-((4-fluoro-2-(trifluoromethyl)benzyl)oxy)benzyl)-1H-indole-4-carboxylic acid | 2-(bromomethyl)-4-chloro-1-((4-fluoro-2-(trifluoromethyl)benzyl)oxy)benzene | 1 | 3.56 | 462 |
| 21 | 1-(5-chloro-2-((2,3,4-trifluorobenzyl)oxy)benzyl)-1H-indole-4-carboxylic acid | 1-((2-(bromomethyl)-4-chlorophenoxy)methyl)-2,3,4-trifluorobenzene | 1 | 3.43 | 446 |
| 22 | 1-(5-bromo-2-((2,3,4-trifluorobenzyl)oxy)benzyl)-1H-indole-4-carboxylic acid | 1-((4-bromo-2-(bromomethyl)phenoxy)methyl)-2,3,4-trifluorobenzene | 1 | 3.45 | 490 |
| 23 | 1-(5-chloro-2-(1-(2,4-difluorophenyl)ethoxy)benzyl)-1H-indole-4-carboxylic acid | 2-(bromomethyl)-4-chloro-1-(1-(2,4-difluorophenyl)ethoxy)benzene | 1 | 3.50 | 442 |
| 24 | 1-(2-((3-bromo-4-fluorobenzyl)oxy)-5-fluorobenzyl)-1H-indole-4-carboxylic acid | 2-bromo-4-((2-(bromomethyl)-4-fluorophenoxy)methyl)-1-fluorobenzene | 1 | 3.39 | 472 |
| 25 | 1-(5-bromo-2-((3-bromo-4-fluorobenzyl)oxy)benzyl)-1H-indole-4-carboxylic acid | 2-bromo-4-((4-bromo-2-(bromomethyl)phenoxy)methyl)-1-fluorobenzene | 1 | 2.94 | 532 |
| 26 | 1-(5-bromo-2-((4-fluoro-2-(trifluoromethyl)benzyl)oxy)benzyl)-1H-indole-4-carboxylic acid | 4-bromo-2-(bromomethyl)-1-((4-fluoro-2-(trifluoromethyl)benzyl)oxy)benzene | 1 | 3.03 | 522 |
| 27 | 1-(5-bromo-2-((2-chloro-4-fluorobenzyl)oxy)benzyl)-1H-indole-4-carboxylic acid | 4-bromo-2-(bromomethyl)-1-((2-chloro-4-fluorobenzyl)oxy)benzene | 1 | 2.96 | 488 |
| 28 | 1-(3-bromo-2-((4-bromo-2-fluorobenzyl)oxy)-5-chlorobenzyl)-1H-indole-4-carboxylic acid | 1-bromo-2-((4-bromo-2-fluorobenzyl)oxy)-3-(bromomethyl)-5-chlorobenzene | 1 | 3.20 | 566 |
| 29 | 1-(5-chloro-2-((2,5-difluorobenzyl)oxy)benzyl)-1H-indole-4-carboxylic acid | 2-(bromomethyl)-4-chloro-1-((2,5-difluorobenzyl)oxy)benzene | 1 | 3.35 | 428 |
| 30 | 1-(5-chloro-2-((2-chloro-5-fluorobenzyl)oxy)benzyl)-1H-indole-4-carboxylic acid | 2-(bromomethyl)-4-chloro-1-((2-chloro-5-fluorobenzyl)oxy)benzene | 1 | 3.52 | 440 |

-continued

| Example | Compound name | Starting compound II | LC-MS Method | $t_R$ (min) | m/z [M + H]⁺ |
|---|---|---|---|---|---|
| 31 | 1-(5-chloro-2-((2-chloro-4,5-difluorobenzyl)oxy)benzyl)-1H-indole-4-carboxylic acid | 2-(bromomethyl)-4-chloro-1-((2-chloro-4,5-difluorobenzyl)oxy)benzene | 1 | 3.64 | 462 |
| 32 | 1-(2-((2,5-difluorobenzyl)oxy)-5-fluorobenzyl)-1H-indole-4-carboxylic acid | 2-(bromomethyl)-4-fluoro-1-((2,5-difluorobenzyl)oxy)benzene | 1 | 3.23 | 412 |
| 33 | 1-(2-((2,6-difluorobenzyl)oxy)-5-fluorobenzyl)-1H-indole-4-carboxylic acid | 2-(bromomethyl)-4-fluoro-1-((2,6-difluorobenzyl)oxy)benzene | 1 | 3.21 | 412 |
| 34 | 1-(5-fluoro-2-((3,4,5-trifluorobenzyl)oxy)benzyl)-1H-indole-4-carboxylic acid | 2-(bromomethyl)-4-fluoro-1-((3,4,5-trifluorobenzyl)oxy)benzene | 1 | 3.34 | 430 |
| 35 | 1-(5-fluoro-2-((4-fluorobenzyl)oxy)benzyl)-1H-indole-4-carboxylic acid | 2-(bromomethyl)-4-fluoro-1-((4-fluorobenzyl)oxy)benzene | 1 | 3.21 | 394 |
| 36 | 1-(2-((2-chloro-4,5-difluorobenzyl)oxy)-5-fluorobenzyl)-1H-indole-4-carboxylic acid | 2-(bromomethyl)-4-fluoro-1-((2-chloro-4,5-difluorobenzyl)oxy)benzene | 1 | 3.43 | 446 |
| 37 | 1-(2-((2,6-difluorobenzyl)oxy)-5-(trifluoromethyl)benzyl)-1H-indole-4-carboxylic acid | 2-(bromomethyl)-4-trifluoromethyl-1-((2,6-difluorobenzyl)oxy)benzene | 1 | 3.40 | 462 |
| 38 | 1-(2-((2-chloro-5-fluorobenzyl)oxy)-5-fluorobenzyl)-1H-indole-4-carboxylic acid | 2-(bromomethyl)-4-fluoro-1-((2-chloro-5-fluorobenzyl)oxy)benzene | 1 | 3.39 | 428 |
| 39 | 1-(2-((2,5-difluorobenzyl)oxy)-5-(trifluoromethyl)benzyl)-1H-indole-4-carboxylic acid | 2-(bromomethyl)-4-trifluoromethyl-1-((2,5-difluorobenzyl)oxy)benzene | 1 | 3.42 | 462 |
| 40 | 1-(3-bromo-5-chloro-2-((2,6-difluorobenzyl)oxy)benzyl)-1H-indole-4-carboxylic acid | 2-(bromomethyl)-6-bromo-4-chloro-1-((2,6-difluorobenzyl)oxy)benzene | 1 | 2.94 | 506 |
| 41 | 1-(5-chloro-2-((3,5-difluorobenzyl)oxy)benzyl)-1H-indole-4-carboxylic acid | 2-(bromomethyl)-4-chloro-1-((3,5-difluorobenzyl)oxy)benzene | 1 | 3.77 | 428 |
| 42 | 1-(1-(5-chloro-2-((4-chloro-2-fluorobenzyl)oxy)phenyl)ethyl)-1H-indole-4-carboxylic acid | 2-(1-bromoethyl)-4-chloro-1-((4-chloro-2-fluorobenzyl)oxy)benzene | 1 | 4.03 | 458 |
| 43 | 1-(5-chloro-2-((2,4-difluorobenzyl)oxy)benzyl)-1H-indole-4-carboxylic acid | 2-(bromomethyl)-4-chloro-1-((2,4-difluorobenzyl)oxy)benzene | 1 | 3.36 | 428 |
| 44 | 1-(2-(benzyloxy)-5-chlorobenzyl)-1H-indole-4-carboxylic acid | 1-(benzyloxy)-2-(bromomethyl)-4-chlorobenzene | 1 | 3.32 | 392 |
| 45 | 1-(5-chloro-2-((2-fluorobenzyl)oxy)benzyl)-1H-indole-4-carboxylic acid | 2-(bromomethyl)-4-chloro-1-((2-fluorobenzyl)oxy)benzene | 1 | 3.35 | 410 |
| 46 | 1-(2-((4-bromo-2-fluorobenzyl)oxy)-5-chlorobenzyl)-1H-indole-4-carboxylic acid | 4-bromo-1-((2-(bromomethyl)-4-chlorophenoxy)methyl)-2-fluorobenzene | 1 | 3.58 | 488 |
| 47 | 1-(5-chloro-2-((2-fluoro-4-(trifluoromethyl)benzyl)oxy)benzyl)-1H-indole-4-carboxylic acid | 2-(bromomethyl)-4-chloro-1-((2-fluoro-4-(trifluoromethyl)benzyl)oxy)benzene | 1 | 3.61 | 478 |

-continued

| | | | | LC-MS | |
|---|---|---|---|---|---|
| Example | Compound name | Starting compound II | Method | $t_R$ (min) | m/z [M + H]$^+$ |
| 48 | 1-(5-chloro-2-((4-chloro-2-fluorobenzyl)oxy)benzyl)-1H-indole-4-carboxylic acid | 2-(bromomethyl)-4-chloro-1-((4-chloro-2-fluorobenzyl)oxy)benzene | 1 | 3.54 | 444 |
| 49 | 1-(2-((3-fluorobenzyl)oxy)-5-(trifluoromethyl)benzyl)-1H-indole-4-carboxylic acid | 2-(bromomethyl)-1-((3-fluorobenzyl)oxy)-4-(trifluoromethyl)benzene | 1 | 3.41 | 444 |
| 50 | 1-(2-((4-bromo-2-fluorobenzyl)oxy)-5-(trifluoromethyl)benzyl)-1H-indole-4-carboxylic acid | 4-bromo-1-((2-(bromomethyl)-4-(trifluoromethyl)phenoxy)methyl)-2-fluorobenzene | 1 | 3.64 | 522 |
| 51 | 1-(2-((2,4-difluorobenzyl)oxy)-5-(trifluoromethyl)benzyl)-1H-indole-4-carboxylic acid | 4-bromo-1-((2-(bromomethyl)-4-(trifluoromethyl)phenoxy)methyl)-2-fluorobenzene | 1 | 3.45 | 462 |
| 52 | 1-(2-((2-fluorobenzyl)oxy)-5-(trifluoromethyl)benzyl)-1H-indole-4-carboxylic acid | 2-(bromomethyl)-1-((2-fluorobenzyl)oxy)-4-(trifluoromethyl)benzene | 1 | 3.41 | 444 |
| 53 | 1-(2-((2,4-difluorobenzyl)oxy)-5-fluorobenzyl)-1H-indole-4-carboxylic acid | 2-(bromomethyl)-1-((2,4-difluorobenzyl)oxy)-4-fluorobenzene | 1 | 3.26 | 412 |
| 54 | 1-(2-((2,4-difluorobenzyl)oxy)benzyl)-1H-indole-4-carboxylic acid | 1-((2-(bromomethyl)phenoxy)methyl)-2,4-difluorobenzene | 1 | 3.26 | 394 |
| 55 | 1-(5-bromo-2-((4-bromo-2-fluorobenzyl)oxy)benzyl)-1H-indole-4-carboxylic acid | 4-bromo-1-((4-bromo-2-(bromomethyl)phenoxy)methyl)-2-fluorobenzene | 1 | 3.01 | 532 |
| 56 | 1-(2-((4-bromo-2-fluorobenzyl)oxy)-5-fluorobenzyl)-1H-indole-4-carboxylic acid | 4-bromo-1-((2-(bromomethyl)-4-fluorophenoxy)methyl)-2-fluorobenzene | 1 | 2.86 | 472 |
| 57 | 1-(5-chloro-2-((4-chloro-2,6-difluorobenzyl)oxy)benzyl)-1H-indole-4-carboxylic acid | 2-((2-(bromomethyl)-4-chlorophenoxy)methyl)-5-chloro-1,3-difluorobenzene | 1 | 2.91 | 462 |
| 58 | 1-(2-((4-bromo-2,6-difluorobenzyl)oxy)-5-chlorobenzyl)-1H-indole-4-carboxylic acid | 5-bromo-2-((2-(bromomethyl)-4-chlorophenoxy)methyl)-1,3-difluorobenzene | 1 | 2.98 | 506 |
| 59 | 1-(3,5-dichloro-2-((4-chloro-2-fluorobenzyl)oxy)benzyl)-1H-indole-4-carboxylic acid | 1-(bromomethyl)-3,5-dichloro-2-((4-chloro-2-fluorobenzyl)oxy)benzene | 1 | 3.12 | 478 |
| 60 | 1-(5-bromo-2-((4-chloro-2,6-difluorobenzyl)oxy)benzyl)-1H-indole-4-carboxylic acid | 2-((4-bromo-2-(bromomethyl)phenoxy)methyl)-5-chloro-1,3-difluorobenzene | 1 | 2.98 | 506 |
| 61 | 1-((3-((4-chloro-2-fluorobenzyl)oxy)pyridin-2-yl)methyl)-1H-indole-4-carboxylic acid | 2-(bromomethyl)-3-((4-chloro-2-fluorobenzyl)oxy)pyridine | 1 | 3.54 | 411 |
| 62 | 3-(1-(5-chloro-2-((4-chloro-2-fluorobenzyl)oxy)benzyl)-1H-indol-4-yl)propanoic acid | 2-(bromomethyl)-1-((3,5-difluorobenzyl)oxy)-4-fluorobenzene | 1 | 3.67 | 472 |
| 63 | 1-(5-chloro-2-(4-chloro-2-fluorophenethyl)benzyl)-1H-indole-4-carboxylic acid | 2-(bromomethyl)-4-chloro-1-(4-chloro-2-fluorophenethyl)benzene | 1 | 4.02 | 442 |

Examples 64 to 78

Using methyl 1H-Indole-5-carboxylate as Stating Material

The next compounds were obtained using the same methodology as in example 1 but using methyl 1H-indole-5-carboxylate as starting material of formula III and the compound II indicated.

| | | | | LC-MS | |
|---|---|---|---|---|---|
| Example | Compound name | Starting compound II | Method | $t_R$ (min) | m/z $[M + H]^+$ |
| 64 | 1-(5-chloro-2-(cyclopropylmethoxy)benzyl)-1H-indole-5-carboxylic acid | 2-(bromomethyl)-4-chloro-1-(cyclopropylmethoxy)benzene | 1 | 3.18 | 356 |
| 65 | 1-(5-fluoro-2-((2,4,5-trifluorobenzyl)oxy)benzyl)-1H-indole-5-carboxylic acid | 1-((2-(bromomethyl)-4-fluorophenoxy)methyl)-2,4,5-trifluorobenzene | 1 | 3.28 | 430 |
| 66 | 1-(2-((2-chloro-4-fluorobenzyl)oxy)-5-fluorobenzyl)-1H-indole-5-carboxylic acid | 2-(bromomethyl)-1-((2-chloro-4-fluorobenzyl)oxy)-4-fluorobenzene | 1 | 3.40 | 428 |
| 67 | 1-(5-chloro-2-((4-fluoro-2-(trifluoromethyl)benzyl)oxy)benzyl)-1H-indole-5-carboxylic acid | 2-(bromomethyl)-4-chloro-1-((4-fluoro-2-(trifluoromethyl)benzyl)oxy)benzene | 1 | 3.58 | 478 |
| 68 | 1-(2-((3-bromo-4-fluorobenzyl)oxy)-5-fluorobenzyl)-1H-indole-5-carboxylic acid | 2-bromo-4-((2-(bromomethyl)-4-fluorophenoxy)methyl)-1-fluorobenzene | 1 | 2.93 | 472 |
| 69 | 1-(5-bromo-2-((4-fluoro-2-(trifluoromethyl)benzyl)oxy)benzyl)-1H-indole-5-carboxylic acid | 4-bromo-2-(bromomethyl)-1-((4-fluoro-2-(trifluoromethyl)benzyl)oxy)benzene | 1 | 3.02 | 522 |
| 70 | 1-(5-bromo-2-((2-chloro-4-fluorobenzyl)oxy)benzyl)-1H-indole-5-carboxylic acid | 4-bromo-2-(bromomethyl)-1-((2-chloro-4-fluorobenzyl)oxy)benzene | 1 | 2.99 | 488 |
| 71 | 1-(5-fluoro-2-((3,4,5-trifluorobenzyl)oxy)benzyl)-1H-indole-5-carboxylic acid | 2-(bromomethyl)-4-fluoro-1-((3,4,5-trifluorobenzyl)oxy)benzene | 1 | 3.33 | 430 |
| 72 | 1-(2-((2-chloro-4,5-difluorobenzyl)oxy)-5-fluorobenzyl)-1H-indole-5-carboxylic acid | 2-(bromomethyl)-4-fluoro-1-((2-chloro-4,5-difluorobenzyl)oxy)benzene | 1 | 3.43 | 446 |
| 73 | 1-(2-((2-chloro-5-fluorobenzyl)oxy)-5-fluorobenzyl)-1H-indole-5-carboxylic acid | 2-(bromomethyl)-4-fluoro-1-((2-chloro-5-fluorobenzyl)oxy)benzene | 1 | 2.80 | 428 |
| 74 | 1-(5-bromo-2-((2,4-difluorobenzyl)oxy)benzyl)-1H-indole-5-carboxylic acid | 4-bromo-2-(bromomethyl)-1-((2,4-difluorobenzyl)oxy)benzene | 1 | 3.40 | 472 |
| 75 | 1-(2-((4-bromo-2-fluorobenzyl)oxy)-5-(trifluoromethyl)benzyl)-1H-indole-5-carboxylic acid | 4-bromo-1-((2-(bromomethyl)-4-(trifluoromethyl)phenoxy)methyl)-2-fluorobenzene | 1 | 3.62 | 522 |
| 76 | 1-(5-chloro-2-((4-chloro-2-fluorobenzyl)oxy)benzyl)-1H-indole-5-carboxylic acid | 2-(bromomethyl)-4-chloro-1-((4-chloro-2-fluorobenzyl)oxy)benzene | 1 | 3.51 | 444 |

-continued

| Example | Compound name | Starting compound II | Method | LC-MS $t_R$ (min) | m/z $[M + H]^+$ |
|---|---|---|---|---|---|
| 77 | 1-(5-chloro-2-((4-fluorobenzyl)oxy)benzyl)-1H-indole-5-carboxylic acid | 2-(bromomethyl)-4-chloro-1-(4-fluorobenzyloxy)benzene | 1 | 3.34 | 410 |
| 78 | Sodium 1-(5-chloro-2-((2,4-difluorobenzyl)oxy)benzyl)-1H-indole-5-carboxylate | 4-chloro-2-(bromomethyl)-1-((2,4-difluorobenzyl)oxy)benzene | 1 | 3.79 | 428 |

Examples 79 to 83

Using (E)-ethyl 3-(1H-indol-4-yl)acrylate as Stating Material

The next compounds were obtained using the same methodology as in example 1 but using (E)-ethyl 3-(1H-indol-4-yl)acrylate as starting material of formula III and the compound II indicated.

| Example | Compound name | Starting compound II | Method | LC-MS $t_R$ (min) | m/z $[M + H]^+$ |
|---|---|---|---|---|---|
| 79 | (E)-3-(1-(2-(benzyloxy)-5-(trifluoromethyl)benzyl)-1H-indol-4-yl)acrylic acid | 1-(benzyloxy)-2-(bromomethyl)-4-(trifluoromethyl)benzene | 1 | 3.45 | 452 |
| 80 | (E)-3-(1-(5-bromo-2-(cyclopropylmethoxy)benzyl)-1H-indol-4-yl)acrylic acid | 4-bromo-2-(bromomethyl)-1-(cyclopropylmethoxy)benzene | 1 | 3.34 | 426 |
| 81 | (E)-3-(1-(5-chloro-2-(cyclopropylmethoxy)benzyl)-1H-indol-4-yl)acrylic acid | 2-(bromomethyl)-4-chloro-1-(cyclopropylmethoxy)benzene | 1 | 3.29 | 382 |
| 82 | (E)-3-(1-(5-chloro-2-((2,4-difluorobenzyl)oxy)benzyl)-1H-indol-4-yl)acrylic acid | 2-(bromomethyl)-4-chloro-1-((2,4-difluorobenzyl)oxy)benzene | 1 | 3.43 | 454 |
| 83 | (E)-3-(1-(5-chloro-2-((4-chloro-2-fluorobenzyl)oxy)benzyl)-1H-indol-4-yl)acrylic acid | 2-(bromomethyl)-4-chloro-1-((4-chloro-2-fluorobenzyl)oxy)benzene | 1 | 3.56 | 470 |

Examples 84 to 86

Using 2-((1H-indol-4-yl)oxy)acetate as Stating Material

The next compounds were obtained using the same methodology as in example 1 but using methyl 2-((1H-indol-4-yl)oxy)acetate as starting material of formula III and the compound II indicated.

| Example | Compound name | Starting compound II | Method | LC-MS $t_R$ (min) | m/z $[M + H]^+$ |
|---|---|---|---|---|---|
| 84 | 2-((1-(2-((4-chloro-2-fluorobenzyl)oxy)-5-(trifluoromethyl)benzyl)- | 2-(bromomethyl)-1-(4-chloro-2-fluorobenzyloxy)-4- | 1 | 3.54 | 508 |

| Example | Compound name | Starting compound II | Method | LC-MS $t_R$ (min) | m/z $[M + H]^+$ |
|---|---|---|---|---|---|
| 85 | 1H-indol-4-yl)oxy)acetic acid 2-((1-(5-chloro-2-(cyclopropylmethoxy)benzyl)-1H-indol-4-yl)oxy)acetic acid | (trifluoromethyl)benzene 2-(bromomethyl)-4-chloro-1-(cyclopropylmethoxy)benzene | 1 | 3.22 | 386 |
| 86 | 2-((1-(5-chloro-2-(cyclopropylmethoxy)benzyl)-1H-indol-4-yl)oxy)acetic acid | 4-bromo-2-(bromomethyl)-1-(4-fluorobenzyloxy)benzene | 1 | 3.34 | 484 |

Example 87

Synthesis of 1-(2-(benzyloxy)-5-bromobenzyl)-1H-indole-6-carboxylic acid)

The title compound (example 87) was obtained from using the same methodology as in example 1 but using methyl 1H-indole-6-carboxylate and 1-(benzyloxy)-4-bromo-2-(bromomethyl)benzene as starting materials.

LCMS: $t_R$=3.33, $[M+H]^+$=438

The next compounds were obtained from using the same methodology and methyl 1H-indole-6-carboxylate the compound II specified

| Example | Compound name | Starting compound II | Method | LC-MS $t_R$ (min) | m/z $[M + H]^+$ |
|---|---|---|---|---|---|
| 88 | Sodium 1-(5-chloro-2-((2,4-difluorobenzyl)oxy)benzyl)-1H-indole-6-carboxylate | 4-chloro-2-(bromomethyl)-1-((2,4-difluorobenzyl)oxy)benzene | 1 | 3.80 | 428 |

Example 89

Synthesis of 3-(1-(5-chloro-2-((4-chloro-2-fluorobenzyl)oxy)benzyl)-1H-indol-4-yl)propanoic acid The title compound (example 89) was obtained using the same methodology as in example 1 but using ethyl 3-(1H-indol-4-yl)propanoate and 2-(bromomethyl)-4-chloro-1-((4-chloro-2-fluorobenzyl)oxy)benzene as starting materials.

$^1$H NMR (400 MHz CDCl$_3$) δ 7.26-7.10 (7H, m), 6.97 (1H, dd), 6.90 (1H, d,), 6.84 (1H, d), 6.59 (1H, dd), 5.29 (2H, s), 5.12 (2H, s), 3.29 (2H, t), 2.85 (2H, t).

LC-MS: $t_R$=9.28, $[M+H]^+$=472 (method 3).

Example 90

Synthesis of 1-(5-chloro-2-((4-chloro-2-fluorobenzyl)oxy)benzyl) -1H-pyrrolo[2,3-b]pyridine-4-carboxylic acid The title compound (example 90) was obtained using the same methodology as in example 1 but using methyl 1H-pyrrolo[2,3-b]pyridine-4-carboxylate and 2-(bromomethyl)-4-chloro-1-((4-chloro-2-fluorobenzyl)oxy)benzene as starting materials.

$^1$H NMR (400 MHz, DMSO) δ 8.35 (1H, d), 7.64 (1H, d), 7.60 (1H, d), 7.56 (2H, t), 7.49 (1H, dd), 7.32 (2H, ddd), 7.21 (1H, d), 6.91 (1H, d), 6.82 (1H, d), 5.49 (2H, s), 5.20 (2H, s).

LC-MS: $t_R$=9.9 $[M+H]^+$=445 (method 3)

The next compounds were obtained using the same methodology and 1H-pyrrolo[2,3-b]pyridine-4-carboxylic acid as staring material of formula III and the compound II specified

| Example | Compound name | Starting compound II | Method | LC-MS $t_R$ (min) | m/z $[M + H]^+$ |
|---|---|---|---|---|---|
| 91 | Sodium 1-(5-chloro-2-((2,4-difluorobenzyl)oxy)benzyl)-1H-pyrrolo[2,3-b]pyridine-4-carboxylate | 4-chloro-2-(bromomethyl)-1-((2,4-difluorobenzyl)oxy)benzene | 1 | 3.55 | 429 |

Example 92

Synthesis of 1-(5-chloro-2-((4-chloro-2-fluorobenzyl)oxy)benzyl)-1H-benzo[d]imidazole-4-carboxylic acid To a suspension of NaH 60% (13 mg, 0.31 mmol) in dry DMF (4 mL) at 0° C. was added dropwise a solution of 1H-benzo[d]imidazole-4-carboxylic acid (50 mg, 0.3 mmol) in DMF (1 mL). After 30 min a solution of 2-(bromomethyl)-4-chloro-1-((4-chloro-2-fluorobenzyl)oxy)benzene (103 mg, 0.28 mmol) in 1 mL of DMF was added dropwise and the mixture kept at RT for 16 h. After evaporation of the solvent the residue was chromatographed on silica gel eluting with DCM:MeOH (9.5:0.5 to 9:1) to gave the title compound (example 92) as a white solid (96 mg, 72% yield).

$^1$H NMR (400 MHz, DMSO) δ 8.29 (1H, d), 7.99 (1H, d), 7.82 (1H, dd), 7.54 (1H, t), 7.48 (1H, d), 7.40 (2H, ddd), 7.31 (1H, t), 7.24 (1H, d), 7.19 (1H, dd), 5.44 (2H, s), 5.22 (2H, s).

LC-MS: $t_R$=7.27; $[M+H]^+$=445 (method 3)

Example 93

Synthesis of 1-(5-chloro-2-((4-chloro-2-fluorobenzyl)oxy)benzyl)indoline-4-carboxylic acid a) To a suspension of $K_2CO_3$ (43 mg, 0.31 mmol) and methyl indoline-4-carboxylate (53 mg, 0.3 mmol) in dry DMF (1 mL) at 0° C. was added dropwise a solution of 2-(bromomethyl)-4-chloro-1-((4-chloro-2-fluorobenzyl) oxy)benzene (114 mg, 0.31 mmol) in DMF (1 mL). The reaction was stirred at RT overnight (TLC analysis showed complete conversion) and then the solution was poured onto crushed ice and extracted with EtAcO (×3). Combined organic extracts were washed with water, brine and dried over $Na_2SO_4$. Column chromatography on silica gel eluting with DCM gave methyl 1-(5-chloro-2-((4-chloro-2-fluorobenzyl)oxy)benzyl)indoline-4-carboxylate as a white solid (111 mg, 81% yield).

$^1$H NMR (400 MHz, CDCl$_3$) δ 7.36 (1H, dd), 7.30 (1H, d), 7.29-7.26 (2H, m), 7.21 (1H, dd), 7.14-7.09 (1H, m), 6.49 (1H, d), 5.09 (2H, s), 4.26 (2H, s), 3.88 (3H, s), 3.49-3.42 (2H, m), 3.41-3.34 (2H, m).

b) In a sealed tube were placed methyl 1-(5-chloro-2-((4-chloro-2-fluorobenzyl)oxy)benzyl)indoline-4-carboxylate (85 mg, 0.19 mmol), EtOH (1.5 mL), THF (0.5 mL) and a solution of LiOH (13 mg, 0.55 mmol) in 0.23 mL of water. The mixture was stirred at 75° C. overnight. Then the mixture was cooled to RT and acidified with HCl 1M to pH-2-3. The reaction mixture was extracted with EtAcO (×3). The organic phases were washed with brine dried over $Na_2SO_4$ and filtered. The solvent was removed in vacuo and the crude was chromatographed on silica-gel eluting with DCM:MeOH (98:2) to give 75 mg (91% yield) of the title compound (example 93) as a slightly yellow solid.

$^1$H NMR (500 MHz, DMSO) δ 7.60 (1H, t), 7.50 (1H, dd), 7.36-7.28 (3H, m), 7.21 (1H, d), 7.10 (1H, d), 7.00 (1H, t), 6.56 (1H, d), 5.20 (2H, s), 4.25 (2H, s), 3.36 (2H, t), 3.22 (2H, t).

LC-MS: $t_R$=2.98 min, $[M+H]^+$=446, (Method 1).

Example 94

Synthesis of 1-(5-chloro-2-((4-chloro-2-fluorobenzyl)oxy)benzyl)-1,2,3,4-tetrahydroquinoline-5-carboxylic acid The title compound (example 94) was obtained following the general procedure described in example 1 using methyl 1,2,3,4-tetrahydroquinoline-5-carboxylate and 2-(bromomethyl)-4-chloro-1-((4-chloro-2-fluorobenzyl)oxy)benzene as starting materials.

$^1$H NMR (400 MHz, DMSO) δ 7.63 (1H, t), 7.51 (1H, dd), 7.34 (1H, dd), 7.30 (1H, dd), 7.22 (1H, d), 6.98 (1H, d), 6.95-6.84 (2H, m), 6.39-6.28 (1H, m), 5.23 (2H, s), 4.40 (2H, s), 3.39-3.32 (2H, m), 2.97 (2H, t), 1.93-1.84 (2H, m).

LC-MS: $t_R$=9.61, $[M+H]^+$=460 (method 3).

The next compounds were obtained using the same methodology and methyl 1,2,3,4-tetrahydroquinoline-5-carboxylate as starting material of formula (III) and the compound II specified

| Example | Compound name | Starting compound II | Method | LC-MS $t_R$ (min) | m/z $[M + H]^+$ |
|---|---|---|---|---|---|
| 95 | 1-(5-chloro-2-((2,4-difluorobenzyl)oxy)benzyl)-1,2,3,4-tetrahydroquinoline-5-carboxylic acid | 2-(bromomethyl)-4-chloro-1-((2,4-difluorobenzyl)oxy)benzene | 1 | 3.82 | 444 |

Example 96

Synthesis of sodium 1-(5-chloro-2-((4-chloro-2-fluorobenzyl)oxy)benzyl)-1H-indole-4-carboxylate a) Methyl 1-(5-chloro-2-((4-chloro-2-fluorobenzyl)oxy)benzyl)-1H-indole-4-carboxylate was obtained following the general method described in example 1, using methyl 1H-indole-4-carboxylate and 2-(bromomethyl)-4-chloro-1-((4-chloro-2-fluorobenzyl)oxy)benzene as starting materials.

b) To a solution of compound obtained above (640 mg, 1.40 mmol) in EtOH, a solution of NaOH 2M (1.75 mL, 3.5 mmol) was added at room temperature. The mixture was stirred at 80° C. until TLC showed there was not starting material left. It was cooled and EtOH was removed in vacuo. The residue was dissolved in EtAcO, washed with water (×3) and brine, and dried with $MgSO_4$. The crude product was purified by $SiO_2$ column chromatography, eluting with a gradient of hexane/EtAcO. Title compound (example 96) was obtained as a white solid (540 mg, 83% yield).

$^1$H NMR (400 MHz, DMSO) δ 7.72 (1H, dd), 7.61 (1H, d), 7.58-7.50 (3H; m), 7.34-7.30 (2H, m), 7.20 (1H, d), 7.13 (1H, t), 6.98 (1H, d), 6.86 (1H, d), 5.39 (2H, s), 5.21 (2H, s).

LC-MS: $t_R$=3.73; [M+H]$^+$=444 (method 1).

Example 97

Synthesis of sodium 1-(5-chloro-2-((2,4-difluorobenzyl)oxy)benzyl)-1H-indole-4-carboxylate The title compound (example 97) was obtained using the same methodology as in Example 96 but using 1-(5-chloro-2-((2,4-difluorobenzyl)oxy)benzyl)-1H-indole-4-carboxylic acid as starting material.

$^1$H NMR (400 MHz, DMF-d$_7$) δ 8.05 (1H, d), 7.92-7.86 (2H, m), 7.79 (1H, d), 7.54-7.30 (6H, m), 7.13 (1H, d,), 5.70 (2H, s), 5.46 (2H, s)

LC-MS: $t_R$=3.95, [M+H]$^+$=428 (method 1).

Examples 98 to 99

Using 2-methyl-7H-pyrrolo[2,3-d]pyrimidine-4-carboxylate as Starting Material

The next compounds were obtained using the same methodology as in Example 96 but using 2-methyl-7H-pyrrolo[2,3-d]pyrimidine-4-carboxylate as starting material of formula III and the compound II indicated.

Example 100

Synthesis of sodium 1-(5-chloro-2-((2,4-difluorobenzyl)oxy)benzyl)-7-fluoro-1H-indole-4-carboxylate The title compound (example 100) was obtained using the same methodology as in Example 96 but using methyl 7-fluoro-1H-indole-4-carboxylate and 2-(bromomethyl)-4-chloro-1-((2,4-difluorobenzyl)oxy)benzene as starting materials.

$^1$H NMR (500 MHz, DMSO) δ 7.71 (1H, dd), 7.60-7.54 (1H, m), 7.53 (1H, d), 7.37-7.28 (2H, m), 7.23 (1H, d), 7.11 (1H, td), 7.06 (1H, t), 6.94 (1H, dd), 6.54 (1H, d), 5.51 (2H, s), 5.19 (2H, s).

LC-MS: $t_R$=3.85; [M+H]$^+$=444 (Method 1)

Example 101

Synthesis of sodium 1-(2-[((2,4-difluorobenzyl)oxy]-5-methoxybenzyl)-1H-indole-4-carboxylate t-BuONa (32 mg, 0.33 mmol) was added to a suspension of 1-{2-[(2,4-difluorobenzyl)oxy]-5-methoxybenzyl}-1H-indole-4-carboxylic acid (140 mg, 0.33 mmol) in MeOH (10 mL) and stirred at room temperature. After 2 h, the solvent was removed out of the clear solution, rendering a white solid that was triturated with Et$_2$O (10 mL) and vacuum dried, affording 130 mg of sodium 1-{2-[(2,4-difluorobenzyl)oxy]-5-methoxybenzyl}-1H-indole-4-carboxylate (87% yield) (example 101).

LC-MS ESI– m/z 422 [M-Na]$^-$, $t_R$=18.14 (Method 2)

$^1$H-NMR (DMSO-d$_6$, 250 MHz, δ): 7.67-7.52 (m, 2H, ArH); 7.40-7.07 (m, 6H, ArH); 6.94 (dd, J=8.0, 7.4 Hz, 1H, ArH); 6.79 (dd, J=8.6, 3.2 Hz, 1H, ArH); 6.29 (d, J=2.8 Hz, 1H, ArH); 5.27 (s, 2H, CH2); 5.14 (s, 2H, CH2); 3.56 (s, 3H, OCH3).

Example 102

Synthesis of sodium 1-[5-chloro-2-(cyclohexylmethoxy)benzyl]-1H-indole-4-carboxylate The title compound (example 102) was obtained using the same methodology as in Example 101 but methyl 1H-in-

| | | | | LC-MS | |
|---|---|---|---|---|---|
| Example | Compound name | Starting compound II | Method | $t_R$ (min) | m/z [M + H]$^+$ |
| 98 | sodium 7-(5-chloro-2-((4-chloro-2-fluorobenzyl)oxy)benzyl)-7H-pyrrolo[2,3-d]pyrimidine-4-carboxylate | 2-(bromomethyl)-4-chloro-1-((4-chloro-2-fluorobenzyl)oxy)benzene | 1 | 3.56 | 446 |
| 99 | sodium 7-(5-chloro-2-((2,4-difluorobenzyl)oxy)benzyl)-7H-pyrrolo[2,3-d]pyrimidine-4-carboxylate | 2-(bromomethyl)-4-chloro-1-((2,4-difluorobenzyl)oxy)benzene | 1 | 3.47 | 430 | dole-4-carboxylate and 2-(bromomethyl)-4-chloro-1-(cyclohexylmethoxy)benzene as starting materials.

LC-MS ESI– m/z 396 [M-Na]⁻, $t_R$=21.18 (Method 2)

¹H-NMR (DMSO-d₆, 250 MHz, δ): 7.57 (dd, J=7.4, 1.0 Hz, 1H, ArH); 7.36-7.18 (m, 4H, ArH); 7.07-6.98 (m, 2H, ArH); 6.64 (d, J=2.7 Hz, 1H, ArH); 5.33 (s, 2H, CH2); 3.85 (d, J=5.5 Hz, 2H, CH2); 1.91-1.60 (m, 6H); 1.38-1.00 (m, 5H).

Example 103

Synthesis of sodium 1-[5-chloro-2-(cyclopentylmethoxy)benzyl]-1H-indole-4-carboxylate The title compound (example 103) was obtained using the same methodology as in Example 15 but methyl 1H-indole-4-carboxylate and 2-(bromomethyl)-4-chloro-1-(cyclopentylmethoxy)benzene as starting materials.

LC-MS ESI– m/z: 382 [M-Na]⁻, $t_R$=20.40 (Method 2)

¹H-NMR (DMSO-d₆, 250 MHz, δ): 7.57 (d, J=7.0 Hz, 1H, ArH); 7.39-7.17 (m, 4H, ArH); 7.10-6.90 (m, 2H, ArH); 6.67 (br s, 1H, ArH); 5.32 (s, 2H, CH2); 3.93 (d, J=6.2 Hz, 2H, CH2); 2.47-2.30 (m, 1H); 1.93-1.11 (m, 8H).

Examples 104 to 113

Using methyl 1H-indole-4-carboxylate as Starting Material

The next compounds were obtained using the same methodology as in Example 96 but using methyl 1H-indole-4-carboxylate as starting material of formula III and the compound II indicated.

| Example | Compound name | Starting compound II | Method | $t_R$ (min) | m/z [M + H]⁺ |
|---|---|---|---|---|---|
| 104 | Sodium 1-(5-fluoro-2-propoxybenzyl)-1H-indole-4-carboxylate | 2-(bromomethyl)-4-fluoro-1-propoxybenzene | 4 | 1.78 | 328 |
| 105 | Sodium 1-(5-chloro-2-(cyclopentyloxy)benzyl)-1H-indole-4-carboxylate | 2-(bromomethyl)-4-chloro-1-(cyclopentyloxy)benzene | 4 | 2.00 | 370 |
| 106 | Sodium 1-(5-chloro-2-propoxybenzyl)-1H-indole-4-carboxylate | 2-(bromomethyl)-4-chloro-1-propoxybenzene | 4 | 1.84 | 344 |
| 107 | Sodium 1-(5-chloro-2-(2-(tetrahydro-2H-pyran-4-yl)ethoxy)benzyl)-1H-indole-4-carboxylate | 4-(2-(2-(bromomethyl)-4-chlorophenoxy)ethyl)tetrahydro-2H-pyran | 1 | 3.44 | 414 |
| 108 | Sodium 1-(5-fluoro-2-isobutoxybenzyl)-1H-indole-4-carboxylate | 2-(bromomethyl)-4-fluoro-1-isobutoxybenzene | 1 | 3.57 | 340* |
| 109 | Sodium 1-(2-isobutoxybenzyl)-1H-indole-4-carboxylate | 1-(bromomethyl)-2-isobutoxybenzene | 2 | 18.65 | 324 |
| 110 | Sodium 1-[5-chloro-2-(2,2-difluoroethoxy)benzyl]-1H-indole-4-carboxylate | 2-(bromomethyl)-4-chloro-1-(2,2-difluoroethoxy)benzene | 2 | 10.11 | 366 |
| 111 | Sodium 1-[5-chloro-2-(2-fluoroethoxy)benzyl]-1H-indole-4-carboxylate | 2-(bromomethyl)-4-chloro-1-(2-fluoroethoxy)benzene | 2 | 15.72 | 348 |
| 112 | Sodium 1-[5-chloro-2-(2,2,2-trifluoroethoxy)benzyl]-1H-indole-4-carboxylate | 2-(bromomethyl)-4-chloro-1-(2,2,2-trifluoroethoxy)benzene | 2 | 16.07 | 384 |
| 113 | Sodium 1-[5-chloro-2-(neopentyloxy)benzyl]-1H-indole-4-carboxylate | 2-(bromomethyl)-4-chloro-1-(neopentyloxy)benzene | 2 | 20.00 | 372 |

*m/z [M − H]⁻ instead of m/z [M + H]⁺

Examples 114 to 115

Using methyl 3-oxo-3,4-dihydro-2H-benzo[b][1,4]oxazine-8-carboxylate as starting material The next compounds were obtained using the same methodology as in Example 96 but using methyl 3-oxo-3,4-dihydro-2H-benzo[b][1,4]oxazine-8-carboxylate as starting material of formula III and the compound II indicated.

| | | | | LC-MS | |
|---|---|---|---|---|---|
| Example | Compound name | Starting compound II | Method | $t_R$ (min) | m/z $[M + H]^+$ |
| 114 | Sodium 4-(5-chloro-2-cyclobutoxybenzyl)-3-oxo-3,4-dihydro-2H-benzo[b][1,4]oxazine-8-carboxylate | 2-(bromomethyl)-4-chloro-1-cyclobutoxybenzene | 4 | 1.67 | 388 |
| 115 | Sodium 4-(5-bromo-2-(4-chloro-2-fluorobenzyloxy)benzyl)-3-oxo-3,4-dihydro-2H-benzo[b][1,4]oxazine-8-carboxylate | 4-bromo-2-(bromomethyl)-1-(4-chloro-2-fluorobenzyloxy)benzene | 4 | 1.88 | 520 |

Examples 116 to 122

Using methyl 3,4-dihydro-2H-benzo[b][1,4]oxazine-8-carboxylate as Starting Material The following compounds were prepared using the same methodology as in example 96 using methyl 3,4-dihydro-2H-benzo[b][1,4]oxazine-8-carboxylate and the compound II specified as starting materials.

| | | | | LC-MS | |
|---|---|---|---|---|---|
| Example | Compound name | Starting compound II | Method | $t_R$ (min) | m/z $[M + H]^+$ |
| 116 | Sodium 4-(5-chloro-2-(2-fluoro-2-methylpropoxy)benzyl)-3,4-dihydro-2H-benzo[b][1,4]oxazine-8-carboxylate | 2-(bromomethyl)-4-chloro-1-(2-fluoro-2-methylpropoxy)benzene | 4 | 1.72 | 394 |
| 117 | Sodium 4-(5-chloro-2-((4-chloro-2-fluorobenzyl)oxy)benzyl)-3,4-dihydro-2H-benzo[b][1,4]oxazine-8-carboxylate | 2-(bromomethyl)-4-chloro-1-((4-chloro-2-fluoro-benzyl)oxy)benzene | 1 | 3.71 | 462 |
| 118 | Sodium 4-(5-chloro-2-((2,4-difluorobenzyl)oxy)benzyl)-3,4-dihydro-2H-benzo[b][1,4]oxazine-8-carboxylate | 2-(bromomethyl)-4-chloro-1-((2,4-difluorobenzyl)oxy)benzene | 1 | 3.60 | 446 |
| 119 | Sodium 4-(2-((4-chloro-2-fluorobenzyl)oxy)benzyl)-3,4-dihydro-2H-benzo[b][1,4]oxazine-8-carboxylate | 1-((2-(bromomethyl)phenoxy)methyl)-4-chloro-2-fluorobenzene | 1 | 3.64 | 428 |

-continued

| Example | Compound name | Starting compound II | LC-MS Method | $t_R$ (min) | m/z $[M + H]^+$ |
|---|---|---|---|---|---|
| 120 | Sodium 4-(2-(benzyloxy)benzyl)-3,4-dihydro-2H-benzo[b][1,4]oxazine-8-carboxylate | 1-(benzyloxy)-2-(bromomethyl)benzene | 1 | 3.39 | 376 |
| 121 | Sodium 4-(2-((2-chloro-4-fluorobenzyl)oxy)-5-fluorobenzyl)-3,4-dihydro-2H-benzo[b][1,4]oxazine-8-carboxylate | 2-(bromomethyl)-1-((2-chloro-4-fluorobenzyl)oxy)-4-fluorobenzene | 1 | 3.57 | 445 |
| 122 | Sodium 4-(2-((2,4-difluorobenzyl)oxy)benzyl)-3,4-dihydro-2H-benzo[b][1,4]oxazine-8-carboxylate | 2-(bromomethyl)-1-((2,4-difluorobenzyl)oxy)benzene | 1 | 3.48 | 412 |

Example 123

Synthesis of sodium 1-(2-((2-chlorobenzyl)oxy)-5-fluorobenzyl)-1H-indazole-4-carboxylate a) To a suspension of NaH 60% (30 mg, 0.75 mmol) in dry DMF (1 mL) at 0° C. was added dropwise a solution of methyl 1H-indazole-4-carboxylate (120 mg, 0.68 mmol) in DMF (2 mL). After 10 min a solution of 2-(bromomethyl)-1-((2-chlorobenzyl)oxy)-4-fluorobenzene (236 mg, 0.72 mmol) in 1.5 mL of DMF was added dropwise. After 16 h at 0° C. water was added and extracted with EtAcO (×3). Combined organic extracts were washed with water, brine and dried over $Na_2SO_4$. The crude was purified by column chromatography using a combiflash system with a RediSep Rf Gold Normal Phase column and using cyclohexane/EtAcO as solvent. Methyl 1-(2-((2-chlorobenzyl)oxy)-5-fluorobenzyl)-1H-indazole-4-carboxylate compound as a slightly brown solid (144 mg, 50% yield).

$^1$H NMR (400 MHz, $CDCl_3$) δ 8.84 (s, 1H), 8.56 (s, 1H), 7.37 (d, J=3.1 Hz, 1H), 7.28 (dd, J=8.8, 2.6 Hz, 1H), 7.18-7.07 (m, 3H), 6.99 (d, J=2.6 Hz, 1H), 6.92 (d, J=8.8 Hz, 1H), 6.70 (dd, J=3.1, 0.8 Hz, 1H), 5.37 (s, 2H), 5.05 (s, 2H).

b) To a suspension of methyl 1-(2-((2-chlorobenzyl)oxy)-5-fluorobenzyl)-1H-indazole-4-carboxylate (120 mg, 0.28 mmol) in EtOH (3 mL), and THF (0.3 mL) a solution of NaOH (34 mg, 0.85 mmol) in $H_2O$ (0.3 mL) was added at room temperature. The mixture was stirred at 80° C. overnight. It was cooled and water was added. The aqueous layer was extracted with EtAcO (×3). The combined organic layers were washed with brine dried ($MgSO_4$) filtered and concentrated.

LC-MS: $t_R$=3.44; $[M+H]^+$=411 (Method 1)

$^1$H NMR (300 MHz, Methanol-d4) δ 8.59 (s, 1H), 7.72 (d, J=7.1 Hz, 1H), 7.55-7.39 (m, 3H), 7.41-7.22 (m, 3H), 7.02 (dtd, J=17.1, 8.9, 3.9 Hz, 2H), 6.57 (dd, J=8.9, 3.0 Hz, 1H), 5.65 (s, 2H), 5.22 (s, 2H).

Examples 124 to 138

Using methyl 1H-indazole-4-carboxylate as Starting Material

The next compounds were obtained using the same methodology as in Example 123 but using the compound II indicated.

| Example | Compound name | Starting compound II | LC-MS Method | $t_R$ (min) | m/z $[M + H]^+$ |
|---|---|---|---|---|---|
| 124 | Sodium 1-(5-chloro-2-((4-chloro-2-fluorobenzyl)oxy)benzyl)-1H-indazole-4-carboxylate | 2-(bromomethyl)-4-chloro-1-((4-chloro-2-fluorobenzyl)oxy)benzene | 1 | 3.65 | 445 |
| 125 | Sodium 1-(5-chloro-2-(2-fluoro-2-methylpropoxy)benzyl)-1H-indazole-4-carboxylate | 2-(bromomethyl)-4-chloro-1-(2-fluoro-2-methylpropoxy)benzene | 1 | 3.21 | 377 |
| 126 | Sodium 1-(5-chloro-2-((2-fluorobenzyl)oxy)benzyl)-1H-indazole-4-carboxylate | 2-(bromomethyl)-4-chloro-1-((2-fluorobenzyl)oxy)benzene | 1 | 3.43 | 411 |
| 127 | Sodium 1-(2-((2-chlorobenzyl)oxy)-5-methylbenzyl)-1H-indazole-4-carboxylate | 2-(bromomethyl)-1-((2-chlorobenzyl)oxy)-4-methylbenzene | 1 | 3.56 | 407 |

-continued

| Example | Compound name | Starting compound II | Method | $t_R$ (min) | m/z $[M + H]^+$ |
|---|---|---|---|---|---|
| 128 | Sodium 1-(5-fluoro-2-((2-fluoro-benzyl)oxy)benzyl)-1H-indazole-4-carboxylate | 2-(bromomethyl)-4-fluoro-1-((2-fluoro-benzyl)oxy)benzene | 1 | 3.33 | 395 |
| 129 | Sodium 1-(2-((2-fluorobenzyl)oxy)-5-methylbenzyl)-1H-indazole-4-carboxylate | 2-(bromomethyl)-1-((2-fluoro-benzyl)oxy)-4-methylbenzene | 1 | 3.43 | 391 |
| 130 | Sodium 1-(5-chloro-2-((2-chloro-benzyl)oxy)benzyl)-1H-indazole-4-carboxylate | 2-(bromomethyl)-4-chloro-1-((2-chloro-benzyl)oxy)benzene | 1 | 3.54 | 427 |
| 131 | Sodium 1-(5-chloro-2-(3-fluoro-2-methylpropoxy)benzyl)-1H-indazole-4-carboxylate | 2-(bromomethyl)-4-chloro-1-(3-fluoro-2-methylpropoxy)benzene | 1 | 3.30 | 377 |
| 132 | Sodium 1-(5-chloro-2-propoxybenzyl)-1H-indazole-4-carboxylate | f 2-(bromomethyl)-4-chloro-1-propoxybenzene | 4 | 1.70 | 345 |
| 133 | Sodium 1-(5-chloro-2-(cyclopentyloxy)benzyl)-1H-indazole-4-carboxylate | 2-(bromomethyl)-4-chloro-1-(cyclopentyloxy)benzene | 4 | 1.79 | 371 |
| 134 | Sodium 1-(5-fluoro-2-isobutoxybenzyl)-1H-indazole-4-carboxylate | 2-(bromomethyl)-4-fluoro-1-isobutoxybenzene | 4 | 1.74 | 343 |
| 135 | Sodium 1-(5-fluoro-2-propoxybenzyl)-1H-indazole-4-carboxylate | 2-(bromomethyl)-4-fluoro-1-propoxybenzene | 4 | 1.60 | 329 |
| 136 | Sodium 1-(5-bromo-2-(4-chloro-2-fluoro-benzyloxy)benzyl)-1H-indazole-4-carboxylate | 4-bromo-2-(bromomethyl)-1-(4-chloro-2-fluoro-benzyloxy)benzene | 4 | 1.95 | 491 |
| 137 | Sodium 1-(5-chloro-2-cyclobutoxybenzyl)-1H-indazole-4-carboxylate | 2-(bromomethyl)-4-chloro-1-cyclobutoxybenzene | 4 | 1.76 | 357 |
| 138 | Sodium 1-(5-chloro-2-(neopentyloxy)benzyl)-1H-indazole-4-carboxylate | 2-(bromomethyl)-4-chloro-1-(neopentyloxy)benzene | 4 | 1.94 | 373 |

Example 139

Using methyl 1H-pyrrolo[3,2-c]pyridine-4-carboxylate as Starting Material

The next compound was obtained using the same methodology as in Example 123 but using methyl 1H-pyrrolo[3,2-c]pyridine-4-carboxylate as starting material and the compound II indicated.

| Example | Compound name | Starting compound II | Method | $t_R$ (min) | m/z $[M + H]^+$ |
|---|---|---|---|---|---|
| 139 | Sodium 1-(5-chloro-2-((4-chloro-2-fluorobenzyl)oxy)benzyl)-1H-pyrrolo[3,2-c]pyridine-4-carboxylate | 2-(bromomethyl)-4-chloro-1-(4-chloro-2-fluorobenzyloxy)benzene | 1 | 3.65 | 445 |

Example 140

Using ethyl 7-fluoro-1H-indole-4-carboxylate as Starting Material

The next compound was obtained using the same methodology as in Example 123 but using ethyl 7-fluoro-1H-indole-4-carboxylate as starting material and the compound II indicated.

| Example | Compound name | Starting compound II | Method | $t_R$ (min) | m/z $[M - H]$ |
|---|---|---|---|---|---|
| 140 | Sodium 1-(2-((2,4-difluorobenzyl)oxy)benzyl)-7-fluoro-1H-indole-4-carboxylate | 1-((2-(bromomethyl)phenoxy)methyl)-2,4-difluorobenzene | 1 | 3.65 | 410 |

Example 141

Synthesis of sodium 1-(5-chloro-2-((4-chloro-2-fluorobenzyl)oxy)benzyl)-3-(hydroxymethyl)-1H-indole-4-carboxylate a) To a suspension of 41.3 mg (1.0 mmol) of NaH 60% in mineral oil in 3 mL of DMF under argon and cooled at 0° C. 200 mg (0.98 mmol) of methyl 3-formyl-1H-indole-4-carboxylate was added as a solution in 3 mL of DMF. The resulting solution was stirred at 0° C. for 15 minutes. Then, a solution of 2-(bromomethyl)-4-chloro-1-((4-chloro-2-fluorobenzyl)oxy)benzene in 4 mL of DMF was added dropwise. Reaction was stirred at 0° C. for 1.5 h. It was quenched with water, extracted with EtAcO and the combined organic extracts were washed with brine, dried over anhydrous $Na_2SO_4$, filtered and the solvent evaporated. The crude was purified by column chromatography over silica gel, eluting with mixtures cyclohexane/EtAcO. Methyl 1-(5-chloro-2-((4-chloro-2-fluorobenzyl)oxy)benzyl)-3-formyl-1H-indole-4-carboxylate (450 mg, 94%) was obtained as a white solid.

b) To a suspension of corresponding aldehyde (195 mg) in ethanol (0.2 M), $NaBH_4$ was added (1.2 eq, 21 mg) at 0° C. Mixture was stirred for 5 minutes and then 1 mL of THF was added to get complete solution. After 30 minutes, TLC showed there was not starting material left. It was quenched with water and extracted with EtOAc (×3). The organic phases were washed with brine and dried over $MgSO_4$. The crude white solid was used without further purification in the follow step reaction.

$^1$H NMR (300 MHz, CDCl3) δ 7.83 (d, 1H), 7.45 (d, 1H), 7.32-7.06 (m, 6H), 6.96-6.79 (m, 2H), 5.25 (s, 2H), 5.08 (s, 2H), 4.77 (s, 2H), 4.00 (s, 3H).

c) To a suspension of 440 mg (0.9 mmol) of methyl 1-(5-chloro-2-((4-chloro-2-fluorobenzyl)oxy)benzyl)-3-(hydroxymethyl)-1H-indole-4-carboxylate in 18 mL of absolute ethanol, 1.12 mL of an aqueous solution of NaOH 2M was added. The resulting mixture was stirred at 80° C. for 1 h. Then water was added and it was extracted with EtAcO. After evaporating the solvent sodium 1-(5-chloro-2-((4-chloro-2-fluorobenzyl)oxy)benzyl)-3-(hydroxymethyl)-1H-indole-4-carboxylate was obtained (385 mg, 86%).

LC-MS: $t_R$=3.71; [M–H]=472 (Method 1)

Examples 142 to 151

Using methyl 3-formyl-1H-indole-4-carboxylate as Starting Material

The next compounds were obtained using the same methodology as in example 141 using methyl 3-formyl-1H-indole-4-carboxylate as starting material and the compound II indicated.

| Example | Compound name | Starting compound II | LC-MS Method | $t_R$ (min) | m/z [M − H] |
|---|---|---|---|---|---|
| 142 | Sodium 1-(5-chloro-2-((2,4-difluorobenzyl)oxy)benzyl)-3-(hydroxymethyl)-1H-indole-4-carboxylate | 2-(bromomethyl)-4-chloro-1-((2,4-difluorobenzyl)oxy)benzene | 1 | 3.57 | 456 |
| 143 | Sodium 1-(2-((2,4-difluorobenzyl)oxy)benzyl)-3-(hydroxymethyl)-1H-indole-4-carboxylate | 2-(bromomethyl)-1-((2,4-difluorobenzyl)oxy)benzene | 1 | 3.20 | 422 |
| 144 | Sodium 1-(2-((4-chloro-2-fluorobenzyl)oxy)benzyl)-3-(hydroxymethyl)-1H-indole-4-carboxylate | 1-((2-(bromomethyl)phenoxy)methyl)-4-chloro-2-fluorobenzene | 1 | 3.53 | 438 |
| 145 | Sodium 1-(2-((2,4-difluorobenzyl)oxy)-5-fluorobenzyl)-3-(hydroxymethyl)-1H-indole-4-carboxylate | 2-(bromomethyl)-1-((2,4-difluorobenzyl)oxy)-4-fluorobenzene | 1 | 3.21 | 440 |
| 146 | Sodium 1-(2-((4-chloro-2-fluorobenzyl)oxy)-5-fluorobenzyl)-3-(hydroxymethyl)-1H-indole-4-carboxylate | 2-(bromomethyl)-1-((4-chloro-2-fluorobenzyl)oxy)-4-fluorobenzene | 1 | 3.53 | 456 |
| 147 | Sodium 1-(5-chloro-2-(2-fluoro-2-methylpropoxy)benzyl)-3-(hydroxymethyl)-1H-indole-4-carboxylate | 2-(bromomethyl)-4-chloro-1-(2-fluoro-2-methylpropoxy)benzene | 1 | 3.25 | 404 |
| 148 | Sodium 1-(2-cyclobutoxy-5-fluorobenzyl)-3-(hydroxymethyl)-1H-indole-4-carboxylate | 2-(bromomethyl)-4-fluoro-1-cyclobutoxybenzene | 1 | 3.30 | 368 |
| 149 | Sodium 1-(5-fluoro-2-((4-fluorobenzyl)oxy)benzyl)-3-(hydroxymethyl)-1H-indole-4-carboxylate | 2-(bromomethyl)-4-fluoro-1-((4-fluorobenzyl)oxy)benzene | 1 | 3.40 | 422 |
| 150 | Sodium 1-(5-chloro-2-((4-fluorobenzyl)oxy)benzyl)-3-(hydroxymethyl)-1H-indole-4-carboxylate | 2-(bromomethyl)-4-chloro-1-((4-fluorobenzyl)oxy)benzene | 1 | 3.50 | 438 |
| 151 | Sodium 1-(5-chloro-2-(3-fluoro-2-methylpropoxy)benzyl)-3-(hydroxymethyl)-1H-indole-4-carboxylate | 2-(bromomethyl)-4-chloro-1-(3-fluoro-2-methylpropoxy)benzene | 1 | 3.36 | 404 |

Examples 152 to 153

Using methyl 3-formyl-1H-pyrrolo[2,3-b]pyridine-4-carboxylate as Starting Material The next compounds were obtained using the same methodology as in example 141 but using methyl 3-formyl-1H-pyrrolo[2,3-b]pyridine-4-carboxylate as starting material and the compound II indicated.

|  |  |  |  | LC-MS | |
|---|---|---|---|---|---|
| Example | Compound name | Starting compound II | Method | $t_R$ (min) | m/z $[M + H]^+$ |
| 152 | Sodium 1-(5-chloro-2-((2,4-difluorobenzyl)oxy)benzyl)-3-(hydroxymethyl)-1H-pyrrolo[2,3-b]pyridine-4-carboxylate | 2-(bromomethyl)-4-chloro-1-((2,4-difluorobenzyl)oxy)benzene | 1 | 3.45 | 459 |
| 153 | Sodium 1-(5-chloro-2-((4-chloro-2-fluorobenzyl)oxy)benzyl)-3-(hydroxymethyl)-1H-pyrrolo[2,3-b]pyridine-4-carboxylate | 2-(bromomethyl)-4-chloro-1-((4-chloro-2-fluorobenzyl)oxy)benzene | 1 | 3.57 | 475 |

Example 154

Synthesis of sodium 1-(5-chloro-2-((4-chloro-2-fluorobenzyl)oxy)benzyl)-3-(2-hydroxyethyl)-1H-indole-4-carboxylate a) To a suspension of 310 mg (0.9 mmol) of (methoxymethyl)triphenylphosphonium chloride in 2 mL of toluene under argon at −0° C. NaHMDS 0.6M in toluene (1.2 mL, 0.72 mmol) was added via syringe. After stirring at 0° C. for 20 min methyl 1-(5-chloro-2-((4-chloro-2-fluorobenzyl)oxy)benzyl)-3-formyl-1H-indole-4-carboxylate was added as a solution in 5 mL of toluene and 3.5 mL of DCM. The resulting mixture was stirred at room temperature for 2 hours. Then it was allowed to warm to room temperature and quenched with a saturated solution of NH$_4$Cl. It was extracted with EtAcO and the combined organic layers were washed with water and brine, dried over MgSO$_4$ and evaporated. The crude was purified by column chromatography eluting with mixtures cyclohexane/EtAcO. Methyl 1-(5-chloro-2-((4-chloro-2-fluorobenzyl)oxy)benzyl)-3-(2-methoxyvinyl)-1H-indole-4-carboxylate was obtained as a yellow oil (230 mg, 99%).

b) To a solution of methyl 1-(5-chloro-2-((4-chloro-2-fluorobenzyl)oxy)benzyl)-3-(2-methoxyvinyl)-1H-indole-4-carboxylate (230 mg, 0.45 mmol) in 9 mL of acetone HCl 1M ((2.1 mL, 2.1 mmol) was added. The resulting mixture was stirred at 50° C. for 1 hour. Then, water was added and it was extracted with EtAcO (×3). The combined organic layers were washed with water and brine, dried over MgSO$_4$. Methyl 1-(5-chloro-2-((4-chloro-2-fluorobenzyl)oxy)benzyl)-3-(2-oxoethyl)-1H-indole-4-carboxylate was obtained (190 mg, 85%).

c) To a solution of methyl 1-(5-chloro-2-((4-chloro-2-fluorobenzyl)oxy)benzyl)-3-(2-oxoethyl)-1H-indole-4-carboxylate (190 mg, 0.38 mmol) in 7.5 mL of THF, NaBH$_4$ (17 mg, 0.46 mmol) was added. Reaction was stirred at room temperature for 1 h. Water was added, and the mixture was extracted with EtAcO, dried over MgSO$_4$. 1-(5-chloro-2-((4-chloro-2-fluorobenzyl)oxy)benzyl)-3,4-dihydrooxepino[5,4,3-cd]indol-6(1H)-one was obtained (120 mg, 65%).

d) To a suspension of 70 mg (0.15 mmol) of 1-(5-chloro-2-((4-chloro-2-fluorobenzyl)oxy)benzyl)-3,4-dihydrooxepino[5,4,3-cd]indol-6(1H)-one in 3 mL of absolute ethanol 0.18 mL of an aqueous solution of NaOH 2M was added. The resulting mixture was stirred at 80° C. for 1 h. Then water was added and it was extracted with EtAcO, dried over MgSO$_4$. Sodium 1-(5-chloro-2-((4-chloro-2-fluorobenzyl)oxy)benzyl)-3-(2-hydroxyethyl)-1H-indole-4-carboxylate was obtained as a yellow solid (63 mg, 83%).

$t_R$=3.61 min; m/x (M+H)$^+$ 488

Examples 155 to 160

Using methyl 3-formyl-1H-indole-4-carboxylate as Starting Material

The next compounds were obtained using the same methodology as in example 141 step a using methyl 3-formyl-1H-indole-4-carboxylate as starting material and the compound II indicated in the table below, followed by the use of the same methodology as in example 154.

|  |  |  |  | LC-MS | |
|---|---|---|---|---|---|
| Example | Compound name | Starting compound II | Method | $t_R$ (min) | m/z $[M + H]^+$ |
| 155 | Sodium 1-(5-chloro-2-((2,4- | methyl 1-(5-chloro-2-(2,4-difluorobenzyl- | 1 | 3.51 | 472 |

| Example | Compound name | Starting compound II | Method | $t_R$ (min) | m/z $[M + H]^+$ |
|---|---|---|---|---|---|
| | difluorobenzyloxy)benzyl)-3-(2-hydroxyethyl)-1H-indole-4-carboxylate | oxy)benzyl)-3-formyl-1H-indole-4-carboxylate | | | |
| 156 | Sodium 1-(5-fluoro-2-isobutoxybenzyl)-3-(2-hydroxyethyl)-1H-indole-4-carboxylate | methyl 1-(5-fluoro-2-isobutoxybenzyl)-3-formyl-1H-indole-4-carboxylate | 1 | 3.38 | 386 |
| 157 | Sodium 1-(5-chloro-2-isobutoxybenzyl)-3-(2-hydroxyethyl)-1H-indole-4-carboxylate | methyl 1-(5-chloro-2-isobutoxybenzyl)-3-formyl-1H-indole-4-carboxylate | 1 | 3.48 | 402 |
| 158 | Sodium 1-(5-chloro-2-(2-fluoro-2-methylpropoxy)benzyl)-3-(2-hydroxyethyl)-1H-indole-4-carboxylate | methyl 1-(5-chloro-2-(2-fluoro-2-methylpropoxy)benzyl)-3-formyl-1H-indole-4-carboxylate | 1 | 3.09 | 420 |
| 159 | Sodium 1-(2-((2,4-difluorobenzyl)oxy)-5-fluorobenzyl)-3-(2-hydroxyethyl)-1H-indole-4-carboxylate | methyl 1-(2-(2,4-difluorobenzyloxy)-5-fluorobenzyl)-3-formyl-1H-indole-4-carboxylate | 1 | 3.40 | 456 |
| 160 | Sodium 1-(5-chloro-2-(3-fluoro-2-methylpropoxy)benzyl)-3-(2-hydroxyethyl)-1H-indole-4-carboxylate | methyl 1-(5-chloro-2-(3-fluoro-2-methylpropoxy)benzyl)-3-formyl-1H-indole-4-carboxylate | 1 | | |

Example 161

Synthesis of sodium (E)-3-(2-carboxylatovinyl)-1-(5-chloro-2-((4-chloro-2-fluorobenzyl)oxy)benzyl)-1H-indole-4-carboxylate a) To a suspension of NaH 60% in mineral oil (19 mg, 0.46 mmol) in 2 mL of DMF under argon and cooled at 0° C. (E)-methyl 3-(3-ethoxy-3-oxoprop-1-en-1-yl)-1H-indole-4-carboxylate (120 mg, 0.44 mmol) was added as a solution in 2 mL of DMF. The resulting solution was stirred at 0° C. for 15 minutes. Then, a solution of 2-(bromomethyl)-4-chloro-1-((4-chloro-2-fluorobenzyl)oxy)benzene (176 mg, 0.48 mmol) in 2 mL of DMF was added dropwise. Reaction was stirred at 0° C. for 3 h. Reaction was quenched with water, extracted with EtAcO and the combined organic extracts were washed with brine, dried over anhydrous $Na_2SO_4$, filtered and the solvent evaporated. The crude was purified by column chromatography over silica gel, eluting with mixtures cyclohexane/EtAcO to yield (E)-methyl 1-(5-chloro-2-((4-chloro-2-fluorobenzyl)oxy)benzyl)-3-(3-ethoxy-3-oxoprop-1-en-1-yl)-1H-indole-4-carboxylate (230 mg, 94%).

b) To a suspension of (E)-methyl 1-(5-chloro-2-((4-chloro-2-fluorobenzyl)oxy)benzyl)-3-(3-ethoxy-3-oxoprop-1-en-1-yl)-1H-indole-4-carboxylate (150 mg, 0.27 mmol) in 4 mL of absolute EtOH, 0.28 mL (0.56 mmol) of an aqueous solution of NaOH 2M was added. The mixture was heated at 80° C. overnight. It was allowed to cool to room temperature. A white solid appeared. It was filtered and washed with cold water. The title compound was obtained (143 mg, 93%).

LC-MS: $t_R$=3.28; $[M+H]^+$=514 (Method 1)

Example 162

Using (E)-methyl 3-(3-ethoxy-3-oxoprop-1-en-1-yl)-1H-indole-4-carboxylate as Starting Material The next compound was obtained using the same methodology as in Example 161 with (E)-methyl 3-(3-ethoxy-3-oxoprop-1-en-1-yl)-1H-indole-4-carboxylate but using the compound II indicated.

| Example | Compound name | Starting compound II | Method | LC-MS $t_R$ (min) | m/z $[M + H]^+$ |
|---|---|---|---|---|---|
| 162 | Sodium (E)-3-(2-carboxylatovinyl)-1-(5-chloro-2-((2,4-difluorobenzyl)oxy)benzyl)-1H-indole-4-carboxylate | 2-(bromomethyl)-4-chloro-1-((2,4-difluorobenzyl)oxy)benzene | 1 | 3.16 | 498 |

Example 163

Synthesis of sodium 1-(5-chloro-2-((2,4-difluorobenzyl)oxy)benzyl)-1H-pyrrolo[2,3-c]pyridine-4-carboxylate a) To a suspension of NaH 60% (19 mg, 0.47 mmol) in dry DMF (1 mL) at 0° C. was added dropwise a solution of 1H-pyrrolo[2,3-c]pyridine-4-carbonitrile (67 mg, 0.45 mmol) in DMF (1 mL). After 10 min a solution of 2-(bromomethyl)-4-chloro-1-((2,4-difluorobenzyl)oxy)benzene (162 mg, 0.47 mmol) in 1 mL of DMF was added dropwise. After 16 h at 0° C. water was added and extracted with EtAcO (×3). Combined organic extracts were washed with water, brine and dried over $Na_2SO_4$. Column chromatography on silica gel eluting with DCM:MeOH (95:5) gave the desired compound as a slightly brown solid (159 mg, 87% yield).

$^1$H NMR (400 MHz, CDCl3) δ 8.83 (s, 1H), 8.55 (s, 1H), 7.37 (d, J=3.1 Hz, 1H), 7.29 (dd, J=8.8, 2.6 Hz, 1H), 7.22-7.14 (m, 1H), 6.99 (d, J=2.6 Hz, 1H), 6.94 (d, J=8.8 Hz, 1H), 6.90-6.82 (m, 2H), 6.70 (dd, J=3.1, 0.8 Hz, 1H), 5.37 (s, 2H), 5.04 (s, 2H).

b) To a suspension of 1-(5-chloro-2-((2,4-difluorobenzyl)oxy)benzyl)-1H-pyrrolo[2,3-c]pyridine-4-carbonitrile (148 mg, 0.36 mmol) in EtOH (3 mL), a solution of NaOH (144 mg, 3.61 mmol) in $H_2O$ (0.75 mL) was added at room temperature. The mixture was stirred at 90° C. overnight. It was cooled and the mixture was acidified with HCl 1 M. Water and EtAcO were added and the aqueous phase was extracted with EtAcO (×3). The combined organic phases were washed with brine and dried with $Na_2SO_4$. The crude product was purified by $SiO_2$ column chromatography, eluting with a gradient of DCM:MeOH (9.5-0.5 to 9-1). Title compound was obtained as a white powder (90 mg, 58% yield).

$^1$H NMR (300 MHz, DMSO) δ 8.95 (s, 1H), 8.68 (s, 1H), 7.67 (d, J=3.0 Hz, 1H), 7.55 (dd, J=15.3, 8.5 Hz, 1H), 7.37 (dd, J=8.8, 2.6 Hz, 1H), 7.34-7.25 (m, 1H), 7.22 (d, J=8.9 Hz, 1H), 7.14 (d, J=2.6 Hz, 1H), 7.09 (td, J=8.5, 1.8 Hz, 1H), 6.90 (d, J=2.8 Hz, 1H), 5.49 (s, 2H), 5.17 (s, 2H).

c) t-BuONa (19 mg, 0.2 mmol) was added to a suspension of 1-(5-chloro-2-((2,4-difluorobenzyl)oxy)benzyl)-1H-pyrrolo[2,3-c]pyridine-4-carboxylic acid (87 mg, 0.2 mmol) in MeOH (5 mL) and stirred at room temperature. After 2 h, the solvent was removed out of the clear solution, rendering a slightly yellow solid that was triturated with $Et_2O$ and vacuum dried, affording 81.5 mg of sodium 1-(5-chloro-2-((2,4-difluorobenzyl)oxy)benzyl)-1H-pyrrolo[2,3-c]pyridine-4-carboxylate (89% yield).

$^1$H NMR (400 MHz, DMSO) δ 8.64 (s, 1H), 8.55 (s, 1H), 7.59 (dd, J=15.3, 8.6 Hz, 1H), 7.45 (d, J=3.0 Hz, 1H), 7.38-7.28 (m, 2H), 7.22 (d, J=8.8 Hz, 1H), 7.16-7.05 (m, 2H), 6.91 (d, J=2.6 Hz, 1H), 5.42 (s, 2H), 5.21 (s, 2H).

LC-MS: $t_R$=3.37 [M+H]$^+$=429 (method 1).

Example 164

Using 1H-pyrrolo[2,3-c]pyridine-4-carbonitrile as Starting Material

The next compound was obtained using the same methodology as in Example 163, but starting with 1H-pyrrolo[2,3-c]pyridine-4-carbonitrile and the compound II indicated.

| Example | Compound name | Starting compound II | Method | LC-MS $t_R$ (min) | m/z $[M + H]^+$ |
|---|---|---|---|---|---|
| 164 | Sodium 1-(5-chloro-2-((4-chloro-2-fluorobenzyl)oxy)benzyl)-1H-pyrrolo[2,3-c]pyridine-4-carboxylate | 2-(bromomethyl)-4-chloro-1-((4-chloro-2-fluorobenzyl)oxy)benzene | 1 | 3.45 | 445 |

Example 165

Synthesis of sodium 1-(5-chloro-2-((2,4-difluorobenzyl)oxy)benzyl)indoline-4-carboxylate a) To a suspension of $K_2CO_3$ (176 mg, 1.27 mmol) and methyl indoline-4-carboxylate (215 mg, 1.21 mmol) in dry DMF (3 mL) at 0° C. was added 2-(bromomethyl)-4-chloro-1-((2,4-difluorobenzyl)oxy)benzene (443 mg, 1.27 mmol) in DMF (3 mL). The reaction was stirred at RT overnight and then the solution was poured onto crushed ice and extracted with EtAcO (×2). Combined organic extracts were washed with water, brine and dried over $Na_2SO_4$. Column chromatography on silica gel eluting with hexane:EtAcO gave the desired compound as a white solid. (430 mg, 80% yield).

$^1$H NMR (400 MHz, Chloroform-d) δ 7.39 (td, J=8.6, 6.3 Hz, 1H), 7.28 (dd, J=15.4, 1.8 Hz, 1H), 7.21 (dd, J=8.6, 2.7 Hz, 1H), 7.04 (t, J=7.8 Hz, 1H), 6.90 (d, J=8.7 Hz, 1H), 6.89-6.79 (m, 2H), 6.49 (dd, J=7.8, 1.0 Hz, 1H), 5.08 (s, 2H), 4.25 (s, 2H), 3.88 (s, 3H), 3.50-3.41 (m, 2H), 3.41-3.32 (m, 2H).

b) To a solution of methyl 1-(5-chloro-2-((2,4-difluorobenzyl)oxy)benzyl)indoline-4-carboxylate (400 mg, 0.9 mmol) in EtOH (8 mL), a solution of NaOH (108 mg, 2.7 mmol) in H$_2$O (2 mL) was added at room temperature. The mixture was stirred at 80° C. overnight. It was cooled and water was added. The aqueous layer was extracted with EtAcO (×3). The combined organic layers were washed with brine dried (Na$_2$SO$_4$) filtered and concentrated. (380 mg, 93% yield).

LC-MS: t$_R$=3.79 [M+H]$^+$=430 (method 1).

$^1$H NMR (400 MHz, DMSO) δ 7.63 (dd, J=15.3, 8.6 Hz, 1H), 7.35-7.27 (m, 3H), 7.20 (d, J=8.6 Hz, 1H), 7.10 (td, J=8.5, 1.7 Hz, 1H), 7.04 (dd, J=7.7, 0.9 Hz, 1H), 6.81 (t, J=7.7 Hz, 1H), 6.27 (d, J=7.0 Hz, 1H), 5.17 (s, 2H), 4.15 (s, 2H), 3.24-3.17 (m, 4H).

Examples 166 to 171

Using methyl indoline-4-carboxylate as Starting Material

The next compounds were obtained using the same methodology as in example 165 but using the compound II indicated.

| | | | | LC-MS | |
| --- | --- | --- | --- | --- | --- |
| Example | Compound name | Starting compound II | Method | t$_R$ (min) | m/z [M + H]$^+$ |
| 166 | Sodium 1-(5-chloro-2-(2-fluoro-2-methyl-propoxy)benzyl)indoline-4-carboxylate | 2-(bromomethyl)-4-chloro-1-(2-fluoro-2-methyl-propoxy)benzene | 1 | 3.45 | 378 |
| 167 | Sodium 1-(5-chloro-2-((4-chloro-2-fluoro-benzyl)oxy)benzyl)indoline-4-carboxylate | 2-(bromomethyl)-4-chloro-1-((4-chloro-2-fluoro-benzyl)oxy)benzene | 1 | 3.92 | 446 |
| 168 | Sodium 1-(2-((2-chloro-4-fluorobenzyl)oxy)-5-fluorobenzyl)indoline-4-carboxylate | 2-(bromomethyl)-1-((2-chloro-4-fluorobenzyl)oxy)-4-fluorobenzene | 1 | 3.72 | 430 |
| 169 | Sodium 1-(5-chloro-2-isobutoxybenzyl)indoline-4-carboxylate | 2-(bromomethyl)-4-chloro-1-isobutoxybenzene | 1 | 3.70 | 360 |
| 170 | Sodium 1-(5-fluoro-2-isobutoxybenzyl)indoline-4-carboxylate | 2-(bromomethyl)-4-fluoro-1-iso-butoxybenzene | 1 | 3.56 | 344 |
| 171 | Sodium 1-(5-chloro-2-cyclobutoxybenzyl)indoline-4-carboxylate | 2-(bromomethyl)-4-chloro-1-cyclobutoxy-benzene | 1 | 3.64 | 358 |

Examples 172 to 182

Using methyl 1,2,3,4-tetrahydroquinoline-5-carboxylate as Starting Material

The next compounds were obtained using the same methodology as in Example 165 but using methyl 1,2,3,4-tetrahydroquinoline-5-carboxylate as starting material and the compound II indicated. In the preparation of compounds 175 to 182 1 equivalent of KI was added to the reaction mixture in step a)

| | | | | LC-MS | |
| --- | --- | --- | --- | --- | --- |
| Example | Compound name | Starting compound II | Method | t$_R$ (min) | m/z [M + H]$^+$ |
| 172 | Sodium 1-(2-((2,4-difluorobenzyl)oxy)benzyl-1,2,3,4-tetrahydroquinoline-5-carboxylate | 1-((2-(bromomethyl)phenoxy)methyl)-2,4-difluorobenzene | 1 | 3.62 | 410 |
| 173 | Sodium 1-(5-chloro-2-((2,4-difluorobenzyl)oxy)benzyl-1,2,3,4-tetrahydroquinoline-5-carboxylate | 2-(bromomethyl)-4-chloro-1-((2,4-difluoro-benzyl)oxy)benzene | 1 | 3.73 | 444 |

| Example | Compound name | Starting compound II | Method | LC-MS $t_R$ (min) | m/z $[M + H]^+$ |
|---|---|---|---|---|---|
| 174 | Sodium 1-(5-chloro-2-(cyclobutylmethoxy)benzyl)-1,2,3,4-tetrahydroquinoline-5-carboxylate | 2-(bromomethyl)-4-chloro-1-(cyclobutylmethoxy)benzene | 4 | 2.10 | 386 |
| 175 | Sodium 1-(5-chloro-2-isobutoxybenzyl)-1,2,3,4-tetrahydroquinoline-5-carboxylate | 2-(bromomethyl)-4-chloro-1-isobutoxybenzene | 2 | 19.06 | 374 |
| 176 | Sodium 1-[5-chloro-2-(1,2-dimethylpropoxy)benzyl]-1,2,3,4-tetrahydroquinoline-5-carboxylate | 2-(bromomethyl)-4-chloro-1-(1,2-dimethylpropoxy)benzene | 2 | 19.52 | 388 |
| 177 | Sodium 1-[5-chloro-2-(2-fluoro-2-methylpropoxy)benzyl]-1,2,3,4-tetrahydroquinoline-5-carboxylate | 2-(bromomethyl)-4-chloro-1-(2-fluoro-2-methylpropoxy)benzene | 2 | 17.09 | 392 |
| 178 | Sodium 1-[5-chloro-2-(cyclobutyloxy)benzyl]-1,2,3,4-tetrahydroquinoline-5-carboxylate | 2-(bromomethyl)-4-chloro-1-(cyclobutyloxy)benzene | 2 | 18.36 | 372 |
| 179 | Sodium 1-{5-chloro-2-[(2-methylprop-2-enyl)oxy]benzyl}-1,2,3,4-tetrahydroquinoline-5-carboxylate | 2-(bromomethyl)-4-chloro-1-[(2-methylprop-2-enyl)oxy]benzene | 2 | 18.02 | 372 |
| 180 | Sodium 1-[5-chloro-2-(3-fluoro-2-methylpropoxy)benzyl]-1,2,3,4-tetrahydroquinoline-5-carboxylate | 2-(bromomethyl)-4-chloro-1-(3-fluoro-2-methylpropoxy)benzene | 2 | 17.46 | 392 |
| 181 | Sodium 1-[5-chloro-2-(2-fluoropropoxy)benzyl]-1,2,3,4-tetrahydroquinoline-5-carboxylate | 2-(bromomethyl)-4-chloro-1-(2-fluoropropoxy)benzene | 2 | 16.25 | 378 |
| 182 | Sodium 1-(5-chloro-2-{[2-(fluoromethyl)prop-2-enyl]oxy}benzyl)-1,2,3,4-tetrahydroquinoline-5-carboxylate | 2-(bromomethyl)-4-chloro-1-{[2-(fluoromethyl)prop-2-enyl]oxy}benzene | 2 | 17.02 | 390 |

Example 183

Synthesis of sodium 1-(5-chloro-2-((4-chloro-2-fluorobenzyl)oxy)benzyl)-1,2,3,4-tetrahydroquinoline-5-sulfonate To a suspension of $K_2CO_3$ (176 mg, 1.28 mmol) and sodium 1,2,3,4-tetrahydroquinoline-5-sulfonate (100 mg, 0.43 mmol) in dry DMF (4 mL) at RT was added 2-(bromomethyl)-4-chloro-1-((4-chloro-2-fluorobenzyl)oxy)benzene (186 mg, 0.51 mmol). The reaction was stirred at RT overnight. Water was added and the solution extracted with EtAcO (×3). Combined organic extracts were concentrated. Column chromatography on C18 column eluting with AcN:Water (2% of AcN to 95% in 10 min) gave the desired compound as a sligthly brown solid.

LC-MS: $t_R$=3.95 [M+H]$^+$=496 (method 1).

$^1$H NMR (400 MHz, Methanol-d4) δ 7.53 (t, J=8.2 Hz, 1H), 7.30-7.17 (m, 4H), 7.08 (d, J=8.7 Hz, 1H), 7.04 (d, J=2.5 Hz, 1H), 6.88 (t, J=8.0 Hz, 1H), 6.36 (dd, J=8.4, 1.1 Hz, 1H), 5.19 (s, 2H), 4.43 (s, 2H), 3.38 (t, 21-f), 3.31 (t, 2H), 2.01 (q, J=8.7, 5.9 Hz, 2H).

Examples 184 to 185

Using sodium 1,2,3,4-tetrahydroquinoline-5-sulfonate as Starting Material

The next compounds were obtained using the same methodology as in Example 183 but using the compound II indicated.

| Example | Compound name | Starting compound II | Method | LC-MS $t_R$ (min) | m/z $[M + H]^+$ |
|---|---|---|---|---|---|
| 184 | Sodium 1-(5-chloro-2-((2,4-difluorobenzyl)oxy)benzyl)-1,2,3,4-tetrahydroquinoline-5-sulfonate | 2-(bromomethyl)-4-chloro-1-((2,4-difluorobenzyl)oxy)benzene | 1 | 3.81 | 480 |
| 185 | Sodium 1-(2-((4-chloro-2-fluorobenzyl)oxy)benzyl)-1,2,3,4-tetrahydroquinoline-5-sulfonate | 1-((2-(bromomethyl)phenoxy)methyl)-4-chloro-2-fluorobenzene | 1 | 3.85 | 462 |

Examples 186 to 187

Using N-((1,2,3,4-tetrahydroquinolin-5-yl)sulfonyl)acetamide as Starting Material The next compounds were obtained using the same methodology as in the Example 183 but using N-((1,2,3,4-tetrahydroquinolin-5-yl)sulfonyl)acetamide and the compound II indicated as starting materials.

| Example | Compound name | Starting compound II | Method | LC-MS $t_R$ (min) | m/z $[M + H]^+$ |
|---|---|---|---|---|---|
| 186 | N-((1-(5-chloro-2-((2,4-difluorobenzyl)oxy)benzyl)-1,2,3,4-tetrahydroquinolin-5-yl)sulfonyl)acetamide | 2-(bromomethyl)-4-chloro-1-((2,4-difluorobenzyl)oxy)benzene | 1 | 3.76 | 521 |
| 187 | N-((1-(5-chloro-2-((4-chloro-2-fluorobenzyl)oxy)benzyl)-1,2,3,4-tetrahydroquinolin-5-yl)sulfonyl)acetamide | 2-(bromomethyl)-4-chloro-1-((4-chloro-2-fluoro-benzyl)oxy)benzene | 1 | 3.92 | 537 |

Example 188

Synthesis of sodium 1-(5-chloro-2-((4-chloro-2-fluorobenzyl)oxy)benzyl)-3-(hydroxymethyl)-1H-indazole-4-carboxylate a) To a solution of methyl 3-formyl-1H-indazole-4-carboxylate (76 mg, 0.4 mmol) in 4.5 mL of DMF at 0° C. NaH 60% in mineral oil (16 mg, 0.4 mmol) and 2-(bromomethyl)-4-chloro-1-((4-chloro-2-fluorobenzyl)oxy)benzene (135 mg, 0.4 mmol) were added. Reaction was stirred at room temperature for 30 min. Then, water was added. The resulting mixture was extracted with EtAcO (×3) and the combined organic layers were washed with a saturated solution of $NH_4Cl$ and brine and dried over $MgSO_4$. After evaporating the solvent the crude was purified by column chromatography over silica gel eluting with mixtures cyclohexane/EtAcO 9:1 to 6:4. Methyl 1-(5-chloro-2-((4-chloro-2-fluorobenzyl)oxy)benzyl)-3-formyl-1H-indazole-4-carboxylate was obtained (76 mg, 42%).

b) To a solution of methyl 1-(5-chloro-2-((4-chloro-2-fluorobenzyl)oxy)benzyl)-3-formyl-1H-indazole-4-carboxylate (76 mg, 0.2 mmol) in 3 mL of THF cooled at 0° C. $NaBH_4$ (12 mg, 0.3 mmol) was added. After 1 h water was added and the resulting mixture was extracted with EtAcO. The combined organic phases were washed with brine, dried over $MgSO_4$. After evaporating the solvent methyl 1-(5-chloro-2-((4-chloro-2-fluorobenzyl)oxy)benzyl)-3-(hydroxymethyl)-1H-indazole-4-carboxylate was added (60 mg, 79%).

c) To a solution of methyl 1-(5-chloro-2-((4-chloro-2-fluorobenzyl)oxy)benzyl)-3-(hydroxymethyl)-1H-indazole-4-carboxylate (60 mg, 0.1 mmol) in absolute EtOH (2.5 mL) an aqueous solution of NaOH 2M was added (0.15 mL, 0.3 mmol). The mixture was stirred at 80° C. for 1 h, then, it was allowed to cool to room temperature. Water was added and the result in mixture was extracted with EtAcO and the organic layers washed with water and dried over $MgSO_4$. After removing the solvent sodium 1-(5-chloro-2-((4-chloro-2-fluorobenzyl)oxy)benzyl)-3-(hydroxymethyl)-1H-indazole-4-carboxylate was obtained (42 mg, 69%). $t_R$=3.60 min, m/z $(M+H)^+$=475.

Example 189

Synthesis of sodium 1-(5-chloro-2-(2-fluoro-2-methylpropoxy)benzyl)-3-(hydroxymethyl)-1H-indazole-4-carboxylate This compound was synthesized using the same methodology as compound 188 using 2-(bromomethyl)-4-chloro-1-(2-fluoro-(2-methylpropyl)oxy)benzene. $t_R$=3.23 min, m/z $(M+H)^+$=407.

Example 190

Synthesis of sodium 1-(5-chloro-2-(propoxy)benzyl)-1,2,3,4-tetrahydroquinoline-5-carboxylate a) To a suspension of methyl 1,2,3,4-tetrahydroquinoline-5-carboxylate hydrochloride (172 mg, 0.75 mmol) in dry THF (5 mL), was added dropwise a solution of 5-chloro-2-propoxybenzaldehyde (150 mg, 0.75 mmol) in THF (3 mL) and AcOH (2 drops). The reaction mixture was stirred at room temperature overnight. At 0° C., NaBH(AcO)$_3$ was added portion wise and the reaction mixture was stirred at room temperature overnight. The solvent was evaporated to dryness, the residue was diluted with H$_2$O and extracted with EtAcO thrice. The combined organic phases were dried over anhydrous Na$_2$SO$_4$, filtered and concentrated. The crude residue was chromatographed on a silica gel flash system (Biotage SP1) using hexanes/EtAcO mixtures of increasing polarity as eluent to afford 94 mg of the desired product (33.3. % yield).

LC-MS (method 4): $t_R$=3.43 min; m/z=374 (MH$^+$).

b) Following a similar procedure to that described in example 123 (section b), but using the compound obtained in previous section as starting material, the desired compound was obtained.

LC-MS (method 4): $t_R$=1.89 [M+H]$^+$=360 (Method 4)

$^1$H NMR (300 MHz, DMSO-d6) δ 7.32-7.25 (m, 1H, ArH); 7.11-6.98 (m, 2H, ArH); 6.75 (t, J=7.7 Hz, 1H, ArH); 6.54 (d, J=6.5 Hz, 1H, ArH); 6.07 (d, J=7.3 Hz, 1H, ArH); 4.39 (s, 2H); 4.05 (t, J=6.4 Hz, 2H); 3.42-3.29 (m, 2H); 2.95 (t, J=6.2 Hz, 2H); 1.97-1.87 (m, 2H); 1.86-1.75 (m, 2H); 1.07 (t, J=7.3, 3H).

Examples 191 to 193

Using methyl 1,2,3,4-tetrahydroquinoline-5-carboxylate hydrochloride as Starting Material The next compounds were obtained using the same methodology as in Example 190 but using the corresponding aldehyde specified as starting materials.

| Example | Compound name | Starting aldehyde | Method | LC-MS $t_R$ (min) | m/z [M + H]$^+$ |
|---|---|---|---|---|---|
| 191 | Sodium 1-(5-chloro-2-(cyclopentyloxy)benzyl)-1,2,3,4-tetrahydroquinoline-5-carboxylate | 5-chloro-2-(cyclopentyloxy)benzaldehyde | 4 | 2.03 | 385 |
| 192 | Sodium 1-(2-(4-chloro-2-fluorobenzyloxy)-5-methylbenzyl)-1,2,3,4-tetrahydroquinoline-5-carboxylate | 2-(4-chloro-2-fluorobenzyloxy)-5-methylbenzaldehyde | 4 | 2.14 | 440 |
| 193 | Sodium 1-(5-chloro-2-(neopentyloxy)benzyl)-1,2,3,4-tetrahydroquinoline-5-carboxylate | 5-chloro-2-(neopentyloxy)benzaldehyde | 4 | 2.13 | 388 |

Examples 194 to 199

Using methyl 3,4-dihydro-2H-benzo[b][1,4]oxazine-8-carboxylate as Starting Material The following compounds were prepared using the same methodology as in Example 190 using methyl 3,4-dihydro-2H-benzo[b][1,4]oxazine-8-carboxylate and the corresponding aldehyde specified as starting materials.

| Example | Compound name | Starting aldehyde | Method | LC-MS $t_R$ (min) | m/z [M + H]$^+$ |
|---|---|---|---|---|---|
| 194 | Sodium 4-(2-(4-chloro-2-fluorobenzyloxy)-5-methylbenzyl)-3,4-dihydro-2H-benzo[b][1,4]oxazine-8-carboxylate | 2-(4-chloro-2-fluorobenzyloxy)-5-methylbenzaldehyde | 4 | 2.03 | 442 |

-continued

| Example | Compound name | Starting aldehyde | LC-MS Method | $t_R$ (min) | m/z [M + H]$^+$ |
|---|---|---|---|---|---|
| 195 | Sodium 4-(5-fluoro-2-isobutoxybenzyl)-3,4-dihydro-2H-benzo[b][1,4]oxazine-8-carboxylate | 5-fluoro-2-isobutoxybenzaldehyde | 4 | 1.79 | 360 |
| 196 | Sodium 4-(5-chloro-2-isobutoxybenzyl)-3,4-dihydro-2H-benzo[b][1,4]oxazine-8-carboxylate | 5-chloro-2-isobutoxybenzaldehyde | 4 | 1.86 | 376 |
| 197 | Sodium 4-(5-chloro-2-cyclobutoxybenzyl)-3,4-dihydro-2H-benzo[b][1,4]oxazine-8-carboxylate | 5-chloro-2-cyclobutoxybenzaldehyde | 4 | 1.83 | 374 |
| 198 | Sodium 4-(5-chloro-2-(cyclopropylmethoxy)benzyl)-3,4-dihydro-2H-benzo[b][1,4]oxazine-8-carboxylate | 5-chloro-2-(cyclopropylmethoxy)benzaldehyde | 4 | 1.79 | 374 |
| 199 | Sodium 4-(5-chloro-2-(neopentyloxy)benzyl)-3,4-dihydro-2H-benzo[b][1,4]oxazine-8-carboxylate | 5-chloro-2-(neopentyloxy)benzaldehyde | 4 | 2.01 | 390 |

Example 200

Synthesis of sodium 1-(5-chloro-2-(3-methoxypropoxy)benzyl)indoline-4-carboxylate a) Following a similar procedure to that described in example 190 (step a), but starting from methyl indoline-4-carboxylate instead of methyl 1,2,3,4-tetrahydroquinoline-5-carboxylate hydrochloride and 5-chloro-2-hydroxybenzaldehyde instead of 5-chloro-2-propoxybenzaldehyde, methyl 1-(5-chloro-2-hydroxybenzyl)-1H-indole-4-carboxylate was obtained (83% yield)

LC-MS (method 4): $t_R$=2.58 min; m/z=318 (MH$^+$).

b) To a solution of the compound obtained in the previous section (250 mg, 0.78 mmol) in DMF (10 mL), potassium carbonate (217 mg, 1.57 mmol) and 1-bromo-3-methoxypropane (181 mg, 1.18 mmol) were added. The reaction mixture was stirred at 60° C. overnight. The reaction mixture was diluted by adding EtAcO and saturated NH$_4$Cl aqueous solution (15 mL) and extracted with EtAcO (3×15 mL). The combined organic phases were dried over anhydrous Na$_2$SO$_4$, filtered and concentrated. The crude residue was chromatographed on a silica gel flash system (Biotage SP1) using hexanes/EtAcO mixtures of increasing polarity as eluent, to afford the desired product in quantitative yield.

LC-MS (method 4): $t_R$=3.09 [M+H]$^+$=390 c) Following a similar procedure to that described in example 123 (section b), but using the compound obtained in previous section as starting material, the desired compound was obtained LC-MS (method 4): $t_R$=1.72 [M+H]$^+$=376

$^1$H NMR (300 MHz, DMSO-d6) δ 7.31-7.23 (m, 2H, ArH); 7.1-6.99 (m, 2H, ArH); 6.87 (t, J=7.68 Hz, 1H, ArH); 6.36 (d, J=7.5 Hz, 1H, ArH); 4.17 (s, 2H); 4.05 (t, J=6.15 Hz, 2H); 3.47 (t, J=6.2 Hz, 2H); 3.4-3.31 (m, 2H); 3.26-3.22 (m, 2H); 3.21 (s, 3H); 2.01-1.88 (m, 2H).

Examples 201 to 206

Using methyl indoline-4-carboxylate as Starting Material

The next compounds were obtained using the same methodology as in example 200, but using in each case the corresponding starting materials:

| Example | Compound name | Starting material (step b) | LC-MS Method | $t_R$ (min) | m/z [M + H]$^+$ |
|---|---|---|---|---|---|
| 201 | Sodium 1-(5-chloro-2-(2-methoxyethoxy)benzyl)indoline-4-carboxylate | 1-bromo-2-methoxyethane | 4 | 1.59 | 362 |
| 202 | Sodium 1-(5-chloro-2-(cyclopropylmethoxy)benzyl)indoline-4-carboxylate | 1.(bromomethyl)cyclopropane | 2. | 3.91 | 4.58 |

-continued

| Example | Compound name | Starting material (step b) | Method | LC-MS $t_R$ (min) | m/z $[M + H]^+$ |
|---------|---------------|----------------------------|--------|-------------------|------------------|
| 203 | Sodium 1-(5-chloro-2-(neo-pentyloxy)benzyl)indoline-4-carboxylate | 1-iodo-2,2-dimethylpropane | 4 | 2.19 | 374 |
| 204 | Sodium 1-(5-chloro-2-((3-methyloxetan-3-yl)methoxy)benzyl)indoline-4-carboxylate | (3-methyloxetan-3-yl)methyl trifluoromethane-sulfonate | 4 | 1.68 | 388 |
| 205 | Sodium 1-(5-chloro-2-((3-ethyloxetan-3-yl)methoxy)benzyl)indoline-4-carboxylate | (3-ethyloxetan-3-yl)methyl trifluoromethane-sulfonate | 4 | 1.80 | 402 |
| 206 | Sodium (S)-1-(5-chloro-2-(3-hydroxy-2-methylpropoxy)benzyl)indoline-4-carboxylate | (S)-3-bromo-2-methylpropan-1-ol | 4 | 1.61 | 376 |

Example 207

Sodium 1-(5-chloro-2-(4-chloro-2-fluorobenzyloxy)benzyl)-3-(methoxymethyl)-1H-indole-4-carboxylate a) To a suspension of 1-(5-chloro-2-((4-chloro-2-fluorobenzyl)oxy)benzyl)-3-(hydroxymethyl)-1H-indole-4-carboxylic acid, obtained as in example 141 but extracting with EOAc at pH=2, (855 mg, 1.8 mmol) in THF (10 mL) at 0° C., NaH 55% (236 mg, 5.41 mmol) and MeI (0.45 mL, 7.21 mmol) were added. The resulting mixture was stirred at room temperature overnight and concentrated to dryness. It was cooled to 0° C., 2M aqueous HCl solution was added up to pH=2 and it was extracted 3 times with DCM. The combined organic phases were dried over $Na_2SO_4$ and concentrated to dryness. The crude residue was washed successively with EtAcO and DCM 236 mg (25.8% yield) of the desired compound were obtained.

LC-MS (method 4): $t_R$=2.05 [M+H]$^-$=486 b) Following a similar procedure to that described in example 123 (section b), but using the compound obtained in previous section as starting material, the desired compound was obtained (quantitative yield).

LC-MS (method 4): $t_R$=2.05 [M+H]$^-$=486
$^1$H NMR (300 MHz, DMSO-d6) δ 7.72-7.55 (m, 2H, ArH); 7.47-7.11 (m, 6H, ArH); 7.04-6.89 (m, 1H, ArH); 6.85-6.74 (m, 1H, ArH); 5.4-5.22 (m, 4H); 4.88-4.78 (m, 2H); 3.31 (s, 3H).

Example 208

Synthesis of sodium 1-(5-chloro-2-(4-chloro-2-fluorobenzyloxy)benzyl)-2-oxoindoline-4-carboxylate a) To a suspension of methyl 1-(5-chloro-2-(4-chloro-2-fluorobenzyloxy)benzyl)-1H-indole-4-carboxylate, obtained in example 48 section a, (785 mg, 1.7 mmol) in DCM (15 mL), N-chlorosuccinimide (240 mg, 1.79 mmol) was added. The resulting mixture was stirred at room temperature for 2 h, then concentrated to dryness. The resulting foamy residue was dissolved in acetic acid (7 mL) and the reaction mixture was heated at 70° C. 85% $H_3PO_4$ (197 mg, 1.71 mmol) was added and the reaction mixture was refluxed for 1 h. The reaction mixture was cooled to room temperature, poured into ice water, basified to pH=11 with $Na_2CO_3$ and extracted with EtAcO (×3). The combined organic phases were dried over $Na_2SO_4$ and concentrated to dryness. The crude residue was chromatographed on a silica gel flash system (Biotage SP1) using hexanes/EtAcO mixtures of increasing polarity as eluent. An abundant white solid appeared during the fraction collection that it was filtered and washed with and diethyl ether to afford 230 mg (28.31% yield) of the desired compound.

LC-MS (method 4): $t_R$=2.99 [M+H]$^+$=474 b) Following a similar procedure to that described in example 123 (section b), but using the compound obtained in previous section as starting material, the desired compound was obtained (93% yield).

LC-MS (method 4): $t_R$=1.94 [M+H]$^+$=460
$^1$H NMR (300 MHz, DMSO-d6) δ 7.77-7.49 (m, 3H, ArH); 7.46-7.25 (m, 3H, ArH); 7.16-7.01 (m, 2H, ArH); 6.64 (d, J=7.6 Hz, 1H, ArH); 5.31 (s, 2H); 4.84 (s, 2H); 3.89 (s, 2H).

Example 209

Synthesis of sodium 1-(2-(4-chloro-2-fluorobenzyloxy)-5-cyclopropylbenzyl)-1H-indazole-4-carboxylate a) To a suspension of methyl 1-(5-bromo-2-(4-chloro-2-fluorobenzyloxy)benzyl)-1H-indazole-4-carboxylate, obtained in example 136, section a, (197 mg, 0.39 mmol) in THF (15 mL), $K_3PO_4$ (166 mg, 0.78 mmol), X-Phos (37 mg, 0.078 mmol), Pd(AcO)$_2$ (8.8 mg, 0.04 mmol) and cyclopropylboronic acid (40 mg, 0.47 mmol) were added. The reaction mixture was refluxed overnight. The crude reaction was filtered through a plug of Celite®, and evaporated to dryness. The crude product was diluted with saturated NaCl aqueous solution (10 mL) and extracted with EtAcO (3×15 mL). The combined organic phases were dried over anhydrous $Na_2SO_4$, filtered and concentrated. The crude residue was cromatographed on a silica gel flash system (SP1 Biotage) using EtAcO/hexanes mixtures of increasing polarity as eluent to afford 70 mg (38.5% yield) of the desired compound.

LC-MS (method 4): $t_R$=3.24 [M+H]$^+$=465 b) Following a similar procedure to that described in example 123 (section b), but using the compound obtained in previous section as starting material, the desired compound was obtained (8.65% yield).

LC-MS (method 4): $t_R$=2.02 [M+H]$^-$=449

$^1$H NMR (300 MHz, DMSO-d6) δ 7.73 (d, J=7 Hz, 1H, ArH); 7.49 (d, J=8.5 Hz, 1H, ArH); 7.22-6.99 (m, 3H, ArH); 6.94-6.8 (m, 3H, ArH); 6.7-6.65 (m, 1H, ArH); 5.48 (s, 2H); 4.94 (s, 2H); 1.52 (m, 1H); 1.34-1.06 (m, 4H).

Example 210

Synthesis of sodium (S)-1-(5-chloro-2-(3-hydroxy-2-methylpropoxy)benzyl)indoline-4-carboxylate a) To a suspension of (S)-methyl 1-(5-chloro-2-(3-hydroxy-2-methylpropoxy)benzyl)indoline-4-carboxylate, obtained as in example 206 (360 mg, 0.9 mmol) in THF (15 mL) at 0° C., NaH 55% (55 mg, 1.38 mmol) and MeI (0.07 mL, 1.1 mmol) were added. The resulting mixture was stirred at room temperature overnight and concentrated to dryness. It was cooled to 0° C., 2M aqueous HCl solution was added up to pH=2 and it was extracted 3 times with EtAcO. The combined organic phases were dried over MgSO$_4$ and concentrated to dryness. The residue was purified by reverse phase chromatography, 24 mg (7% yield) of 1-(5-chloro-2-(4-chloro-2-fluorobenzyloxy)benzyl)-3-(methoxymethyl)-1H-indole-4-carboxylic acid was obtained.

LC-MS (method 4): $t_R$=1.89 [M+H]$^+$=390 b) Following a similar procedure to that described in example 123 (section b), but using the compound obtained in previous section as starting material, the desired compound was obtained (97% Yield).

LC-MS (method 4): $t_R$=1.89 [M+H]$^-$=390

$^1$H NMR (300 MHz, DMSO-d6) δ 7.3-7.22 (m, 2H, ArH); 7.1-6.98 (m, 2H, ArH); 6.87 (t, J=7.65 Hz, 1H, ArH); 6.36 (d, J=7.5 Hz, 1H, ArH); 3.98-3.84 (m, 2H); 3.47-3.24 (m, 6H); 3.21 (s, 3H); 2.24-1.99 (m, 1H); 0.99 (d, J=6.9 Hz, 3H).

Example 211

Synthesis of sodium 1-{5-chloro-2-[(4-chloro-2-ethylbenzyl)oxy]benzyl}-1H-indole-4-carboxylate a) A mixture of methyl 1-(5-chloro-2-hydroxybenzyl)-1H-indole-4-carboxylate (0.20 g, 0.63 mmol), K$_2$CO$_3$ (0.13 g, 0.95 mmol) and 1-(bromomethyl)-4-chloro-2-ethylbenzene (0.18 g, 0.76 mmol) in DMF (8 mL) was stirred at room temperature for 17 h. The reaction mixture was poured over EtAcO (40 mL) and washed with water (2×20 mL); the organic layer was dried over anhydrous Na$_2$SO$_4$ and filtered. After removal of the solvent, the residue was purified by column chromatography on silica gel (10% EtAcO/hexanes), affording 0.20 g of methyl 1-{5-chloro-2-[(4-chloro-2-ethylbenzyl)oxy]benzyl}-1H-indole-4-carboxylate [Rf=0.50 (20% EtAcO/hexanes), white solid, 68% yield].

$^1$H-NMR (CDCl$_3$, 250 MHz, δ): 7.89 (d, J=6.6 Hz, 1H, ArH); 7.40 (d, J=8.3 Hz, 1H, ArH); 7.28-7.09 (m, 7H, ArH); 6.89 (d, J=8.8 Hz, 1H, ArH); 6.74 (d, J=2.4 Hz, 1H, ArH); 5.28 (s, 2H); 5.02 (s, 2H); 3.99 (s, 3H); 2.63 (q, J=7.5 Hz, 2H); 1.22 (t, J=7.5 Hz, 3H).

b) NaOH (aqueous solution 10%, 0.3 mL) was added to a solution of methyl 1-{5-chloro-2-[(4-chloro-2-ethylbenzyl)oxy]benzyl}-1H-indole-4-carboxylate (0.19 g, 0.41 mmol) in EtOH (10 mL) and heated at 80° C. for 2 h. After removal of the volatiles by rotatory evaporation, the resulting residue was dissolved in DCM (20 mL), acidified with HCl (aqueous solution 10%, 5 mL), and washed with water (20 mL). The organic layer was dried over anhydrous Na$_2$SO$_4$ and filtered. After removal of the solvent, the residue was purified by column chromatography on silica gel (5→75% EtAcO/hexanes), affording 0.12 g of 1-{5-chloro-2-[(4-chloro-2-ethylbenzyl)oxy]benzyl}-1H-indole-4-carboxylic acid, white solid, 65% yield.

LC-MS ESI+ m/z: 454 (M+1, 93%) (Method 5).

c) t-BuONa (25 mg, 0.26 mmol) was added to a suspension of 1-{5-chloro-2-[(4-chloro-2-ethylbenzyl)oxy]benzyl}-1H-indole-4-carboxylic acid (11.7 mg, 0.26 mmol) in MeOH (8 mL) and stirred at room temperature. After 1.5 h, the solvent was removed out of the clear solution, rendering a pale yellow solid that was triturated with Et$_2$O (2×5 mL) and vacuum dried, affording 90 mg of sodium 1-{5-chloro-2-[(4-chloro-2-ethylbenzyl)oxy]benzyl}-1H-indole-4-carboxylate, white solid, 74% yield.

LC-MS ESI+ m/z: 454 (M+2-Na, 92%) (Method 2).

$^1$H-NMR (DMSO-d$_6$, 250 MHz, δ): 7.56-7.46 (m, 2H, ArH); 7.39-7.15 (m, 7H, ArH); 6.94 (t, J=7.7 Hz, 1H, ArH); 6.61 (br s, 1H, ArH); 5.32 (s, 2H); 5.20 (s, 2H); 2.72 (q, J=7.3 Hz, 2H); 1.20 (t, J=7.3 Hz, 3H).

Example 212

Synthesis of sodium 1-{5-chloro-2-[(4-chloro-2-fluorobenzyl)oxy]benzyl}-1H-pyrazolo[3,4-b]pyridine-4-carboxylat a) Hydrazine monohydrate (0.78 mL, 15.94 mmol) was added dropwise to a suspension of 2-fluoro-4-iodonicotinaldehyde (2.00 g, 7.97 mmol) in 2-propanol (20 mL) and heated at 60° C. After 2 h, the solvent was removed by rotatory evaporation and the residue dissolved in EtAcO (40 mL) and washed with water (30 mL). The organic layer was dried over anhydrous Na$_2$SO$_4$ and filtered. After removal of the solvent, the residue was purified by column chromatography on silica gel (10→40% EtAcO/hexanes), affording 1.62 g of 4-iodo-1H-pyrazolo[3,4-b]pyridine, [Rf=0.30 (20% EtAcO/hexanes), white solid, 82% yield].

LC-MS ESI+ m/z: 246 (M+1, 99%) (Method 5).

$^1$H-NMR (CDCl$_3$, 250 MHz, δ): 12.45 (br s, 1H); 8.23 (d, J=5.0 Hz, 1H, ArH); 7.98 (s, 1H, ArH); 7.61 (d, J=5.0 Hz, 1H, ArH).

b) Following the general procedure described in example 1, section a, 1-{5-chloro-2-[(4-chloro-2-fluorobenzyl)oxy]benzyl}-4-iodo-1H-pyrazolo[3,4-b]pyridine was obtained in 31% yield (white solid) after 3 h, using 4-iodo-1H-pyrazolo[3,4-b]pyridine (0.17 g, 0.69 mmol), NaH (33 mg, 0.82 mmol) and 2-(bromomethyl)-4-chloro-1-[(4-chloro-2-fluorobenzyl)oxy]benzene (0.30 g, 0.83 mmol) as starting materials.

LC-MS ESI+ m/z: 528 (M+1, 87%) (Method 5).

$^1$H-NMR (CDCl$_3$, 250 MHz, δ): 8.05 (d, J=4.6 Hz, 1H, ArH); 7.90 (s, 1H, ArH); 7.53 (d, J=4.6 Hz, 1H, ArH); 7.36-7.05 (m, 4H, ArH); 6.94 (d, J=2.4 Hz, 1H, ArH); 6.86 (d, J=8.6 Hz, 1H, ArH); 5.69 (s, 2H); 5.04 (s, 2H).

c) A suspension of 1-{5-chloro-2-[(4-chloro-2-fluorobenzyl)oxy]benzyl}-4-iodo-1H-pyrazolo[3,4-b]pyridine (0.30 g, 0.56 mmol), dppf (31 mg, 0.06 mmol) and TEA (0.16 mL, 1.13 mmol) in EtOH (8 mL) was thoroughly purged with argon; Pd(AcO)$_2$ (13 mg, 0.06 mmol) was added and the mixture was purged again with carbon monoxide. The reaction was heated at reflux under carbon monoxide pressure (balloon) for 3 h. After removal of the solvent, the residue was purified by column chromatography on silica gel (5→10% EtAcO/hexanes), affording 105 mg of ethyl 1-{5-chloro-2-[(4-chloro-2-fluorobenzyl)oxy]benzyl}-1H-pyrazolo[3,4-b]pyridine-4-carboxylate [Rf=0.60 (20% EtAcO/hexanes), white solid, 40% yield].

LC-MS ESI+ m/z: 474 (M+1, 73%) (Method 5).

d) Following the general procedure described in example 211, section b, 1-{(5-chloro-2-[(4-chloro-2-fluorobenzyl)oxy]benzyl}-1H-pyrazolo[3,4-b]pyridine-4-carboxylic acid was obtained in 58% yield (pale pink solid), using ethyl 1-{5-chloro-2-[(4-chloro-2-fluorobenzyl)oxy]benzyl}-1H-pyrazolo[3,4-b]pyridine-4-carboxylate (0.17 g, 0.37 mmol) as starting material.

LC-MS ESI+ m/z: 446 (M+1, 96%) (Method 5).

e) Following the general procedure described in example 211, section c, sodium 1-{5-chloro-2-[(4-chloro-2-fluorobenzyl)oxy]benzyl}-1H-pyrazolo[3,4-b]pyridine-4-carboxylate was obtained in 95% yield (pale brown solid), using 1-{5-chloro-2-[(4-chloro-2-fluorobenzyl)oxy]benzyl}-1H-pyrazolo[3,4-b]pyridine-4-carboxylic acid (96 mg, 0.22 mmol) as starting material.

LC-MS ESI+ m/z: 446 (M+2-Na, 98%) (Method 2).

$^1$H-NMR (CD$_3$OD, 250 MHz, δ): 8.50 (s, 1H, ArH); 8.45 (d, J=5.0 Hz, 1H, ArH); 7.58 (d, J=5.0 Hz, 1H, ArH); 7.37-7.11 (m, 4H, ArH); 7.05 (d, J=8.8 Hz, 1H, ArH); 6.87 (d, J=2.6 Hz, 1H, ArH); 5.70 (s, 2H); 5.07 (s, 2H).

Examples 213 to 214

Using 4-iodo-1H-pyrazolo[3,4-b]pyridine as Starting Material

The next compound was obtained using the same methodology as in Example 212 but using the compound II indicated.

late was obtained forming part of an uncharacterized mixture, using ethyl 2-oxo-1,2,3,4-tetrahydroquinoline-5-carboxylate (0.17 g, 0.54 mmol), NaH (37 mg, 0.93 mmol) and 2-(bromomethyl)-4-chloro-1-[(4-chloro-2-fluorobenzyl)oxy]benzene (0.34 g, 1.01 mmol) as starting materials.

c) Following the general procedure described in example 211, section b, 1-{5-chloro-2-[(4-chloro-2-fluorobenzyl)oxy]benzyl}-2-oxo-1,2,3,4-tetrahydroquinoline-5-carboxylic acid was obtained in 26% yield (white solid), using the mixture obtained in the previous step as starting material.

LC-MS ESI+ m/z: 474 (M+1, 98%) (Method 5).

d) Following the general procedure described in example 211, section c, sodium 1-{5-chloro-2-[(4-chloro-2-fluorobenzyl)oxy]benzyl}-2-oxo-1,2,3,4-tetrahydroquinoline-5-carboxylate was obtained in 85% yield (white solid), using 1-{5-chloro-2-[(4-chloro-2-fluorobenzyl)oxy]benzyl}-2-oxo-1,2,3,4-tetrahydroquinoline-5-carboxylic acid (62 mg, 0.13 mmol) as starting material.

LC-MS ESI+ m/z: 474 (M+2-Na, 98%) (Method 2).

$^1$H-NMR (CD$_3$OD, 250 MHz, δ): 7.58 (t, J=8.5 Hz, 1H, ArH); 7.33-7.02 (m, 6H, ArH); 6.88 (d, J=2.5 Hz, 1H, ArH); 6.73 (d, J=8.0 Hz, 1H, ArH); 5.22 (s, 2H); 5.12 (s, 2H); 3.22-3.10 (m, 2H); 2.75-2.65 (m, 2H).

Example 216

Synthesis of sodium 1-{5-chloro-2-[(4-chloro-2-fluorobenzyl)oxy]benzyl}-2,3-dihydro-1H-pyrrolo[2,3-b]pyridine-4-carboxylate a) Freshly prepared LDA (1.44 mmol) was added to a solution of 2-fluoro-3-iodopyridine (0.32 g, 1.44 mmol) in

| | | | | LC-MS | |
|---|---|---|---|---|---|
| Example | Compound name | Starting compound II | Method | $t_R$ (min) | m/z [M + H]$^+$ |
| 213 | Sodium 1-[5-chloro-2-(2-fluoro-2-methylpropoxy)benzyl]-1H-pyrazolo[3,4-b]pyridine-4-carboxylic acid | 2-(bromomethyl)-4-chloro-1-(2-fluoro-2-methylpropoxy)benzene | 2 | 14.43 | 378 |
| 214 | Sodium 1-[5-chloro-2-(cyclobutyloxy)benzyl]-1H-pyrazolo[3,4-b]pyridine-4-carboxylate | 2-(bromomethyl)-4-chloro-1-(cyclobutyloxy)benzene | 2 | 15.09 | 358 |

Example 215

Synthesis of sodium 1-{5-chloro-2-[(4-chloro-2-fluorobenzyl)oxy]benzyl}-2-oxo-1,2,3,4-tetrahydroquinoline-5-carboxylate a) Following the general procedure described in example 212, section c, ethyl 2-oxo-1,2,3,4-tetrahydroquinoline-5-carboxylate was obtained in 61% yield (pale orange solid) after 4 h, using 2-oxo-1,2,3,4-tetrahydroquinolin-5-yl trifluoromethanesulfonate (66 mg, 0.22 mmol) as starting material. The latter was obtained from the known 5-hydroxy-3,4-dihydroquinolin-2(1H)-one under standard conditions.

$^1$H-NMR (CDCl$_3$, 250 MHz, δ): 8.36 (br s, 1H, NH); 7.59 (d, J=7.7 Hz, 1H, ArH); 7.23 (t, J=7.8 Hz, 1H, ArH); 6.93 (d, J=7.8 Hz, 1H, ArH); 4.36 (q, J=7.1 Hz, 2H); 3.43-3.35 (m, 2H); 2.65-2.56 (m, 2H); 1.40 (t, J=7.1 Hz, 3H).

b) Following the general procedure described in example 1, section a, ethyl 1-{5-chloro-2-[(4-chloro-2-fluorobenzyl)oxy]benzyl}-2-oxo-1,2,3,4-tetrahydroquinoline-5-carboxy- THF (12 mL) cooled at −78° C. After 1.5 h, a solution of 3-{5-chloro-2-[(4-chloro-2-fluorobenzyl)oxy]benzyl}-1,2,3-oxathiazolidine 2,2-dioxide (0.70 g, 1.72 mmol) in 8 mL of THF was transferred via canula to the anion solution, allowing to reach room temperature (overnight). TLC showed an intense polar spot corresponding to the sulfamic acid intermediate. The solvent was evaporated and the resulting residue was dissolved in 1,4-dioxane (6 mL) and treated with 1.0 mL of HCl (4 M in 1,4-dioxane), stirring at room temperature. After, 16 h, the reaction was cooled to 0° C. and slowly basified with NaOH (aqueous solution 10%, 5 mL). The mixture was poured over EtAcO (40 mL) and washed with brine (2×20 mL); the organic layer was dried over anhydrous Na$_2$SO$_4$ and filtered. After removal of the solvent, the residue was purified by column chromatography on silica gel (10□30% EtAcO/hexanes), affording 0.51 g of N-{5-chloro-2-[(4-chloro-2-fluorobenzyl)oxy]benzyl}-N-[2-(2-fluoro-4-iodopyridin-3-yl)ethyl]amine [Rf=0.70 (10% MeOH/DCM), colorless oil, 64% yield].

LC-MS ESI+ m/z: 549 (M+1, 90%) (Method 5).

¹H-NMR (CDCl₃, 250 MHz, δ): 7.68 (d, J=5.1 Hz, 1H, ArH); 7.58 (d, J=5.1 Hz, 1H, ArH); 7.43-7.11 (m, 5H, ArH); 6.83 (d, J=8.8 Hz, 1H, ArH); 5.07 (s, 2H); 3.82 (s, 2H); 3.01-2.74 (m, 4H).

b) A mixture of N-{5-chloro-2-[(4-chloro-2-fluorobenzyl)oxy]benzyl}-N-[2-(2-fluoro-4-iodopyridin-3-yl)ethyl]amine (0.51 g, 0.92 mmol) and K₂CO₃ (0.15 g, 1.10 mmol) in DMF (10 mL) was heated at 100° C. for 4 h. The reaction was allowed to reach room temperature, poured over EtAcO (40 mL) and washed with water (2×20 mL); the organic layer was dried over anhydrous Na₂SO₄ and filtered. After removal of the solvent, the residue was purified by column chromatography on silica gel (10□20% EtAcO/hexanes), affording 0.34 g of 1-{(5-chloro-2-[(4-chloro-2-fluorobenzyl)oxy]benzyl}-4-iodo-2,3-dihydro-1H-pyrrolo[2,3-b]pyridine [Rf=0.65 (20% EtAcO/hexanes), white solid, 69% yield].

LC-MS ESI+ m/z: 529 (M+1, 99%) (Method 5).

¹H-NMR (CDCl₃, 250 MHz, δ): 7.47-7.37 (m, 2H, ArH); (m, 4H, ArH); 6.86 (d, J=8.5 Hz, 1H, ArH); 6.76 (d, J=5.4 Hz, 1H, ArH); 5.05 (s, 2H); 4.55 (s, 2H); 3.46 (t, J=8.4 Hz, 2H); 2.91 (t, J=8.4 Hz, 2H).

c) Following the general procedure described in example 212, section c, ethyl 1-{5-chloro-2-[(4-chloro-2-fluorobenzyl)oxy]benzyl}-2,3-dihydro-1H-pyrrolo[2,3-b]pyridine-4-carboxylate was obtained in 71% yield (pale yellow solid) after 7 h, using 1-{5-chloro-2-[(4-chloro-2-fluorobenzyl)oxy]benzyl}-4-iodo-2,3-dihydro-1H-pyrrolo[2,3-b]pyridine (0.33 g, 0.61 mmol) as starting material.

LC-MS ESI+ m/z: 475 (M+1, 97%) (Method 5).

¹H-NMR (CDCl₃, 250 MHz, δ): 7.90 (d, J=5.8 Hz, 1H, ArH); 7.41 (t, J=8.7 Hz, 1H, ArH); 7.27-7.07 (m, 4H, ArH); 6.92-6.84 (m, 2H, ArH); 5.06 (s, 2H); 4.63 (s, 2H); 4.35 (q, J=7.2 Hz, 2H); 3.55-3.28 (m, 4H); 1.39 (t, J=7.2 Hz, 3H).

d) Following the general procedure described in example 211, section b, 1-{5-chloro-2-[(4-chloro-2-fluorobenzyl)oxy]benzyl}-2,3-dihydro-1H-pyrrolo[2,3-b]pyridine-4-carboxylic acid was obtained in 96% yield (white solid), using ethyl 1-{5-chloro-2-[(4-chloro-2-fluorobenzyl)oxy]benzyl}-2,3-dihydro-1H-pyrrolo[2,3-b]pyridine-4-carboxylate (0.20 g, 0.42 mmol) as starting material.

LC-MS ESI− m/z 445 (M−1, 92%) (Method 5).

e) Following the general procedure described in example 211, section c, sodium 1-{5-chloro-2-[(4-chloro-2-fluorobenzyl)oxy]benzyl}-2,3-dihydro-1H-pyrrolo[2,3-b]pyridine-4-carboxylate was obtained in 90% yield (white solid), using 1-{5-chloro-2-[(4-chloro-2-fluorobenzyl)oxy]benzyl}-2,3-dihydro-1H-pyrrolo[2,3-b]pyridine-4-carboxylic acid (0.18 g, 0.40 mmol) as starting material.

LC-MS ESI+ m/z: 447 (M+2-Na, 97%) (Method 2).

¹H-NMR (CD₃OD, 250 MHz, δ): 7.64 (d, J=6.1 Hz, 1H, ArH); 7.49 (t, J=8.0 Hz, 1H, ArH); 7.28-7.03 (m, 5H, ArH); 6.79 (d, J=5.4 Hz, 1H, ArH); 5.14 (s, 2H); 4.55 (s, 2H); 3.48-3.21 (m, 4H).

Examples 217 to 222

Using Different Starting Materials

The next compound was obtained using the same methodology as in Example 216 but using the corresponding starting material as indicated.

| Example | Compound name | Starting material | Method | LC-MS t_R (min) | m/z [M + H]+ |
|---|---|---|---|---|---|
| 217 | Sodium 1-{5-chloro-2-[(2,4-difluorobenzyl)oxy]benzyl}-2,3-dihydro-1H-pyrrolo[2,3-b]pyridine-4-carboxylate | 3-{5-chloro-2-[(2,4-difluorobenzyl)oxy]benzyl}-1,2,3-oxathiazolidine 2,2-dioxide | 2 | 16.59 | 431 |
| 218 | Sodium 1-{5-chloro-2-[(4-chlorobenzyl)oxy]benzyl}-2,3-dihydro-1H-pyrrolo[2,3-b]pyridine-4-carboxylate | 3-{5-chloro-2-[(4-chlorobenzyl)oxy]benzyl}-1,2,3-oxathiazolidine 2,2-dioxide | 2 | 17.34 | 429 |
| 219 | Sodium 1-{5-chloro-2-[(2-fluorobenzyl)oxy]benzyl}-2,3-dihydro-1H-pyrrolo[2,3-b]pyridine-4-carboxylate | 3-{5-chloro-2-[(2-fluorobenzyl)oxy]benzyl}-1,2,3-oxathiazolidine 2,2-dioxide | 2 | 16.61 | 413 |
| 220 | Sodium 1-{5-chloro-2-[(4-fluorobenzyl)oxy]benzyl}-2,3-dihydro-1H-pyrrolo[2,3-b]pyridine-4-carboxylate | 3-{5-chloro-2-[(4-fluorobenzyl)oxy]benzyl}-1,2,3-oxathiazolidine 2,2-dioxide | 2 | 16.03 | 413 |
| 221 | Sodium 1-[5-chloro-2-(2-fluoro-2-methylpropoxy)benzyl]-2,3-dihydro-1H-pyrrolo[2,3-b]pyridine-4-carboxylate | 3-[5-chloro-2-(2-fluoro-2-methylpropoxy)benzyl]-1,2,3-oxathiazolidine 2,2-dioxide | 2 | 14.81 | 379 |

-continued

| Example | Compound name | Starting material | Method | LC-MS $t_R$ (min) | m/z $[M + H]^+$ |
|---|---|---|---|---|---|
| 222 | Sodium 1-(5-chloro-2-isobutoxybenzyl)-2,3-dihydro-1H-pyrrolo[2,3-b]pyridine-4-carboxylate | 3-(5-chloro-2-isobutoxybenzyl)-1,2,3-oxathiazolidine 2,2-dioxide | 2 | 16.47 | 361 |

Example 223

Synthesis of 1-{5-chloro-2-[(4-chloro-2-fluorobenzyl)oxy]benzyl}-4-(1H-tetrazol-5-yl)-2,3-dihydro-1H-pyrrolo[2,3-b]pyridine sodium salt a) A solution of 1-{5-chloro-2-[(4-chloro-2-fluorobenzyl)oxy]benzyl}-4-iodo-2,3-dihydro-1H-pyrrolo[2,3-b]pyridine (0.14 g, 0.26 mmol) and $Zn(CN)_2$ (37 mg, 0.31 mmol) in DMF (4 mL) was thoroughly purged with argon; $Pd(PPh_3)_4$ (6 mg, 0.01 mmol) was added and the mixture was purged again and heated at 90° C. After 16 h, the reaction was allowed to reach room temperature, poured over EtAcO (20 mL) and washed with water (2×10 mL); the organic layer was dried over anhydrous $Na_2SO_4$ and filtered. After removal of the solvent, the residue was purified by column chromatography on silica gel (10→15% EtAcO/hexanes), affording 0.10 g 1-{5-chloro-2-[(4-chloro-2-fluorobenzyl)oxy]benzyl}-2,3-dihydro-1H-pyrrolo[2,3-b]pyridine-4-carbonitrile [Rf=0.35 (20% EtAcO/hexanes), pale yellow solid, 90% yield].

LC-MS ESI+ m/z 428 (M+1, 99%) (Method 5).

b) $TMSN_3$ (91 □L, 0.69 mmol) was added to a suspension of 1-{5-chloro-2-[(4-chloro-2-fluorobenzyl)oxy]benzyl}-2,3-dihydro-1H-pyrrolo[2,3-b]pyridine-4-carbonitrile (100 mg, 0.23 mmol) and $Bu_2SnO$ (17 mg, 0.07 mmol) in toluene and heated at 120° C. in a sealed tube. An abundant white solid appeared during the reaction. After 22 h, the reaction was allowed to reach room temperature, and toluene was removed by rotatory evaporation; the solid residue was dissolved in Me-THF (30 mL) and washed with water (10 mL) and HCl (aqueous solution 10%, 5 mL). The organic layer was dried over anhydrous $Na_2SO_4$ and filtered. After removal of the solvent, the residue was purified by column chromatography on silica gel (3→10% MeOH/DCM), affording 40 mg of 1-{5-chloro-2-[(4-chloro-2-fluorobenzyl)oxy]benzyl}-4-(1H-tetrazol-5-yl)-2,3-dihydro-1H-pyrrolo[2,3-b]pyridine [Rf=0.25 (10% MeOH/DCM), pale yellow solid, 37% yield].

LC-MS ESI+ m/z 471 (M+1, 83%) (Method 5).

c) Following the general procedure described in example 211, section c, 1-{5-chloro-2-[(4-chloro-2-fluorobenzyl)oxy]benzyl}-4-(1H-tetrazol-5-yl)-2,3-dihydro-1H-pyrrolo[2,3-b]pyridine sodium salt was obtained in 71% yield (pale yellow solid), using 1-{5-chloro-2-[(4-chloro-2-fluorobenzyl)oxy]benzyl}-4-(1H-tetrazol-5-yl)-2,3-dihydro-1H-pyrrolo[2,3-b]pyridine (40 mg, 0.085 mmol) as starting material.

LC-MS ESI+ m/z: 471 (M+2-Na, 98%) (Method 2).

$^1$H-NMR (DMSO-d6, 250 MHz, δ): (diluted) 7.78-7.45 (m, 3H, ArH); 7.38-7.07 (m, 5H, ArH); 5.20 (s, 2H); 4.49 (s, 2H). The signals of CH2 are under the peak of water.

Example 224

Synthesis of sodium 8-{5-chloro-2-[(2,4-difluorobenzyl)oxy]benzyl}-5,6,7,8-tetrahydro-1,8-naphthyridine-4-carboxylate a) Freshly prepared LDA (8.97 mmol) was added to a solution of 2-fluoro-3-iodopyridine (2.00 g, 8.97 mmol) in THF (15 mL) cooled at −78° C. After 1 h, 1-chloro-3-iodopropane (0.96 mL, 8.97 mmol) was added to the anion solution, allowing to reach room temperature (overnight). The reaction volume was reduced to ca. 10 mL and the mixture was poured over EtAcO (60 mL) and washed with water (2×20 mL); the organic layer was dried over anhydrous $Na_2SO_4$ and filtered. After removal of the solvent, the residue was purified by column chromatography on silica gel (2→4% EtAcO/hexanes), affording 1.88 g of 3-(3-chloropropyl)-2-fluoro-4-iodopyridine [Rf=0.70 (5% EtAcO/hexanes), colorless oil, 70% yield].

LC-MS ESI+ m/z: 300 (M+1, 98%) (Method 5).

$^1$H-NMR (CDCl$_3$, 250 MHz, δ): 7.70 (d, J=5.2 Hz, 1H, ArH); 7.61 (d, J=5.2 Hz, 1H, ArH); 3.62 (t, J=6.5 Hz, 2H); 2.99-2.90 (m, 2H); 2.10-1.97 (m, 2H).

b) A mixture of 3-(3-chloropropyl)-2-fluoro-4-iodopyridine (0.23 g, 0.77 mmol), 1-{5-chloro-2-[(2,4-difluorobenzyl)oxy]phenyl}methanamine (0.26 g, 0.92 mmol), KI (0.15 g, 0.92 mmol) and $K_2CO_3$ (0.22 g, 1.62 mmol) in DMF (10 mL) was heated at 80° C. for 24 h. The reaction was allowed to reach room temperature, poured over EtAcO (40 mL) and washed with water (2×10 mL); the organic layer was dried over anhydrous $Na_2SO_4$ and filtered. After removal of the solvent, the residue was purified by column chromatography on silica gel (5→10% EtAcO/hexanes), affording 0.29 g of 1-{5-chloro-2-[(2,4-difluorobenzyl)oxy]benzyl}-5-iodo-1,2,3,4-tetrahydro-1,8-naphthyridine [Rf=0.65 (20% EtAcO/hexanes), white solid, 71% yield];

LC-MS ESI+ m/z 527 (M+1, 92%) (Method 5).

$^1$H-NMR (CDCl$_3$, 250 MHz, δ): 7.50-7.37 (m, 2H, ArH); 7.16 (dd, J=8.5, 2.6 Hz, 1H, ArH); 7.11 (d, J=2.6 Hz, 1H, ArH); 6.97-6.79 (m, 4H, ArH); 5.05 (s, 2H); 4.84 (s, 2H); 3.36-3.27 (m, 2H); 2.81-2.73 (m, 2H); 2.00-1.88 (m, 2H).

c) Following the general procedure described in example 212, section c, ethyl 8-{5-chloro-2-[(2,4-difluorobenzyl)oxy]benzyl}-5,6,7,8-tetrahydro-1,8-naphthyridine-4-carboxylate was obtained in 74% yield (pale yellow solid) after 6 h, using 1-{5-chloro-2-[(2,4-difluorobenzyl)oxy]benzyl}-5-iodo-1,2,3,4-tetrahydro-1,8-naphthyridine (0.28 g, 0.53 mmol) as starting material.

LC-MS ESI+ m/z 473 (M+1, 83%) (Method 5).

$^1$H-NMR (CDCl$_3$, 250 MHz, δ): 7.96 (d, J=5.2 Hz, 1H, ArH); 7.49-7.38 (m, 1H, ArH); 7.16 (dd, J=8.6, 2.6 Hz, 1H, ArH); 7.09 (d, J=2.6 Hz, 1H, ArH); 6.93-6.77 (m, 4H, ArH);

5.06 (s, 2H); 4.87 (s, 2H); 4.35 (q, J=7.2 Hz, 2H); 3.39-3.31 (m, 2H); 3.09-3.01 (m, 2H); 1.99-1.87 (m, 2H); 1.39 (t, J=7.2 Hz, 3H).

d) Following the general procedure described in example 211, section b, 8-{5-chloro-2-[(2,4-difluorobenzyl)oxy]benzyl}-5,6,7,8-tetrahydro-1,8-naphthyridine-4-carboxylic acid was obtained in 60% yield (white solid), using ethyl 8-{5-chloro-2-[(2,4-difluorobenzyl)oxy]benzyl}-5,6,7,8-tetrahydro-1,8-naphthyridine-4-carboxylate (0.15 g, 0.32 mmol) as starting material.

LC-MS ESI+ m/z: 445 (M+1, 91%) (Method 5).

e) Following the general procedure described in example 211, section c, Sodium 8-{5-chloro-2-[(2,4-difluorobenzyl)oxy]benzyl}-5,6,7,8-tetrahydro-1,8-naphthyridine-4-carboxylate was obtained in 79% yield (white solid), using 8-{5-chloro-2-[(2,4-difluorobenzyl)oxy]benzyl}-5,6,7,8-tetrahydro-1,8-naphthyridine-4-carboxylic acid (85 mg, 0.19 mmol) as starting material.

LC-MS ESI+ m/z: 445 (M+2-Na, 98%) (Method 2).

$^1$H-NMR (CD$_3$OD, 250 MHz, δ): 7.70 (d, J=5.6 Hz, 1H, ArH); 7.64-7.53 (m, 1H, ArH); 7.20 (dd, J=8.6, 2.7 Hz, 1H, ArH); 7.10-6.95 (m, 4H, ArH); 6.52 (d, J=5.6 Hz, 1H, ArH); 5.15 (s, 2H); 4.75 (s, 2H); 3.41-3.34 (m, 2H); 2.95-2.87 (m, 2H); 2.01-1.88 (m, 2H).

Examples 225

Using a Different Starting Material

The next compound was obtained using the same methodology as in Example 224 but using the corresponding starting material as indicated.

b) A mixture of 3-bromo-4-(3-chloropropyl)-5-fluoropyridine (0.60 g, 2.38 mmol), 1-{5-chloro-2-[(4-chloro-2-fluorobenzyl)oxy]phenyl}methanamine (0.93 g, 3.09 mmol), KI (0.39 g, 2.38 mmol) and K$_2$CO$_3$ (0.82 g, 5.94 mmol) in DMF (10 mL) was heated at 150° C. for 5 h. The reaction was allowed to reach room temperature, poured over EtAcO (60 mL) and washed with brine (2×25 mL); the organic layer was dried over anhydrous Na$_2$SO$_4$ and filtered. After removal of the solvent, the residue was purified by column chromatography on silica gel (12% EtAcO/hexanes), affording 0.68 g of 5-bromo-1-{5-chloro-2-[(4-chloro-2-fluorobenzyl)oxy]benzyl}-1,2,3,4-tetrahydro-1,7-naphthyridine [Rf=0.35 (20% EtAcO/hexanes), white solid, 58% yield].

LC-MS ESI+ m/z: 496 (M+1, 98%) (Method 5).

$^1$H-NMR (CDCl$_3$, 250 MHz, δ): 7.96 (s, 1H, ArH); 7.60 (s, 1H, ArH); 7.38 (t, J=8.2 Hz, 1H, ArH); 7.23-7.10 (m, 3H, ArH); 7.05 (d, J=2.4 Hz, 1H, ArH); 6.89 (d, J=8.5 Hz, 1H, ArH); 5.10 (s, 2H); 4.46 (s, 2H); 3.40-3.33 (m, 2H); 2.86-2.79 (m, 2H); 2.09-1.98 (m, 2H).

c) A suspension of 5-bromo-1-{5-chloro-2-[(4-chloro-2-fluorobenzyl)oxy]benzyl}-1,2,3,4-tetrahydro-1,7-naphthyridine (0.50 g, 1.01 mmol), dppf (28 mg, 0.05 mmol) and TEA (0.42 mL, 3.03 mmol) in EtOH (60 mL) was thoroughly purged with argon; Pd(AcO)$_2$ (11 mg, 0.05 mmol) was added and the mixture was purged again with carbon monoxide. The mixture was placed in a stainless steel pressure reactor and heated at 130° C. under carbon monoxide pressure (30 bar) for 16 h. The reaction was allowed to reach room temperature and carbon monoxide was released. After removal of the solvent, the residue was purified by column chromatography on silica gel (20–25%

| | | | | LC-MS | |
|---|---|---|---|---|---|
| Example | Compound name | Starting material | Method | t$_R$ (min) | m/z [M + H]$^+$ |
| 225 | Sodium 8-{5-chloro-2-[(4-chloro-2-fluorobenzyl)oxy]benzyl}-5,6,7,8-tetrahydro-1,8-naphthyridine-4-carboxylate | 1-{5-chloro-2-[(4-chloro-2-fluorobenzyl)oxy]phenyl}methanamine | 2 | 18.03 | 461 |

Example 226

Sodium 1-{5-chloro-2-[(4-chloro-2-fluorobenzyl)oxy]benzyl}-1,2,3,4-tetrahydro-1,7-naphthyridine-5-carboxylate a) Freshly prepared LDA (20.46 mmol) was added to a solution of 3-bromo-5-fluoropyridine (3.00 g, 17.05 mmol) in THF (20 mL) cooled at −78° C. After 40 min, a solution of 1-chloro-3-iodopropane (6.98 g, 34.09 mmol) in THF (10 mL) was transferred via cannula was added to the anion solution, allowing to reach room temperature. After 1 h, the volatiles were removed by rotatory evaporation and the residue was dissolved in EtAcO (60 mL) and washed with water (2×30 mL); the organic layer was dried over anhydrous Na$_2$SO$_4$ and filtered. After removal of the solvent, the residue was purified by column chromatography on silica gel (2–4% EtAcO/hexanes), affording 3.07 g of 3-bromo-4-(3-chloropropyl)-5-fluoropyridine [Rf=0.60 (20% EtAcO/hexanes), colorless oil, 71% yield].

LC-MS ESI+ m/z: 300 (M+1, 98%) (Method 5).

$^1$H-NMR (CDCl$_3$, 250 MHz, δ): 8.50 (s, 1H, ArH); 8.33 (s, 1H, ArH); 3.59 (t, J=6.7 Hz, 2H); 3.05-2.92 (m, 2H); 2.16-1.98 (m, 2H).

EtAcO/hexanes), affording 0.42 g of ethyl 1-{5-chloro-2-[(4-chloro-2-fluorobenzyl)oxy]benzyl}-1,2,3,4-tetrahydro-1,7-naphthyridine-5-carboxylate [Rf=0.50 (40% EtAcO/hexanes), pale yellow solid, 85% yield].

LC-MS ESI+ m/z: 489 (M+1, 98%) (Method 5).

$^1$H-NMR (CDCl$_3$, 250 MHz, δ): 8.32 (s, 1H, ArH); 7.78 (s, 1H, ArH); 7.43-7.35 (m, 1H, ArH); 7.22-7.11 (m, 3H, ArH); 7.04 (d, J=2.5 Hz, 1H, ArH); 6.89 (d, J=8.7 Hz, 1H, ArH); 5.11 (s, 2H); 4.49 (s, 2H); 4.36 (q, J=7.1 Hz, 2H); 3.42-3.36 (m, 2H); 3.18-3.10 (m, 2H); 2.07-1.96 (m, 2H); 1.39 (t, J=7.1 Hz, 3H).

d) Following the general procedure described in example 211, section b, 1-{5-chloro-2-[(4-chloro-2-fluorobenzyl)oxy]benzyl}-1,2,3,4-tetrahydro-1,7-naphthyridine-5-carboxylic acid was obtained in 91% yield (pale yellow solid), using ethyl 1-{5-chloro-2-[(4-chloro-2-fluorobenzyl)oxy]benzyl}-1,2,3,4-tetrahydro-1,7-naphthyridine-5-carboxylate (0.40 g, 0.82 mmol) as starting material.

LC-MS ESI+ m/z: 461 (M+1, 99%) (Method 5).

e) Following the general procedure described in example 211, section c, sodium 1-{5-chloro-2-[(4-chloro-2-fluorobenzyl)oxy]benzyl}-1,2,3,4-tetrahydro-1,7-naphthyridine-5-carboxylate was obtained in 99% yield (white solid), using 1-{5-chloro-2-[(4-chloro-2-fluorobenzyl)oxy]benzyl}-1,2,3,4-tetrahydro-1,7-naphthyridine-5-carboxylic acid (0.33 g, 0.72 mmol) as starting material.

LC-MS ESI+ m/z: 461 (M+2-Na, 99%) (Method 2).

$^1$H-NMR (CD$_3$OD, 250 MHz, δ): 7.81 (s, 1H, ArH); 7.55 (t, J=7.5 Hz, 1H, ArH); 7.44 (s, 1H, ArH); 7.31-7.20 (m, 3H, ArH); 7.10 (d, J=8.6 Hz, 1H, ArH); 7.04 (d, J=2.8 Hz, 1H, ArH); 5.20 (s, 2H); 4.49 (s, 2H); 3.46-3.39 (m, 2H); 3.03-2.95 (m, 2H); 2.07-1.94 (m, 2H).

Examples 227

Using 1-{5-chloro-2[(2,4-difluorobenzyl)oxy]phenyl}methanamine Material

The next compound was obtained using the same methodology as in Example 226 but using the corresponding starting material as indicated.

| | | | | LC-MS | |
|---|---|---|---|---|---|
| Example | Compound name | Starting material | Method | $t_R$ (min) | m/z [M + H]$^+$ |
| 227 | Sodium 1-{5-chloro-2-[(2,4-difluorobenzyl)oxy]benzyl}-1,2,3,4-tetrahydro-1,7-naphthyridine-5-carboxylate | 1-{5-chloro-2-[(2,4-difluorobenzyl)oxy]phenyl}methanamine | 2 | 16.91 | 445 |

Example 228

1-{5-chloro-2-[(2,4-difluorobenzyl)oxy]benzyl}-1,2,3,4-tetrahydro-1,6-naphthyridine-5-carboxylic acid a) n-BuLi [0.93 mL (1.6 M in hexanes), 1.50 mmol] was added dropwise to a solution of 4-chloro-N,N-diisopropylpyridine-2-carboxamide (0.30 g, 1.25 mmol) in THF (6 mL) cooled at −78° C. After 1.5 h, 1-chloro-3-iodopropane (0.33 mL, 1.75 mmol) was added to the anion solution, allowing to reach room temperature. After 30 min, the volatiles were removed by rotatory evaporation and the residue was dissolved in EtAcO (40 mL) and washed with brine (2×15 mL); the organic layer was dried over anhydrous Na$_2$SO$_4$ and filtered. After removal of the solvent, the residue was purified by column chromatography on silica gel (25% EtAcO/hexanes), affording 0.31 g of 4-chloro-3-(3-chloropropyl)-N,N-diisopropylpyridine-2-carboxamide [Rf=0.65 (50% EtAcO/hexanes), colorless oil, 77% yield].

LC-MS ESI+ m/z 317 (M+1, 93%) (Method 5).

$^1$H-NMR (CDCl$_3$, 250 MHz, δ): 8.32 (d, J=5.4 Hz, 1H, ArH); 7.28 (d, J=5.4 Hz, 1H, ArH); 3.68-3.42 (m, 4H); 3.33 (t, J=6.4 Hz, 2H); 2.29-2.12 (m, 2H); 1.58 (d, J=6.5 Hz, 6H); 1.16 (d, J=6.5 Hz, 6H).

b) A mixture of 4-chloro-3-(3-chloropropyl)-N,N-diisopropylpyridine-2-carboxamide (0.70 g, 2.21 mmol), 1-{5-chloro-2-[(2,4-difluorobenzyl)oxy]phenyl}methanamine (0.75 g, 2.65 mmol), KI (0.44 g, 2.65 mmol) and K$_2$CO$_3$ (0.61 g, 4.41 mmol) in DMF (15 mL) was heated at 100° C. for 15 h. The reaction was allowed to reach room temperature, poured over EtAcO (100 mL) and washed with water (2×60 mL); the organic layer was dried over anhydrous Na$_2$SO$_4$ and filtered. After removal of the solvent, the residue was purified by column chromatography on silica gel (20□70% EtAcO/hexanes), affording 0.82 g of 1-{5-chloro-2-[(2,4-difluorobenzyl)oxy]benzyl}-N,N-diisopropyl-1,2,3,4-tetrahydro-1,6-naphthyridine-5-carboxamide [Rf=0.50 (70% EtAcO/hexanes), pale yellow solid, 70% yield].

LC-MS ESI+ m/z: 528 (M+1, 95%) (Method 5).

$^1$H-NMR (CDCl$_3$, 250 MHz, δ): 7.92 (d, J=5.7 Hz, 1H, ArH); 7.48-7.36 (m, 1H, ArH); 7.22 (dd, J=8.6, 2.6 Hz, 1H, ArH); 7.00 (d, J=2.6 Hz, 1H, ArH); 6.97-6.81 (m, 3H, ArH); 6.15 (d, J=5.7 Hz, 1H, ArH); 5.09 (s, 2H); 4.43 (s, 2H); 3.73-3.44 (m, 2H); 3.42-3.34 (m, 2H); 2.75 (br s, 2H); 2.05-1.94 (m, 2H); 1.58 (d, J=6.8 Hz, 6H); 1.16 (d, J=6.8 Hz, 6H).

c) A solution of DIBAL-H [1.52 mL (1.5 M in toluene), 2.29 mmol] was added dropwise to a solution of 1-{5-chloro-2-[(2,4-difluorobenzyl)oxy]benzyl}-N,N-diisopropyl-1,2,3,4-tetrahydro-1,6-naphthyridine-5-carboxamide (0.81 g, 1.52 mmol) in THF (15 mL) cooled at −78° C. After 1 h, the reaction mixture was warmed to room temperature, and, after 5 h, quenched by dropwise addition of HCl (aqueous solution 10%, 2 mL). The volatiles were removed by rotatory evaporation and the residue was dissolved in EtAcO (50 mL) and washed with water (2×25 mL); the organic layer was dried over anhydrous Na$_2$SO$_4$ and filtered. After removal of the solvent, the residue was purified by column chromatography on silica gel (5% MeOH/DCM), affording 0.17 g of 1-{5-chloro-2-[(2,4-difluorobenzyl)oxy]benzyl}-1,2,3,4-tetrahydro-1,6-naphthyridine-5-carbaldehyde [Rf=0.50 (10% MeOH/DCM), pale yellow oil, 25% yield].

LC-MS ESI+ m/z: 429 (M+1, 78%) (Method 5).

d) H$_2$O$_2$ (aqueous solution 30%, 0.07 mL, 0.77 mmol) was added dropwise to a solution of 1-{5-chloro-2-[(2,4-difluorobenzyl)oxy]benzyl}-1,2,3,4-tetrahydro-1,6-naphthyridine-5-carbaldehyde (0.17 g, 0.38 mmol) in formic acid (5 mL) and stirred at room temperature for 22 h. Another 0.07 mL of H$_2$O$_2$ were added and stirring was continued for additional 20 h. The reaction mixture was diluted with DCM (30 mL) and washed with water (2×10 mL); the organic layer was dried over anhydrous Na$_2$SO$_4$ and filtered. After removal of the solvent, the residue was purified by column chromatography on silica gel (4□15% MeOH/DCM), affording 0.08 g of 1-{5-chloro-2-[(2,4-difluorobenzyl)oxy]benzyl}-1,2,3,4-tetrahydro-1,6-naphthyridine-5-carboxylic acid, orange solid, 48% yield.

LC-MS ESI+ m/z 445 (M+1, 99%) (Method 2).

$^1$H-NMR (CD$_3$OD, 250 MHz, δ): 7.59 (d, J=6.5 Hz, 1H, ArH); 7.54-7.42 (m, 1H, ArH); 7.36 (dd, J=8.6, 2.0 Hz, 1H, ArH); 7.22-7.15 (m, 2H, ArH); 7.05-6.92 (m, 2H, ArH); 6.72 (d, J=6.5 Hz, 1H, ArH); 5.11 (s, 2H); 4.68 (s, 2H); 3.48-3.40 (m, 2H); 3.22-3.12 (m, 2H); 1.98-1.85 (m, 2H).

Examples 229

Using 4-chloro-3-(3-chloropropyl)-N,N-diisopropylpyridine-2-carboxamide and 1-{5-chloro-2-[(4-chloro-2-fluorobenzyl)oxy]phenyl}methanamine as Starting Materials

| Example | Compound name | Starting material | Method | LC-MS $t_R$ (min) | m/z [M + H]+ |
|---|---|---|---|---|---|
| 229 | Sodium 1-{5-chloro-2-[(4-chloro-2-fluorobenzyl)oxy]benzyl}-1,2,3,4-tetrahydro-1,6-naphthyridine-5-carboxylate | 1-{5-chloro-2-[(4-chloro-2-fluorobenzyl)oxy]phenyl}methanamine | 2 | 19.01 | 461 |

Example 230

Synthesis of sodium 1-{5-chloro-2-[(4-chloro-2-fluorobenzyl)oxy]benzyl}-1,2,3,4-tetrahydroquinoxaline-5-carboxylate a) A solution of 2-aminoethanol (0.70 mL, 11.50 mmol) and methyl 2-chloro-3-nitrobenzoate (0.62 g, 2.88 mmol) in DMF (7 mL) was heated at 70° C. for 30 min. The reaction was allowed to reach room temperature, poured over EtAcO (40 mL) and washed with water (2×30 mL) and brine (20 mL); the organic layer was dried over anhydrous $Na_2SO_4$ and filtered. After removal of the solvent, 0.68 g of methyl 2-[(2-hydroxyethyl)amino]-3-nitrobenzoate were obtained [Rf=0.30 (30% EtAcO/hexanes), yellow-orange solid, 99% yield], that were used without further purification.

LC-MS ESI+ m/z: 241 (M+1, 85%) (Method 5).

NOTE: Prolonged reaction times lead to intramolecular cyclization.

b) A mixture of 0.25 g of Pd (5%, charcoal) and methyl 2-[(2-hydroxyethyl)amino]-3-nitrobenzoate (0.56 g, 2.33 mmol) in THF (12 mL) was stirred under hydrogen atmosphere (balloon) at room temperature. After 14 h, the reaction was filtered through a pad of celite and the solvent was removed by rotatory evaporation. The residue was purified by column chromatography on silica gel (70% EtAcO/hexanes), affording 0.36 g of methyl 3-amino-2-[(2-hydroxyethyl)amino]benzoate [Rf=0.15 (50% EtAcO/hexanes), colorless oil, 80% yield, 2 steps].

LC-MS ESI+ m/z: 211 (M+1, 99%) (Method 5).

c) MsCl (0.64 mL, 0.83 mmol) was added dropwise to a solution of methyl 3-amino-2-[(2-hydroxyethyl)amino]benzoate (0.18 g, 0.83 mmol) and TEA (0.35 mL, 2.50 mmol) in THF (10 mL) cooled at 0° C., while a white suspension appeared. After 5 min, TLC showed complete conversion of the starting material; the reaction was warmed to room temperature and stirred for additional 6 h. The volatiles were removed by rotatory evaporation and the residue was dissolved in EtAcO (20 mL) and washed with water (2×10 mL); the organic layer was dried over anhydrous $Na_2SO_4$ and filtered. After removal of the solvent, the residue was purified by column chromatography on silica gel (30% EtAcO/hexanes), affording 99 mg of methyl 1,2,3,4-tetrahydroquinoxaline-5-carboxylate [Rf=0.45 (40% EtAcO/hexanes), yellow oil, 62% yield].

LC-MS ESI+ m/z: 193 (M+1, 99%) (Method 5).

$^1$H-NMR (CDCl$_3$, 250 MHz, δ): 7.55 (br s, 1H, NH); 7.30 (d, J=8.0 Hz, 1H, ArH); 6.58 (d, J=7.4 Hz, 1H, ArH); 6.46-6.38 (m, 1H, ArH); 3.83 (s, 3H); 3.59-3.50 (m, 2H); 3.40-3.33 (m, 2H).

d) Following the general procedure described in example 165, methyl 1-{5-chloro-2-[(4-chloro-2-fluorobenzyl)oxy]benzyl}-1,2,3,4-tetrahydroquinoxaline-5-carboxylate was obtained in 55% yield (yellow foam) after 3 h, using methyl 1,2,3,4-tetrahydroquinoxaline-5-carboxylate (95 mg, 0.49 mmol), $K_2CO_3$ (89 mg, 0.64 mmol), KI (82 mg, 0.49 mmol) and 2-(bromomethyl)-4-chloro-1-[(4-chloro-2-fluorobenzyl)oxy]benzene (234 mg, 0.64 mmol) as starting materials.

LC-MS ESI+ m/z: 475 (M+1, 97%) (Method 5).

$^1$H-NMR (CDCl$_3$, 250 MHz, δ): 7.46-7.11 (m, 6H, ArH); 6.89 (d, J=8.8 Hz, 1H, ArH); 6.45-6.36 (m, 2H, ArH); 5.10 (s, 2H); 4.40 (s, 2H); 3.84 (s, 3H); 3.63-3.56 (m, 2H); 3.45-3.38 (m, 2H).

e) Following the general procedure described in example 211, section b, 1-{5-chloro-2-[(4-chloro-2-fluorobenzyl)oxy]benzyl}-1,2,3,4-tetrahydroquinoxaline-5-carboxylic acid was obtained in 68% yield (yellow solid), using methyl 1-{5-chloro-2-[(4-chloro-2-fluorobenzyl)oxy]benzyl}-1,2,3,4-tetrahydroquinoxaline-5-carboxylate (0.32 g, 0.67 mmol) as starting material.

LC-MS ESI+ m/z: 461 (M+1, 96%) (Method 5).

f) Following the general procedure described in example 211, section c, sodium 1-{5-chloro-2-[(4-chloro-2-fluorobenzyl)oxy]benzyl}-1,2,3,4-tetrahydroquinoxaline-5-carboxylate was obtained in 99% yield (pale yellow solid), using 1-{5-chloro-2-[(4-chloro-2-fluorobenzyl)oxy]benzyl}-1,2,3,4-tetrahydroquinoxaline-5-carboxylic acid (53 mg, 0.11 mmol) as starting material.

LC-MS ESI+ m/z: 461 (M+2-Na, 96%) (Method 2).

$^1$H-NMR (CD$_3$OD, 250 MHz, δ): 7.53 (t, J=3.3 Hz, 1H, ArH); 7.30-7.13 (m, 5H, ArH); 7.06 (d, J=3.3 Hz, 1H, ArH); 6.36 (t, J=7.8 Hz, 1H, ArH); 6.26 (d, J=7.8 Hz, 1H, ArH); 5.17 (s, 2H); 4.36 (s, 2H); 3.51-3.33 (m, 4H).

Example 231

Synthesis of sodium 1-{5-chloro-2-[2-(2,4-difluorophenyl)ethoxy]benzyl}-1H-indole-4-carboxylate a) A mixture of 5-chloro-2-hydroxybenzaldehyde (3.0 g, 19.2 mmol), $K_2CO_3$ (3.4 g, 24.9 mmol) and MEM-Cl (2.4 mL, 21.1 mmol) in DMF (20 mL) was stirred at room temperature for 18 h. The reaction mixture was poured over EtAcO (100 mL) and washed with water (50 mL) and NaOH(aqueous solution 10%, 3×5 mL); the organic layer was dried over anhydrous $Na_2SO_4$ and filtered. After removal of the solvent, 3.8 g of 5-chloro-2-[(2-methoxyethoxy)methoxy]benzaldehyde were obtained [Rf=0.20

(20% EtAcO/hexanes), pale yellow oil, 81% yield], that were used without further purification.

b) NaBH$_4$ (0.59 g, 15.5 mmol) was added in small portions to a solution of 5-chloro-2-[(2-methoxyethoxy) methoxy]benzaldehyde (3.80 g, 15.5 mmol) in MeOH (25 mL) cooled at 0° C., observing abundant gas evolution. After 20 min, the solvent was removed by rotatory evaporation and the resulting residue was dissolved in Et$_2$O (50 mL) and washed with water (50 mL). The organic layer was dried over anhydrous Na$_2$SO$_4$ and filtered. After removal of the solvent, the residue was purified by column chromatography on silica gel (30% EtAcO/hexanes), affording 3.15 g of {5-chloro-2-[(2-methoxyethoxy)methoxy]phenyl}methanol [Rf=0.33 (10% EtAcO/hexanes), colorless oil, 82% yield].

$^1$H-NMR (CDCl$_3$, 250 MHz, δ): 7.32 (d, J=2.6 Hz, 1H, ArH); 7.20 (dd, J=8.8, 2.6 Hz, 1H, ArH); 7.06 (d, J=8.8 Hz, 1H, ArH); 5.30 (s, 2H); 4.65 (d, J=6.0 Hz, 2H); 3.84-3.79 (m, 2H); 3.57-3.51 (m, 2H); 3.35 (s, 3H); 2.38 (t, J=6.0, 1H, OH).

c) MsCl (1.00 mL, 12.89 mmol) was added dropwise to a solution of {5-chloro-2-[(2-methoxyethoxy)methoxy] phenyl}methanol (2.65 g, 10.74 mmol) and TEA (2.98 mL, 21.48 mmol) in DCM, cooled at 0° C., and the mixture allowed to reach room temperature. After 20 h, the reaction mixture was diluted with DCM (25 mL) and washed with HCl (aqueous solution 5%, 30 mL). The organic layer was dried over anhydrous Na$_2$SO$_4$ and filtered. After removal of the solvent, 1.73 g of 4-chloro-2-(chloromethyl)-1-[(2-methoxyethoxy)methoxy]benzene were obtained [Rf=0.65 (40% EtAcO/hexanes), colorless oil, 50% yield], that were used without further purification.

d) NaH [0.21 g (60% in mineral oil), 5.23 mmol] was added to a solution of methyl 1H-indole-4-carboxylate (0.76 g, 4.36 mmol) in DMF (10 mL) cooled at 0° C., leading to the formation of a yellow mixture. After 30 min, a solution of 4-chloro-2-(chloromethyl)-1-[(2-methoxyethoxy) methoxy]benzene (5 mL of DMF) was added, and the mixture was stirred for additional 2 h. The reaction was poured into EtAcO (50 mL) and washed with water (2×30 mL); the organic layer was dried over anhydrous Na$_2$SO$_4$ and filtered. After removal of the solvent, the residue was dissolved in 25 mL of MeOH, H$_2$SO$_4$ (0.23 mL, 4.36 mmol) was added and the reaction was heated at reflux for 2 h; it was allowed to reach room temperature and MeOH was eliminated in the rotatory evaporator. The residue was dissolved in DCM (100 mL) and washed with water (50 mL). The organic layer was dried over anhydrous Na$_2$SO$_4$ and filtered. After removal of the solvent, the residue was purified by column chromatography on silica gel (30% EtAcO/hexanes), affording 1.22 g of methyl 1-(5-chloro-2-hydroxybenzyl)-1H-indole-4-carboxylate [Rf=0.50 (40% EtAcO/hexanes), white solid, 88% yield].

LC-MS ESI+ m/z 316 (M+1, 99%) (Method 5).

$^1$H-NMR (CDCl$_3$, 250 MHz, δ): 7.94-7.89 (m, 1H, ArH); 7.58-7.53 (m, 1H, ArH); 7.32 (d, J=8.1 Hz, 1H, ArH); 7.24-7.17 (m, 2H, ArH); 7.10 (dd, J=8.6, 2.5 Hz, 1H, ArH); 6.76 (d, J=2.8 Hz, 1H, ArH); 6.72 (d, J=8.6 Hz, 1H, ArH); 5.33 (s, 2H); 3.99 (s, 3H).

e) A mixture of methyl 1-(5-chloro-2-hydroxybenzyl)-1H-indole-4-carboxylate (0.19 g, 0.59 mmol), K$_2$CO$_3$ (0.12 g, 0.88 mmol) and 2-(2,4-difluorophenyl)ethyl 4-methylbenzenesulfonate (0.24 g, 0.77 mmol) in DMF (10 mL) was stirred at 60° C. for 16 h. The reaction mixture was allowed to reach room temperature and poured over EtAcO (40 mL) and washed with water (2×20 mL); the organic layer was dried over anhydrous Na$_2$SO$_4$ and filtered. After removal of the solvent, the residue was purified by column chromatography on silica gel. (10% EtAcO/hexanes), affording 0.25 g of methyl 1-{5-chloro-2-[2-(2,4-difluorophenyl)ethoxy] benzyl}-1H-indole-4-carboxylate [Rf=0.60 (20% EtAcO/ hexanes), yellow oil, 92% yield].

$^1$H-NMR (CDCl$_3$, 250 MHz, δ): 7.91 (dd, J=7.7, 1.1 Hz, 1H, ArH); 7.41 (d, J=8.0 Hz, 1H, ArH); 7.24-7.13 (m, 5H, ArH); 6.85-6.75 (m, 3H, ArH); 6.64 (d, J=2.7 Hz, 1H, ArH); 5:23 (s, 2H); 4.19 (t, J=6.7 Hz, 2H); 4.00 (s, 3H); 3.10 (t, J=6.7 Hz, 2H).

f) Following the general procedure described in example 211, section b, 1-{5-chloro-2-[2-(2,4-difluorophenyl) ethoxy]benzyl}-1H-indole-4-carboxylic acid was obtained in 62% yield (white solid), using methyl 1-{5-chloro-2-[2-(2,4-difluorophenyl)ethoxy]benzyl}-1H-indole-4-carboxylate (0.25 g, 0.54 mmol) as starting material.

LC-MS ESI+ m/z: 442 (M+1, 95%) (Method 5).

g) Following the general procedure described in example 211, section c, sodium 1-{5-chloro-2-[2-(2,4-difluorophenyl)ethoxy]benzyl}-1H-indole-4-carboxylate was obtained in 91% yield (white solid), using 1-{5-chloro-2-[2-(2,4-difluorophenyl)ethoxy]benzyl}-1H-indole-4-carboxylic acid (0.15 g, 0.33 mmol) as starting material.

LC-MS ESI+ m/z: 442 (M+2-Na, 95%) (Method 2).

$^1$H-NMR (DMSO-d$_6$, 250 MHz, δ): 7.61-7.46 (m, 2H, ArH); 7.32-6.91 (m, 8H, ArH); 6.59 (br s, 1H, ArH); 5.20 (s, 2H); 4.28 (t, J=7.2 Hz, 2H); 3.14 (t, J=7.2 Hz, 2H).

Example 232

Synthesis of 1-{5-chloro-2-[(4-chloro-2-fluorobenzyl)oxy]benzyl}-N-(methylsulfonyl)-1H-indole-4-carboxamide A mixture of EDCl (100 mg, 0.52 mmol), methanesulfonamide (49 mg, 0.52 mmol), DMAP (5 mg, 0.04 mmol) and 1-{5-chloro-2-[(4-chloro-2-fluorobenzyl)oxy]benzyl}-1H-indole-4-carboxylic acid (0.19 g, 0.43 mmol) in DCM (6 mL) was stirred at room temperature for 18 h. The reaction mixture was diluted with DCM (20 mL) and washed with water (20 mL) and brine (10 mL); the organic layer was dried over anhydrous Na$_2$SO$_4$ and filtered. After removal of the solvent, the residue was purified by column chromatography on silica gel (5% MeOH/DCM), affording 1-{5-chloro-2-[(4-chloro-2-fluorobenzyl)oxy]benzyl}-N-(methylsulfonyl)-1H-indole-4-carboxamide as a pale yellow solid. This solid was triturated with Et$_2$O (2×5 mL) and vacuum dried, rendering a white solid in 58% yield.

LC-MS ESI+ m/z: 521 (M+1, 99%) (Method 2).

$^1$H-NMR (CD$_3$OD, 250 MHz, δ): 7.60-7.53 (m, 2H, ArH); 7.40-6.99 (m, 8H, ArH); 6.82 (d, J=2.0 Hz, 1H, ArH); 5.40 (s, 2H); 5.15 (s, 2H); 3.40 (s, 3H).

Example 233

Synthesis of 1-{5-chloro-2-[(4-chloro-2-fluorobenzyl)oxy]benzyl}-N-(methylsulfonyl)-1H-indole-4-carboxamide sodium salt Following the general procedure described in example 211, section c, 1-{5-chloro-2-[(4-chloro-2-fluorobenzyl) oxy]benzyl}-N-(methylsulfonyl)-1H-indole-4-carboxamide sodium salt was obtained in 93% yield (white solid), using 1-{5-chloro-2-[(4-chloro-2-fluorobenzyl)oxy]benzyl}-N-(methylsulfonyl)-1H-indole-4-carboxamide (53 mg, 0.10 mmol) as starting material.

LC-MS ESI+ m/z: 521 (M+2-Na, 98%) (Method 2).

¹H-NMR (CD₃OD, 250 MHz, δ): 7.72 (d, J=8.3 Hz, 1H, ArH); 7.43-7.03 (m, 9H, ArH); 6.69 (d, J=2.0 Hz, 1H, ArH); 5.36 (s, 2H); 5.17 (s, 2H); (s, 3H).

Example 234

Synthesis of 1-(5-chloro-2-isobutoxybenzyl)-N-(methylsulfonyl)-2,3-dihydro-1H-pyrrolo[2,3-b]pyridine-4-carboxamide sodium salt a) A mixture of EDCl (180 mg, 0.94 mmol), methanesulfonamide (89 mg, 0.94 mmol), DMAP (8 mg, 0.07 mmol) and 1-(5-chloro-2-isobutoxybenzyl)-2,3-dihydro-1H-pyrrolo[2,3-b]pyridine-4-carboxylic acid (242 mg, 0.67 mmol) in DCM (10 mL) was stirred at room temperature for 21 h. The reaction mixture was diluted with DCM (20 mL) and washed with water (20 mL) and brine (15 mL); the organic layer was dried over anhydrous Na₂SO₄ and filtered. After removal of the solvent, the residue was purified by column chromatography on silica gel (1☐5% MeOH/DCM), affording 115 mg of 1-(5-chloro-2-isobutoxybenzyl)-N-(methylsulfonyl)-2,3-dihydro-1H-pyrrolo[2,3-b]pyridine-4-carboxamide [Rf=0.50 (10% MeOH/DCM), pale yellow solid, 39% yield].

LC-MS ESI+ m/z: 438 (M+1, 97%) (Method 5).

b) Following the general procedure described in example 211, section c, sodium 1-(5-chloro-2-isobutoxybenzyl)-N-(methylsulfonyl)-2,3-dihydro-1H-pyrrolo[2,3-b]pyridine-4-carboxamide was obtained in 98% yield (pale yellow solid), using 1-(5-chloro-2-isobutoxybenzyl)-N-(methylsulfonyl)-2,3-dihydro-1H-pyrrolo[2,3-b]pyridine-4-carboxamide (115 mg, 0.26 mmol) as starting material.

LC-MS ESI+ m/z: 438 (M+2-Na, 99%) (Method 2).

¹H-NMR (DMSO-d6, 250 MHz, δ): 7.71 (d, J=5.2 Hz, 1H, ArH); 7.25 (dd, J=8.7, 2.5 Hz, 1H, ArH); 7.18 (d, J=2.5 Hz, 1H, ArH); 7.00 (d, J=8.7 Hz, 1H, ArH); 6.85 (d, J=5.2 Hz, 1H, ArH); 4.47 (s, 2H); 3.77 (d, J=6.3 Hz, 2H); 3.46-3.18 (m, 4H); 2.81 (s, 3H); 2.10-1.93 (m, 1H); 0.98 (d, J=6.6 Hz, 6H).

Example 235

Synthesis of 1-{5-chloro-2-[(4-chloro-2-fluorobenzyl)oxy]benzyl}-N-(methylsulfonyl)-1,2,3,4-tetrahydroquinoline-5-carboxamide sodium salt a) A mixture of CDI (99 mg, 0.61 mmol) and 1-{5-chloro-2-[(4-chloro-2-fluorobenzyl)oxy]benzyl}-1,2,3,4-tetrahydroquinoline-5-carboxylic acid (0.20 g, 0.43 mmol) in DCM (10 mL) was stirred at 0° C. After 1 h, DBU (0.09 mL, 0.61 mmol) and methanesulfonamide (59 mg, 0.61 mmol) were added, and the reaction was allowed to reach room temperature. After 16 h, more DBU (0.09 mL, 0.61 mmol) and methanesulfonamide (59 mg, 0.61 mmol) were added, and the mixture was heated at 35° C. for 4 h. The reaction mixture was diluted with DCM (20 mL) and washed with water (20 mL) and HCl (aqueous solution 10%, 10 mL); the organic layer was dried over anhydrous Na₂SO₄ and filtered. After removal of the solvent, the residue was purified by column chromatography on silica gel (1☐3% MeOH/DCM), affording 0.19 g 1-{5-chloro-2-[(4-chloro-2-fluorobenzyl)oxy]benzyl}-N-(methylsulfonyl)-1,2,3,4-tetrahydroquinoline-5-carboxamide [Rf=0.45 (5% MeOH/DCM), white solid, 81% yield].

LC-MS ESI+ m/z: 537 (M+1, 95%) (Method 5).

¹H-NMR (CDCl₃, 250 MHz, δ): 7.47-6.86 (m, 7H, ArH); 6.70 (d, J=7.2 Hz, 1H, ArH); 6.44 (d, J=8.0 Hz, 1H, ArH); 5.11 (s, 2H); 4.44 (s, 2H); 3.54-3.34 (m, 5H); 3.07-2.95 (m, 2H); 2.12-1.96 (m, 2H).

b) Following the general procedure described in example 211, section c, 1-{5-chloro-2-[(4-chloro-2-fluorobenzyl)oxy]benzyl}-N-(methylsulfonyl)-1,2,3,4-tetrahydroquinoline-5-carboxamide sodium salt was obtained in 99% yield (white solid), using 1-{5-chloro-2-[(4-chloro-2-fluorobenzyl)oxy]benzyl}-N-(methylsulfonyl)-1,2,3,4-tetrahydroquinoline-5-carboxamide (0.14 g, 0.25 mmol) as starting material.

LC-MS ESI+ m/z: 536 (M+1-Na, 96%) (Method 2).

¹H-NMR (CD₃OD, 250 MHz, δ): 7.55 (t, J=8.5 Hz, 1H, ArH); 7.31-6.99 (m, 5H, ArH); 6.84 (t, J=8.0 Hz, 1H, ArH); 6.65 (dd, J=7.5, 1.2 Hz, 1H, ArH); 6.21 (d, J=7.5 Hz, 1H, ArH); 5.19 (s, 2H); 4.41 (s, 2H); 3.41-3.33 (m, 2H); 3.09 (s, 3H); 3.01-2.91 (m, 2H); 2.05-1.93 (m, 2H).

Example 236

Synthesis of 1-{5-chloro-2-[(4-chloro-2-fluorobenzyl)oxy]benzyl}-N-[(dimethylamino)sulfonyl]-1,2,3,4-tetrahydroquinoline-5-carboxamide A mixture of CDI (0.12 g, 0.76 mmol) and 1-{5-chloro-2-[(4-chloro-2-fluorobenzyl)oxy]benzyl}-1,2,3,4-tetrahydroquinoline-5-carboxylic acid (0.25 g, 0.54 mmol) in DCM (15 mL) was stirred at 0° C. After 1 h, the solvent was removed and the residue was dissolved in 1,4-dioxane (15 mL); DBU (0.12 mL, 0.76 mmol) and N,N-dimethylsulfamide (94 mg, 0.76 mmol) were added and the reaction was heated at 100° C. for 7 h and 80° C. overnight. The reaction mixture was allowed to reach room temperature and the volatiles were removed by rotatory evaporation. The residue was dissolved in EtAcO (30 mL) and washed with water (30 mL) and HCl (aqueous solution 10%, 10 mL); the organic layer was dried over anhydrous Na₂SO₄ and filtered. After removal of the solvent, the residue was purified by column chromatography on silica gel (10☐20% EtAcO/hexanes), affording 0.15 g 1-{5-chloro-2-[(4-chloro-2-fluorobenzyl)oxy]benzyl}-N-[(dimethylamino)sulfonyl]-1,2,3,4-tetrahydroquinoline-5-carboxamide [Rf=0.40 (40% EtAcO/hexanes), white solid, 50% yield].

LC-MS ESI+ m/z: 566 (M+1, 99%) (Method 2).

¹H-NMR (DMSO-d6, 250 MHz, δ): 11.69 (s, 1H); 7.69-7.49 (m, 2H, ArH); 7.39-7.19 (m, 3H, ArH); 6.99-6.88 (m, 2H, ArH); 6.58 (d, J=7.3 Hz, 1H, ArH); 6.30 (d, J=8.4 Hz, 1H, ArH); 5.23 (s, 2H); 4.40 (s, 2H); 2.88 (s, 6H); 2.83-2.73 (m; 2H); 1.99-1.85 (m, 2H). One of the CH2 is under the peak of water.

Example 237

Synthesis of 1-{5-chloro-2-[(4-chloro-2-fluorobenzyl)oxy]benzyl}-N-[(dimethylamino)sulfonyl]-1,2,3,4-tetrahydroquinoline-5-carboxamide sodium salt Following the general procedure described in example 211, section c, the title compound was obtained in 87% yield (white solid), using 1-{5-chloro-2-[(4-chloro-2-fluorobenzyl)oxy]benzyl}-N-[(dimethylamino)sulfonyl]-1,2,3,4-tetrahydroquinoline-5-carboxamide (95 mg, 0.17 mmol) as starting material.

LC-MS ESI+ m/z 566 (M+2-Na, 99%) (Method 2).

¹H-NMR (CD₃OD, 250 MHz, δ): 7.56 (t, J=8.4 Hz, 1H, ArH); 7.33-7.00 (m, 5H, ArH); 6.84 (t, J=7.8 Hz, 1H, ArH);

J=7.6 Hz, 1H, ArH); 6.20 (d, J=8.0 Hz, 1H, ArH); 5.19 (s, 2H); 4.42 (s, 2H); 3.42-3.34 (m, 2H); 3.04-2.95 (m, 2H); 2.83 (s, 6H); 2.06-1.93 (m, 2H).

Example 238

Synthesis of N-({1-(5-chloro-2-[(4-chloro-2-fluorobenzyl)oxy]benzyl})-1,2,3,4-tetrahydroquinolin-5-yl]amino}carbonyl)methanesulfonamide sodium salt a) DPPA (0.06 mL, 0.28 mmol) was added to a suspension of 1-{5-chloro-2-[(4-chloro-2-fluorobenzyl)oxy]benzyl}-1,2,3,4-tetrahydroquinoline-5-carboxylic acid (105 mg, 0.23 mmol), methanesulfonamide (22 mg, 0.23 mmol) and DIPEA (0.08 mL, 0.46 mmol) in toluene (8 mL) and heated at 85° C. After 19 h, the reaction mixture was allowed to reach room temperature and the volatiles were removed by rotatory evaporation. The residue was dissolved in EtAcO (25 mL) and washed with water (2×15 mL); the organic layer was dried over anhydrous $Na_2SO_4$ and filtered. After removal of the solvent, the residue was purified by column chromatography on silica gel (5% MeOH/DCM), affording 52 mg of N-({1-(5-chloro-2-[(4-chloro-2-fluorobenzyl)oxy]benzyl})-1,2,3,4-tetrahydroquinolin-5-yl]amino}carbonyl)methanesulfonamide [Rf=0.60 (10% MeOH/DCM), yellow solid, 10.41% yield].

LC-MS ESI+ m/z 552 (M+1, 77%) (Method 5).

b) Following the general procedure described in example 211, section c, N-({1-(5-chloro-2-[(4-chloro-2-fluorobenzyl)oxy]benzyl})-1,2,3,4-tetrahydroquinolin-5-yl]amino}carbonyl)methanesulfonamide sodium salt was obtained in 65% yield (pale yellow solid), using N-({1-(5-chloro-2-[(4-chloro-2-fluorobenzyl)oxy]benzyl})-1,2,3,4-tetrahydroquinolin-5-yl]amino}carbonyl)methanesulfonamide (61 mg, 0.11 mmol) as starting material.

LC-MS ESI+ m/z: 552 (M+2-Na, 95%) (Method 2).

$^1$H-NMR (DMSO-d6, 250 MHz, δ): 7.69-6.94 (m, 7H, ArH); 6.68 (t, J=7.8 Hz, 1H, ArH); 5.82 (d, J=8.2 Hz, 1H, ArH); 5.22 (s, 2H); 4.33 (s, 2H); 3.33-3.18 (m, 2H); 2.73 (s, 3H); 1.97-1.79 (m, 2H). One of the CH2 is under the peak of water.

Example 239

Synthesis of 1-{5-chloro-2-[(4-chloro-2-fluorobenzyl)oxy]benzyl}-N-(methylsulfonyl)-2,3-dihydro-1H-pyrrolo[2,3-b]pyridine-4-carboxamide sodium salt a) A mixture of EDCl (111 mg, 0.58 mmol), methanesulfonamide (55 mg, 0.58 mmol), DMAP (5 mg, 0.04 mmol) and 1-{5-chloro-2-[(4-chloro-2-fluorobenzyl)oxy]benzyl}-2,3-dihydro-1H-pyrrolo[2,3-b]pyridine-4-carboxylic acid (185 mg, 0.41 mmol) in DCM (8 mL) was stirred at room temperature for 17 h. The reaction mixture was diluted with DCM (20 mL) and washed with water (10 mL) and HCl (aqueous solution 10%, 2 mL); the organic layer was dried over anhydrous $Na_2SO_4$ and filtered. After removal of the solvent, the residue was purified by column chromatography on silica gel (0→5% MeOH/DCM), affording 83 mg of 1-{5-chloro-2-[(4-chloro-2-fluorobenzyl)oxy]benzyl}-N-(methylsulfonyl)-2,3-dihydro-1H-pyrrolo[2,3-b]pyridine-4-carboxamide [Rf=0.60 (10% MeOH/DCM), pale yellow solid, 39% yield].

LC-MS ESI+ m/z: 524 (M+1, 99%) (Method 5).

b) Following the general procedure described in example 211, section c, sodium 1-{5-chloro-2-[(4-chloro-2-fluorobenzyl)oxy]benzyl}-N-(methylsulfonyl)-2,3-dihydro-1H-pyrrolo[2,3-b]pyridine-4-carboxamide was obtained in 91% yield (pale yellow solid), using 1-{5-chloro-2-[(4-chloro-2-fluorobenzyl)oxy]benzyl}-N-(methylsulfonyl)-2,3-dihydro-1H-pyrrolo[2,3-b]pyridine-4-carboxamide (78 mg, 0.15 mmol) as starting material.

LC-MS ESI– m/z: 522 (M-Na, 99%) (Method 2).

$^1$H-NMR (DMSO-d6, 250 MHz, δ): 7.73-7.60 (m, 2H, ArH); 7.50 (dd, J=10.0, 2.5 Hz, 1H, ArH); 7.35-7.27 (m, 2H, ArH); 7.22 (d, J=2.5 Hz, 1H, ArH); 7.17 (d, J=8.8 Hz, 1H, ArH); 6.85 (d, J=5.7 Hz, 1H, ArH); 5.19 (s, 2H); 4.46 (s, 2H); 3.41-3.17 (m, 4H); 2.81 (s, 3H).

Examples 240 to 246

Using Different Starting Materials

The next compound were obtained using the same methodology as in Example 224 but using the corresponding starting material as indicated.

| | | | | LC-MS | |
| --- | --- | --- | --- | --- | --- |
| Example | Compound name | Starting material | Method | $t_R$ (min) | m/z [M + H]⁺ |
| 240 | Sodium 1-{2-[(4-chloro-2-fluorobenzyl)oxy]benzyl}-1,2,3,4-tetrahydro-1,7-naphthyridine-5-carboxylate | 1-{2-[(4-chloro-2-fluorobenzyl)oxy]phenyl}methanamine | 2 | 17.09 | 427 |
| 241 | Sodium 1-{2-[(2,4-difluorobenzyl)oxy]benzyl}-1,2,3,4-tetrahydro-1,7-naphthyridine-5-carboxylate | 1-{2-[(2,4-difluorobenzyl)oxy]phenyl}methanamine | 2 | 16.14 | 411 |
| 242 | Sodium 1-[5-chloro-2-(2-fluoro-2-methylpropoxy)benzyl]-1,2,3,4-tetrahydro-1,7-naphthyridine-5-carboxylate | 1-[5-chloro-2-(2-fluoro-2-methylpropoxy)phenyl]methanamine | 2 | 15.18 | 393 |

| Example | Compound name | Starting material | Method | LC-MS $t_R$ (min) | m/z $[M + H]^+$ |
|---|---|---|---|---|---|
| 243 | Sodium 1-{2-[(2,4-difluorobenzyl)oxy]-5-fluorobenzyl}-1,2,3,4-tetrahydro-1,7-naphthyridine-5-carboxylate | 1-{2-[(2,4-difluorobenzyl)oxy]-5-fluorophenyl}methanamine | 2 | 16.06 | 429 |
| 244 | Sodium 1-(2-((2,4-difluorobenzyl)oxy)-5-methylbenzyl)-1,2,3,4-tetrahydro-1,7-naphthyridine-5-carboxylate | 1-{2-[(2,4-difluorobenzyl)oxy]-5-methylphenyl}methanamine | 2 | 16.86 | 425 |
| 245 | Sodium 1-{2-[(4-chloro-2-fluorobenzyl)oxy]-5-fluorobenzyl}-1,2,3,4-tetrahydro-1,7-naphthyridine-5-carboxylate | 1-{2-[(4-chloro-2-fluorobenzyl)oxy]-5-fluorophenyl}methanamine | 2 | 17.22 | 445 |
| 246 | Sodium 1-{2-[(4-chloro-2-fluorobenzyl)oxy]-5-methylbenzyl}-1,2,3,4-tetrahydro-1,7-naphthyridine-5-carboxylate | 1-{2-[(4-chloro-2-fluorobenzyl)oxy]-5-methylphenyl}methanamine | 2 | 17.78 | 441 |

Example 247

Synthesis of sodium 4-(2-cyclobutoxy-5-fluorobenzyl)-3,4-dihydro-2H-benzo[b][1,4]oxazine-8-carboxylate a) Following a similar procedure to that described in example 190 (step a), but starting from methyl 3,4-dihydro-2H-benzo[b][1,4]oxazine-8-carboxylate instead of methyl 1,2,3,4-tetrahydroquinoline-5-carboxylate hydrochloride and 5-fluoro-2-hydroxybenzaldehyde instead of 5-chloro-2-propoxybenzaldehyde, the desired compound was obtained (31% yield)

LC-MS (method 4): $t_R$=2.05 min; m/z=318 (MH$^+$).

b) To a solution of the compound obtained in the previous section (250 mg, 0.78 mmol) in DMF (10 mL), potassium carbonate (217 mg, 1.57 mmol) and bromocyclobutane (160 mg, 1.18 mmol) were added. The reaction mixture was stirred at 60° C. overnight. The reaction mixture was diluted by adding EtAcO and saturated NH$_4$Cl aqueous solution (15 mL) and extracted with EtAcO (3×15 mL). The combined organic phases were dried over anhydrous Na$_2$SO$_4$, filtered and concentrated. The crude residue was chromatographed on a silica gel flash system (Biotage SP1) using hexanes/EtAcO mixtures of increasing polarity as eluent, to afford the desired product (96% yield).

LC-MS (method 4): $t_R$=2.9 [M+H]$^+$=372 c) Following a similar procedure to that described in example 123 (section b), but using the compound obtained in previous section as starting material, the desired compound was obtained (79% yield).

LC-MS (method 4): $t_R$=1.72 [M+H]$^+$=358

$^1$H NMR (300 MHz, DMSO-d6) δ: 7.08-6.78 (m, 3H, ArH); 6.6-6.41 (m, 2H, ArH); 6.32-6.22 (m, 1H, ArH); 4.87-4.6 (m, 1H); 4.34 (s, 2H); 4.24-4.04 (m, 2H); 3.57-3.22 (m, 2H); 2.51-2.33 (m, 2H); 2.21-1.96 (m, 2H); 1.91-1.51 (m, 2H).

Example 248

Synthesis of sodium 1-{5-chloro-2-[(4-chloro-2-fluorobenzyl)oxy]benzyl}-2,3-dihydro-1H-pyrrolo[2,3-c]pyridine-4-carboxylate a) Freshly prepared LDA (0.90 mmol) was added to a solution of 3-bromo-5-fluoropyridine (0.15 g, 0.82 mmol) in THF (10 mL) cooled at −78° C. After 30 min, a solution of 3-{5-chloro-2-[(4-chloro-2-fluorobenzyl)oxy]benzyl}-1,2,3-oxathiazolidine 2,2-dioxide (0.37 g, 0.90 mmol) in 3 mL of THF was transferred via cannula to the anion solution. After 20 min, TLC showed an intense polar spot corresponding to the sulfamic acid intermediate. The solvent was evaporated and the resulting residue was dissolved in 1,4-dioxane (10 mL) and treated with 0.40 mL of HCl (4 M in 1,4-dioxane), stirring at room temperature. After 17 h, the reaction was cooled to 0° C. and slowly basified with NaOH (aqueous solution 10%, 4 mL). The mixture was poured over EtAcO (40 mL) and washed with water (30 mL); the organic layer was dried over anhydrous Na$_2$SO$_4$ and filtered. After removal of the solvent, the residue was purified by column chromatography on silica gel (20☐ and filtered. After removal of the solveN-[2-(3-bromo-5-fluoropyridin-4-yl)ethyl]-N-{5-chloro-2-[(4-chloro-2-fluorobenzyl)oxy]benzyl}amine [Rf=0.70 (5% MeOH/DCM), pale yellow oil, 74% yield].

LC-MS ESI+ m/z: 503 (M+1, 93%) (Method 5).

$^1$H-NMR (CDCl$_3$, 250 MHz, δ): 8.48 (s, 1H, ArH); 8.31 (s, 1H, ArH); 7.42-7.33 (m, 1H, ArH); 7.25-7.10 (m, 4H, ArH); 6.84 (d, J=8.5 Hz, 1H, ArH); 5.06 (s, 2H); 3.81 (s, 2H); 3.03-2.93 (m, 2H); 2.86-2.78 (m, 2H).

b) A mixture of N-[2-(3-bromo-5-fluoropyridin-4-yl)ethyl]-N-{5-chloro-2-[(4-chloro-2-fluorobenzyl)oxy]benzyl}amine (0.30 g, 0.60 mmol) and $K_2CO_3$ (0.10 g, 0.72 mmol) in DMF (10 mL) was heated at 120° C. for 12 h and 140° C. for 2 h. The reaction was allowed to reach room temperature, poured over EtAcO (60 mL) and washed with water (60 mL); the organic layer was dried over anhydrous $Na_2SO_4$ and filtered. After removal of the solvent, the residue was purified by column chromatography on silica gel (5□ and filtered. After removal of 0.18 g of 4-bromo-1-{5-chloro-2-[(4-chloro-2-fluorobenzyl)oxy]benzyl}-2,3-dihydro-1H-pyrrolo[2,3-c]pyridine [Rf=0.75 (40% EtAcO/hexanes), white solid, 65% yield].

LC-MS ESI+ m/z: 483 (M+1, 97%) (Method 5).

$^1$H-NMR (CDCl$_3$, 250 MHz, δ): 7.96 (s, 1H, ArH); 7.60 (s, 1H, ArH); 7.37-7.08 (m, 5H, ArH); 6.89 (d, J=8.5 Hz, 1H, ArH); 5.08 (s, 2H); 4.27 (s, 2H); 3.52-3.42 (m, 2H); 3.06-2.98 (m, 2H).

c) A suspension of 4-bromo-1-{5-chloro-2-[(4-chloro-2-fluorobenzyl)oxy]benzyl}-2,3-dihydro-1H-pyrrolo[2,3-c]pyridine (0.18 g, 0.37 mmol), dppf (11 mg, 0.02 mmol) and TEA (0.15 mL, 1.11 mmol) in EtOH (60 mL) was thoroughly purged with argon; Pd(AcO)$_2$ (4 mg, 0.02 mmol) was added and the mixture was purged again with carbon monoxide. The mixture was placed in a stainless steel pressure reactor and heated at 120° C. under carbon monoxide pressure (30 bar) for 16 h. The reaction was allowed to reach room temperature and carbon monoxide was released. After removal of the solvent, the residue was purified by column chromatography on silica, gel (15□25% EtAcO/hexanes), affording 0.15 g of ethyl 1-{5-chloro-2-[(4-chloro-2-fluorobenzyl)oxy]benzyl}-2,3-dihydro-1H-pyrrolo[2,3-c]pyridine-4-carboxylate [Rf=0.50 (40% EtAcO/hexanes), pale yellow solid, 84% yield].

LC-MS ESI+ m/z: 475 (M+1, 99%) (Method 5).

$^1$H-NMR (CDCl$_3$, 250 MHz, δ): 8.49 (s, 1H, ArH); 7.79 (s, 1H, ArH); 7.37-7.08 (m, 5H, ArH); 6.89 (d, J=8.4 Hz, 1H, ArH); 5.09 (s, 2H); 4.37 (q, J=7.2 Hz, 2H); 4.31 (s, 2H); 3.50-3.37 (m, 4H); 1.40 (t, J=7.2 Hz, 3H).

d) Following the general procedure described in example 211, section b, 1-{5-chloro-2-[(4-chloro-2-fluorobenzyl)oxy]benzyl}-2,3-dihydro-1H-pyrrolo[2,3-c]pyridine-4-carboxylic acid was obtained in 88% yield (pale yellow solid), using ethyl 1-{5-chloro-2-[(4-chloro-2-fluorobenzyl)oxy]benzyl}-2,3-dihydro-1H-pyrrolo[2,3-c]pyridine-4-carboxylate (0.14 g, 0.29 mmol) as starting material.

LC-MS ESI+ m/z: 448 (M+1, 99%) (Method 5).

e) Following the general procedure described in example 211, section c, sodium 1-{5-chloro-2-[(4-chloro-2-fluorobenzyl)oxy]benzyl}-2,3-dihydro-1H-pyrrolo[2,3-c]pyridine-4-carboxylate was obtained in 80% yield (white solid), using 1-{5-chloro-2-[(4-chloro-2-fluorobenzyl)oxy]benzyl}-2,3-dihydro-1H-pyrrolo[2,3-c]pyridine-4-carboxylic acid (0.11 g, 0.25 mmol) as starting material.

LC-MS ESI+ m/z: 447 (M+1-Na, 99%) (Method 2).

$^1$H-NMR (CD$_3$OD, 250 MHz, δ): 8.22 (s, 1H, ArH); 7.55 (s, 1H, ArH); 7.50-7.07 (m, 6H, ArH); 5.14 (s, 2H); 4.32 (s, 2H); 3.49-3.28 (m, 4H).

Examples 249 to 250

Using a Different starting material

The next compounds were obtained using the same methodology as in Example 208 but using the corresponding starting material as indicated.

| Example | Compound name | Starting material | Method | $t_R$ (min) | m/z $[M + H]^+$ |
|---|---|---|---|---|---|
| 249 | Sodium 1-(5-chloro-2-cyclobutoxybenzyl)-2-oxoindoline-4-carboxylate | methyl 1-(5-chloro-2-cyclobutoxybenzyl)-1H-indole-4-carboxylate | 4 | 1.69 | 371 |
| 250 | Sodium 1-(5-chloro-2-(2-fluoro-2-methylpropoxy)benzyl)-2-oxoindoline-4-carboxylate | methyl 1-(5-chloro-2-(2-fluoro-2-methylpropoxy)benzyl)-1H-indole-4-carboxylate | 4 | 1.61 | 391 |

Examples of Biological Activity

In the following examples the biological activity of compounds of formula (I) towards EP1 receptors is shown.

Test 1: Human EP1 Receptor Radioligand Binding Assay

To investigate binding properties of EP1 receptor ligands to human EP1 receptor, transfected HEK-293 cell membranes and [3H]-PGE2 (Perkin Elmer) were used. In 96-well plates the assay was carried out with a total reaction volume of 250 µl, containing 25 µl of membrane suspension (30 µg protein/well), 25 µl of [3H]-PGE2 (10 nM) in either absence or presence of 25 µl of either buffer or PGE2 (10 µM) for total and non-specific binding, respectively. Binding buffer contained 10 mM MES, 1 mM MgCl2 and 1 mM EDTA at pH 6.0. Plates were incubated at 25° C. for 60 minutes. After the incubation period, 200 µl of incubate were transferred to MultiScreen HTS, FB plates (Millipore), filtered and plates were washed 6 times with ice-cold 10 mM MES, 1 mM MgCl2 and 1 mM EDTA at pH 6.0. Filters were dried and counted in a MicroBeta scintillation counter (Perkin-Elmer) using EcoScint liquid scintillation cocktail.

Percentage inhibition was calculated relating compounds activity to the 0% inhibition of the wells incubated with 10 nM [3H]-PGE2 alone (total binding) and 100% inhibition of the wells incubated with 10 nM [3H]-PGE2 plus 10 µM PGE2 (non-specific binding).

Test 2: Measurement of IP1 responses by Homogeneous Time Resolved Fluorescence

IP1 measurements on HEK-293 cells that stably expressed human EP1 receptors were performed by using a system based on Homogeneous Time Resolved Fluorescence (HTRF) (Gabriel et al., 2003). This technology allows the direct measurement of IP1 in living cells. The principle of this assay is based on competition between IP1 produced by cells and IP1-d2 conjugate for the binding with monoclonal anti-IP1-cryptate conjugate. The HTRF IP1 kit from CisBio was used according to the manufacturer's directions. The experimental procedure was performed as stated below.

Suspended cells (30,000 cells per well) were added to 96-well culture plates in 40 μl of stimulation buffer (supplied by the kit). Compounds were then added in 20 μl of stimulation buffer and incubated at 37° C. for 15 minutes followed by 10 μl of PGE2 to a final concentration of 30 nM. After 90 minutes at 37° C., the reaction was stopped lysing the cells with a mixture of 15 μl of cryptate and 15 μl of IP1-d2 prepared in the lysis buffer supplied by the manufacturer. Plates were incubated for an additional hour at room temperature and read at 665 nm/620 nm using an UltraEvolution Plate reader (Tecan).

Antagonist percentage inhibition was calculated relating compounds activity to the 0% inhibition of the wells incubated with 10 nM PGE2 alone and 100% inhibition of the wells incubated with 10 nM PGE2 plus 1 μM of the reference antagonist.

Test 3: Measurement of IP1 Responses by Homogeneous Time Resolved Fluorescence

IP1 measurements on HEK-293 cells that stably expressed human EP1 receptors were performed by using a system based on Homogeneous Time Resolved Fluorescense (HTRF) (Gabriel et al., 2003). This technology allows the direct measurement of IP1 in living cells. The principle of this assay is based on competition between IP1 produced by cells and IP1-d2 conjugate for the binding with monoclonal anti-IP1-cryptate conjugate. The HTRF IP1 kit from CisBio was used according to the manufacturer's directions. The experimental procedure was performed as stated below.

40,000 cells per well were added to 96-well culture plates in 40 μl of Optimem and incubated o/n at 37° C. Optimem was replaced by 40 μl of stimulation buffer (supplied by the kit) and compounds were then added in 20 μl of stimulation buffer and incubated at 37° C. for 15 minutes followed by 10 μl of PGE2 to a final concentration of 10 nM. After 90 minutes at 37° C., the reaction was stopped lysing the cells with a mixture of 15 μl of cryptate and 15 μl of IP1-d2 prepared in the lysis buffer supplied by the manufacturer. Plates were incubated for an additional hour at room temperature and read at 665 nm/620 nm using an UltraEvolution Plate reader (Tecan).

Antagonist percentage inhibition was calculated relating compounds activity to the 0% inhibition of the wells incubated with 10 nM PGE2 alone and 100% inhibition of the wells incubated with 10 nM PGE2 plus 10 μM of the reference antagonist.

The results obtained in the biological assays disclosed in tests 1, 2 and 3 with representative compounds of formula (I) are shown in the Table below.

| Example no | Results of Test 1* | Results of Test 2** | Results of Test 3** |
|---|---|---|---|
| 2 |  | $ |  |
| 3 |  | $ |  |
| 4 |  | $ |  |
| 5 |  | $ |  |
| 6 |  | $ |  |
| 7 |  | $ |  |
| 8 |  | $ |  |
| 9 |  | $ |  |
| 10 |  | $$ |  |
| 11 | # | $ |  |
| 12 | # | $ |  |
| 13 | ## | $ |  |
| 14 | # | $ |  |
| 15 | # |  |  |
| 16 | # |  |  |
| 17 | ## | $ |  |
| 18 |  | $ |  |
| 19 | ## | $ |  |
| 20 |  | $ |  |
| 21 | ## | $ |  |
| 22 | ## |  |  |
| 23 |  | $ |  |
| 24 | ## | $ |  |
| 25 | ## | $ |  |
| 26 | # |  |  |
| 27 | # |  |  |
| 28 |  | $$ |  |
| 29 | # | $ |  |
| 30 | ## |  |  |
| 31 | ## |  |  |
| 32 | ## |  |  |
| 33 | ## | $ |  |
| 34 | ## | $ |  |
| 35 |  | $ |  |
| 36 |  | $$ |  |
| 37 |  | $ |  |
| 38 |  | $ |  |
| 39 |  | $ |  |
| 40 |  | $$ |  |
| 41 |  | $ |  |
| 42 |  | $ |  |
| 43 |  | $ |  |
| 44 | # |  |  |
| 45 | # | $ |  |
| 46 |  | $ |  |
| 47 | # | $ |  |
| 48 | # | $ |  |
| 49 | ## | $ |  |
| 50 | # |  |  |
| 51 | ## | $ |  |
| 52 |  | $ |  |
| 53 |  | $ |  |
| 54 | ## | $ |  |
| 55 | # | $ |  |
| 56 | # |  |  |
| 57 | # |  |  |
| 58 |  | $ |  |
| 59 |  | $$ |  |
| 60 |  | $ |  |
| 61 |  | $$ |  |
| 62 |  | $ |  |
| 63 |  | $ |  |
| 64 |  | $ |  |
| 65 |  | $ |  |
| 66 |  | $ |  |
| 67 |  | $$ |  |
| 68 | ## | $ |  |
| 69 | ## | $ |  |
| 70 |  | $ |  |
| 71 |  | $$ |  |
| 72 |  | $ |  |
| 73 |  | $$ |  |
| 74 |  | $$ |  |
| 75 | ## | $ |  |
| 76 |  | $$ |  |
| 78 |  | $ |  |
| 79 |  | $ |  |
| 80 |  | $ |  |
| 81 |  | $ |  |
| 82 |  | $ |  |
| 83 |  | $ |  |
| 84 |  | $ |  |
| 85 |  | $ |  |
| 86 |  | $$ |  |
| 87 |  | $ |  |
| 89 |  | $$ |  |

| Example no | Results of Test 1* | Results of Test 2** | Results of Test 3** |
|---|---|---|---|
| 90 |  | $ |  |
| 91 | # |  |  |
| 92 |  | $$ |  |
| 93 |  | $ |  |
| 94 |  | $ |  |
| 95 |  | $ |  |
| 96 |  |  |  |
| 97 |  |  |  |
| 98 | # |  |  |
| 99 | # | $ |  |
| 100 |  | $ |  |
| 101 | ## |  |  |
| 104 | ## |  |  |
| 105 | # |  |  |
| 106 | ## |  |  |
| 108 | ## |  |  |
| 111 | ## |  |  |
| 112 | # |  |  |
| 115 | # |  | $ |
| 117 | # |  | $ |
| 119 | # |  | $ |
| 121 | # |  | $ |
| 122 | # |  | $ |
| 124 | # |  | $ |
| 125 | # |  | $ |
| 133 | # |  |  |
| 135 | ## |  |  |
| 136 | # |  | $ |
| 137 | # |  | $ |
| 138 | # |  | $ |
| 140 | ## |  |  |
| 141 | # |  | $ |
| 142 | # |  | $ |
| 144 | # |  | $ |
| 145 | # |  | $ |
| 146 | # |  | $ |
| 147 | # |  | $ |
| 148 | # |  | $ |
| 149 | # |  | $ |
| 151 | # |  | $ |
| 152 | # |  | $ |
| 153 | # |  | $ |
| 157 | # |  | $ |
| 158 | # |  |  |
| 159 | # |  |  |
| 166 | # |  | $ |
| 169 | # |  | $ |
| 170 | # |  | $ |
| 171 | # |  | $ |
| 175 | # |  | $ |
| 176 | ## |  |  |
| 177 | # |  | $ |
| 178 | # |  | $ |
| 182 | # |  | $ |
| 188 | # |  | $ |
| 194 | # |  | $ |
| 195 | # |  | $ |
| 196 | # |  | $ |
| 197 | # |  | $ |
| 201 | ## |  |  |
| 203 | ## |  |  |
| 207 | # |  | $ |
| 208 | # |  | $ |
| 212 | # |  | $ |
| 213 | # |  |  |
| 214 | ## |  |  |
| 216 | # |  | $ |
| 217 | # |  | $ |
| 220 | # |  | $ |
| 221 | # |  | $ |
| 226 | # |  | $ |
| 227 | # |  | $ |
| 234 | # |  | $ |
| 237 | # |  | $$ |
| 240 | # |  | $ |
| 242 | # |  | $ |
| 243 | # |  | $ |
| 248 | # |  | $ |

*Binding assay (Test 1) at 10 µM
% inh > 75,
45 < % inh < 75;
**Functional assay (Test 2 and 3) at 10 µM
$ % inh > 75
$$ 45 < % inh < 75.

REFERENCES

Abe T, Kunz A, Shimamura M, Zhou P, Anrather J, Iadecola C. (2009) The neuroprotective effect of prostaglandin E2 EP1 receptor inhibition has a wide therapeutic window, is sustained in time and is not sexually dimorphic. J Cereb Blood Flow Metab. 29(1):66-72.

Asbóth G, Phaneuf S, Europe-Finner G N, Tóth M, Bernal A L. (1996) Prostaglandin E2 activates phospholipase C and elevates intracellular calcium in cultured myometrial cells: involvement of EP1 and EP3 receptor subtypes. Endocrinology. 137(6):2572-9.

Baba H, Kohno T, Moore K A, Woolf C J. (2001) Direct activation of rat spinal dorsal horn neurons by prostaglandin E2 The Journal of Neuroscience, 21(5):1750-1756.

Banfi, L.; Narisano, E.; Riva, R.; Stiasni, N.; Hiersemann, M. "Sodium Borohydride" in Encyclopedia of Reagents for Organic Synthesis (Ed: L. Paquette) 2004.

Breyer M D, Breyer R M. (2000) Prostaglandin receptors: their role in regulating renal function. Curr Opin Nephrol Hypertens. 2000 January; 9(1):23-9.

Candelario-Jalil E, Slawik H, Ridelis I, Waschbisch A, Akundi R S, Hull M, Fiebich B L. (2005) Regional distribution of the prostaglandin E2 receptor EP1 in the rat brain: accumulation in Purkinje cells of the cerebellum. J Mol Neurosci. 27(3):303-10.

Coleman, R. A., Prostanoid Receptors. IUPHAR compendium of receptor characterization and classification, 2$^{nd}$ edition, 338-353, 2000.

Dirig D M, Yaksh T L. (1999) In vitro prostanoid release from spinal cord following peripheral inflammation: effects of substance P, NMDA and capsaicin. Br J Pharmacol. 126(6):1333-40.

Durrenberger P F, Facer P, Casula M A, Yiangou Y, Gray R A, Chessell I P, Day N C, Collins S D, Bingham S, Wilson A W, Elliot D, Birch R, Anand P. (2006) Prostanoid receptor EP1 and Cox-2 in injured human nerves and a rat model of nerve injury: a time-course study. BMC Neurol. 4; 6:1.

Gabriel D, Vernier M, Pfeifer M J, Dasen B, Tenaillon L, Bouhelal R. (2003) High throughput screening technologies for direct cyclic AMP measurement. *Assay Drug Dev. Technol.* 1: 291-303.

Giblin G M, Bit R A, Brown S H, Chaignot H M; Chowdhury A, Chessell I P, Clayton N M, Coleman T, Hall A, Hammond B, Hurst D N, Michel A D, Naylor A, Novelli R, Scoccitti T, Spalding D, Tang S P, Wilson A W, Wilson R. (2007) The discovery of 6-[2-(5-chloro-2-{[(2,4-difluorophenyl)methyl]oxy}phenyl)-1-cyclopenten-1-yl]-2-pyridinecarboxylic acid, GW848687X, a potent and selective prostaglandin EP1 receptor antagonist for the treatment of inflammatory pain. Bioorg Med Chem Lett. 17(2):385-9.

T. W. Greene and P. G. M. Wuts "Protective groups in organic synthesis" (John Wiley & sons 10 1999)

Guay J., Bateman, K., Gordon R., Mancini J., Riendeau D. (2004) Carrageenan-induced paw edema in rat elicits a predominant prostaglandin E2 (PGE2) response in the central nervous system associated with the induction of microsomal PGE2 synthase-1 J. Biol Chem 2004. 279, 24866-24872.

Hall, A., Billinton A., Giblin G. M. (2007) EP1 antagonists for the treatment of inflammatory pain. Curr Opin. Drug Discov. Devel. 10 (2007) 597-612.

Hall A, Brown S H, Budd C, Clayton N M, Giblin G M, Goldsmith P, Hayhow T G, Hurst D N, Naylor A, Anthony Rawlings D, Scoccitti T, Wilson A W, Winchester W J. (2009) Discovery of GSK345931A: An EP(1) receptor antagonist with efficacy in preclinical models of inflammatory pain. Bioorg Med Chem Lett. 19(2):497-501.

Hönemann C W, Heyse T J, Möllhoff T, Hahnenkamp K, Berning S, Hinder F, Linck B, Schmitz W, van Aken H. (2001) The inhibitory effect of bupivacaine on prostaglandin E(2) (EP(1)) receptor functioning: mechanism of action. Anesth Analg. 93(3):628-634.

J. Wiley & Sons, New York.; and Seyden-Penne, J. "Reductions by the Alumino- and Borohydrides in Organic Synthesis"; VCH-Lavoisier: Paris, 1991

Johansson T, Narumiya S, Zeilhofer H U. (2011) Contribution of peripheral versus central EP1 prostaglandin receptors to inflammatory pain. Neurosci Lett. 495(2):98-101.

Kawahara H, Sakamoto A, Takeda S, Onodera H, lmaki J, Ogawa R. (2001) A prostaglandin E2 receptor subtype EP1 receptor antagonist (ONO-8711) reduces hyperalgesia, allodynia, and c-fos gene expression in rats with chronic nerve constriction. Anesth Analg. 93(4):1012-7.

P. J. Kocienski "Protecting Groups" (Georg Thieme Verlag 1994)

Richard Larock, *Comprehensive Organic Transformations,* 2nd edition, Wiley-VCH, ISBN 0-471-19031-4.

Lee T, Hedlund P, Newgreen D, Andersson K E. (2007) Urodynamic effects of a novel EP(1) receptor antagonist in normal rats and rats with bladder outlet obstruction. J Urol. 177(4):1562-1567.

Lee C. M, Genetos D C, You Z, Yellowley C E. (2007b) Hypoxia regulates PGE(2) release and EP1 receptor expression in osteoblastic cells. J Cell Physiol. 212(1):182-188

Li X, Cudaback E, Keene C D, Breyer R M, Montine T J. (2011) Suppressed microglial E prostanoid receptor 1 signaling selectively reduces tumor necrosis factor alpha and interleukin 6 secretion from toll-like receptor 3 activation. Glia. 59(4):569-576

Lin C R, Amaya F, Barrett L, Wang H, Takada J, Samad T A, Woolf C J (2006) Prostaglandin E2 receptor EP4 contributes to inflammatory pain hypersensitivity. J Pharmacol Exp Ther. 319(3):1096-103.

Ma W, Eisenach J C. (2003) Four PGE2 EP receptors are up-regulated in injured nerve following partial sciatic nerve ligation. Exp Neurol. 183(2):581-92.

Miki, T.; Matsunami, M.; Okada, H.; Matsuya, H.; Kawabata, A (2010) ONO-8130, an EP1 antagonist, strongly attenuates cystitis-related bladder pain caused by cyclophosphamide in mice. J Pharmacol Sci 112(Suppl. 1): Abst P1J-1-2

Minami T, Uda R., Horiguchi S., Ito S. Hyodo M., Hayaishi O. (1994) Allodynia evoked by intrathecal administration fo prostaglandin E2 to conscious mice. Pain, 1994, 57: 217-223.

Minami T, Nakano H, Kobayashi T, Sugimoto Y, Ushikubi F, Ichikawa A, Narumiya S, Ito S. (2001) Characterization of EP receptor subtypes responsible for prostaglandin E2-induced pain responses by use of EP1 and EP3 receptor knockout mice. Br J Pharmacol. 133(3):438-44.

Mizuguchi S, Ohno T, Hattori Y, Ae T, Minamino T, Satoh T, Arai K, Saeki T, Hayashi I, Sugimoto Y, Narumiya S, Saigenji K, Majima M. (2010) Roles of prostaglandin E2-EP1 receptor signaling in regulation of gastric motor activity and emptying. Am J Physiol Gastrointest Liver Physiol. 299(5):G1078-1086

Moriyama T, Higashi T, Togashi K, Iida T, Segi E, Sugimoto Y, Tominaga T, Narumiya S, Tominaga M. (2005) Sensitization of TRPV1 by EP1 and IP reveals peripheral nociceptive mechanism of prostaglandins. Mol Pain. 1: 3.

Nakayama Y, Ornote K, Namiki A. (2002) Role of prostaglandin receptor EP1 in the spinal dorsal horn in carrageenan-induced inflammatory pain. Anesthesiology. 97(5): 1254-62.

Nakayama Y, Omote K, Kawamata T, Namiki A. (2004) Role of prostaglandin receptor subtype EP1 in prostaglandin E2-induced nociceptive transmission in the rat spinal dorsal horn. Brain Res. 1010(1-2):62-8.

Narumiya S., Sugimoto Y., Ushikubi F. (1999) Protanoid receptors: structures, properties, and functions. Physiol Rev. 79 (1999) 1193-1226.

Niho N, Mutoh M, Kitamura T, Takahashi M, Sato H, Yamamoto H, Maruyama T, Ohuchida S, Sugimura T, Wakabayashi K. (2005) Suppression of azoxymethane-induced colon cancer development in rats by a prostaglandin E receptor EP1-selective antagonist. Cancer Sci. 96(5):260-264.

Oidda H., Namba T., Sugimoto Y., Ushikubi F., Ohishi H., Ichikawa A. et al (1995) In situ hybridization studies of prostacyclin receptor mRNA expression in various mouse organs. Br J Pharmacol 1995, 116, 2828-2837.

Oka T, Oka K, Saper CB. (2003) Contrasting effects of E type prostaglandin (EP) receptor agonists on core body temperature in rats. Brain Res. 968(2):256-262.

Oka T, Hosoi M, Oka K, Hori T. (1997) Biphasic alteration in the trigeminal nociceptive neuronal responses after intracerebroventricular injection of prostaglandin E2 in rats. Brain Res. 749(2):354-7. Erratum in: Brain Res 757(2):299.

Okada, H., Konemura, T., Maruyama, T (2010) ONO-8539, a novel ep1 receptor antagonist, suppresses bladder hyperactivity via excessive production of prostaglandin e2 (pge2) induced by intravesical instillation of atp in urodynamic evaluation of cynomolgus monkeys. Eur Urol Suppl 9(2):72

Omote K, Yamamoto H, Kawamata T, Nakayama Y, Namiki A. (2002) The effects of intrathecal administration of an antagonist for prostaglandin E receptor subtype EP(1) on mechanical and thermal hyperalgesia in a rat model of postoperative pain. Anesth Analg. 95(6):1708-12.

Omote K, Kawamata T, Nakayama Y, Kawamata M, Hazama K, Namiki A. (2001) The effects of peripheral administration of a novel selective antagonist for prostaglandin E receptor subtype EP(1), ONO-8711, in a rat model of postoperative pain. Anesth Analg.92(1):233-238.

Rahal S, McVeigh L I, Zhang Y, Guan Y, Breyer M D, Kennedy C R. (2006) Increased severity of renal impairment in nephritic mice lacking the EP1 receptor. Can J Physiol Pharmacol. 84(8-9):877-885.

Sarkar S, Hobson A R, Hughes A, Growcott J, Woolf C J, Thompson D G, Aziz Q. (2003) The prostaglandin E2 receptor-1 (EP-1) mediates acid-induced visceral pain hypersensitivity in humans. Gastroenterology. 124(1):18-25.

Samad T A, Sapirstein A, Woolf C J. (2002) Prostanoids and pain: unraveling mechanisms and revealing therapeutic targets. Trends Mol Med. 2002 August; 8(8):390-6.

Schlötzer-Schrehardt U, Zenkel M, Nüsing R. M. (2002) Expression and Localization of FP and EP Prostanoid. Invest. Ophthalmol. Vis. Sci. 43(5) 1475-1487.

Syriatowicz J P, Hu D, Walker J S, Tracey D J. (1999) Hyperalgesia due to nerve injury: role of prostaglandins. Neuroscience. 94(2):587-94.

Teramura, T.; Kawatani, M.; Maruyama, T. (2000) Prostaglandin E1 facilitate primary afferent activity from the urinary bladder in the rat using selective EP1-receptor antagonist (ONO-8711). BJU Int 86(Suppl. 3): Abst P6.3.19

L. G. Wade, Jr., *Organic Chemistry*, 6th ed., p. 477, Pearson/Prentice Hall, Upper Saddle River, New Jersey, USA, 2005.

Watanabe K, Kawamori T, Nakatsugi S, Ohta T, Ohuchida S, Yamamoto H, Maruyama T, Kondo K, Ushikubi F, Narumiya S, Sugimura T, Wakabayashi K. (1999) Role of the prostaglandin E receptor subtype EP1 in colon carcinogenesis. Cancer Res. 59(20):5093-5096.

Wilbraham D., Masuda T., Deacon S., Kuwayama T., Vincent S. (2010) Safety, tolerability and pharmacokinetic of multiple ascending doses of the ep-1 receptor antagonist ono-8539, a potential new and novel therapy to overactive bladder in healthy young and elderly subjects Eur Urol Suppl 9(2):250.

Woodward D F, Regan J W, Lake S, Ocklind A. (1997) The molecular biology and ocular distribution of prostanoid receptors. Sury Ophthalmol. 41 Suppl 2:S15-21.

Zhang M, Ho H C, Sheu T J, Breyer M D, Flick L M, Jonason J H, Awad H A, Schwarz E M, O'Keefe R J. J (2011) EP1(−/−) mice have enhanced osteoblast differentiation and accelerated fracture repair. Bone Miner Res. 26(4): 792-802.

What is claimed is:

1. A compound of general formula I:

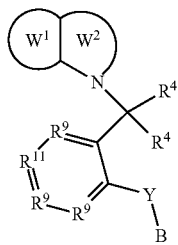

wherein:
$W^1$ is a phenyl ring;
$W^2$ is a 6-membered heterocyclic ring that contains at least 1 N atom and can additionally contain 1 or 2 heteroatoms selected from the group consisting of N, O, and S; wherein said 6-membered heterocyclic ring is aromatic, partially unsaturated or saturated, and which is optionally substituted by one or more $R^3$;
$R^1$ is $-R^6-R^7$;
each $R^2$ is independently selected from the group consisting of H, halogen, $C_{1-6}$-alkyl, $C_{1-6}$-haloalkyl, $-O-C_{1-6}$-alkyl, $-O-C_{1-6}$-haloalkyl, hydroxy$C_{1-6}$-alkyl, CN, $-NR^{14}COR^{15}$, $-NR^{14}SO_2R^{15}$ and $-SO_2R^{15}$;
each $R^3$ is independently selected from the group consisting of H, halogen, $C_{1-6}$-alkyl $C_{1-6}$-haloalkyl, $-O-C_{1-6}$-alkyl, $-O-C_{1-6}$-haloalkyl, hydroxy$C_{1-6}$-alkyl, $-C_{1-4}$-alkylene-$OR^{14}$, $-C_{2-4}$-alkenylene-COOH, =O and CN;

each $R^4$ is independently selected from the group consisting of H and $C_{1-6}$-alkyl, or both $R^4$ together with the C atom to which they are bonded form a $C_{3-6}$cycloalkyl;
$R^5$ is selected from the group consisting of H, halogen, $C_{1-6}$-haloalkyl, $-O-C_{1-6}$-alkyl, $-O-C_{1-6}$-haloalkyl, -OH, $C_{1-6}$-alkyl, $C_{3-6}$cycloalkyl and $-SO_2R^{15}$;
$R^6$ is selected from the group consisting of a direct bond, $-C_{1-4}$-alkylene-, $-O-C_{1-4}$-alkylene-and $-C_{2-4}$-alkenylene-;
$R^7$ is selected from the group consisting of $-CO_2H$, $-SO_3H$, 5-tetrazolyl, $-OPO_3H_2$, $-PO_3H_2$, $-CONR^{12}R^{12}$, $-CONH-SO_2R^{12}$, $-NR^{14}CONR^{14}-SO_2R^{15}$ and $-SO_2-NHCOR^{15}$
Y is selected from the group consisting of $-C_{2-4}$-alkylene-, $-O-C_{1-4}$-alkylene-, $-C_{2-4}$-alkenylene-, $-C_{1-4}$-alkylene-O-, $-NR^{13}-C_{1-4}$-alkylene- and $-C_{1-4}$-alkylene-$NR^{13}-$;
B is selected from the group consisting of $C_{2-6}$-alkyl, $C_{2-6}$ alkenyl and Cy, any of them optionally substituted by one or more $R^8$;
each $R^8$ is independently selected from the group consisting of halogen, $C_{1-6}$-haloalkyl, $-O-C_{1-6}$-alkyl, $-O-C_{1-6}$-haloalkyl, $C_{1-6}$-alkyl, $-OH$, $-CN$, $-CH_2OR^{14}$ and $-CONR^{12}R^{12}$;
each $R^9$ is independently selected from the group consisting of $CR^{10}$ and N;
each $R^{10}$ is independently selected from the group consisting of H, halogen, $C_{1-6}$-alkyl, $C_{1-6}$-haloalkyl, $-O-C_{1-6}$-alkyl, $-O-C_{1-6}$-haloalkyl and hydroxy$C_{1-6}$-alkyl;
$R^{11}$ is $CR^5$ or N,
each $R^{12}$ is independently selected from the group consisting of H, $C_{1-6}$-alkyl, $C_{1-6}$-haloalkyl, $-NR^{14}R^{14}$ and $C_{3-6}$cycloalkyl;
each $R^{13}$ is independently selected from the group consisting of H, $C_{1-6}$-alkyl, $C_{1-6}$-haloalkyl, and $C_{3-6}$cycloalkyl;
each $R^{14}$ is independently selected from the group consisting of H and $C_{1-6}$-alkyl;
each $R^{15}$ is independently selected from the group consisting of $C_{1-6}$-alkyl;
Cy is a 3-6 membered monocyclic or 8-12 membered polycyclic ring which can be carbocyclic or heterocyclic containing 1 to 3 heteroatoms selected from N, O and S and which can be aromatic, partially unsaturated or saturated and wherein one or more C or S atoms in Cy can be oxidized to form CO, SO or $SO_2$;
with the proviso that when W1 and W2 is a benzimidazole, R6 and R7 are not at the same time respectively a $-O-C_{1-4}$-alkylene- and a $-CO_2H$ or that $R^7$ is not $-CONH-SO_2R^{12}$;
and the salts and prodrugs thereof.

2. The compound according to claim 1 wherein each $R^9$ is $CR^{10}$ and each $R^{10}$ is H.

3. The compound according to claim 1, wherein each $R^4$ is H.

4. The compound according to claim 1, wherein Y is $-O-CH_2-$ or $-CH_2-O-$, preferably $-O-CH_2-$.

5. The compound according to claim 1, where $R^{11}$ is $CR^5$ and $R^5$ is selected from the group consisting of H, halogen and —$C_{1-6}$-haloalkyl.

6. The compound according to claim 1, wherein B is phenyl, $C_{3-6}$-cycloalkyl, $C_{2-6}$-alkyl, $C_{2-6}$ alkenyl or is a 5-6 membered monocyclic heterocycle containing 1 or 2 N atom which can be aromatic, partially unsaturated or saturated, any of them optionally substituted by one or more $R^8$.

7. The compound according to claim 1, wherein B is phenyl optionally substituted by 1 to 5 $R^8$.

8. The compound according to claim 1, wherein

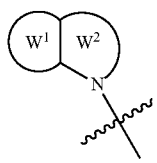

represents

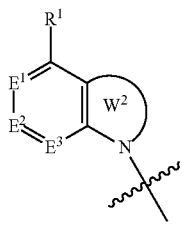

where $E^1$, $E^2$ and $E^3$ are $CR^2$; or one of $E^1$, $E^2$ or $E^3$ is N and the others are $CR^2$; or two of $E^1$, $E^2$ or $E^3$ are N and the other is $CR^2$.

9. The compound according to claim 1, wherein

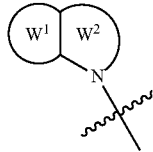

represents

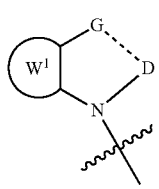

where G is selected from the group consisting of $CR^3$, $CR^3R^3$, $OCR^3R^3$; $OCR^3$; $CR^3R^3$—$CR^3R^3$ and N;
D is selected from the group consisting of $CR^3$, $CR^3R^3$ and N;
- - - represents a single bond or a double bond.

10. The compound according to claim 1 wherein

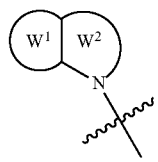 [SMILES: *NCC]

is selected from the group consisting of

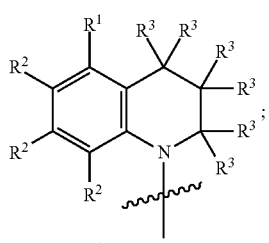

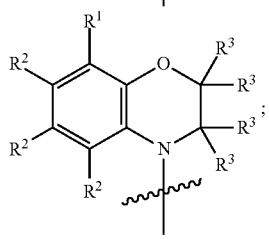

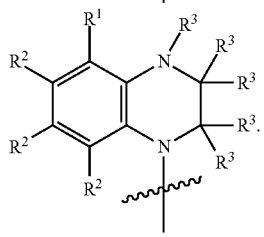

11. The compound according to claim 10 wherein

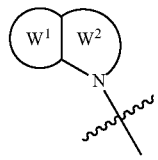 [SMILES: *NCC]

represents

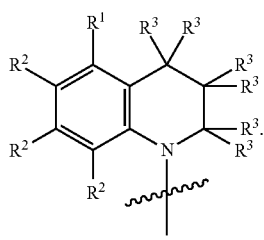

12. The compound according to claim 1, wherein $R^6$ is a direct bond and $R^7$ is —$CO_2H$.

13. The compound according to claim 1, wherein each $R^2$ is independently selected from the group consisting of H and halogen and each $R^3$ is H.

14. A compound according to claim 1 selected from:
1-(5-chloro-2-((4-chloro-2-fluorobenzyl)oxy)benzyl)-1,2,3,4-tetrahydroquinoline-5-carboxylic acid,
1-(5-chloro-2-((2,4-difluorobenzyl)oxy)benzyl)-1,2,3,4-tetrahydroquinoline-5-carboxylic acid,
4-(5-chloro-2-cyclobutoxybenzyl)-3-oxo-3,4-dihydro-2H-benzo[b][1,4]oxazine-8-carboxylic acid,
4-(5-bromo-2-(4-chloro-2-fluorobenzyloxy)benzyl)-3-oxo-3,4-dihydro-2H-benzo[b][1,4]oxazine-8-carboxylic acid,
4-(5-chloro-2-(2-fluoro-2-methylpropoxy)benzyl)-3,4-dihydro-2H-benzo[b][1,4]oxazine-8-carboxylic acid,
4-(5-chloro-2-((4-chloro-2-fluorobenzyl)oxy)benzyl)-3,4dihydro-2H-benzo[b][1,4]oxazine-8-carboxylic acid,
4-(5-chloro-2-((2,4-difluorobenzyl)oxy)benzyl)-3,4-dihydro-2H-benzo[b][1,4]oxazine-8-carboxylic acid,
4-(2-((4-chloro-2-fluorobenzyl)oxy)benzyl)-3,4-dihydro-2H-benzo[b][1,4]oxazine-8-carboxylic acid,
4-(2-(benzyloxy)benzyl)-3,4-dihydro-2H-benzo[b][1,4]oxazine-8-carboxylic acid,
4-(2-((2-chloro-4-fluorobenzyl)oxy)-5-fluorobenzyl)-3,4-dihydro-2H-benzo[b][1,4]oxazine-8-carboxylic acid,
4-(2-((2,4-difluorobenzyl)oxy)benzyl)-3,4-dihydro-2H-benzo[b][1,4]oxazine-8-carboxylic acid,
1-(2-((2,4-difluorobenzyl)oxy)benzyl)-1,2,3,4-tetrahydroquinoline-5-carboxylic acid,
1-(5-chloro-2-((2,4-difluorobenzyl)benzyl)-1,2,3,4-tetrahydroquinoline-5-carboxylic acid,
1-(5-chloro-2-(cyclobutylmethoxy)benzyl)-1,2,3,4-tetrahydroquinoline-5-carboxylic acid,
1-(5-chloro-2-isobutoxybenzyl)-1,2,3,4-tetrahydroquinoline-5-carboxylic acid,
1-[5-chloro-2-(1,2-dimethylpropoxy)benzyl]-1,2,3,4-tetrahydroquinoline-5-carboxylic acid,
1-[5-chloro-2-(2-fluoro-2-methylpropoxy)benzyl]-1,2,3,4-tetrahydroquinoline-5-carboxylic acid,
1-[5-chloro-2-(cyclobutyloxy)benzyl]-1,2,3,4-tetrahydroquinoline-5-carboxylic acid,
1-{5-chloro-2-[(2-methylprop-2-enyl)oxy]benzyl}-1,2,3,4-tetrahydroquinoline-5-carboxylic acid,
1-[5-chloro-2-(3-fluoro-2-methylpropoxy)benzyl]-1,2,3,4-tetrahydroquinoline-5-carboxylic acid,
1-[5-chloro-2-(2-fluoropropoxy)benzyl]-1,2,3,4-tetrahydroquinoline-5-carboxylic acid,
1-(5-chloro-2-{[2-(fluoromethyl)prop-2-enyl]oxy}benzyl)-1,2,3,4-tetrahydroquinoline-5-carboxylic acid,
1-(5-chloro-2-((4-chloro-2-fluorobenzyl)oxy)benzyl)-1,2,3,4-tetrahydroquinoline-5-sulfonic acid,
1-(5-chloro-2-((2,4-difluorobenzyl)oxy)benzyl)-1,2,3,4-tetrahydroquinoline-5-sulfonic acid,
1-(2-((4-chloro-2-fluorobenzyl)oxy)benzyl)-1,2,3,4-tetrahydroquinoline-5-sulfonic acid,
N-((1-(5-chloro-2-((2,4-difluorobenzyl)oxy)benzyl)-1,2,3,4-tetrahydroquinolin-5-yl)sulfonyl)acetamide,
N-((1-(5-chloro-2-((4-chloro-2-fluorobenzyl)oxy)benzyl)-1,2,3,4-tetrahydroquinolin-5-yl)sulfonyl)acetamide,
1-(5-chloro-2-(cyclopentyloxy)benzyl)-1,2,3,4-tetrahydroquinoline-5-carboxylic acid,
1-(5-chloro-2-(propooxy)benzyl)-1,2,3,4-tetrahydroquinoline-5-carboxylic acid,
1-(2-(4-chloro-2-fluorobenzyloxy)-5-methylbenzyl)-1,2,3,4-tetrahydroquinoline-5-carboxylic acid,
1-(5-chloro-2-(neopentyloxy)benzyl)-1,2,3,4-tetrahydroquinoline-5-carboxylic acid,
4-(2-(4-chloro-2-fluorobenzyloxy)-5-methylbenzyl)-3,4-dihydro-2H-benzo[b][1,4]oxazine-8-carboxylic acid,
4-(5-fluoro-2-isobutoxybenzyl)-3,4-dihydro-2H-benzo[b][1,4]oxazine-8-carboxylic acid,
4-(5-chloro-2-isobutoxybenzyl)-3,4-dihydro-2H-benzo[b][1,4]oxazine-8-carboxylic acid,
4-(5-chloro-2-cyclobutoxybenzyl)-3,4-dihydro-2H-benzo[b][1,4]oxazine-8-carboxylic acid,
4-(5-chloro-2-(cyclopropylmethoxy)benzyl)-3,4-dihydro-2H-benzo[b][1,4]oxazine-8-carboxylic acid,
4-(5-chloro-2-(neopentyloxy)benzyl)-3,4-dihydro-2H-benzo[b][1,4]oxazine-8-carboxylic acid,
1-{5-chloro-2-[(4-chloro-2-fluorobenzyl)oxy]benzyl}-2-oxo-1,2,3,4-tetrahydroquinoline-5-carboxylic acid,
8-{5-chloro-2-[(2,4-difluorobenzyl)oxy]benzyl}-5,6,7,8-tetrahydro-1,8-naphthyridine-4-carboxylic acid,
8-{5-chloro-2-[(4-chloro-2-fluorobenzyl)oxy]benzyl}-5,6,7,8-tetrahydro-1,8-naphthyridine-4-carboxylic acid,
1-{5-chloro-2-[(4-chloro-2-fluorobenzyl)oxy]benzyl}-1,2,3,4-tetrahydro-1,7-naphthyridine-5-carboxylic acid,
1-{5-chloro-2-[(2,4-difluorobenzyl)oxy]benzyl}-1,2,3,4-tetrahydro-1,7-naphthyridine-5-carboxylic acid,
1-{5-chloro-2-[(2,4-difluorobenzyl)oxy]benzyl}-1,2,3,4-tetrahydro-1,6-naphthyridine-5-carboxylic acid,
1-{5-chloro-2-[(4-chloro-2-fluorobenzyl)oxy]benzyl}-1,2,3,4-tetrahydro-1,6-naphthyridine-5-carboxylic acid,
1-{5-chloro-2-[(4-chloro-2-fluorobenzyl)oxy]benzyl}-1,2,3,4-tetrahydroquinoxaline-5-carboxylic acid,
1-{5-chloro-2-[(4-chloro-2-fluorobenzyl)oxy]benzyl}-N-(methylsulfonyl)-1,2,3,4-tetrahydroquinoline-5-carboxamide,
1-{5-chloro-2-[(4-chloro-2-fluorobenzyl)oxy]benzyl}-N-[(dimethylamino)sulfonyl]-1,2,3,4-tetrahydroquinoline-5-carboxamide,
1-{5-chloro-2-[(4-chloro-2-fluorobenzyl)oxy]benzyl}-N-[(dimethylamino)sulfonyl]-1,2,3,4-tetrahydroquinoline-5-carboxamide,
N-({1-(5-chloro-2-[(4-chloro-2-fluorobenzyl)oxy]benzyl})-1,2,3,4-tetrahydroquinolin-5-yl]amino}carbonyl)methanesulfonamide,
4-(2-cyclobutoxy-5-fluorobenzyl)-3,4-dihydro-2H-benzo[b][1,4]oxazine-8-carboxylic acid,
and the salts and prodrugs thereof.

15. A medicament comprising at least a compound according to claim 1.

16. Pharmaceutical composition comprising at least one compound according to claim 1 and at least one pharmaceutically acceptable carrier, additive, adjuvant or vehicle.

* * * * *